(12) United States Patent
Johnson et al.

(10) Patent No.: US 7,841,982 B2
(45) Date of Patent: *Nov. 30, 2010

(54) APPARATUS AND METHOD FOR IMAGING OBJECTS WITH WAVEFIELDS

(75) Inventors: Steven A. Johnson, Salt Lake City, UT (US); David T. Borup, Salt Lake City, UT (US); James Wiskin, Salt Lake City, UT (US); Michael J. Berggren, Salt Lake City, UT (US)

(73) Assignee: Techniscan, Inc., Salt Lake City, UT (US)

( * ) Notice: Subject to any disclaimer, the term of this patent is extended or adjusted under 35 U.S.C. 154(b) by 1202 days.

This patent is subject to a terminal disclaimer.

(21) Appl. No.: 11/223,084

(22) Filed: Sep. 9, 2005

(65) Prior Publication Data

US 2006/0084859 A1   Apr. 20, 2006

Related U.S. Application Data

(63) Continuation of application No. 10/615,569, filed on Jul. 7, 2003, now Pat. No. 7,570,742, which is a continuation of application No. 10/024,035, filed on Dec. 17, 2001, now Pat. No. 6,636,584, which is a continuation of application No. 09/471,106, filed on Dec. 21, 1999, now Pat. No. 6,587,540, which is a continuation-in-part of application No. 08/706,205, filed on Aug. 29, 1996, now abandoned, which is a continuation-in-part of application No. 08/486,971, filed on Jun. 22, 1995, now abandoned.

(51) Int. Cl.
*A61B 5/00* (2006.01)
*G01N 23/00* (2006.01)

(52) U.S. Cl. .................. 600/437; 600/442; 600/443; 600/448; 181/101

(58) Field of Classification Search ................. 600/437, 600/438, 442, 448
See application file for complete search history.

(56) References Cited

U.S. PATENT DOCUMENTS

| | | | |
|---|---|---|---|
| 3,805,596 | A | 4/1974 | Klahr |
| 3,885,224 | A | 5/1975 | Klahr |
| 4,047,520 | A | 9/1977 | Soldner et al. |

(Continued)

OTHER PUBLICATIONS

P.R. Williamson, "Tomographic inversion in reflection seismology," Geophys. J. Int. 100, pp. 255-274, 1990.

(Continued)

*Primary Examiner*—Long V Le
*Assistant Examiner*—Vani Gupta
(74) *Attorney, Agent, or Firm*—Thorpe North & Western LLP

(57) ABSTRACT

A transmission wave field imaging method, comprising the transmission of an incident wave field into an object, the incident wave field propagating into the object and, at least, partially scattering. Also includes the measuring of a wave field transmitted, at least in part, through an object to obtain a measured wave field, the measured wave field based, in part, on the incident wave field and the object. Additionally, the processing of the measured wave field utilizing a parabolic approximation reconstruction algorithm to generate an image data set representing at least one image of the object.

33 Claims, 74 Drawing Sheets

U.S. PATENT DOCUMENTS

| | | | |
|---|---|---|---|
| 4,074,564 | A | 2/1978 | Andersen |
| 4,075,883 | A | 2/1978 | Glover |
| 4,100,916 | A | 7/1978 | King |
| 4,105,018 | A | 8/1978 | Greenleaf et al. |
| 4,109,642 | A | 8/1978 | Reid et al. |
| 4,109,644 | A | 8/1978 | Kojima |
| 4,120,291 | A | 10/1978 | Paton et al. |
| 4,222,274 | A | 9/1980 | Johnson |
| 4,317,369 | A | 3/1982 | Johnson |
| 4,341,222 | A | 7/1982 | Gardineer et al. |
| 4,594,662 | A | 6/1986 | Devaney |
| 4,662,222 | A | 5/1987 | Johnson |
| 4,727,550 | A | 2/1988 | Chang et al. |
| 4,798,209 | A | 1/1989 | Klingenbeck et al. |
| 5,227,797 | A | 7/1993 | Murphy |
| 5,588,032 | A | 12/1996 | Johnson et al. |
| 5,667,893 | A | 9/1997 | De Hoop et al. |
| 6,005,916 | A * | 12/1999 | Johnson et al. ............... 378/87 |
| 6,587,540 | B1 | 7/2003 | Johnson et al. |
| 6,636,584 | B2 | 10/2003 | Johnson et al. |
| 6,693,558 | B2 | 2/2004 | Hedrick |
| 7,285,092 | B2 | 10/2007 | Duric et al. |
| 2004/0064046 | A1 | 4/2004 | Shehada |

OTHER PUBLICATIONS

W.W. Kim D.T. Borup, S.A. Johnson, M.J. Berggren, and Y. Chou, "Accelerated Inverse Scattering Algorithms for Highter Contract Objects," in 1987 IEEE Ultrasonics Symposium, 903-906, (IEEE Cat. No. 87ch2492-7).

S.J. Norton, "iterative Seismic Inversion," Geophysical Journal, No. 94, pp. 457-468 (1988).

T.K. Sarkar, E. Arvas, and S.M. Rao (1986) "Application of FFT and the Conjugate Gradient Method for the Solution of Electromagnetic Radiation from Electrically Large and Small Conducting Bodies," IEEE Trans. Antennas Propagat., vol. AP-34, pp. 635-640, May.

R.J. Wombell and M.A. Fiddy (1988), "Inverse Scattering Within the Distorted-wave Born Approximation," Inverse Problems 4 (1988).

Y. Zhou, S.A. Johnson, M.J. Berggren, B.V. Carruth, and W.W. Kim, "Constrained Reconstruction of Object Acoustic Parameters from Noisy Ultrasound Scattering Data," Proc. of the IEEE 1987 Ultrasonics Symposium pp. 897-901 (1987).

Kostas T. Ladas and A. J. Devaney, "Iterative Methods in Geophysical Diffraction Tomography," Inverse Problems 8 (1992).

M.J. Berggren, S.A. Johnson, W.W. Kim, D.T. Borup, R.S. Eidens and Y. Zhou, "Acoustic Inverse Scattering Images from Simulated Higher Contrast Objects and from Laboratory Test Objects," Acoustical Imaging 16, Chicago, Illinois, Jun. 1987.

Brent S. Robinson and James F. Greenleaf, "An Experimental Study of Diffraction Tomography Under the Born Approximation," Acoustical Imaging 18, No. 18, Jun. 1990.

M.J. Berggren, S.A. Johnson, B.L. Carruth, W.W. Kim, F. Stenger and P.L. Kuhn, "Performance of Fast Inverse Scattering Solutions for the Exact Helmholtz Equation Using Multiple Frequencies and Limited Views," Acoustical Imaging 15, Halifax, Nova Scotia, Jul. 1986.

W.W. Kim, S.A. Johnson, M.J. Bergrren, F. Stenger and C.H. Wilcox, "Analysis of Inverse Scattering Solutions from Single Frequency, Combined Transmission and Reflection Data for the Helmholtz and Riccati Exact Wave Equations," Acoustical Imaging 15, pp. 359-369, Plenum Press (1987).

E.J. Ayme-Bellegarda and T.M. Habashy, "Forward Ultrasonic Scattering from Multidimensional Solid or Fluids Inclusions Buried in Multilayered Elastic Structures," IEEE Trans. Ultras., Ferro., and Freq. Cont., vol. 39, No. 1, Jan. 1992.

E.J. Ayme-Bellegarda, and T.M. Habashy, "Ultrasonic Inverse Scattering of Multidimensional Objects Buried in Multilayered Elastic Background Structures," IEEE Trans. Ultras., Ferro, and Freq. Cont., vol. 39, No. 1, Jan. 1992.

J.K. Cohen and F.G. Hagin, "Velocity Inversion Using a Stratified Reference," Geophysics, 50, 11, 1985.

E. Crase, A. Pica, M. Noble, J. McDonald, and A. Tarantola, "Robust Elastic Nonlinear Waveform Inversion: Application to Real Data," Geophysics, 55, 5 (May 1990).

Peter Mora, "Nonlinear Two-dimensional Elastic Inversion of Multioffset Seismic Data," Geophysics, vol. 52, Sep. 9, 1987.

G.S. Pan, R.A Phinney and R.I. Odom, "Full-waveform Inversion of Plane-wave Seismograms in Stratified Acoustic Media: Theory and Feasibility," Geophysics, vol. 53, 1 (1988).

G.R. Franssens, "Calculation of the Elasto-dynamic Green's Function in Layered Media by Means of a Modified Propagator Matrix Method," Geophys. J.R. astr. Soc. 1983.

B.L.N. Kennett and N.J. Kerry, "Seismic Waves in a Stratified Half Space," Geophys. J.R. astr. Soc. 57, pp. 557-583, 1979.

Bolemy, J.C., and Pichot, C., (Apr. 1991) "Some Applications of Diffraction Tomography to Electromagnetics—The Particular Case of Microwaves," in *Inverse Problems in Scattering and Imaging*, edited by M. Bertero and E. R. Pike, Adam Higler (Publisher), New York 1992. Presented at the Proceedings of a Nato Advance Research Workshop, Cape Cod, Apr. 1991.

Borup, D.T., (1989) *Fast-Fourier-Transform Based INteracatoin Methods for Solving the Electric Field Intergral Equation for Anatomically Detailed Man Models*, Ph.D. Dissertion. Unviersity of Utah. Salt Lake City, Utah.

Borup, D.T., and Gandhi, O.P., (1984) Fast-Fourier-Transform method for the calculation of SAR distributions in finely discretized models of biological bodies. *IEEE Trans. Microwave Therory Tech., MIT-32*, 355-360.

Borup, D.T., and Gandhi, O.P., (1985) "Calculation of High-Resolution SAR Distribution in Biological Bodies Using the FFT Algorithm and the Conjugate Gradient Method." *IEEE Trans, Microwave Theory Tech., MIT -33*, 417-419.

Borup, D.T., S.A. Johnson J.W. Wiskin, and M.J.Berggren, "An Integral Equation Method for Nonlinear Imaging of Acoustic and Elastic Parameters," Poster session at the SEG Research Workshop on Recording and Processing of Vector Wave Field Data held at Snowbird, Utah, Aug. 13-17, 1989.

Borup. D.T., Johnosn, S.A., Kim, W.W., and Berggren, M.J., (1992) "Nonperturbative fifraciton Tomography via Gauss-Newton iteration applied ot the Scattering Integral Equaiton." *Ultrasonic Imaging* 14, pp. 69-85. Jan.

Broquetas, A., Romeu, J., Rius, J.M., Elis-Fuste, A.R., Cardama, A. and Jofre, L., (1991) "Cylindrical Geometry: A Further Step in Active Microwave Tomograph." *IEEE Trans Microwave Theroy Tech.*, vol. 39 No. 5, pp. 836-844. May.

Candy, J.V., and Pichot, C., (1991) "Active Microwave Imaging: A Model Based Approach." *IEEE Trans Antennas Propagat.*, vol. 39 No. 3, pp. 285-290. Mar.

Cavicchi, T.J., Johnson, S.A., and O'Brien, Jr., W.D., (1988) Application of the Sinc Basis Moment Method to the Reconstruciton of Infinited Circular Cyclinders, *IEEE Trans Ultrasonics, Ferroelectri., Freq. Control, UFFC-35*, 22-23.

Chew, W.C. and Wang, Y.M., (Jan. 1990) "Reconstruciot nof Two-Dimensional Permittivity Distribution Using the DIstored Born Iterative Method." *IEEE Trans Microwave Theroy Tech.*, pp. 218-225.

Chew, W.C. and Wang, Y.M., (May 1990) "A Fast Algorithm for Solution of a Scattering Problem Using a Recursive Aggregate Tau Matrix Method," *Microwave and Opt. Tech Let.* vol. 3 No. 5, pp. 164-169, May.

Datta. A.N. and Bandyopadhyay, B., (1986) "Nonlinear Extension ot a Moment Method Iterative Reconstruction Algorithm for Microwave Tomography." *Proceed. IEEE*, vol. 74, No. 4, pp. 604-606. Apr.

Johnson, S. A. et al., "Inverse Scattering Solutions by a Sinc Basis, Multiple Source, Moment Method—Part I: Theory", Ultrasonic Imaging, vol. 5, pp. 361-375. Johnson, S. A. et al., "Inverse Scattering Solutions by a Sinc Basis, Multiple Source, Moment Method—Part II: Numerical Evaluations", Ultrasonic Imaging, vol. 5, pp. 376-392.

Johnson, S. A. et al., "Inverse Scattering Solutions by a Sinc Basis, Multiple Source, Moment Method—Part III: Fast Algorithms", Ultrasonic Imaging, vol. 6, pp. 103-116, Academic Press (1984).

Johnson, S.A., Zhou, Y., Berggren M.J., and Tracy, M.L. (1983) "Acoustical Inverse Scattering Solutions by Moment Methods and Backprojection." in *Confernece on Inverse Scattering: Theory and Aplication*. SIAM, Philadlephia.

Muller, Gl., "The Reflectivity Method: a Tutorial." *J. Geophys* 58: 153, 1985.

Tracy, M.L., et al. (1983) "Invense Scattering Solutions by a Sinc Basis, Multiple Source, Moment Method—Part II: Numerical Evaluations." *Ultrasonic Imaging* 5, 376-392.

Wannamaketer, P.E., G.W. Hohmann, and W.A. Filipo, "Electromagnetic Modeling of Three-Dimensional Bodies in Layered Earth using Integral Equations."

Wilcox, C.H., "Ultrasound Imaging at the AIM Laboratory, Univeristy of Utah." Lecture at IMACS International Symposium of Computational Acourstics. Harvard University Jun. 1991.

Wiskin, J.W., "Geometric and Integral Equation Mehtods for Scatteing in Layered Media." Ph. D. dissertation. Dept. Math. University of Utah, publ. Oct. 15, 1991.

Carrion, Philip M. et al., A Method for Computation of Velocity Profiles by Inversion of Large-Offset Records; Geophysics, (1984) pp. 1249-1258 vol. 49, No. 8.

Cheng, Guan and Shimon Coen, The Relationship between Born Inversion, Rytov Inversion, and Migration for Both CMP Stacked and Slant Stacked Data, Abstract of presentation made at 54th Annual Meeting & Exposition of the Society of Exploration Geophysicists, Atlanta, Dec. 2-6, 1984 pp. 575-579.

Cohen, J.K. and F.G. Hagin. "Velocity Inverison using a Stratifeid Reference." *Geophysics*, (1985) pp. 1689-1700, vol. 50, No. 11.

De Figueiredo, Rui J.P., "Approximation-Theoretic Methods for Nonlinear Deconvolution and Inversion", Information Sciences, pp. 209-220 (1983) vol. 31, No. 3.

Foster, Douglas J. et al., "Linear Inversion Applied to Real Seismic Data", Abstract of presentation made at the 54th Annual Meeting & Exposition of the Society of Exploration Geophysicists, Atlanta, Dec. 2-6, 1984.

Tarantola, Albert et al., "Nonlinear Inversion of Seismic Reflection Data", Abstract of presentation made at the 54th Annual Meeting & Exposition of the Society of Exploration Geophysicists held at Atlanta, Dec. 2-6, 1984, pp. 645-658.

Goutsias et al., "A 2-D Stochastic Earth Model for Seismic Inversion", Abstract of presentation made at the 54th Annual Meeting and Exposition of the Society of Exploration Geophysicists held at Atlanta, Ga., Dec. 2-6, 1984, pp. 385-386.

Greenleaf, James F., edited by D. W. McLaughlin Computer Tomography from Ultrasound Scattered by Biological Tissues, SIAM-AMS Proceedings (1984) pp. 53-63.

Hanson, Douglas W., "Multiparameter Seismic Inversion of Noisy Data", Abstract of presentation made at the 54th Annual Meeting and Exposition of the Society of Exploration Geophysicists held at Atlanta, Ga., Dec. 2-6, 1984.

Harkrider, David G., "Synthetics and Theoretical Seismology", Reviews of Geophysics and Space Physics, (1983) vol. 21, No. 6, pp. 1299-1308.

Johnson, S. A. et al., "Acoustic Inverse Scattering Solutions by Moment Methods and Backpropagation", Conference on Inverse Scattering: Theory and Application, SIAM, (1983) pp. 144-155, Philadelphia.

Johnson, S. A. et al., "Fast Iterative Algorithms for Inverse Scattering Solutions of the Helmholtz and Riccati Wave Equations", Acoustical Imaging, vol. 13, pp. 75-87.

Johnson, S.A., Zhou, Y., Tracy, M.K., Berggren, M.J. and Stenger, F.F., (1984) "inverse Scattering Solutions by a Sinc Basis. Multiple Source Moment Method—Part III: Fast Algorithms." *Ultrasonic Imaging* (1984), pp. 103-116.

Johnson, S.A., Zahou Y., Tracy, M.L. Bergrren, M.J. and Stenger, F. "Inverse Scattering Solutions by aSinc Basis, Multiple Source, Moemnt Method—Part I: Theory." *Ultrasonic Imaging* (1983), pp. 361-375.

Johnson, Steven A. et al., "Ultrasound Tomography by Galerkin or Moment Methods", Lecture Notes in Medical Informatics, (1984) vol. 23, pp. 254-276.

Kaman, E. J., "Detailed Inversion of Reservoir Data by Constrained Parameter Estimation and Resolution Analysis," Abstract of presentation made at 54th Annual Meeting and Exposition of the Society of Exploration Geophysicists at Atlanta, Ga., Dec. 2-6, 1984.

La Bras, L. et al., "Presentation of a Born Inversion for Multioffset Reflection Data: Tests on Synthetic Seismograms," Abstract of presentation made at 54th Annual Meeting and Exposition of the Society of Exploration Geophysicists at Atlanta, Ga., Dec. 2-6, 1984.

Lailly, P., "Migration Methods: Practical but Efficient Solutions to the Seismic Inverse Problem," Inverse Problems of Acoustic and Elastic Waves, pp. 182-214.

Lines, Larry R. et al., "Inversion with a Grain of Salt," Abstract of presentation made at 54th Annual Meeting and Exposition of the Society of Exploration Geophysicists at Atlanta, Ga., Dec. 2-6, 1984, pp. 638-640.

MacDonald, Calum et al., "Nonlinear Seismic Inversion", Abstract of presentation made at 54th Annual Meeting and Exposition of the Society of exploration Geophysicists at Atlanta, Ga., Dec. 2-6, 1984, pp. 655-657.

McClary, W. Keith, "Fast Seismic Inversion", Geophysics, (1983) vol. 48, No. 10, pp. 1371-1372.

Morley, Lawrence C., "Invertibility of Elastic Layered Earth Parameters from Precritical P-Wave Reflection Amplitudes", Abstract of presentation at 54th Annual Meeting and Exposition of the Society of Exploration Geophysicists at Atlanta, Ga., Dec. 2-6, 1984, pp. 641-643.

Nercessian, A., "Linearized Inversion of Multioffset Seismic Reflection Data," Abstract of presentation at 54th Annual Meeting and Exposition of the Society of Exploration Geophysicists at Atlanta, Ga., Dec. 2-6, 1984.

P. D. Corl et al., "A Digital Synthetic Focus Acoustic Imaging System", Acoustical Imaging, 8th Int'l. Conference, Jun. 1978, pp. 39-53.

S. A. Johnson et al., High Resolution Ultrasound Echo and Reconstruction Imaging from Temporal and Spatial Projections by Adaptive Ray Tracing, Proceedings of the $4^{th}$ International Joint Conference Pattern Recognition, Feb. 1978 pp. 846-850.

S. A. Johnson et al., Quantitative Synthetic Aperture Reflection Imaging Correction for Refraction and Attenuation: Appl. Seismic Tech. in Medicine, Feb. 1978, pp. 337-349.

S. A. Johnson et al., Ultrasound Images Corrected for Refraction and Attenuation: Comparison of High Resolution Methods, Aug. 1979, pp. 55-71.

S. A. Johnson, et al., "Algebraic and Anly. Inversion Acou. Data Partially or Fully Enclosing Apertures", Acoustical Imaging, Jun. 1978 pp. 577-598.

Sigalov, Ya. B. et al., "On the Solution of the Two-Dimensional Inverse Dynamic Problem of Seismometry by the Finite-Difference Method, Part 1." Geophysical Journal, (1984) vol. 5, No. 4, pp. 508-521.

Tarantola, A. et al., "Generalized Nonlinear Inverse Problems Solved Using the Lease Squares Criterion," Review of Geophysics and Space Physics, (1982) vol. 20, No. 2, pp. 219-232.

Tarantola, A. et al., "Inverse Problems: Quest of Information", J. Geophysics, (1982) vol. 50, No. 3, pp. 159-170.

Tarantola, A., "Inversion of Seismic Reflection Data in the Acoustic Approximation", Geophysics, (1984) vol. 49, No. 8, pp. 1259-1266.

Tarantola, A., "Linearized Inversion of Seismic Reflection Data," Geophysical Prospecting, (1984) vol. 32, pp. 998-1015.

Verwest, B. J. et al., "Prestack Inversion of Plane-Layered Viscoacoustic Earth Parameters," Abstract of presentation at 54th Annual Meeting and Exposition of the Society of the Exploration Geophysicist at Atlanta, Ga., Dec. 2-6, 1984.

* cited by examiner

Hermitian Conjugate of the second
Lippman-Schwinger operator
$(I - G^*\Upsilon^*)f_{\omega\phi} = f_{\omega\phi}^{inc}$
Input $G^*$ is the complex conjugate of the Fourier Transform of $G$, $\bar{\gamma}$, or $\gamma^*$ is the complex conjugate of $\gamma$ Form the pointwise product of the complex conjugate of the scattering potential estimate, with the input to this subroutine $\gamma \cdot f_{\omega\phi}$ store in vector $y(i,j)$ — 1242

Take the Fast Fourier Transform — 1244

Pointwise multiply by $G_\omega^*$ - the conjugate of the Fast Fourier Transform of the Green's function at frequency omega — 1246

Take the Inverse Fast Fourier Transform of the product — 1248

Form the difference $f_{\omega\phi}(i,j) - y(i,j)$ — 1252

$f_{\omega\phi}(i,j) - y(i,j)$

FIG. 15

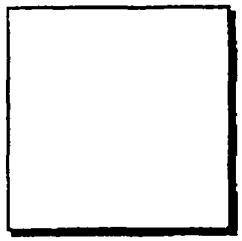
N/2
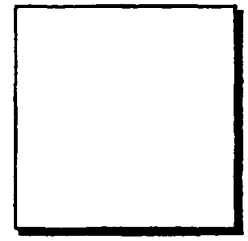
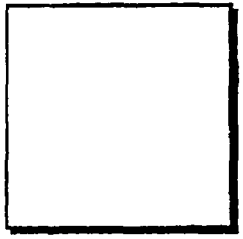
1
1
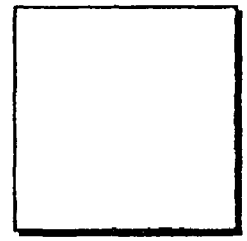
N/2
FIG. 18

APPARATUS AND METHOD FOR IMAGING OBJECTS WITH WAVEFIELDS

PRIORITY CLAIM

This is a continuation of U.S. patent application Ser. No. 10/615,569, filed Jul. 7, 2003, now U.S. Pat. No. 7,570,742 which is a continuation of U.S. patent application Ser. No. 10/024,035, filed on Dec. 17, 2001, now U.S. Pat. No. 6,636,584, which is a continuation of U.S. patent application Ser. No. 09/471,106, filed on Dec. 21, 1999, now U.S. Pat. No. 6,587,540, which is a continuation-in-part of U.S. patent application Ser. No. 08/706,205, filed on Aug. 29, 1996, now abandoned, which is a continuation-in-part of U.S. patent application Ser. No. 08/486,971, filed on Jun. 22, 1995, now abandoned; which are all herein incorporated by reference.

INCORPORATION BY REFERENCE

Material on one (1) compact disc accompanying this patent and labeled COPY 1, a copy of which is also included and is labeled as COPY 2, is incorporated herein by reference. The compact disc has a software appendix thereon in the form of the following three (3) files:
Appendix A.txt, Size: 16 Kbytes, Created: Aug. 13, 2001;
Appendix B.txt, Size: 19 Kbytes, Created: Aug. 13, 2001; and
Appendix C.txt, Size: 1 Kbytes, Created: Aug. 13, 2001.

COPYRIGHT NOTICE

A portion of the disclosure of this patent document contains material to which a claim of copyright protection is made. The copyright owner(s) has/have no objection to the facsimile reproduction by any one of the patent document or the patent disclosure as it appears in the Patent and Trademark Office patent file or records, but reserves all other rights in the copyrighted word.

BACKGROUND OF THE INVENTION

It has long been known that elastic, electromagnetic or acoustic waves in homogeneous and layered environments in the frequency range of a fraction of a cycle per second up to hundreds of millions of cycles per second and higher can be propagated through many solids and liquids. Elastic waves are waves that propagate through solids, and have components of particle motion both parallel (longitudinal, or pressure, wave) and perpendicular (shear wave) to the direction of propagation of the wave energy itself. In contrast to this, acoustic waves are those waves that generate particle motion that is exclusively parallel to the propagation of wave energy. Electromagnetic waves have components of variation of field strength solely in the direction perpendicular to the direction of propagation. All of these types of waves may be used to image the acoustic longitudinal wavespeed and absorption, the electromagnetic wavespeed and absorption, the shear wavespeed, and the density of the material through which the wave energy has travelled.

It is also known that scattering is produced not only by spatial fluctuations in acoustic impedance, which is the product of mass density times wavespeed, but also by independent fluctuations in electromagnetic permeability, permittivity and conductivity, elastic compressibility, shear modulus, density, and absorption. These lead to variations in phase speed (which is the speed of propagation of fronts of constant phase) and in impedance (for the electromagnetic case, the ratio of the electric to the magnetic field strength). The net property of an object which describes the phenomenon of scattering in a given modality, is called the "scattering potential".

Other imaging methods have been applied to one or the other modality, or restricted to acoustic or elastic media, the method described in this patent is applicable to any type of wave motion, whether electromagnetic, elastic (including shear wave effects) or acoustic (scalar approximation valid in liquid and gases).

Furthermore, the ambient media may have some forms of structure (layering) or microstructure (porosity) relevant to the medical, geophysical, or nondestructive imaging applications envisioned for this technology. In the prior art the presence of this layering or porosity has greatly diminished the effectiveness of the imaging program. The method of this patent minimizes the obscuring effect of such structures in the ambient media. In addition, we have made several changes to the previous U.S. Pat. No. 4,662,222 that significantly extend the applicability and speed of our algorithm. These changes are described, in part, below:

As discussed in U.S. Pat. No. 4,662,222, by one of the present authors, these principles can be used to image scattering bodies within a given medium. Some definitions will clarify the procedures and methods used:

The direct or forward scattering problem is concerned with a determination of the scattered energy or fields when the elastic or electromagnetic properties of the scattering potential are known.

The inverse scattering problem, by contrast, consists in the use of scattered electromagnetic, elastic, or acoustic waves to determine the internal material properties of objects embedded in a known (ambient) medium. An incident wave field is imposed upon the ambient medium and the scatterer. The scattered field is measured at detectors placed a finite distance from the scattering objects. The material parameters of the scatterer are then reconstructed from the information contained in the incident and scattered fields. In other words, as defined herein, acoustic or electromagnetic imaging using inverse scattering techniques is intended to mean electronic or optical reconstruction and display of the size shape, and unique distribution of material elastic or electromagnetic and viscous properties of an object scanned with acoustic, electromagnetic or acoustic energy, i.e., reconstruction of that scattering potential which, for a given incident field and for a given wave equation, would replicate a given measurement of the scattered field for any source location.

The description of prior art summarized in U.S. Pat. No. 4,662,222 (referred to as "the previous patent") is also relevant here. It is sufficient to say here, that the use of the conjugate gradient algorithms discussed in the previous patent brought the attainment of inverse scattering into a practical reality. Previous to that patent (U.S. Pat. No. 4,662,222), only linear approximations to the full inverse scattering problem were amenable to solution, even with the aid of modern high speed digital computers. The resolution achievable with the inverse scattering methods described in the previous patent was far superior to any ultrasound imaging in medicine previous to that time.

This invention is designed to provide improved imaging of bodies using wave field energy such as ultrasound energy, electromagnetic energy, elastic wave energy or Biot wave energy. In particular it is designed to provide improved imaging for medical diagnostic applications, for geophysical imaging applications, for environmental imaging applications, for seismic applications, for sonar applications, for radar applications and for similar applications where wave field energy is used to probe and image the interior of objects.

In particular, this invention has important applications to the field of medical diagnosis with specific value to improved breast cancer detection and screening. The present method of choice is mammography. This choice is not supported by the outstanding performance of mammography, but rather because it is the most diagnostically effective for its present cost per exam. Another reason for the wide spread use of mammography is the inertia of changing to other modalities. It is known that hand-probe-based, clinical reflection ultrasound can match the performance of mammography in many cases, but only in the hands of specially trained ultrasound radiologists. Today and in the foreseeable future, there are more mammography machines and radiologists trained to use them than there are trained ultrasound radiologists that have access to high quality ultrasound scanners. Sophisticated breast cancer diagnostic centers use both mammography and ultrasound to compensate for weakness in either approach when used alone. When used alone, ultrasound and mammography require a biopsy to remove a sample of breast tissue for pathology lab analysis to determine whether a sampled lesion is cancerous or benign.

Even when mammography and ultrasound are used together, the specificity for discriminating between cancer and fibrocystic condition or between cancerous tumor and a fibroadenoma is not high enough to eliminate the need for biopsy in 20 to 30 percent of lesions. Given that early diagnosis of breast cancer can ensure survival and that one woman in eight will have breast cancer in her life, it is important to the general population for cancer to be detected as early as possible. Detection of cancer in an early stage for biopsy is thus very important. However, biopsy of benign lesions is traumatic to the patient and expensive. A mammogram costs about $90 but a biopsy is about ten times more expensive. Thus, it is important that a breast cancer diagnostic system have high specificity and sensitivity to eliminate unnecessary biopsies. Increasing the rate of diagnostic true positives to near 100 percent will identify all lesions as a cancer that are cancer without the need to biopsy. However, it is also necessary to increase the rate of true negatives to near 100 percent to eliminate biopsy of benign lesions. Neither mammography or ultrasound or their joint use has provided the combination of sensitivity and specificity to eliminate biopsy or to detect all cancers early enough to insure long term survival after breast cancer surgery for all women that have had breast exams.

There does not seem to be any obvious improvements in present mammography or hand-probe-based, clinical reflection ultrasound that can significantly improve these statistics. However, there is reason to believe that inverse scattering ultrasound tomography or electric impedance tomography can provide improved diagnostic sensitivity or specificity when used separately or jointly with themselves and with ultrasound and/or mammography. Inverse scattering ultrasound imaging provides several advantages over present clinical reflection ultrasound that uses hand held ultrasound probes. A hand held probe is a transducer assembly that scans an area of the patient's body below the probe. Probes consisting of mechanical scanning transducers and probes comprising electronically scanned arrays of transducer elements are both well developed technologies.

Inverse scattering has the following advantages over said clinical reflection ultrasound. Inverse scattering images have the following features: (1) two separate images can be made, one of speed of sound and one of acoustic absorption; (2) these images are a quantitative representation of actual acoustic bulk tissue properties; (3) the images are machine independent; (4) the images are operator independent; (5) the images are nearly free of speckle and other artifacts; (6) all orders of scattering tend to be used to enhance the images and do not contribute to artifacts or degrade the images; (7) the images of speed of sound and absorption create a separation of tissues into classes (fat, benign fluid filled cyst, cancer, and fibroadenoma), although the cancer and fibroadenoma values tend to overlap; (8) the speed of sound and acoustic absorption images have excellent spatial resolution of 0.3 to 0.65 mm at or below 5 MHz; and (9) the speed of sound images can be used to correct reflection tomography for phase aberration artifacts and improve ultrasound reflectivity spatial resolution. Inverse scattering easily discriminates fat from other tissues, while mammography and present clinical ultrasound cannot.

Because of the similar values of speed of sound and acoustic absorption between cancer and fibrocystic condition (including fibroadenoma), it is not known whether inverse scattering will provide the required high level of specificity to eliminate biopsy. Perhaps this performance could be achieved if inverse scattering were combined with reflection ultrasound (including reflection tomography) or with mammography or with both.

A traditional problem with inverse scattering imaging is the long computing times required to make an image. Diffraction Tomography is an approximation to inverse scattering that uses a first order perturbation expansion of some wave equation. Diffraction Tomography is extremely rapid in image computation, but suffers the fatal flaw for medical imaging of producing images that are blurred and not of acceptable quality for diagnostic purposes and it is not quantitatively accurate. In our last patent application, we addressed the computational speed problem with inverse scattering and showed how to increase the calculation speed by two orders of magnitude over finite difference methods and integral equation methods. This speed up in performance was achieved by use of a parabolic marching method. This improvement in speed was sufficient to allow single 2D slices to be imaged at frequencies of 2 MHz using data collected in the laboratory. However, making a full 3-D image with a 3D algorithm or even from several, stacked 2-D image slices made with a 2D algorithm would have required computing speed not available then and only becoming available now.

Another imaging modality that has been investigated for detecting breast cancer is EIT (electrical impedance tomography). This modality has been investigated for many years and many of its features are well known. One of its great advantages for breast cancer detection is its high selectivity between cancer and fibrocystic conditions including fibroadenoma. Cancer has high electrical conductivity (low electrical impedance) while fibrocystic conditions and fibroadenoma have low electrical conductivity (high electrical impedance). However, EIT has poor spatial resolution. Also EIT requires the use of inversion algorithms similar (in a general sense) to those of inverse scattering. In addition EIT algorithms have mostly been used to make 2-D images. Work on making 3-D EIT images is less developed because of the increased computer run time of 3-D algorithms.

Other problems with mammography may be listed, such as the pain associated with compressing the breast between two plates to reduce the thickness of the breast in order to improve image contrast and cancer detection potential. Another problem is the accumulated ionizing radiation dose over years of mammography. It is true that a single mammogram has a very low x-ray dose, especially with modern equipment. However, if mammograms are taken every year from age 40 or earlier, by age 60 to 70 the accumulated dose begins to cause breast cancer. The effect is slight, and the benefits of diagnosis outweigh this risk. Nevertheless, it would be an advantage to eliminate this effect. Mammography is not useful in many younger women (because of the tendency for greater breast density) or older women with dense breasts (such as lactating women). About 15 percent of women have breasts so dense that mammography has no value and another 15 percent of women have breasts dense enough that the value of mammography is questionable. Thus 30 percent of all mammograms are of questionable or zero value because of image artifacts from higher than normal breast density.

SUMMARY OF THE INVENTION

The present invention describes a transmission wave field imaging method. The method consist of the transmitting of an incident wave field into an object wherein the incident wave field propagates into the object and, at least, partially scatters. The method further consists of the measuring of a wave field transmitted, at least in part, through the object to obtain a measured wave field. The measured wave field is defined, in part, by the incident wave field and the object. The method further consists of the processing of the measured wave field utilizing a parabolic approximation reconstruction algorithm to generate an image data set representing at least one image of the object.

The method above further describes the parabolic approximation reconstruction algorithm which calculates a predicted total wave field utilizing a single independent variable wherein the single independent variable represents scattering potential. The algorithm may also utilize a parabolic binomial approximation.

The method above further describes the object as tissue, the incident wave field is an acoustic wave field and the parabolic approximation reconstruction algorithm models acoustic wave propagation through the tissue.

The method above further describes a parabolic approximation reconstruction algorithm which models forward wave propagation of the incident wave field.

The method above further describes the object is a breast scanner wherein the processing generates the image of a breast during the breast scan. The image represents quantitative estimates of a speed-of-sound and/or an attenutation associated with the object.

The method above further describes an incident wave field which represents an ultrasound wave field and the displaying of at least one image or transmissive image as at least two images co-displayed wherein the at least two images include a speed-of-sound image and an attenuation image. The incident wave field comprises at least one of acoustic energy, elastic energy, electromagnetic energy and microwave energy.

The method above further describes the transmitting and receiving performed by a transmitter and receiver, respectively, wherein at least one of the transmitter and receiver are movable with respect to the object. The transmitting and receiving are repeated at multiple slices within the object to generate a 3D volume of data and/or the displaying 2-D images representative of slices through the object and/or a 3-D image of at least a portion of the object.

The method above further describes the obtaining of speed-of-sound and attenuation values from the image data set wherein the speed-of-sound values correspond to a speed of ultrasound wave field through tissue and the attenuation values correspond to an amount of attenuation of ultrasound wave fields propagated through the tissue. A speed-of-sound image and attenuation image are constructed from the measured wave field and displayed.

The invention also describes a transmission wave field imaging device. The device comprises a transmitter for transmitting an incident wave field into an object wherein the incident wave field propagates into the object and, at least, partially scatters. The device also comprises a receiver measuring a total wave field transmitted, at least in part, through the object to obtain a measured wave field, the measured wave field being defined, in part, by the incident wave field and the object. The device also comprises a processing module for processing the measured wave field. The processor utilizes a parabolic approximation reconstruction algorithm to generate an image data set representing at least one image of the object.

The imaging device above also describes a processor module comprising a plurality of processors operated in parallel and a PCI bus interconnecting the processing module and the transmitter and/or the receiver. The processor module is implemented on either a personal computer, a hand-held device, a multi-processor system and/or a network PC. The transmitter operates in a pulse echo mode to perform reflective tomography and is rotated about the object to obtain measured data at multiple receive positions around the object. The measured data defines the measured wave field and a display for displaying the image based on the image data set uses the speed of sound image and/or the attenuation image.

The imaging device above also describes the receiver and/or the transmitter as including transducer elements arranged in at least one of a circular array, a linear array, a 2D planar array and a checkerboard 2D array. The transmitter sequentially transmits first and second incident wave fields into the object having different first and second fundamental frequencies, respectively and sequentially transmits a high frequency incident wave field and a low frequency incident wave field.

The present invention also describes a transmission wave field imaging system. The system comprises a transmitter for transmitting an incident wave field into an object wherein the incident wave field is propagated into the object and, at least, partially scatters. The system includes a receiver measuring a total wave field transmitted, at least in part, through the object to obtain a measured wave field. The measured wave field is defined, in part, by the incident wave field, a scattering potential and the object. The measured wave field includes at least one of speed of sound information and attenuation information characterizing the object. The system also includes a processing module for processing, on-site and in real-time, the measured wave field to generate an image of the object. The image comprises pixel values based on at least one of the speed of sound information and the attenuation information characterizing the object. The system further comprises a display for displaying, on-site and in real-time, the image containing at least one of the speed of sound information and the attenuation information of the object.

The wave field imaging system above also describes a breast scanner including the transmitter and receiver, and the processing module that generates the image substantially during a breast scan. The processor module calculates a scattering potential from the measured wave field. The scattering potential includes a real component and an imaginary component, the real component defining the speed of sound information and the imaginary component defining the attenuation information.

The wave field imaging system above also describes a phase detector joined to the receiver wherein the phase detector outputs real and imaginary signal components. The transmitter and receiver repeat the transmitting and receiving operations at multiple slices within the object to collect a 3D volume of data and the display displays 2-D images representative of slices through the object. The display may also display a 3-D image of at least a portion of the object.

The wave field imaging system above also describes a movable carriage supporting the transmitter and receiver wherein the movable carriage rotates about an axis of a cylindrical chamber and is configured to receive the object. The movable carriage supporting the transmitter and receiver is vertically adjusted along an axis of the cylindrical chamber. The chamber is configured to receive the object and a fluid tank is configured to receive at least the object, the transmitter, and/or the receiver.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 4A illustrates, with the use of an array processor, the scanning of an object using multiple frequencies, the frequency of an oscillator being changed several times at each illustrated transmitter position, so that sequential multiple frequencies may be transmitted by changing the frequency of the oscillator;

FIG. 4C shows n transducer elements in a circular array closely spaced to form a continuous array surrounding a body for use in the present inventive method of electronically multiplexing the array elements to eliminate the need for mechanical rotation;

FIG. 4D illustrates the transducers arranged in a linear fashion for pure electronic multiplexing of a linear transducer array according to the present invention.

FIG. 4E is an electrical schematic diagram showing how the elements in FIGS. 4C and 4D may be switched to act as either a transmitter or receiver by use of an active switch.

FIG. 4F shows how a passive network of diodes and resistors may be used to allow a single element to act as either a transmitter or a receiver, or in both capacities by the use of diode networks to isolate the transmitter from the receiver circuits according to the present invention;

FIG. 5A shows multiple frequency signals transmitted by selecting and generating a type of waveform which inherently includes multiple frequencies, and using a parallel processor, so as to produce repetitive narrow bandwidth signals or a wide bandwidth signal, which differs from the system shown in FIG. 4A in that the amplified analog signals output by a preamplifier are digitized by a high-speed analog-to-digital converter rather than being input to a phase detector;

FIG. 5B shows a waveform generator having five basic components;

FIGS. 11A-1, 11A-2 show the generic solution to the forward problem (or any square system) using a biconjugate gradient algorithm according to the present invention;

FIGS. 11B-1, 11B-2 show the generic solution to the forward problem using the stabilized conjugate gradient algorithm, according to the present invention;

FIG. 15 illustrates the application of Hermitian conjugate of the second Lippmann Schwinger Operators. FIG. 15 also illustrates a subroutine for the Top Loop Box in FIG. 8, according to the present invention;

FIG. 18 illustrates a N-by-N scattering coalesced region according to the present invention;

FIG. 45 2.5 MHz to 5 MHz bandwidth time signal through a cylinder; and

DEFINITIONS

Figure 1:
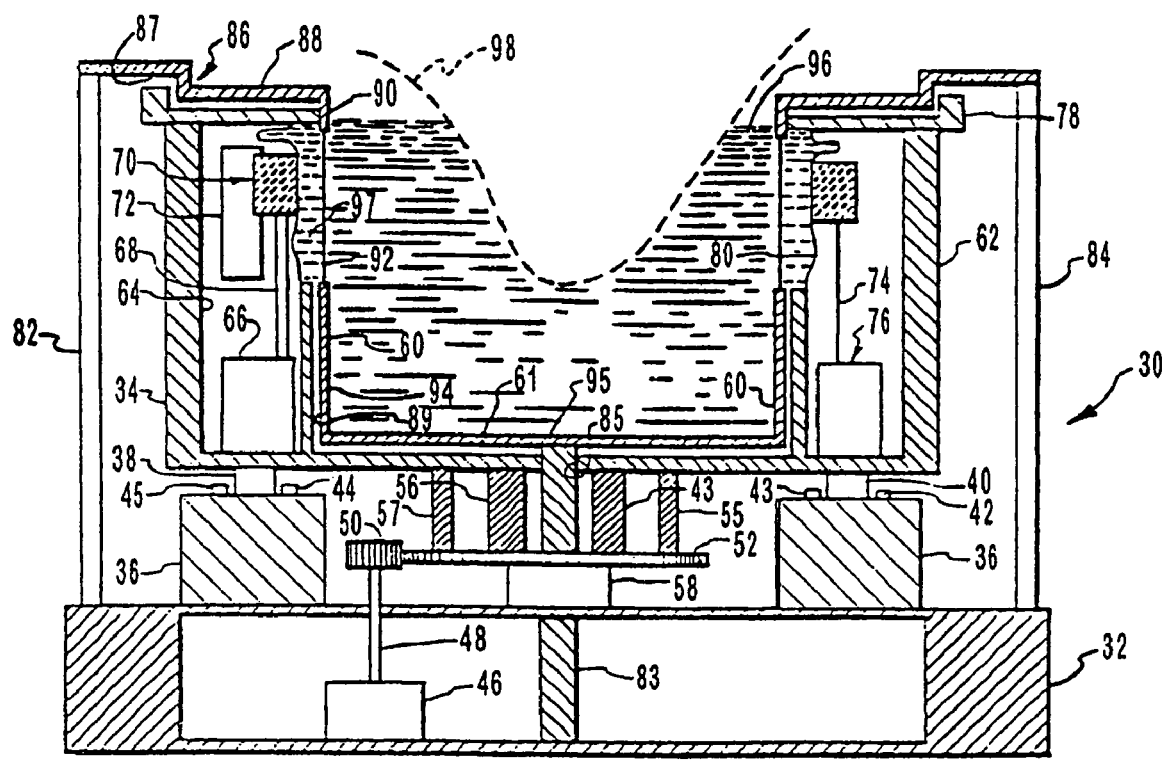
FIG. 1 is a side-elevational view shown partially in cross section which schematically illustrates an acoustic scanner which may be used with the apparatus and method of the present invention.

Definition 1. An inverse scattering imaging method is any imaging method which totally or partially uses wave equation modeling and which utilizes a nonlinear operator relating the inversion data to the image components.

Definition 2. The inversion data is defined by that transformation of the wavefield data which is the range of the nonlinear operator. The domain of the nonlinear operator is the image components.

Definition 3. A parabolic propagation step is an arithmetic operation which computes the wavefield on a set of surfaces given the wavefield on another, disjoint set of surfaces using a parabolic differential (or difference?) equation in the derivation of the arithmetic operation.

Definition 4. By $\lambda$ we mean the wavelength in the imbedding medium for the maximum temporal frequency in the wavefield energy.

Definition 5. By $\Delta$ we mean the average spatial separation of the points used to discretize the discretized wavefield in the computer implementation of the method.

Definition 6. By a short convolution operation we mean a discrete convolution which is faster if done by direct summation rather than by FFT.

DETAILED DESCRIPTION OF INVENTION

The following explanation of notation is given to facilitate obtaining an understanding of the invention. Unless otherwise noted, the notation will essentially be the same as U.S. Pat. No. 4,662,222. The scattering potential $\gamma$ changes from point to point within an object or body as well as changing with frequency of the incident field. Thus, $$\gamma_{\omega j} \equiv \gamma_\omega(x_j), x_j \in R^3 \text{ or } R^3$$

is used to signify the scattering potential at pixel j or point j, for the incident field at frequency $\omega \cdot \gamma_\omega$ can be considered to be the vector composed of all values of j, i.e. for all pixels:

$$\gamma_\omega \equiv (\gamma_{\omega 1} \gamma_{\omega 2} \cdots \gamma_{\omega N})^T,$$

where T indicates "transpose". For our purposes of exposition and simplicity, we will hence forth consider the case where $\gamma$ is independent of frequency, although this is not necessary. This convention also is essentially the same as that employed in the U.S. Pat. No. 4,662,222.

Notation

Vector Field Notation

The following notation will be used throughout the patent to denote a vector field describing elastic waves, or electromagnetic waves:

$$f(r) \equiv \begin{pmatrix} f_x(x, y, z) \\ f_y(x, y, z) \\ f_z(x, y, z) \end{pmatrix} \equiv (f_x f_y f_z)^T$$

(T-denotes "transpose") is used to represent the total field.

$$f^i(r) \equiv \begin{pmatrix} f_x^i(x, y, z) \\ f_y^i(x, y, z) \\ f_z^i(x, y, z) \end{pmatrix} \equiv (f_x^i f_y^i f_z^i)^T$$

(T-denotes "transpose") is used to denote the incident field. The incident field is the field that would be present if there was no object present to image. In the case of layering in the ambient medium, it is the field that results from the unblemished, piecewise constant layering.

The scattered field is the difference between the total field and the incident field, it represents that part of the total field that is due to the presence of the inhomogeneity, i.e. the "mine" for the undersea ordnance locater, the hazardous waste cannister for the hazardous waste locator, the school of fish for the echo-fish locator/counter, and the malignant tumor for the breast scanner:

$$f^s(r) \equiv \equiv f(r) - f^i(r)$$

$$f^s(r) \equiv \begin{pmatrix} f_x^s(x, y, z) \\ f_y^s(x, y, z) \\ f_z^s(x, y, z) \end{pmatrix} \equiv (f_x^s f_y^s f_z^s)^T$$

T-denotes "transpose" $f_{\omega\phi}^{inc}(r)$ denotes the scalar incident field coming from direction (source position) $\Phi$ at frequency $\omega$. The r could represent either a 3 dimensional, or a 2 dimensional vector of position.

Scalar Field Notation

A scalar field is indicated by a nonbold f(r), $r \in R^3$

EXAMPLE 1

Acoustic Scattering—Scalar Model Equations

This first example is designed to give the basic structure of the algorithm and to point out why it is so fast in this particular implementation compared to present state of the art. The background medium is assumed to be homogeneous medium (no layering). This example will highlight the exploitation of convolutional form via the FFT, the use of the Frechet derivative in the Gauss-Newton and FR—RP algorithms, the use of the biconjugate gradient algorithm (BCG) for the forward problems, the independence of the different view, and frequency, forward problems. It will also set up some examples which will elucidate the patent terminology. The field can be represented by a scalar quantity f. The object is assumed to have finite extent The speed of sound within the object is $c=c(x)$. The speed of sound in the background medium is the constant $c_o$. The mass density is assumed to be constant. The attenuation is modelled as the imaginary part of the wavespeed. These are simplifying assumptions, which we make so as to focus on the important aspects of the imaging algorithm. By no means is the imaging algorithm restricted to the scalar case, either in theory, or, more importantly, in practical implementation.

We consider the two dimensional case first of all (equivalently the object and incident fields are assumed to be constant in one direction). Given an acoustic scatterer with constant mass density and constant cross-section in z, illuminated by a time harmonic incident field, $f_{\omega\phi}^{inc}$, with $e^{i\omega t}$ dependence and source position (incident angle), $\phi$, the total field satisfies the following integral equation.

$$f_{\omega\phi}^{inc}(\bar{\rho}) = f_{\omega\phi}(\bar{\rho}) - \int\int \gamma(\bar{\rho}') f_{\omega\phi}(\bar{\rho}') g_\omega(1\bar{\rho} - \bar{\rho}1) dx' dy' \quad (1)$$

where $$\gamma = \frac{c_0^2}{c^2} - 1$$

where $$\bar{\rho} = (x, y)$$

and where $$f \equiv f_{\omega\phi}$$

is the field internal to the object at frequency ω and resulting from the incident field from source position φ, $f_{\omega\phi}^{inc}$. The 2-D Helmholtz Green's function is given by:

$$g_\omega(|\bar{p}-\bar{p}'|) = \frac{k_\omega^2}{4i} H_0^{(2)}(k_\omega|\bar{p}-\bar{p}'|), \quad k_\omega = \frac{\omega}{c_0}$$

where $H_o^{(2)}$ is the Hankel function of the second kind, and zeroth order.

Now it is required to compare the field measured at the detectors, with the field as predicted by a given guess, $\gamma^{(n)}$ for γ. To accomplish this, first define the scattered field at the detectors as the total field minus the incident field.

$$f_{\omega\phi}^{sc}(\bar{\rho}) \equiv f_{\omega\phi}(\bar{\rho}) - f_{\omega\phi}^{inc}(\bar{\rho})$$

This represents the field due entirely to the scattering potential. Using this relation to rewrite (1), gives $$f_{\omega\phi}^{sc}(\bar{\rho}) = \iint \gamma(\bar{\rho}') f_{\omega\phi}(\bar{\rho}') g_\omega(|\bar{\rho}=p|) dx' dy' \quad (2)$$

These two equations, (1) and (2) are the basis of the imaging algorithm. They must be discretized, then exported to the computer in order to solve practical imaging problems. The purpose of the apparatus and method herein described, is to solve the discretized form of these equations without making any linearizing assumptions (such as used in conventional diffraction tomography), and in real time, with presently available computers.

Discretization of the Acoustic Free-Space Lippmann Schwinger Integral Equation and Green's function—2D Free Space Case Let us for a moment drop the frequency and source position subscripts. The scalar field "γf" is given by $$\gamma f \begin{pmatrix} x' \\ y' \end{pmatrix} \equiv \gamma \begin{pmatrix} x' \\ y' \end{pmatrix} f \begin{pmatrix} x' \\ y' \end{pmatrix}$$

Discretization of the Integral Equation is Achieved by First Decomposing this Function into a Linear Combination of Certain (Displaced) Basis Functions $$\gamma f \begin{pmatrix} x' \\ y' \end{pmatrix} \approx \sum_{n'=1}^{N_x} \sum_{m'=1}^{N_y} a_{n'm'} s \begin{pmatrix} x'-n\delta \\ y'-m'\delta \end{pmatrix} \quad (3)$$

where it has been assumed that the scatterer γ lies within the support $[0, N_x\delta] \times [0, N_y\delta]$—a rectangular subregion.

The basis functions S can be arbitrary except that we should have cardinality at the grid nodes:

$$S\begin{pmatrix} 0 \\ 0 \end{pmatrix} = 1$$

whereas for all other choices of n',m', $$s\begin{pmatrix} n'\delta \\ m'\delta \end{pmatrix} = 0, \quad n'm' \neq 0$$

An example of such a function is the 2-D "hat" function. Our algorithm uses the "sinc" function has its basic building block—the Whittaker sinc function which is defined as:

$$\sin c(x) = \frac{\sin(\pi x)}{\pi x}$$

The two dimensional basis functions are defined by the tensor product:

$$s\begin{pmatrix} x'-n'\delta \\ y'-m'\delta \end{pmatrix} = \text{sinc}((x'-n'\delta)/\delta) \cdot \text{sinc}((y'-m'\delta)/\delta) \quad (4)$$

If the equality in equation (3) is presumed to hold at the grid points x=nδ, y=mδ: the coefficients $\alpha_{nm}$ can be determined to be precisely the value of the field γf:

$$\gamma f \begin{pmatrix} x' \\ y' \end{pmatrix} \equiv \sum_{n'=1}^{N_x} \sum_{m'=1}^{N_y} \gamma \begin{pmatrix} n'\delta \\ m'\delta \end{pmatrix} f \begin{pmatrix} n'\delta \\ m'\delta \end{pmatrix} s \begin{pmatrix} x'-n'\delta \\ y'-m'\delta \end{pmatrix} \quad (5)$$

Now this expression for the product γf can be substituted into (1):

$$f^i \begin{pmatrix} x \\ y \end{pmatrix} = \quad (6)$$

$$f \begin{pmatrix} x \\ y \end{pmatrix} - \frac{k_\omega^2}{4i} \sum_{n'} \sum_{m'} \gamma_{n'm'} f_{n'm'} \int H_o^{(2)}(k_\omega|\bar{p}-\bar{p}'|) s\begin{pmatrix} x'-n'\delta \\ y'-m'\delta \end{pmatrix} d^2\rho'$$

In particular this equation holds at $$\begin{pmatrix} x \\ y \end{pmatrix} = \begin{pmatrix} n\delta \\ m\delta \end{pmatrix}$$

for which we get:

$$f_{nm}^i = f_{nm} - \sum_{n'=1}^{N_x} \sum_{m'=1}^{N_y} \gamma_{n'm'} f_{n'm'} f_{n-n',m-m'}, \quad (7)$$

$$n = 1, \ldots, N_x \quad m = 1, \ldots, N_y$$

where the 2-D discrete Green's function is defined as:

$$g(n-n', m-m') \equiv \frac{k^2}{4i} \int H_0^2\left(k\left|\begin{pmatrix} n\delta-x' \\ m\delta-y' \end{pmatrix}\right|\right) s\begin{pmatrix} x'-n'\delta \\ y'-m'\delta \end{pmatrix} d^2\rho' \quad (8)$$

Although it is not clear that the dependence of g on m and n is as so stated, in is indeed the case, since we have by the substitution of the transformation x'→x'+nδ y'→y'+m'δ into this last equation shows explicitly that the discretized Green's function "g", does in fact depend only on the differences n–n', and m–m''. Thus the discrete equation (7) has inherited the convolutional form of the continuous equation (1). It is this fact which allows the use of the 2-D FFT to compute the summation in (8) in only order $N_x N_y \log_2(N_x N_y)$ arithmetic operations and is therefore critical to the real-time speed of the algorithm.

Expression of the Discretized Lippmann—Schwinger Equation in Compact Notation

The discretized Lippmann-Schwinger equation can be rewritten using a compact operator notation. We write (7) as:

$$f_{\omega\phi}^i = (I - G_\omega[\gamma])f_{\omega\phi} \quad (9)$$

where $G_\omega$ represents 2-D discrete convolution with the discrete, 2-D Green's function for frequency ω and [γ] denotes the operator consisting of pointwise multiplication by the 2-D array γ. I denotes the identity operator.

In exactly the same manner, and with the same definitions, we can write the scattered field equation (2) as:

$$f_{\omega\phi}^{sc} = G_\omega[\gamma]f_{\omega\phi} \quad (10)$$

for the scattered field inside of the object, and finally $$f_{\omega\phi}^{meas} = T(f_{\omega\phi}^{sc}) = T(G_\omega[\gamma]f_{\omega\phi}) \quad (11)$$

for the measured value of the scattered field at the detectors. The T operator is used to indicate the "truncation" of the calculated scattered field, calculated on the entire convolution range (a rectangle of samples $[1,N_x] \times [1,N_y]$ covering γ), onto the detectors which lie outside the support of γ. (see FIGS. 1A/B/C.). In other words T is simply the operation of "picking" out of the rectangular range of the convolution, those points which coincide with receiver locations.

Extension of the Method to Remote Receivers with Arbitrary Characteristics

In the event that the receivers do not lie within the range of the convolution and/or they are not simple point receivers, we need to modify the measurement equations (11). It is well known that, given source distributions within an enclosed boundary, the scattered field everywhere external to the boundary can be computed from the values of the field on the boundary by an application of Green's theorem with a suitably chosen Green's function, i.e.:

$$f^s(\bar{p}) = \oint_B f^s(\bar{p}')p(\bar{p}, \bar{p}')dl', \bar{p} \text{ outside boundary } B \quad (12)$$

where P is the Green's function the integral is about the boundary, and dl' is the differential arclength (in the 3-D case, the integral is on an enclosing surface). Equation (12) allows for the construction of a matrix operator which maps the boundary values of the rectangular support of the convolution ($2N_x + 2N_y - 4$ values in the discrete case) to values of the scattered field external to the rectangle. Furthermore, this "propagator matrix" can be generalized to incorporate more complex receiver geometries. For example, suppose that the receiver can be modeled as an integration of the scattered field over some support function, i.e.;

$$v_n \equiv \text{signal from receiver } n = \int\int f^s(\bar{p})S_n(\bar{p})ds \quad (13)$$

where $S_n$ is the support of receiver n. Then from (12):

$$v_n = \oint_B f^s(\bar{p}')\left\{\int\int S_n(\bar{p})P(\bar{p},\bar{p}')ds\right\}dl', \bar{p}$$

outside boundary $$B(14) = \oint_B f^s(\bar{p}')P'(n,\bar{p}')dl', P'(n,\bar{p}') = \int\int S_n(\bar{p})P(\bar{p},\bar{p}')ds$$

Discretizing the integral gives the matrix equation:

$$v_n = \sum_{i=1}^{N_b} P_{nl'}f^s, n = 1, \ldots, N_d \quad (15)$$

where $$N_b = 2N_x + 2N_y - 4$$

is the number of boundary (border) pixels and $N_d$ is the number of receivers. Equation (15) defines the matrix that we shall henceforth refer to as P or the "propagator matrix" for a given distribution of external receivers. The equation:

$$v_{\omega\phi}^{meas} = P_{107}(G_\omega[\gamma]f_{\omega\phi}) \quad (16)$$

includes (11) as a special case for which the receivers are point receivers inside the convolution support. Note that P is a function of frequency, but is not a function of source position. $v_{\omega\phi}^{meas}$ is a vector of dimension $N_d$.

The added flexibility of this propagator matrix formulation is particularly advantageous when interfacing our algorithms with real laboratory or field data. Often times the precise radiation patterns of the transducers used will not be known a priori. In this event, the transducers must be characterized by measurements. The results of these measurements can be easily incorporated into the construction of the propagator matrix P allowing the empirically determined transducer model to be accurately incorporated into the inversion. Equations (9) and (16) then provide in compact notation the equations which we wish to solve for the unknown scattering potential, γ. First we consider the forward problem, i.e. the determination of the field $f_{\omega\phi}$ for a known object function γ and known incident field, $f_{\omega\phi}^i$. Then we establish how this forward problem is then incorporated into the solution of the inverse problem, i.e., the determination of γ when the incident fields, and the received signals from a set of receivers are known. Note that the internal field to the object is also—along with the object function γ, an unknown in the inverse problem.

Since (9) is linear in $f_{\omega\phi}$ it can be solved by direct inversion of the linear system:

$$f = (I - G[\gamma])^{-1} f^i \qquad (17)$$

In discrete form, this is just a matrix equation (after linearly ordering the 2-D supports of the domain and range into vectors). Since the dimension of the range and domain of the linear system is $N_x N_y$, the dimension of the linear system is the same giving a total of $(N_x N_y)^2$ elements. The arithmetic required to solve the system by standard direct means is thus order $(N_x N_y)^3$. In other words, a doubling of the edge dimension of the problem space will increase the CPU time required by a factor $2^6 = 64$ times! The arithmetic work required will quickly become intolerable as the size of the problem increases. It is precisely this large growth rate which has convinced many researchers not to pursue inverse scattering approaches based on integral equations. One could, of course, go to an iterative method. A single iteration of an iterative linear system solver, such as bi-conjugate gradients requires order $(N_x N_y)^2$ operations (essentially a matrix-vector product). It can be shown that the growth rate in the number of required iterations for sufficient convergence for the BCG algorithm is order N for this equation. Thus, the overall computational complexity is order $N^5$—only one order of N has been saved over direct inversion. Since inverse problems in 2-D generally require order N views, the iteration must be done N times and we are back to order $N^6$ computation for BCG.

The key to overcoming this objection is the convolutional form of (7). If this is exploited by use of the FFT algorithm, the computation needed to perform a matrix-vector product is only order $N_x N_y \log_2(N_x N_y)$ This allows the BCG algorithm to be applied to a single view with order $N^3 \log_2(N)$ operations and to all views with order $N^4 \log_2(N)$ operations. Due to the slow growth rate of $\log_2(N)$, this is essentially a reduction of two orders of N over nonconvolutional methods. Also, this convolutional approach avoids the necessity of storing the order $N^4$ computer words needed to contain the linear system in full matrix form. Only order $N^2$ words are needed due to the shift invariance of the discrete Green's kernel in (7). It is these two savings, more than any other advance that we have made, that allows us to perform inverse scattering in reasonable time for meaningfully sized problems. The use of BCG over the original CG algorithm also represents a major advance since it converges in essentially the square root of the number of iterations needed by CG. This combination of FFT and CG algorithm was originally developed in [Borup, 1989, Ph.D. dissertation, Univ. of Utah, Salt Lake City], herein incorporated by reference.

The Imaging or Inverse Problem

In order to solve the imaging problem, we need a set of equations relating the unknown scattering potential, $\gamma$, and total fields, $f_{\omega\phi}$ with measurements of the scattered field on a set of external detectors. These detector equations are given in (16). Equation (16), and the internal field equations (9) are the equations which are solved simultaneously to determine $\gamma$ and the $f_{\omega\phi}$. There are $N_x N_y$ unknowns corresponding to the $\gamma$ values at each of the grid points, and $N_x \times N_y \times \Omega \times \Phi$, unknowns corresponding to the unknown fields, $\Omega$ is the number of frequencies, and D is the number of source positions (angles). We have improved upon the state of the art by considering the internal field equations to define $f_{\omega\phi}$, for a given $\gamma$. Thus the total number of unknowns is reduced to $N_x N_y$.

The total number of measurement equations is $N_d \times \Omega \times \Phi$ where $N_d$ is the number of detectors. In the general case, where, the sources and detectors do not completely surround the object, the problem of determining $\gamma$ is "ill-posed", in a precise mathematical sense, therefore, in order to guarantee a solution, the number of equations $N_d \times \Omega \times \Phi > N_x N_y$, is chosen to be larger than the number of pixel values for over determination. Then the system is solved in the least squares sense. More specifically the solution of (9,16) for $\gamma$ and the set of fields, $f_{\omega\phi}$, in the least squares sense is obtained by minimizing the real valued, nonlinear functional:

$$\min_\gamma \sum_{\omega\phi} \|r_{\omega\phi}\|^2 \equiv \min_\gamma \sum_{\omega\phi} \|v_{\omega\phi}^{meas} - P_\omega G_\omega [f_{\omega\phi}] \gamma\|^2 \qquad (18)$$

subject to the satisfaction of the total field equations, (9), as constraints. The vector $r_{\omega\phi}$ of dimension $N_d$ is referred to as the "residual" for frequency, $\omega$, and angle, $\phi$.

The methods used to solve the nonlinear optimization problem in our inverse scattering algorithms are, thus far, all "gradient methods" in that second derivative information is not used (as it is in the full Newton and quasi-Newton methods). The principal computation involves the calculation of the gradient vector of (18). A straight forward calculation gives the gradient formula: $\nabla f(x) = J^H(x) r(x)$ where the superscript H denotes the Hermitian transpose (complex conjugate transpose of the matrix) and J is the Jacobian of the nonlinear system:

$$J(x) = \begin{bmatrix} \frac{\partial}{\partial x_1} a_1 & \cdots & \frac{\partial}{\partial x_N} a_1 \\ \vdots & \ddots & \vdots \\ \frac{\partial}{\partial x_1} a_M & \cdots & \frac{\partial}{\partial x_N} a_M \end{bmatrix}. \qquad (19)$$

The simplest gradient algorithm is the Gauss-Newton (GN) iteration. The GN iteration for finding a solution to $\nabla f = 0$ is given by:

$$r^n = y - a(x)^{(n)} \qquad (20.1)$$

$$\delta x^{(n)} = (J_n^H J_n)^{-1} J_n^H r^{(n)} \qquad (20.2)$$

$$x^{(n+1)} = x^{(n)} + \delta x^{(n)} \qquad (20.3)$$

where a is the vector of nonlinear equations. This iteration is well defined assuming that the columns of $J_n$ remain linearly independent. Since (20.2) is equivalent to the quadratic minimization problem:

$$\min_{\delta x^{(n)}} \|J_n \delta x^{(n)} - r^{(n)}\| M^2 \qquad (21)$$

it can be solved by the minimum residual conjugate gradient method (MRCG). This approach also ensures that small singular values in $J_n$ will not amplify noise if care is taken not to overconverge the iteration.

In the previous patent U.S. Pat. No. 4,662,222 the fields $f_{\omega\phi}$ were considered to be independent variables. In this present patent these fields are considered to be dependent variables, with dependence upon $\gamma$ given implicitly by $$f_{\omega\phi}{}^{(n)} = (I - G_\omega [\gamma^{(n)}])^{-1} f_{\omega\phi}{}^{inc}$$

In order to find the Jacobian expression we must then differentiate the residual vector defined in (18) with respect to γ. The details of this calculation are given in [Borup, 1992.]. The result is:

$$J_{\omega\phi} = \frac{\delta r_{\omega\phi}}{\delta \gamma} = P_\omega (I - [\gamma]G_\omega)^{-1}[f_{\omega\phi}] \quad (22)$$

The final Gauss-Newton algorithm for minimizing (18) subject to equality constraints (9) is:

GN 1. Select an initial guess, $\gamma^{(0)}$
GN 2. Set n = 0
GN 3. Solve the forward problems using (biconjugate gradients) BCG:

$$f_{\omega\phi}^{(n)} = (I - G_\omega[\gamma^{(n)}])^{-1} f_{\omega\phi'}^{inc} \quad \begin{array}{l} \omega = 1, \ldots, \Omega \\ \phi = 1, \ldots, \Phi \end{array}$$

GN 4. Compute the detector residuals:

$$r_{\omega\phi}^{(n)} = v_{\omega\phi}^{meas} - P_\omega G_\omega [f_{\omega\phi}^{(n)}]\gamma^{(n)}, \quad \begin{array}{l} \omega = 1, \ldots, \Omega \\ \phi = 1, \ldots, \Phi \end{array}$$

GN 5. If $\sum_{\omega\phi} \|r_{\omega\phi}^{(n)}\|^2 < \epsilon$, stop.

GN 6. Use MRCG to find the least squares solution to the quadratic minimization problem.

$$\min_{\delta\gamma^{(n)}} \sum_{\omega\phi} \left\| r_{\omega\phi}^{(n)} + P_\omega G_\omega (I - [\gamma^{(n)}]G_\omega)^{-1} [f_{\omega\phi}^{(n)}]\delta\gamma^{(n)} \right\|^2 \text{ for } \delta\gamma^{(n)}$$

GN 7. Update $\gamma$: $\gamma^{(n+1)} = \gamma^{(n)} + \delta\gamma^{(n)}$.
GN 8. Set n = n + 1, go to GN 3

The crux of the GN iteration is GN 6 where the overdetermined quadratic minimization problem is solved for the scattering potential correction. This correction is approximated by applying a set of M iterations of the MRCG algorithm. The details of GN 6 are:

GN.6.1 Initialize the zeroth iterate of MRCG: $\delta\gamma^0 = 0$
GN.6.2 Initialize the MRCG residuals equal to the GN outer loop residuals: $r_{\omega\phi}^0 = r_{\omega\phi}^{(n)}$
Note that iterates pertaining to the MRCG iteration are indexed without the ( ) in order to distinguish them from outer GN loop iterates.
GN.6.3 Compute the gradient of the MRCG quadratic functional:

$$g^0 = \sum_{\omega\phi} [f_{\omega\phi}^{*(n)}](I - G_\omega * [\gamma *^{(n)}])^{-1} G_\omega * P_\omega^H r_{\omega\phi}^0$$

GN.6.4 Set the initial search direction equal to minus the gradient: $p^0 = -g^0$
GN.6.5 Set m = 0
GN.6.6 Compute $t_{\omega\phi}^n = p_\omega G_\omega (I - [\gamma^{(n)}]G_\omega)^{-1}[f_{\omega\phi}^{(n)}]p^m m \quad \begin{array}{l} \omega = 1, \ldots, \Omega \\ \phi = 1, \ldots, \Phi \end{array}$ GN.6.7 Compute the quadratic step length:

$$\alpha^m = \sum_{\omega\phi} \|t_{\omega\phi}^m\|^2 / \|g^m\|^2$$

GN.6.8 Update the solution of the quadratic minimization:
$\delta\gamma^{m+1} = \delta\gamma^m + \alpha^m p^m$
GN.6.9 Update the MRCG search residuals:
$r_{\omega\phi}^{m+1} = r_{\omega\phi}^m + \alpha^m t_{\omega\phi}^m$
GN.6.10 Compute the gradient of the MRCG quadratic functional:

$$g^{m+1} = \sum_{\omega\phi} [f_{\omega\phi}^{*(n)}](I - G_\omega * [\gamma *^{(n)}])^{-1} G_\omega * P_\omega^H r_{\omega\phi}^{n+1}$$

GN.6.11 Compute $\beta^m = \|g^{m+1}\|^2 / \|g^m\|^2$
GN.6.12 Update the MRCG search direction: $p^{m+1} = -g^{m+1} + \beta^m p^m$
GN.6.13 If m = M, go to CN.6.15
GN.6.14 m = m + 1. go to GM.6.8
GN.6.15 Equate the solution of the quadratic minimization problem with the last iterate of MRCG: $\delta\gamma^{(n)} = \delta\gamma^M$
GN.6.16 Return to the GN algorithm at GN 7

A problem with the algorithm above is the presence of the inverse of the transposed total field equation $(I-[\gamma^{(n)}]G_\omega)^{-1}$ in the computation of the Jacobian and its adjoint in 6.3 and 6.10 Since we do not invert (or even store) these large linear systems, the occurrence of these inverse operators must be dealt with. This problem can however be overcome by computing the action of this operator on a given vector, as needed during the MRCG iteration, by a few iterations of BCG. When performed in this way, the shift invariance of the Green's function is exploited in a maximal way. No large matrices need to be inverted or stored. This is because the Jacobian implementation now consists exclusively of shift invariant kernels (diagonal kernels such as pointwise multiplication by γ or f and the shift invariant kernel composed of convolution with the Green's function) Such shift invariant kernels can be implemented efficiently with the FFT as previously described.

An even greater increase in numerical efficiency can be obtained in cases for which the approximation:

$$(I-[\gamma^{(n)}]G_\omega)^{-1} \approx (I+[\gamma^{(n)}]G_\omega) \quad (23)$$

(which is similar to the Born approximation of the forward problem) can be used in the Jacobian. This has been found to be the case for many acoustic scattering problems for biological tissue, and for EM problems for which the contrast in dielectric contrast is small. The other two gradient algorithms that are used to solve the inverse scattering equations are the Fletcher-Reeves and Ribiere-Polak algorithms. For the inverse scattering equations, they are given by the iteration:

RP 1. Select an initnal guess, $\gamma^{(0)}$
RP 2. Solve the forward problems using (biconjugate gradients) BCG $$f_{\omega\phi}^{inc} = (I - G_\omega[\gamma^{(0)}])f_{\omega\phi'}^{(0)} \quad \begin{array}{l} \omega = 1, \ldots, \Omega \\ \phi = 1, \ldots, \Phi \end{array}$$

for the internal fields, $f_{\omega\phi}^{(0)}$

RP 3 Compute the detector residuals:

$$r_{\omega\phi}^{(0)} = P_\omega G_\omega [f_{\omega\phi}^{(0)}]\gamma^{(0)} - v_{\omega\phi}^{meas}, \quad \begin{array}{l} \omega = 1, \ldots, \Omega \\ \phi = 1, \ldots, \Phi \end{array}$$

RP 4 Compute the gradient $$r_{\omega\phi}^{(0)} = P_\omega G_\omega [f_{\omega\phi}^{(0)}]\gamma^{(0)} - v_{\omega\phi}^{meas}, \quad \begin{array}{l} \omega = 1, \ldots, \Omega \\ \phi = 1, \ldots, \Phi \end{array}$$

-continued

| | |
|---|---|
| RP 5 | computer the search direction: $p^{(0)} = -g^{(0)}$ |
| RP 6 | $n = 0$ |
| RP 7 | compute the Jacobian operating on the search direction: |
| | $t_{\omega\phi}^{(0)} = P_\omega G_\omega (I - [\gamma^{(n)}]G_\omega)^{-1}[f_{\omega\phi}^{(0)}]p^{(0)}, \begin{array}{l}\omega = 1, \ldots, \Omega \\ \phi = 1, \ldots, \Phi\end{array}$ |
| RP 8 | compute the step length (quadratic approximation): |
| | $\alpha_n = -\text{Re}\sum_{\omega\phi}(r_{\omega\phi}^{(n)}, t_{\omega\phi}^{(n)}) \Big/ \sum_{\omega\phi}\|t_{\omega\phi}^{(n)}\|^2$ |
| RP 9 | update the solution: $\gamma^{(n+1)} = \gamma^{(n)} + \alpha_n p^{(n)}$ |
| RP 10 | Solve the forward problems using (biconjugate gradients) BCG: |
| | $f_{\omega\phi}^{inc} = (I - G_\omega[\gamma^{(n+1)}])f_{\omega\phi'}^{(n+1)} \begin{array}{l}\omega = 1, \ldots, \Omega \\ \phi = 1, \ldots, \Phi\end{array}$ |
| RP 11 | Compute the detector residuals: |
| | $r_{\omega\phi}^{(n+1)} = P_\omega G_\omega [f_{\omega\phi}^{(n+1)}]\gamma^{(n+1)} - v_{\omega\phi}^{meas}, \begin{array}{l}\omega = 1, \ldots, \Omega \\ \phi = 1, \ldots, \Phi\end{array}$ |
| RP 12 | If $\sum_{\omega\phi}\|t_{\omega\phi}^{(n)}\|^2 < \epsilon$, stop |
| RP 13 | Compute the gradient |
| | $g^{(n+1)} = \sum_{\omega\phi}[f_{\omega\phi}^{*(n+1)}](i - G_\omega^*[\gamma^{*(n+1)}])^{-1}G_\omega^* P_\omega^H r_{\omega\phi}^{(n+1)}$ |
| RP 14 | Compute: |
| | $\beta_n = \begin{cases} \|g^{(n+1)}\|^2 / \|g^{(n)}\|^2 \\ \langle g^{(n+1)}, g^{(n+1)} - g^{(n)}\rangle / \|g^{(n)}\|^2, \end{cases}$ |
| | Fletcher - Reeves |
| | Ribere - Pollack |
| RP 15 | Update the search direction: $p^{(n+1)} = -g^{(n+1)} = \beta_n p^{(n)}$ |
| RP 16 | $n = n + 1$, go to RP 7 |

The distinction between FR and RP lies in the calculation of β in RP 14. It is generally believed that the RP calculation is more rapidly convergent. Our experience indicates that this is true and so we generally use the RP iteration rather than FR. Comparison of the linear MRCG iteration and the nonlinear RP iteration reveals that they are very similar. In fact, RP is precisely a nonlinear version of MRCG. Note that the only difference between them lies in the fact that the RP residuals, computed in steps RP.10 and RP.11 involve recomputation of the forward problems while the MRCG residuals are simply recurred in 6.9 (additional, trivial, differences exist in the computation of the α and β's). In other words, the RP iteration updates the actual nonlinear system at each iteration, while the MRCG simply iterates on the quadratic functional (GN linearization). The overall GN-MRCG algorithm contains two loops—the outer linearization loop, and the inner MRCG loop, while the RP algorithm contains only one loop. Sine the RP algorithm updates the forward solutions at each step, it tends to converge faster than GN with respect to total iteration count (number of GN outer iterations times the number, M, of inner loop MRCG iterates). The GN method is, however, generally faster since an MRCG step is faster than an RP step due to the need for forward recomputation in the RP step. The overall codes for the GN-MRCG algorithm and the RP algorithm are so similar that a GN-MRCG code can be converted to an RP code with about 10 lines of modification.

Before leaving this example it is important to note that the examples given in this patent all assume that the different frequencies, ω, and views, φ are all computed in serial fashion. It is important to note however, that another important link in the real time implementation of our algorithm, is the fact that the different frequencies and different views are independent in both the forward problem and Jacobian calculations, and therefore can be computed independently and in parallel. This should be clear by examining, for example, the computations in GN.3 and GN.6.3. The forward problem calculations, GN.3 are completely independent and in the gradient calculation, GN.6.3, the computations are independent in frequency and view up to the point at which these contributions are summed to give the gradient. The GN and RP algorithms could thus be executed on a multinode machine in parallel with node intercommunication required only 2 to 3 times per step in order to collect sums over frequency and view number and to distribute frequency/view independent variables, such as scattering potential iterates, gradient iterates, etc., to the nodes.

EXAMPLE 2

Image Reconstruction in Layered Ambient Media Using Optimization of A Bilinear or Quadratic Objective Function Containing All Detector Measurement Equations, and With Internal Fields Represented as a Function of the Scattering Potential The examples in the previous patent U.S. Pat. No. 4,662,222 were characterized by the consideration of both the internal fields, and the object function γ to be independent variables of equal importance. The example given above, however, has the distinguishing characteristic that the object function γ is considered to be the sole independent variable, and the internal field resulting from the incident field and γ interaction is considered to be a function of this γ. We may write $$f_{\theta\omega}^{sc} \equiv f_{\theta\omega}^{sc}(\gamma) \forall \begin{array}{l}\theta = 1, \ldots, \Theta \\ \omega = 1, \ldots, \Omega\end{array} \quad (24)$$

for the scattered field.

The difference between this example, and the previous one is that the background medium, in which the object is assumed to be buried, is assumed to be homogeneous in the previous case, whereas it is here assumed that the background is layered. The residual is defined in the same way as the previous example, with $d_{\theta\omega}$ used to represent the $N_d$-length vector of measured scattered field at the detector positions. That is, the residual vectors for all ω, θ are defined in the following way.

$$r_{\theta\omega} \equiv f_{\theta\omega}^{sc}(\gamma) - d_{\theta\omega} = 0 \forall \begin{array}{l}\theta = 1, \ldots, \Theta \\ \omega = 1, \ldots, \Omega\end{array} \quad (25)$$

The functional F(γ), dependent upon γ is defined in the same way as example 1:

$$F(\gamma) = \Sigma_{\theta\omega}\|r_{\theta\omega}\|_2^2 \quad (26)$$

This is the functional, dependent upon the object function γ in a highly nonlinear manner, which must be minimized in order to determine the γ values at each gridpoint in the object space. It is again necessary to compute the Jacobian:

$$\left(\frac{\partial f^{sc}_{\theta\omega}}{\partial \gamma}\right) = T_o((I - G_\omega \cdot [\gamma])^{-1}(G_\omega \cdot [f_{\theta\omega}]))\forall \begin{array}{l} \theta = 1, \ldots, \Theta \\ \omega = 1, \ldots, \Omega \end{array} \quad (27)$$

where θ again refers to the multiple views and the ω to the multiple frequencies available to us. That is, we again assume that the noise level in the system is zero. We apply the Gauss Newton algorithm to the associated least squares problem and get the same result. This leads to the overdetermined system described above (the notation is identical to the previous example, the difference lies in the actual form of the layered Green's function).

$$[T_o([I - G_k \cdot [\gamma]]^{-1} G_k)_\otimes I_{\theta x\theta}] \begin{bmatrix} [f_{1k}] \\ \vdots \\ [f_{\theta k}] \end{bmatrix} \delta\gamma^{(n)} = - \begin{bmatrix} [r^{(n)}_{1k}] \\ \vdots \\ [r^{(n)}_{\theta k}] \end{bmatrix} \forall k: \quad (28)$$

which must be solved for the γ-update δγ The left hand side of the above formula is given by $$[T_o([I - G_k \cdot [\gamma]]^{-1} G_k)_\otimes I_{\theta x\theta}] \equiv \quad (29)$$

$$\left\{ \begin{bmatrix} [TG_k(1 - [\gamma^{(n)}]G_k)^{-1} & 0 \ldots \\ 0 & \ldots \\ \vdots & \ldots \\ \vdots & \ldots \\ 0 & \ldots 0TG_k(I - [\gamma^{(n)}]G_k)^{-1} \end{bmatrix} \right\}$$

Again, we can use the complex analytic version of the Hestenes overdetermined conjugate gradient algorithm, adapted for least squares problems to iteratively solve this system. This is equivalent to finding the minimum norm solution.

The formula for the Jacobian in the layered medium situation in the presence of multiple frequencies, is, $$\left(\frac{\partial f^{sc}_{\theta\omega}}{\partial \gamma}\right) = T_o((I - G_\omega \cdot [\gamma])^{-1}(G_\omega \cdot [f_{\theta\omega}]))\forall \begin{array}{l} \theta = 1, \ldots, \Theta \\ \omega = 1, \ldots, \Omega \end{array} \quad (30)$$

where $G_\omega$ is the Layered Green's function for the frequency ω. Therefore, in effect, to determine the γ-update, δγ, we merely solve the multiple view problem for each particular frequency, that is, we solve the overdetermined system:

$$[T_o([I - G_k \cdot [\gamma]]^{-1} G_k)_\otimes I_{\theta x\theta}] \begin{bmatrix} [f_{1k}] \\ \vdots \\ [f_{\theta k}] \end{bmatrix} \delta\gamma^{(n)} = \begin{bmatrix} [r^{(n)}_{1k}] \\ \vdots \\ [r^{(n)}_{\theta k}] \end{bmatrix} \forall k = 1, \ldots, \Omega \quad (31)$$

which in component form is $$:[T \circ ([I - G_k \cdot [\gamma]]^{-1} G_k)][f_{jk}]\delta\gamma^{(n)=} - [r^{(n)}_{jk}]\forall \begin{array}{l} k + 1, \ldots, \Omega \\ j + 1 \ldots, \Theta \end{array} \quad (32)$$

See also the computer code in this patent for the complete description of this procedure. For multiple view and multiple frequency inversion then, the inversion scheme in layered media reads:

STEP 1. Choose an initial guess for the scattering potential, $\gamma^{(o)}$.

STEP 2. Set n = 0

STEP 3. solve the forward problems $$(I - G[\gamma])f_{\theta\omega} = f^{inc}_{\theta\omega}, \forall \begin{array}{l} \theta = 1, \ldots, \Theta \\ \omega = 1, \ldots, \Omega \end{array}$$

using biconjugate gradients, and use the result to compute the φ - forward maps $\phi_{\theta\omega}(\gamma^{(n)})$ and $$r^{(n)}_{\omega\phi} \equiv \phi_{\theta\omega}(\gamma^{(n)}) - d_{\theta\omega} = 0\forall \begin{array}{l} \theta = 1, \ldots, \Theta \\ \omega = 1, \ldots, \Omega \end{array}$$

STEP 4. Determine the $L_2$ norm of the total residual vector:

$$tr^{(n)} \equiv \begin{bmatrix} r^{(n)}_{11} \\ \cdot \\ \cdot \\ \cdot \\ r^{(n)}_{\theta} \\ \ddots \\ \ddots \\ r^{(n)}_{1\Omega} \\ \cdot \\ \cdot \\ \cdot \\ r^{(n)}_{\theta\Omega} \end{bmatrix}$$

STEP 5. If $\|tr^{(n)}\|^2 \equiv \sum_{\omega=1}^{\Omega} \sum_{\theta=1}^{\Theta} \|r^{(n)}_{\theta\omega}\|^2 < \epsilon$ then stop.

Step 6. Solve the $N_d\theta\Omega$ by N overdetermined system:

$$T \circ \begin{bmatrix} ([I - G_1 \cdot [g]]^{-1}G_1)_\otimes I_{\theta x\theta} & \cdots & 0 \\ \vdots & \ddots & \vdots \\ 0 & \cdots & ([I - G_\Omega \cdot [g]]^{-1}G_\Omega)_\otimes I_{\theta x\theta} \end{bmatrix}$$

in the least squares sense for $\delta\gamma^{(n)}$, using the conjugate gradient algorithm adapted for least squares problems.

STEP 7. Update γ via the formula
$\gamma^{(n+1)} = \gamma^{(n)} + \delta\gamma^{(n)}$ STEP 8. Set n = n + 1, go to begin The actual values of the angles of incidence θ are chosen to diminish as much as possible the ill conditioning of the problem. Equally spaced values 0<θ<2π are ideal, but experimental constraints may prohibit such values, in which case the multiple frequencies are critical. For biological contrasts (γ<0.15 say) the following approximation, which is essentially identical to the assumption in the previous example, is valid:

$$[I - G_\omega[\gamma]]^{-1} = [I + G_\omega[\gamma]] \quad (33)$$

This is the same Born-like approximation restricted to the Jacobian calculation only, that is assumed in example 1. This approximation has a much larger radius of convergence than the standard born approximation, but substantially reduces the computational complexity of the problem.

How to Implement the Convolution and Correlation in Layered Medium Imaging

All of the above calculations have been carried out without using the fact that the operation of matrix multiplication with G is in fact the sum of a convolution and a correlation, which is transformed into a pair of convolutions. Symbolically $G^L = G_R + G_V$, where $G_R$ is the correlation and $G_V$ is a convolution operator. The actual numerical implementation of the above formulas, therefore, is somewhat different than would naively appear. The implementation of the correlation with convolution is a little more challenging than the convolution in the homogeneous case, in that a change of variables must be used to convert the correlation to a convolution before the Fast Fourier Transform (FFT)s can be applied. A "reflection" operator must be applied to y before the convolution is applied, this operator is denoted by Z, and is defined by:

$$(zf)(x, y, z,) \equiv f(x, y, h = z) \begin{bmatrix} \begin{bmatrix} [f_{11}] \\ \vdots \\ [f_{\theta 1}] \end{bmatrix} \\ \ddots \\ \ddots \\ \begin{bmatrix} [f_{1\Omega}] \\ \vdots \\ [f_{\Theta\Omega}] \end{bmatrix} \end{bmatrix} \delta_g^{(n)} = - \begin{bmatrix} \begin{bmatrix} [r_{11}^{(n)}] \\ \vdots \\ [r_{\theta 1}^{(n)}] \end{bmatrix} \\ \ddots \\ \ddots \\ \begin{bmatrix} [r_{1\Omega}^{(n)}] \\ \vdots \\ [r_{\Theta\Omega}^{(n)}] \end{bmatrix} \end{bmatrix} \quad (34)$$

The use of this operator is incorporated into the action of the Lippmann-Schwinger equation on the field f That is, the equation for the internal fields, which in example 1 read:

$$(I - G\gamma)f = f^{inc}(I - G\gamma)$$

Now becomes $$(I - G_V\gamma = G_R Z\gamma)f = f^{inc}$$

This change has non-trivial ramifications for the construction of the algorithms discussed above. The FFT implementation of this is given below. To prevent the notation from getting out of hand we use [ ] to indicate that a diagonal matrix is constructed out of an n vector, so that $[\gamma^{(n)}]f_\phi^{(n)}$ denotes pointwise multiplication of the vectors γ and f. Also F is used to denote the Fourier transform, and * is used to indicate "convolution". In this notation, the Lippmann-Schwinger equation becomes, in the symbolic form adopted above, $$(I - G_V\gamma - G_R Z\gamma)f = (f - G_V * ([\gamma]f) - G_R * Z([\gamma]f)) = (f - F^{-1}\{(F(G_V) \cdot F([\gamma]f)) - (F(G_R) \cdot F\{Z([\gamma]f)\})\}) \quad (35)$$

Substantial savings is achieved through the observation that the Fourier Transforms of $G_V$ and $G_R$ need only be done once, then stored, and finally, that the reflection operator, Z, will commute with Fourier transformation in the x and y (horizontal) directions, since it only involves reflection in the z (vertical) direction.

There are changes also, for example in the computation of f. The biconjugate gradient algorithm requires the use of the adjoint in the solution of the above equation. This adjoint differs from the homogeneous ambient medium case with the introduction of the correlation operator. Also, there are substantial changes in the implementation of the overdetermined conjugate gradient algorithm used to solve (in the least squares sense) the overdetermined system of equations. In this section, as before, we incorporate the $k_{sc}^2$ factor into the $G_V$ and $G_R$ terms. Of course, rather than carry out the inversion of a matrix, we use biconjugate gradients and Fast Fourier Transforms (FFT's), which require the Lippmann Schwinger operator, which we denote by LS, and its adjoint, which are defined by the following formulas:

$$(LS)f \equiv (I - F^{-1}[(\overline{G}_V \cdot F) + (\overline{G}_R \cdot F \bigcirc Z)])([\gamma]f) \quad (36)$$

Where $$\overline{G}_V \equiv F(G_V) \text{ and } \overline{G}_R \equiv F(G_R)$$

are the Fourier Transforms of $G_V$ and $G_R$ and need only be calculated once, then stored. The unitarity of F is used below to determine the adjoint $(LS)^H$.

$$(LS)^H \equiv ((I - F^{-1}[(\overline{G}_V \cdot F) + (\overline{G}_R \cdot F \bigcirc Z)])[\gamma])^H = [\overline{\gamma}](I - [(F^{-1}\overline{G}_V^H) + (Z^H F^{-1}\overline{G}_R^H)](F^{-1})^H) = (\overline{\gamma})(I - [(F^{-1}\overline{G}_V) + (ZF^{-1}\overline{G}_R)]F) \quad (37)$$

where we have used the unitarity of Fourier Transformation F: $F^H = F^{-1}$, and the fact that point wise multiplication is used, and the fact that $Z^H = Z$. For practical problems it is best to obtain a reasonable first guess using low frequency data, then to build on this using the higher frequency information.

The Actual Construction of the Layered Greens Function

Up to this point, we have assumed the existence of the layered Green's function, but have not shown explicitly how to construct it. This is an essential step. For simplicity we deal with the scalar case, although the inclusion of shear wave phenomena is conceptually no more difficult than this case. The details are given in [Wiskin, 1991]. The general idea is based upon standard ideas in the literature concerning reflection coefficients in layered media. See for example [Muller, G., 1985, Journal of Geophysics, vol. 58] which is herein incorporated by reference. The novelty is the combination of the reflection coefficients into a bona fide Green's function, and the utilization of this in a forward problem, then more importantly, in the inverse problem solution. The procedure involves decomposing the point response in free space into a continuum of plane waves. These plane waves are multiply reflected in the various layers, accounting for all reverberations via the proper plane wave reflection/transmission coefficients. The resulting plane waves are then resummed (via a Weyl-Sommerfeld type integral) into the proper point response, which in essence, is the desired Green's function in the layered medium. The final result is:

$$G_V(x - x'; |\Delta z - \Delta z'|) = \int_{-\infty}^{\infty} e^{i\omega u(x-x')} C(u) \left[ e^{-i\omega b_{sc}|\Delta z - \Delta z'|} + R^+ R^- e^{i\omega b_{sc}|\Delta z - \Delta z'|} \right] du, \quad (38)$$

and $$G_R(x - x'; \Delta z - \Delta z) = \int_{-\infty}^{\infty} e^{i\omega u(x-x')} C(u) \left[ R^+ e^{-i\omega b_{sc}(\Delta z - \Delta z')} + R^- e^{i\omega b_{sc}(\Delta z - \Delta z')} \right] du, \quad (39)$$

where $$C(u) = (1 - R^+ R^-)^{-1} \frac{i\omega u}{b_{sc}},$$

$R^-$ and $R^{30}$ are the recursively defined reflectivity coefficients described in Muller's paper, u is the horizontal slowness, $$u \equiv \frac{\sin\theta}{c}$$

Recall that Snell's law guarantees that u will remain constant as a given incident plane wave passes through several layers.

ω is the frequency $b_{sc}$ is the vertical slowness for the particular layer hosting the scattering potential This Green's function for imaging inhomogeneities residing within Ambient Layered Media must be quantized by convolving with the sinc (really Jinc) basis functions described below. This is done analytically in [Wiskin, 1991], and the result is given below.

Discretization of Layered Medium Lippmann—Schwinger Equation

Unfortunately the basis functions that were used in the free space case (example 1) cannot be used to give the discretization in the layered medium case because of the arbitrary distribution of the layers above and below the layer which contains the scattering potential. The sinc functions may continue to be used in the horizontal direction, but the vertical direction requires the use of a basis function with compact support (i.e. should be nonzero only over a finite region). The sampled (i.e. discrete) Green's operator in the layered case is defined by $$G^L(y,k,m) = G^L(j\delta, k\delta, m\delta) \quad (40)$$

where the three dimensional basis functions are of the form:

$$B(x) = B(x,y,z) = S_{j,\delta}(x) S_{k,\delta}(y) \Lambda_m(z), \quad (41)$$

(I is the set of integers) and where:

$$x = \begin{pmatrix} x \\ y \\ z \end{pmatrix} \in R^3 \quad x_{jkm} \equiv \begin{pmatrix} j\delta \\ k\delta \\ m\delta \end{pmatrix} j, k, m \in I$$

The basis functions in the horizontal (x-y) plane $S_{(j,\delta)}$ are based upon the Whittaker $$\sin c(x) = \frac{\sin(\pi x)}{\pi x}$$

The basis functions in the vertical (z) direction, on the other hand, are given by $$\Lambda_m(Z) = \Lambda(z = m\delta),$$

where $\Lambda(z)$ is the "tent" function:

$$\Lambda(z) = \begin{cases} \frac{1}{\delta}(z+\delta) & z \in [-\delta, 0] \\ -\frac{1}{\delta}(z-\delta) & z \in [0, \delta] \end{cases}$$

The form of the discretized Lippmann Schwinger equation is $$f^{inc}\begin{pmatrix} n\delta \\ m\delta \\ l\delta \end{pmatrix} \equiv f^{inc}_{nml} = f\begin{pmatrix} n\delta \\ m\delta \\ l\delta \end{pmatrix} - k^2_{sc} \sum_{n'm'l'} G^V_{\pi/\delta}\begin{pmatrix} n-n' \\ m-m' \\ l-l' \end{pmatrix} \gamma_f\begin{pmatrix} n'\delta \\ m'\delta \\ l'\delta \end{pmatrix} - \quad (42)$$

$$k^2_{sc} \sum_{n'm'l'} \hat{G}^R_{\pi/\delta}\begin{pmatrix} n-n' \\ m-m' \\ l-l' \end{pmatrix} \gamma_f\begin{pmatrix} n'\delta \\ m'\delta \\ l'\delta \end{pmatrix}$$

with the vectors $G_{\pi/\delta}^R$ and $G_{\pi/\delta}^V$ are the result of first convolving the Green's function with the basis functions, and then sampling at the gridpoints. The superscript R refers to the correlation part whereas the superscript V refers to the convolution part of the Green's function. Both are computed via Fast Fourier Transforms, and are very fast. In the free space case the correlation part is zero. That is, we make the definition for L=V or R—(ie. convolution or correlation):

$$G^L_{\pi/\delta}(n,m,l) \equiv \int\int\int_{R^3} S(x')S(y')\Lambda(z')G^L\begin{pmatrix} n\delta - x' \\ m\delta - y' \\ l\delta - z' \end{pmatrix} dx'dy'dz', \quad (43)$$

substitution into equation (17) yields thee form (42). In matix notation, this equation gives:

$$f(I - k_{sc}^2 G_V^* \gamma_L - k_{sc}^2 \hat{G}_R^* Z \gamma_1)^{-1} f^{inc} \quad (44)$$

where now * represents discrete convolution in 3D. Now that we have constructed the Integral equations in discrete form, we must derive the closed form expression for the layered Green's operators. The construction of the closed form expression of the sampled and convolved acoustic layered Green's function $G_{\pi/\delta}^L$ from the layered Green's function given in equations (38 and 39) above is given by performing the integration in (43) analytically. This process is carried out in [Wiskin, 1991]. The final result is, for the convolutional part, $$G_V(m,n) = A\int_{u=0}^{u\delta} J_0 C(u) \frac{2}{i\omega b_{sc}} \left\{ R^- R^+ \left\{ -1 + \frac{(e^{i\omega b} SC^\delta - 1)}{i\omega b_{sc} C^\delta} \right\} + \quad (45) \right.$$

$$\left. \left\{ 1 - e^{-i\omega b} SC^\delta \frac{(e^{i\omega b} SC^\delta - 1)}{i\omega b_{sc} C^\delta} \right\} \right\} du \quad n = 0$$

$$A\int_{u=0}^{u\delta} J_0 C(u) \frac{1}{\omega^2 b_{sc}^2 \delta} \{2 - e^{i\omega b} SC^\delta - e^{-i\omega b} SC^\delta\}$$

$$\{e^{-i\omega b} SC^{|n\delta|} + R^- R^+ e^{i\omega b} SC^{|n\delta|}\} du \quad |n| \geq 1$$

$$\forall m \in [0, M-1], \forall n \in [-N+1, N-1]$$

and $$G_r(m,n) = A\int_{u=0}^{u\delta} J_0 C(u) \frac{\{2 - e^{i\omega b} m^\delta - e^{-i\omega b} m^\delta\}}{\omega^2 b_{sc}^2 \delta} \quad (46)$$

$$\{R^+ (e^{\omega b} sc^{(h+2d)} e^{-i\omega b} SC^{n\delta}) + R^- (e^{i\omega b} sc^{(h+2d)} e^{i\omega b} SC^{n\delta})\} du$$

$$\forall m \in [0, M-1], \forall n \in [-N+1, N-1]$$

In the above formulas $$J_o = J_o(u\omega|m|\delta)$$

is the zero$^{th}$ order Bessel Function, and the upper limit $u\delta$ is defined as:

$$u\delta = 1/c\delta = k\delta \frac{1}{\omega} = \frac{\pi/\delta}{\omega}$$

for wavenumber $$k\delta = \pi/\delta.$$

Also, $$C(u) \equiv (1 - R^- R^+)^{-1} S^c$$

where $\quad S^c = \frac{i\omega u}{b_{sc}}$ with $b_{sc}$ defined as the vertical slowness in the layer containing the scattering point. When this layer is assumed to have acoustic wave velocity, it is given explicitly by:

$$b_{sc}\sqrt{\frac{1}{\beta_{sc}^2} - u^2}.$$

These expressions give the discretized 3D Acoustic layered Green's function, which is used in the layered media discretized Lippmann-Schwinger equation to obtain the solution field within the inhomogeneity. It is also used in the detector equations (9), which correspond to the detector equations (11).

This patent differs from the previous art in the important aspect of including the correlation part of the green's function. This correlation part is zero for the free space case. This correlational part is directly applicable as it occurs above to the fish echo-locator/counter, and to the mine detection device in the acoustic approximation. (There are specific scenarios, where the acoustic approximation will be adequate, even though shear waves are clearly supported to some degree in all sediments). The inclusion of shear waves into the layered media imaging algorithm (the technical title of the algorithm at the heart of the hazardous waste detection device, the fish echo-locator, and the buried mine identifier) is accomplished in Example 6 below. Actually a generalized Lippmann-Schwinger equation is proposed. This general equation is a vector counterpart to the acoustic Layered Green's function, and must be discretized before it can be implemented. The process of discretization is virtually identical to the method revealed above. Furthermore, the BCG method for solving the forward problem, the use of the sinc basis functions, and the use of the Fast Fourier Transform (FFT) are all carried out identically as they in the acoustic (scalar) case.

EXAMPLE 3

Imaging with Electromagnetic Wave Energy

The use of electromagnetic energy does not greatly affect the basic idea behind the imaging algorithm, as this example will demonstrate. Furthermore, we will see that it is possible to combine the layered Green's function with the electromagnetic free space Green's function to image materials within layered dielectrics. In fact this process of combining the layered Green's function with Green's functions derived for other structures and/or modalities than the free space acoustic case can be extended almost indefinitely. Another example is given below, where the combination of the Acoustic Biot Green's function with the layered Green's function is carried out. Further extensions that are not detailed here, are: (1) Combining Elastic (including shear wave energy) Wave equations with the layered Green's function, (3) Combining the Elastic Biot equations with the layered Green's function, (4) Combining the elastic and electromagnetic wave equations to model transducers. For simplicity, we consider a homogeneous, isotropic, non-magnetic background material. The time dependence will be $e^{i\omega t}$, the magnetic properties of free space are summarized in $\hat{z}_o = i\omega\mu_o$, and the electric properties are summarized in $\hat{y}_o = i\omega\epsilon_o$. Within the object being imaged the magnetic properties are $\hat{z} \equiv \hat{z}_o = i\omega\mu_o$ (the equivalence with the free space value is the nonmagnetic media assumption). The electric properties of the object being imaged are summarized in $$\hat{y} = \sigma + \hat{y}_o = \sigma i\omega\epsilon_r\epsilon_o,$$

which is the complex admittivity of the object. The larger $\sigma$ is, the less able the medium is able to support electromagnetic wave transport. These properties are combined in $$k_o^2 \equiv -\hat{y}_o\hat{z}_o = \omega^2\mu_o\epsilon_o \equiv \frac{\omega^2}{c_o^2} \tag{47}$$

which is a measure of the number of wave cycles present per unit distance for a given frequency $\omega$, when the wave speed of propagation is $c_o$. The object's electrical properties (recall it is assumed non-magnetic for simplicity) are summarized in the "object function", $\gamma$. (the normalized difference from the surrounding medium):

$$\gamma(r) \equiv \frac{\hat{y} - \hat{y}_o}{\hat{y}_o} = \frac{\sigma + i\omega\epsilon_r\epsilon_o}{i\omega\epsilon_o} - 1 = -i\frac{\sigma}{\omega\epsilon_o} + \epsilon_r - 1 \tag{48}$$

The total electric field equations are:

$$E^i(r) = E(r) - (k_o^2 + \nabla\nabla\cdot)\int \gamma(r')E(r')\frac{e^{-ik_o|r-r'|}}{4\pi|r-r'|}d^3r' \tag{49}$$

where $E^i(r)$ is the 3-D incident field, $E(r)$ is the 3-D total field.

The construction of the sinc basis discretization and the GN and RP algorithms for this 3-D EM case is essentially equivalent to the 2-D scalar acoustic case described above. See [Borup, 1989] for the details of the discretization and solution of the forward problem by FFT-BCG. The vector-tensor nature of the fields—Green's function is the only new feature and this is easily dealt with.

For simplicity, we now look at the situation where there is no z dependence in either the object function, i.e. $\gamma(x,y,z)=\gamma(x,y)$, neither in the incident field. The vector $\rho=(x,y)$ is used for the position vector in (x,y)-space.

$$E^i(\rho) = (\rho) - (k_o^2 + \nabla\nabla\cdot)\int \gamma(\rho')E(\rho')\frac{1}{4i}H_0^{(2)}(k_o|\rho-\rho'|)d^2\rho' \tag{50}$$

in matrix form the equation (50) looks like:

$$E'(\rho) = \tag{51}$$

$$E(\rho) - \begin{bmatrix} k_0^2 + \frac{\partial^2}{\partial x^2} & \frac{\partial^2}{\partial x \partial y} & \\ \frac{\partial^2}{\partial y \partial x} & k_0^2 + \frac{\partial^2}{\partial y^2} & \\ & & k_o^2 \end{bmatrix} \int \gamma(\rho')E(\rho')\frac{1}{4i}H_o^2(k_o|\rho-\rho'|)d^2\rho'$$

From this form of the equation, it is clear that the electric field in the z-direction is uncoupled with the electric field in the x-y plane. Thus, in this situation the field consists of two parts. The so-called transverse electric (TE) mode, in which the electric field is transverse to the z direction, and the transverse magnetic (TM) mode, in which the electric field has a nonzero component only in the z direction. The TM mode is governed by the scalar equation:

$$E_z^i(\rho) = E_z(\rho) - \frac{k_0^2}{4i} \int \gamma(\rho') E_z(\rho') H_0^{(2)}(k_o|\rho - \rho'|) d^2\rho' \quad (52)$$

where $$E^i(\rho) \equiv \begin{pmatrix} E_x^i \\ E_y^i \\ E_z^i \end{pmatrix} \text{ and } E(\rho) \equiv \begin{pmatrix} E_x \\ E_y \\ E_z \end{pmatrix}(x, y)$$

which is identical to the 2-D acoustic equation discussed previously. Thus, the 2-D TM electromagnetic imaging algorithm is identical to the 2-D acoustic case discussed in detail above. The TE mode is given by the following equation:

$$\begin{pmatrix} E_x^i(\rho) \\ E_y^i(\rho) \end{pmatrix} = \begin{pmatrix} E_x(\rho) \\ E_y(\rho) \end{pmatrix} - \quad (53)$$

$$\frac{1}{4i} \begin{bmatrix} k_0^2 + \frac{\partial^2}{\partial x^2} & \frac{\partial^2}{\partial x \partial y} \\ \frac{\partial^2}{\partial y \partial x} & k_0^2 + \frac{\partial^2}{\partial y^2} \end{bmatrix} \int \gamma(\rho') \begin{pmatrix} E_x(\rho') \\ E_y(\rho') \end{pmatrix} H_0^2(k_o|\rho-\rho'|) d^2\rho'$$

The field is a two component vector and the Green's function is a 2×2 tensor Green': function:

$$G = \begin{bmatrix} g_{xx} & g_{xy} \\ g_{xy} & g_{yy} \end{bmatrix} = \frac{1}{4i} \begin{bmatrix} k_0^2 + \frac{\partial^2}{\partial x^2} & \frac{\partial^2}{\partial x \partial y} \\ \frac{\partial^2}{\partial y \partial x} & k_0^2 + \frac{\partial^2}{\partial y^2} \end{bmatrix} H_0^2(k_o|\rho - \rho'|) \quad (54)$$

In compact notation:

$$E^i(I - G\Gamma)E \quad (55)$$

where:

$$E^i = \begin{bmatrix} E_x^i \\ E_y^i \end{bmatrix}, E = \begin{bmatrix} E_x \\ E_y \end{bmatrix}, I = \begin{bmatrix} I & 0 \\ 0 & I \end{bmatrix}$$

and $$\Gamma = \begin{bmatrix} \gamma & 0 \\ 0 & \gamma \end{bmatrix}$$

This equation also has a convolution form and can thus be solved by the FFT-BCG algorithm as described in [Borup, 1989] The construction of the GN-MRCG MRCG and RP imaging algorithms for this case is identical to the 2-D acoustic case described above with the exception that the fields are two component vectors and the Green's operator is a 2×2 component Green's function with convolutional components.

Finally, note that the presence of layering parallel to the z direction can also be incorporated into these 2-D algorithms in essentially the same manner as above. Special care must be taken, of course, to insure that the proper reflection coefficient is in fact, used. The reflection coefficient for the TM case is different from the TE case.

The Electromagnetic Imaging Algorithm

The electromagnetic imaging algorithm is virtually the same as the imaging algorithm for the scalar acoustic mode shown in the previous example, and therefore, will not be shown here. The Microwave Nondestructive Imager is one particular application of this imaging technology, another example is the advanced imaging optical microscope.

EXAMPLE 4

Advanced Imaging Microscope

Figure 6A:
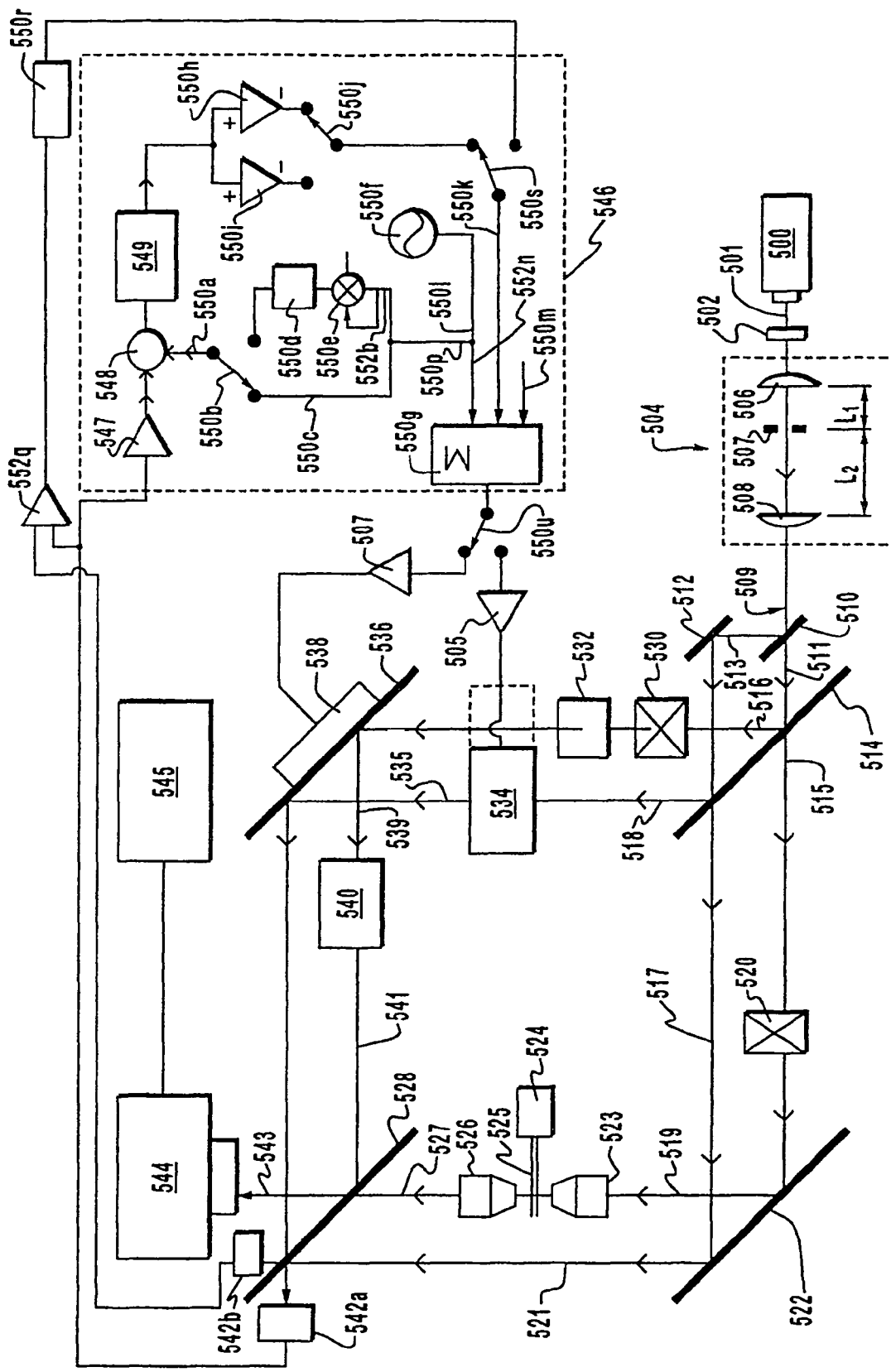
FIG. 6A is a system block diagram of an optical microscope used with the apparatus and method of the present invention.

The microscope imaging algorithm requires the complex scattered wave amplitude or phasor of the light (not the intensity, which is a scalar) at one or more distinct pure frequencies (as supplied by a laser). Since optical detectors are phase insensitive, the phase must be obtained from an interference pattern. These interference patterns can be made using a Mach-Zehnder interferometer. From a set of such interference patterns taken from different directions (by rotating the body for example), the information to compute the 3-D distribution of electromagnetic properties can be extracted. A prototype microscope system is shown in FIG. 6A and discussed in the Detailed Description Of The Drawings. There are two interferometer paths A and B where A is the path containing the microscope objective lenses and sample and B is the reference path containing a beam expander to simulate the effect of the objective lenses in path A. These paths are made to be nearly identical. If the paths are equal in length and if the beam expander duplicates the objective lenses, then the light from these two paths has equal amplitude and phase. The resulting interference pattern will be uniformly bright. When any path is disturbed and interference pattern will result. In particular if path A is disturbed by placing a sample between the objective lenses, an interference pattern containing information of the object will result. When path B has an additional phase shift of 90 degrees inserted, then the interference pattern will change by shifted (a spatial displacement) corresponding to 90 degrees.

The problem of extracting the actual complex field on a detector (such as a CCD array face) from intensity measurements can be solved by analysis of the interference patterns produced by the interferometer. It is possible to generate eight different measurements by: (1) use of shutters in path A and path B of the interferometer; (2) inserting or removing the sample from path A; and (3) using 0 or 90 degree phase shifts in path B. It is seen that all eight measurements are necessary.

The procedure to extract amplitude and phase from the interference patterns can be seen after defining variables to describe the eight measurements. Let:

$$f_o^{(det)}\phi\omega xA = A_{o\phi\omega x} e^{i\omega t + i\alpha(\phi,\omega,x)}$$

be the incident field on the detector from path A (with no energy in path B) when no sample is in place, $$A_{o\phi\omega x} = |A_{o\phi\omega x}|,$$

$$f_o^{det}\phi\omega xB = B_{1\phi\omega n} e^{i\omega t + i\beta(\phi\omega x)}$$

be the incident field on the detector from reference path $B_1$ when no additional phase shift is introduced in path B (with no energy in path A), $$B_{1\phi\omega x} = |B_{1\phi\omega x}|$$

$$f_1^{(det)}100_{\omega xB} = B_{2\phi\omega x} e^{i\omega t + i\beta(\phi,\omega,x) + i\pi/2}$$

be the incident field on the detector from reference path B when $\pi/2$ additional phase shift is introduced in path B (with no energy in path A), $$B_{2\phi\omega x} = |B_{2\phi\omega x}|,$$

$$f_o^{(det)}\phi\omega x C = C_{o1\phi\omega x} e^{i\omega t + i\theta(\phi,\omega,x)}$$

be the field on the detector when both path A and path $B_1$ are combined when no sample is in place, $$C_{o1\phi\omega x} = |C_{o1\phi\omega x}|,$$

$$f_o^{(det)}\phi\omega x C = C_{o2\phi\omega x} e^{i\omega t + i\theta(\phi,\omega,x) + i\pi/2}$$

be the field on the detector when both path A and path $B_2$ are combined when no sample is in place, $$C_{o2\phi\omega x} = |C_{o2\phi\omega x}|,$$

$$f^{(det)}\phi\omega x A = A_{1\phi\omega x} e^{i\omega t + i\phi(\phi,\omega,x)}$$

be the field on the detector from path A (with no energy in path B) when a sample is present, $$A_{\phi\omega x} = |A_{\phi\omega x}|,$$

$$f^{(det)}\phi\omega x C = C_{1\phi\omega x} e^{i\omega t + i\sigma(\phi,\omega,x)}$$

be the field on the detector when both path A and path $B_1$ are combined when the sample is in place, $$C_{1\phi\omega x} C = C_{1\phi\omega x} e^{i\omega t + i\sigma(\phi,\omega,x)}$$

$$f^{(det)}{}_{\phi\omega x} C = C_{2\phi\omega x} e^{i\omega t + i\sigma 2(\phi,\omega,x)}$$

be the field on the detector when both path A and path $B_2$ are combined when the sample is in place, $$C_{2\phi\omega x} = |C_{2\phi\omega x}|,$$

$\phi$ be the rotation angle of the sample holder
$\omega$ be the frequency of the light
x be the 2-D address of a pixel on the detector.

Now consider the one pixel for one rotation angle and at one frequency of light so that we may suppress these indices temporarily. The measurement made by the CCD camera is not of the field but rather of the square of the modulus of the field (i.e., the intensity). Thus, eight intensity fields can be measured on the detector:

$$M_1^2 = A_0^2 \phi\omega x \quad M_2^2 = B_1^2 \phi\omega x$$

$$M_3^2 = B_2^2 \phi\omega x \quad M_4^2 = C_{01}^2 \phi\omega x$$

$$M_5^2 = C_{o2}^2 \phi\omega x \quad M_6^2 = A^2 \phi\omega x$$

$$M_7^2 = C_1^2 \phi\omega x \quad M_8^2 = C_2^2 \phi\omega x$$

Because of the nature of an interferometer, the eight measurements are not independent. In particular, $M_4^2$ is dependent on $M_1^2$ and $M_2^2$. $M_5^2$ is dependent on $M_1^2$ and $M_3^2$ $M_7^2$ is dependent on $M_1^2$, $M_2^2$, $M_4^2$ and $M_6^2$ $M_8^2$ is dependent on $M_1^2$, $M_3^2$, $M_5^2$ and $M_6^2$. Also, $$M_3^2 = K M_2^2 \text{ (where, K=1 for a perfect phase shifter)}.$$

Thus, $$B_2^2 = K B_1^2$$

There are four ways to add the two beams on specifying sample in or sample out and specifying 0-degree phase shift or 90-degree phase shift. For sample out:

$$M_4^2 = C_{o1\phi\omega x}^2 = |A_o e^{i\omega t + i\alpha(\phi,\omega,x)} + B_1 e^{i\omega t + i\beta(\phi m \omega x)}|^2 = A_0^1 + B_1^2 + 2A_0 B_1 \cos(\beta - \alpha), M_5^2 = C_{o2\phi\omega x}^2 = |A_o e^{i\omega t + i\alpha(\phi,\omega,x)} + B_2 e^{i\omega t + i\beta(\phi,\omega,x) + i\pi/2}|^2 = A_o^2 + B_2^2 + 2A_o B_2 \cos(\beta - \alpha + \pi/2) = A_o^2 + B_2^2 + 2A_o B_2 \sin(\beta - \alpha)$$

$$(\beta - \alpha) = -\arctan\{M_3[M_4^2 - M_1^2 - M_2^2]/M_5^2 - M_1^2 - M_3^2]\}$$

For sample in:

$$M_7^2 = C_{1\phi\omega x}^2 = |A_{\phi\omega x} e^{i\omega t + i\phi(\phi,\omega,x)} + B_{1\phi\omega x} e^{i\omega t + i\beta(\phi,\omega,x)}|^2 = A^2 B_1^2 + 2AB_1 \cos(\beta - \Psi), M_8^2 = C_{2\phi\omega x}^2 = |A_{\phi\omega x} e^{i\omega t + i\phi(\phi,\omega,x)} + B_{2\phi\omega x} e^{i\omega t + i\beta(\phi,\omega,x)}|^2 = A^2 + B_2^2 + 2AB_2 \cos(\beta - \Psi + \pi/2) = A^2 + B_2^2 - 2AB_2 \sin(\beta - \Psi).$$

$$(\beta - \Psi) = -\arctan\{M_3[M_7^2 - M_6^2 - M_2^2]/M_2[M_8^2 - M_6^2 - M_3^2]\}$$

$(\beta - \alpha) - (\beta - \Psi) = (\Psi - \alpha) = $ phase shift introduced by sample The scattering equations are $$f(x) = f^{inc}(x) + C(x-y) * ([\gamma(y)]_D f(y)), f(x)$$

$$f^{(sc-det)}(z) = f^{(det)}(z) - f^{(inc)}(z) = D(z-x) * ([f(x)]_D \gamma(x))$$

Here, the symbol * means convolution and the symbol $[.]_D$ means the vector [.] is replaced by a diagonal matrix. When written in terms of the phase shift introduced by the sample these equations become:

$$(f(x)/f^{(inc)}(x)) - 1 = C(x-y) * ([\gamma(y)]_D (f(y)/f^{(inc)}(x))) f^{(sc-det)}(z) = f^{(inc)}(z) = ([f^{(det)}(z)/f^{(inc)}(z)) - 1 = D(z-x) * ([f(x)/f^{(inc)}(z)]_D \gamma(x))$$

If the incident field is known then these equations can be solved. If the incident field is not known explicitly, but is known to be a plane wave incident normal to the detector, then the phase and amplitude is constant and can be divided out of both pairs of equations. It is the latter case that is compatible with the data collected by the interferometer. If the incident field is not a plane wave then, the amplitude and phase everywhere must be estimated, but the constant (reference) phase and amplitude will still cancel. The incident field can be estimated by inserting known objects into the microscope and solving for the incident field from measured interference patterns or from inverse scattering images.

The basic microscope has been described in its basic and ideal form. A practical microscope will incorporate this basic form but will also include other principles to make it easier to use or easier to manufacture. One such principle is immunity to image. degradation due to environmental factors such as temperature changes and vibrations. Both temgerature changes and vibration can cause anomalous differential phase shifts between the probing beam and reference beam in the interferometer. There effects are minimized by both passive and active methods. Passive methods isolate the microscope from vibrations as much as possible by adding mass and viscous damping (e.g. an air supported optical table). Active methods add phase shifts in one leg (e.g. the reference leg) to cancel the vibration or temperature induced phase shifts. One such method we propose is to add one or more additional beams to actively stabilize the interferometer. This approach will minimize the degree of passive stabilization that is required and enhance the value of minimal passive stabilization.

Stabilization will be done by adjusting the mirrors and beam splitters to maintain parallelness and equal optical path length. A minimum of three stabilizing beams per/mirror is necessary to accomplish this end optimally (since three points determine a plane uniquely including all translation). These beams may be placed on the edge of the mirrors and beam splitters at near maximum mutual separation. The phase difference between the main probing and main reference beam occupying the center of each mirror and beam splitter, will remain nearly constant if the phase difference of the two component beams for each stabilizing beam is held constant. Note that one component beam propagates clockwise in the interferometer, while the other propagates counterclockwise. Stabilization can be accomplished by use of a feed back loop that senses the phase shift between the two component beams for each stabilizing beam, and then adjusts the optical elements (a mirror in our case) to hold each phase difference constant. This adjustment of the optical elements may be done by use of piezoelectric or magnet drivers.

We now describe how use of the several stabilizing beams operates to stabilize the interferometer and the microscope. Since the stabilization of a single beam is known to those working with optical interferometers, the description given here will be brief. The description is easily seen by a simple mathematical analysis of the interaction of the two components of the stabilizing beam. The electric field of the light at a point in space may be represented $E=E_o\exp(i2\pi ft)$, where $E_o$ contains the spatial dependence and $\exp(i2\pi ft)$ contains the temporal component, where f is the frequency of oscillation and t is time. For the remainder of this discussion we assume $\exp(i2\pi ft)$ time dependence at a single frequency f and this factor will be omitted. Let the electric field of the output of the interferometer for one component beam be A and let the electric field output of the second component be B exp iθ. Then the combined output is [A+B exp(iθ)]. The light intensity of the combined output that is detected is $$|A+B \exp(i\theta)|^2 = A^2 + B^2 + 2AB \cos\theta.$$

The feedback conditions can be easily derived from the above equation. The feedback signal can be derived by: (1) synchronous detection of the summed beams when one of the beams, say beam B, is modulated; or (2) by use of the differences in intensity of the transmitted and reflected beam exiting the final beam splitter. We now describe the operation of the first method of synchronous detection.

Let $\theta = (\theta_o + \in \sin(\omega t))$ represent phase modulation of phase θ around equilibrium phase $\theta_o$ by amount $\in$ at frequency ω. The frequency ω is typically 100 Hz to 1000 Hz. Suppose that phase difference of zero degrees between beam A and beam B is required. Setting $\theta_o = \delta$ and noting that both $\in$ and δ are small we see that $\cos\theta = \cos(\delta + \in \sin(\omega t))$. By use of the trigonometric identity for the cosine of the sum of two angles we get $\cos\theta = \cos\delta \cos(\in \sin(\omega t)) - \sin\delta \sin(\in \sin(\omega t))$. On expanding this expression to second order in δ we obtain $$\cos\theta = (1-\delta^2/2) - \frac{1}{2} \in^2 (1-\delta^2)\sin^2(\omega t) - \delta \in \sin(\omega t).$$

We wish to force δ to zero for optimal phase lock. There are two ways to accomplish this end: (1) by maximizing the modulus of the signal component $\in^2(1-\delta^2)\sin^2(\omega t)$; or (2) by minimizing the modulus of the signal component $\delta \in \sin(\omega t)$. The former method is accomplished by mixing (multiplying) $|A+B\cos\theta|^2$ by $\sin^2(\omega t)$, low pass filtering and then maximizing the signal by feedback changes to δ.

To lock the phase difference to π/2 a modification of the above procedure may be used. Set $$\theta = \pi/2 + \delta + \in \sin(\omega t).$$

Then $$\cos\theta = \cos(\pi/2 + \delta + \in \sin(\omega t)) = -\sin(\delta + \in \sin(\omega t)) = -\sin\delta \cos(\in \sin(\omega t)) + \cos\delta \sin(\in \sin(\omega t)).$$

On expanding this expression to second order in a we obtain $$\cos\theta = (1-\delta^2/2) \in \sin(\omega t) - \delta\left(1 - \frac{1}{2}\in^2 \sin^2(\omega t)\right).$$

Again, we wish to force δ to zero for optimal phase lock. There are again two ways to accomplish this end: (1) by maximizing the modulus of the signal component $(1-\delta^2/2)\in\sin(\omega t)$; or (2) by minimizing the modulus of the signal component $$\delta\left(1 - \left(\frac{1}{2}\right)\in^2 \sin^2\sin^2(\omega t)\right).$$

The former method is accomplished by mixing $|A+B\cos\theta|^2$ with $\sin(\omega t)$, low pass filtering and maximizing the result by changing to δ through feedback. The latter method is accomplished by mixing $|A+B\cos\theta|^2(\omega)$, low pass filterings and minimizing the resulting signal by feedback to change δ.

We now describe a second or non-hetrodyning method of phase locking beam A and B to a constant phase difference. The net intensity of the respective transmitted and reflected beams from a beam splitter have different dependency of the phase difference from the that combines two beams. Let the two beams coincident on the beamsplitter be A and B cos θ Then the two exit beams from the beam splitter have respective intensities $|A+B\cos\theta|^2$ and $|A-B\cos\theta|^2$. This follows from a difference in phase of 180 degrees in the reflected beam depending on whether the incident medium has a higher or lower dielectric constant than the medium beyond the reflecting surface. The difference of the signals from detectors that detect transmitted and reflected beams is given by $|A+B\cos\theta^2|-|A-B\cos\theta|^2 = 4AB\cos\theta$. If the desired phase angle is π/2 and the error is δ then $4AB\cos\theta = -4AB\sin\delta \approx -4AB\delta 4$. Thus, the error signal δ can be used in a feedback loop to drive the difference in the two optical paths to π/2. This technique can be refined by dividing by the product of A and B. Since A is proportional to B dividing by A.sup.2 will be equivalent. The value of A is proportion to the sampled laser power that is used to generate beam A and beam B cos θ.

EXAMPLE 5

Extension to Biot Theory (Acoustic Approximation)

In the article [Boutin, 1987, Geophys. J. R. astr. Soc., vol. 90], herein incorporated by reference, a greens function for the determination of a point response to a scattering point located in an isotropic, homogeneous, porous medium that supports elastic waves is developed. The implementation of this Greens' function into an imaging algorithm has never been carried out before. In this section, we have adapted their approach to derive an acoustic approximation to the fully elastic Biot theory that enables us to present a simplified practical tool for the imaging of porosity-like parameters in a geophysical context. The implementation of the full elastic Biot imaging algorithm using the Green's function of [Boutin, 1987] in place of the one derived in [Wiskin, 1992] is no different from the discretization employed here. The use of the sinc basis functions, the FFT's, the biconjugate gradients, and so on, is identical.

We have developed a model that incorporates the parameters of fluid content, porosity, permeability, etc, but instead of the 3+1 degrees of freedom of the two phase elastic model, has only 1+1, corresponding to the two independent variables, $P_{s'}$ and $P_{f'}$ the pressure field within the solid (modelled as a liquid in this approximation) and truly liquid phase respectively. As with the previous example. The use of the Biot theory Green's function can be combined profitably with layering, to image material in a layered background.

Define (see [Boutin, 1987], for more complete discussion of the parameters):

$\omega$ as the frequency of the interrogating wave
$\rho_1$ as the density of the liquid phase
$\rho_s$ as the density of the solid phase
n as a saturation parameter
$K(\omega)$ as the generalized, explicitly frequency-dependent Darcy coefficient introduced via homogenization theory.
$\alpha_o$, $\theta$, $\rho$ are parameter's defined in the following way:
$\rho=(1-n)\rho_s+\rho_1\lfloor n+\rho_1\omega^2 K(\omega)/i\omega\rfloor$
$\theta=K(\omega)/i(\omega)$
$\alpha_o=\alpha+\rho_1\omega^2 K(\omega)/i\omega=\alpha+\rho_1\omega^2\theta$ The "acoustic two phase Green's function" is the Green's function obtained by solving the above system with a distributional right hand side, where $\delta(x)$ is the Dirac delta distribution. That is we seek the solution to the following matrix operator equation:

$BG_{Biot}+I_{2\times 2}\delta(x)=0$ where $BG_{Biot}$:

$R^{2,3} \to R^2$ is a function on $R^3$ or $R^2$ and $I_{2\times 2}$ is the two dimensional identity matrix. B is given by:

$$B = \begin{bmatrix} \theta\nabla^2-\beta & -\alpha_0 \\ -\alpha_0\nabla^2 & \lambda\nabla^2+\omega^2\rho \end{bmatrix}$$

This author obtained $$G_{Biot} \frac{1}{4\pi\theta\lambda} \frac{\alpha_0}{(\delta_2^2-\delta_1^2)} \left\{ (\omega \cdot d)\begin{bmatrix} \lambda & 0 \\ \alpha_0 & \theta \end{bmatrix} + (\omega \cdot v)\begin{bmatrix} \overline{\rho}\omega^2 & \alpha_0 \\ 0 & -\overline{\beta} \end{bmatrix} \right\}$$

where w: $R^3 \to R^2$ is the 2D vector defined by:

$$w \equiv \begin{pmatrix} \frac{e^{-i\delta_1|x|}}{|x|} \\ \frac{e^{-i\delta_2|x|}}{|x|} \end{pmatrix}$$

and $x \in R^3$ for the acoustic two-phase 3D model, and where d and v are 2 component vectors (representing the two phases) given by $$d = \begin{pmatrix} -\delta_1^2 \\ \delta_2^2 \end{pmatrix}, v = \begin{pmatrix} 1 \\ -1 \end{pmatrix}$$

A very similar analysis gives an equation and corresponding Green's Operator for the acoustic two-phase 2D (two spatial independent variables) case, in which w: $R^2 \to R^2$ and $x \in R^2$ The operator is very similar except that the w vector contains Hankel functions of the zeroth order:

$$w = \begin{pmatrix} \frac{i}{4}H_0^{(2)}(\delta_1|x|) \\ \frac{i}{4}H_0^{(2)}(\delta_2|x|) \end{pmatrix}$$

Notice the existence of the two wavenumbers $\delta_1$ and $\delta_2$ in this acoustic approximation to Biot theory guarantee the existence of a fast and slow compressional wave—a distinguishing characteristic of the classical elastic Biot theory.

More importantly this algorithm provides us with a computationally feasible means of inverting for phenomenological parameters derived from the classical elastic two phase Biot Theory.

Finally, it is important to point out that convolving the above functions with the sinc basis function analytically is done in exactly the same manner with $G_{BIot}=G_{2\times 2}$ above as it was done above because x only occurs in the form of the scalar acoustic Green's operator. This is why it is possible to create very efficient algorithms based upon the sinc-Galerkin method and FFT's as described in [Borup, 1992], using the Green's Operator described above.

It is now possible to obtain an algorithm for the inversion of the 2D Biot porous medium by analogy with the algorithm based upon the Lippmann-Schwinger equation used earlier. This new algorithm is based upon a "two phase" Lippmann-Schwinger type equation derived in a future publication.

$$r_0(x) = r(x) - \begin{bmatrix} -\overline{b}_1 & 0 \\ 0 & b_2 \end{bmatrix} \int\int\int G_{2\times 2}(x-\xi)D'(\xi)r(\xi)d^3\xi \text{ where } D'(x) =$$

$$\begin{bmatrix} \gamma_1 & 0 \\ 0 & \gamma_2 \end{bmatrix}$$

the object functions $\gamma_j$ are given by $$\gamma_j(x) \equiv (-1)^j\left(\frac{b_j(x)}{\overline{b}_j}-1\right) j = 1, 2$$

This equation is discretized in the same manner as above, and the convolution character is preserved. With the explicit form of the discretized Biot Lippmann-Schwinger Integral Equation the imaging problem is solved by applying the analogous conjugate gradient iterative solution method to the Gauss-Newton Equations in a manner exactly analogous to the discussion above (see future publication for details).

Finally, as mentioned above, it is certainly possible to construct, using the above principles, a layered Green's function for the Biot theory in exact analogy with the construction for the acoustic layered Green's Operator. This operator will be a matrix operator (as is the acoustic two phase Green's Operator constructed above), and will consist of a convolutional and correlational part (as does the acoustic single phase Green's Operator constructed earlier). Because of these convolutional and correlational parts, the FFT methods discussed above are directly applicable, making the algorithm feasible from a numerical standpoint.

EXAMPLE 6

Non-Perturbative Inversion of Elastic Inhomogeneous Structures Buried Within a Layered Half Space In elastic media (by convention in this patent, media that supports shear wave activity) the relevant parameters are $\gamma$, $\mu$, (Lame' parameters), $\rho$ (density) and absorption. The inversion for these elastic parameters (i.e. the first and second Lame' parameters, $\gamma$ and $\mu$ follows virtually the same prescription as was outlined above for the acoustic scalar case. In a manner similar to the Electromagnetic Inversion problem discussed above, it is possible to break up the arbitrary 3 dimensional vector u(x,y,z), representing the displacement into components that propagate independently. The exact description of this procedure is given in [Wiskin, 1991], and [Muller, 1985]. This example will not deal with this decomposition since the idea behind this is more easily seen by looking at the electromagnetic example given earlier.

The idea here is to incorporate the above solution to the layered inversion problem directly into the Green's operator. As before, in the electromagnetic and the acoustic case, this Green's function is used in the integral equation formulation of the inversion problem of imaging an inhomogeneous body extending over an arbitrary number of layers.

The following is the general elastic partial differential equation which governs the displacement vector field u in the general case where $\lambda$ and $\mu$ both depend upon $x \in R^3$. When $\lambda$ and $\mu$ are independent of x, we have the homogeneous elastic case.

$$-\omega^2 \rho(x) u^i(x) - \frac{\partial}{\partial x^i}\left[\lambda(x) \frac{\partial}{\partial x^k} u^k(x)\right] + \frac{\partial}{\partial x^i}\left[\mu(x)\left\{\frac{\partial}{\partial x^i} u^k(x) + \frac{\partial}{\partial x^k} u^i(x)\right\}\right] = f^i(x)$$

$f^i(x)$ represents the applied body force, and $\mu(x)$ and $\lambda(x)$ are the Lame' parameters, their dependence upon $x \in R^3$ is the result of both the inhomogeneity to be imaged and the ambient layered medium. In particular $u_i(\vec{y}) \vec{y} \in R^3$ is the $i^{th}$ component (i=1,2,3) of the displacement field at point $\vec{y} \in R^3$ $u_i^0(\vec{y})$ is the $i^{th}$ component of the incident field.

$\rho_1(\vec{x}) + \rho_0(z) = \rho(\vec{x})$ is the total density variation, it consists of the 3-D variation in $\rho_1$ and the vertical 1-D variation in $\rho_0$ $\lambda_1(\vec{x}) + \lambda_0(z) = \lambda(\vec{x})$ is the total variation in $\lambda$ the first Lame' parameter, $\lambda_1$ has 3-D variation, and $\lambda_0$ has 1-D vertical variation.

$\mu_1(\vec{x}) + \mu_0(z) = \mu(\vec{x})$ is the total variation in the second Lame' parameter .mu. The $\mu_1$ has variation in 3-D, the $\mu_2$ has variation in 1-D (vertical).

$(\vec{x})$=density=$\rho_1(\vec{x}) + \rho_0(z)$, where $\rho_0(\vec{x})$ represents the layered medium without the object, and $\rho_1(\vec{x})$ represents the object to be imaged.

$\mu_0(z)$ and $\mu_0(z)$ are the z-dependent Lame' parameters representing the layered medium $\lambda_1(\vec{x})$ and $\mu_1(\vec{x})$ are the Lame' parameters representing the object to be imaged The above differential equation is converted to the following elastic "Generalized Lippmann-Schwinger equation $$u_i(\vec{y}) = u_i^0(\vec{y}) - \iiint_{vol} \{G_{im}^{(LAY)}(\vec{y}, \vec{x})\} u_m(\vec{x}) d\vec{x}, \ i = 1, 2, 3$$

by means of the kernel $G_{im}^{(LAY)}(\vec{y}, \vec{x})$, which is constructed below. Where the volume integral is performed over the finite volume that contains the image space (and the object being imaged, for example, an ore body, submarine mine, oil reservoir, etc). This is the basic integral equation which forms the theoretical foundation for the Layered Green's Operator approach to Inverse Scattering in a layered medium.

This kernel is a 3 by 3 matrix of functions which is constructed by a series of steps:

STEP 1:
Beginning with the acoustic (scalar or compressional) Green's function given by $$G(k_0|r - r'|) = \frac{e^{-ik_0|r-r'|}}{4\pi|r - r'|}$$

STEP 2:
The free space elastic Green's matrix is a 3 by 3 matrix of functions, built up from the free space Green's function. It's component functions are given as $$G_{im}(k_T k_L|r - r'|) = \mu G(k_T|r - r'|)\delta_{im} + \frac{\mu}{k_T^2}\frac{\partial^2}{\partial x^i \partial x^m}[G(k_T|r - r'|) - G(k_L|r - r'|)]$$

STEP 3:
Next the layered Green's function, $$G_{im}^L(\vec{y}, \vec{x}),$$

for a layered elastic medium is defined. It is defined in terms of $G_{im}$, the components i, m = 1, . . . , 3, of the elastic Green's function in homogeneous elastic media given above. The components of the layered Green's matrix are integrals over Bessel functions and reflection coefficients in essentially the same manner as the acoustic layered Green's function consisted of integrals over wavenumber, of the acoustic reflection coefficients. This dyadic is patterned after [Muller, 1985], in the manner discussed in [Wiskin, 1992].

STEP 4:
Finally the layered Green's kernel $G_{im}^{(LAY)}$, is constructed $\vec{x} \in R^3$ $$G_{im}^{(LAY)}(\vec{y}, \vec{x}) = -\omega^2 G_{im}^L(\vec{y}, \vec{x})\rho_1(\vec{x}) - \frac{\partial}{\partial x^m}\left\{\left(\frac{\partial}{\partial x^j}G_{ij}^L(\vec{y}, \vec{x})\right)\lambda_1(\vec{x})\right\} + \frac{\partial}{\partial x^j}\left\{\left(\frac{\partial}{\partial x^m}G_{ij}^L(\vec{y}, \vec{x}) + \frac{\partial}{\partial x^j}G_{im}^L(\vec{y}, \vec{x})\right)\mu_1(\vec{x})\right\}$$

where $$G_{im}^L(\vec{y}, \vec{x})$$

-continued is layered Green's function for the elastic layered medium. The progressive constructions can be represented in the following way, beginning with the acoustic free space Green's function:

$$G(k_0|r-r'|) = \frac{e^{-ik_0|r-r'|}}{4\pi|r-r'|} \to \to G_{im}(\vec{y}, \vec{x}) \to \to G_{im}^L(\vec{y}, \vec{x}) \to \to$$

$$G_{im}^{(LAY)}(\vec{y}, \vec{x})$$

Alternatively, in words:

| Acoustic free space Green's function | elastic free space Greens function | elastic layered Green's function | kernel for elastic layered Lippmann-Schwinger equation |
|---|---|---|---|

Using the last "kernel" in this series in the generalized elastic layered Lippmann-Schwinger Equation gives the vector displacement.

$$u_i(\vec{y}) = u_i^0(\vec{y}) = \iiint_{vol} \{G_{im}^{(LAY)}(\vec{y}, \vec{x})\} u_m(\vec{x}) d\vec{x}$$

which is then discretized, using the sinc basis in exactly the same way as for the previous examples, and, the FFT, and biconjugate gradient, and conjugate gradient algorithms are then applied to this vector equation, in the same way as done above. Thus the elastic modality (including shear waves) is accounted for.

The construction of the layered Green's function in the full elastic case (with shear wave energy included is slightly more complicated than the purely scalar case. For this reason, we look at the construction in more detail, see also [Wiskin, 1993]

For discretization of the resulting equations see the electromagnetic case discussed in example 3.

The Construction of the Continuous Form of the Layered Green's Operator $G^L$-3D and with full elastic mode conversion Case, Now we proceed with the construction of the continuous variable form of the Layered Green's operator. The closed form expression for the discretized form of the bandlimited approximation to this continuous variable Green's operator is constructed in a manner exactly analogous to the vector electromagnetic case discussed in example 3.

By analogy with the acoustic (scalar) situation, the construction of the layered Green's operator can be viewed as a series of steps beginning with the 3D free space Green's operator.

Step a) Decompose a unit strength point source into a plane wave representation (Weyl-Sommerfeld Integral). For the elastodynamic (vector) case we must consider the three perpendicular directions of particle motion, which we take to be the horizontal direction, the direction of propagation, and the direction perpendicular to the previous two. Muller has given the representation for a point source in elastic media in [Muller, 1985]

Step b) Propagate and reflect the plane waves through the upper and lower layers to determine the total field at the response position. The total field will consist of two parts: $u^{up}(r)$, the upward propagating particle velocity, and $u^d(r)$, the downward propagating particle velocity at position r. This propagation and reflection is carried out analytically by means of the reflection coefficients, which in the elastic case, are the matrices $R^-$ and $R^+$ ($R^-$ and $R^+$ are 2×2 matrices), and the scalars, $r^-$, and $r^+$. The matrices correspond to the P-SV (compressional and shear vertical polarized waves) for the case of horizontal stratification. (x is the horizontal, and z is the vertical coordinate, z is positive downward). The scalar coefficients correspond to the SH (horizontally polarized) shear waves, which propagate without mode conversion to the other types for the case of horizontally layered media.

$R^-$ and $r^-$, represent the wave field reflected from the layers below the source position, and $R^+$, and $r^+$ represent the cumulative reflection coefficient from the layers above the source position, for the matrix and scalar cases respectively.

These total reflection coefficients are formed recursively from the standard reflection coefficients found in the literature (e.g. Muller [1985], and Aki and Richards, Quantitative Seismology, Freeman and Co., 1980, herein included as a reference].

Figure 27:
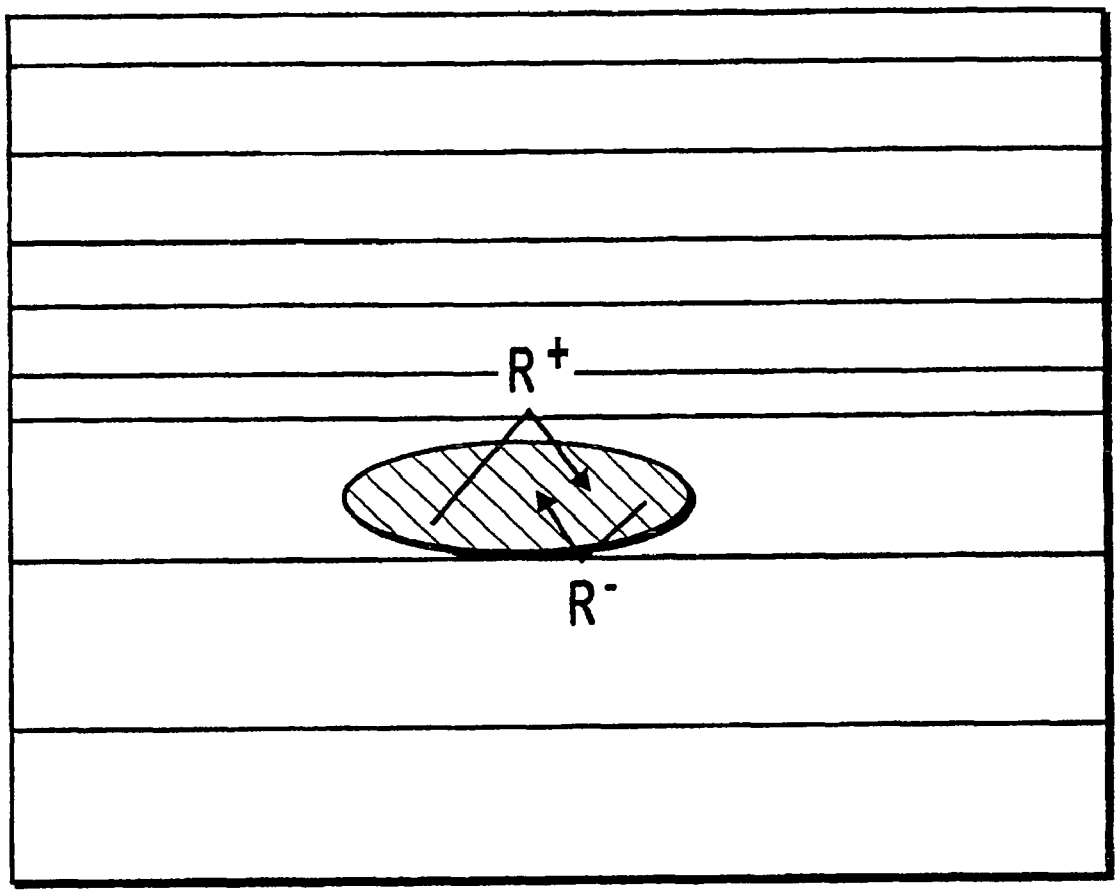
FIG. 27 shows the relavant geometry for the illustrates R reflection coefficients.

FIGS. 1-C and 27 should be kept in mind throughout the following discussion. As in the scalar case, in order to have a single reference position $R^+$ and $R^-$ are both given with respect to the top of layer that contains the scattering point, which is denoted by "sc". That is, $R^+$ represents the reflection coefficient for an upgoing wave at the interface between layer sc and sc−1. FIG. 27 displays the relevant geometry.

In our case the expressions $S^u$ and $S^d$, $S^d$ and $S^u$, and are those derived from the Sommerfeld integral representation of a point source of unit strength, given in Muller. [see also Aki and Richards, 1980]. For example:

$$S^d = e^{iwb_{sc}(z'-z_{sc})} = e^{iwb_{sc}\Delta z'}$$

$$S^u = e^{iwb_{sc}(z'-z_{sc})} = e^{iwb\Delta z'}$$

for the scalar case.

As shown in detail, by Muller, the total contribution of the upward travelling wave is given by $$S^u + R^-R^+S^u + R^-R^+R^-R^+S^u + R^-R^+R^-R^+S^u + \ldots = [1+R^-R^+ + R^-R^+R^-R^+ + R^-R^+R^-R^+R^-R^+ + \ldots] S^u = [1-R^-R^+]^{-1}S^u$$

for the transverse shear wave (SH or horizontal shear wave), and $$S^u + R^-R^+S^u + R^-R^+R^-R^+S^u + R^-R^+R^-R^+S^u + \ldots = [1+R^-R^+ + R^-R^+R^-R^+ + R^-R^+R^-R^+R^-R^+ + \ldots] S^u = [1-R^-R^+]^{-1}S^u$$

for the P-SV matrix case. Note that some care must be exercised in the convergence of the matrix series, however, for practical situations we can omit this detail.

Step c) The process of forming the total field at the response point must be broken up into two cases:

Case 1: the response point is above the scatter point, that is $\Delta z - \Delta z' < 0$ ($\Delta z$ is the distance from the interface above the scattering layer, to the response point, the z axis is positive downward), and Case 2, where the response point is below the scattering point $\Delta z - \Delta z' < 0$.

Furthermore each case consists of an upward travelling, and a travelling wave:

Upward travelling wavefield:

First, in case 1:

$[1-R^-R^+]^{-1}S^u$ and $[1-R^-R^+]^{-1}S^u$ represent the contribution to u.sup.up from the upward travelling part of the source. A similar expression can be formed for the contribution from the downward travelling part of the source, it is $$[1-R^-R^+]^{-1}R^-S^d, \text{ and } [1-R^-R^+]^{-1}R^-S^d$$

Thus, the total upward component of the wave field at the response point is formed from:

$$u^{up} \equiv \begin{pmatrix} (1-R^-R^+)^{-1}(S^u + R^-S^d) \\ (1-r^-r^+)^{-1}(S^u + r^-S^d) \end{pmatrix}$$

Case 2: the response point is below the scatter point, that is $\Delta z - \Delta z' > 0$ The result here is similar, the change occurring in the coefficient of the $S^u$, and $S^u$.

$$u^{up} \equiv \begin{pmatrix} (1-R^-R^+)^{-1}(R^-R^+S^u + R^-S^d) \\ (1-r^-r^+)^{-1}(S^u + r^-S^d) \end{pmatrix}$$

Downward Component of Wavefield

Case 1: A similar expression gives the downward component of the total wave field at the response point r, for case 1:

$$u^{down} \equiv u^d \equiv$$

$$\begin{pmatrix} (1-R^+R^-)^{-1}(R^+R^-S^d) \\ (1-r^+r^-)^{-1}(r^+r^-S^d) \end{pmatrix} + \begin{pmatrix} (1-R^+R^-)^{-1}R^+S^u \\ (1-r^+r^-)^{-1}r^+S^u \end{pmatrix} \text{ or }$$

$$u^{down} \equiv u^d \equiv \begin{pmatrix} (1-R^+R^-)^{-1}(R^+R^-S^d + R^+S^u) \\ (1-r^+r^-)^{-1}(r^+r^-S^d + r^+S^u) \end{pmatrix}$$

Case 2: For case 2, the result is similar, here the response point resides below the scatter point, that is $\Delta z - \Delta z' > 0$ $$u^{down} \equiv u^d \equiv \begin{pmatrix} (1-R^+R^-)^{-1}(S^d + R^+S^u) \\ (1-r^+r^-)^{-1}(r^+r^-S^d + r^+S^u) \end{pmatrix}$$

Step d) The final step in the process is the recombination of the plane waves to obtain the total wavefield (upgoing and downgoing waves) at the response position:

For the scalar case 1 $\Delta z - \Delta z' < 0$, and:

$$G^L(x-x', y-y', z/z') = f^u = f^u,$$

with $$u^{up} = \int J_0(u\omega/r-4)[1-R^-R^+]^{-1}[S^u + R^-S^d]\exp^{i\omega b_{sc}(z-z_{sc})} du$$

$$u^d = \int J_0(u\omega/r-r'])[1-R^-R^+]^{-1}[R^+S^u + R^+R^-S^d]\exp^{-i\omega b_{sc}(z-z_{sc})} du$$

so that $$G^L(x-x', y-y', z/z') = \int J_0(u\omega/r-r'])[1-R^-R^+]^{-1}[S^u + R^-S^d] \{e^{i\omega b_{sc}(z-z_{sc})} + R^+e^{i\omega b_{sc}(z-z_{sc})}\} du$$

While for case 2, $\Delta z - \Delta z' > 0$, similar algebra gives:

$$G^L(x-x', y-y', z/z') = \int J_0(u\omega/r-r'])[1-R^-R^+]^{-1}[R^+S^u + S^d[e^{i\omega b_{sc}(z-z_{sc})} + R^-e^{i\omega b_{sc}(z-z_{sc})}]] du$$

For case 1 this can be rewritten as:

$$G^L(r-r', z/z') + A\int_{u=0}^{\infty} C(u; r-r')$$
$$\{S^u e^{i\omega b_{sc}\Delta z} + R^-S^d e^{i\omega b_{sc}\Delta z} + R^+S^u e^{-i\omega b_{sc}\Delta z} + R^+R^-S^s e^{i\omega b_{sc}\Delta z}\} du$$

where the coefficient function $C(u;r-r')$ is given by:

$$C(u; r-r') = J_0(u\omega|r-r'|)(1-R^-R^+)^{-1}\frac{i\omega u}{b_{sc}}$$

For case 2, $G^L$ can be written as:

$$G^L(x-x', y-y', z/z') = \int J_0(u\omega/r-r'])^{-1}\{R^+R^-S^u e^{i\omega b_{sc}\Delta z} + R^-S^d e^{i\omega b_{sc}\Delta z} + R^+S^u e^{-i\omega b_{sc}\Delta z} + S^d e^{-i\omega b_{sc}\Delta z}\} du$$

Finally, using the definitions for $S^u$ and $S^d$ and recognizing that products such as $S^d e^{i\omega b_{sc}\Delta z}$ can be rewritten as $$S^d e^{i\omega b_{sc}\Delta z} = e^{i\omega b_{sc}\Delta z'} e^{i\omega b_{sc}\Delta z} = e^{i\omega b_{sc}(\Delta z + \Delta z')}$$

the operator $G^L$ turns out (after rearrangement of the above equations) to be the sum of a convolution and a correlation kernel:

$$G^L(r-r', z/z) = G_R(r-r', z+z) + G_v(r-r', z-z').$$

Case I has $(\Delta z - \Delta z') \leq 0$, where $\Delta z = z - z_{sc}$ and $\Delta z' = z' - z_{sc}$ with $z_{sc}$ being the z co-ordinate of the top part of the layer that contains the scatterer. In fact $G_R$ and $G_v$ turn out to be given by the following formulae (they appear to differ from the integrals above because of the rearrangement that leads to the decomposition into convolutional and correlational parts):

$$G_R(r-r', \Delta z/\Delta z') =$$
$$A\int_{u=0}^{\infty} J_0(u\omega|r-r'|)C(u)\{R^+ e^{-i\omega b_{sc}(\Delta z + \Delta z')} R^- e^{i\omega b_{sc}(\Delta z + \Delta z')}\} du$$

$$G_V(r-r', \Delta z/\Delta z') =$$
$$A\int_{u=0}^{\infty} J_0(u\omega|r-r'|)C(u)\{R^+R^- e^{-i\omega b_{sc}(\Delta z + \Delta z')} + e^{i\omega b_{sc}(\Delta z + \Delta z')}\} du$$

where, now:

$$C(u) = (1-R^+R^-)^{-1}b_{sc}^{i\omega b}$$

$R^-$ and $R^+$ are the recursively defined reflectivity coefficients described in Muller's paper, u is the horizontal slowness, $$u \equiv \frac{\sin\theta}{c}$$

Recall that Snell's law guarantees that u will remain constant as a given incident plane wave passes through several layers.

$\omega$ is the frequency $b_{sc}$ is the vertical slowness for the particular layer hosting the scattering potential Case II consists of the case where $(\Delta z - \Delta z') \geqq 0$. The $G_R$ and $G_V$ are now given by the following:

$$G_V(r - r', \Delta z/\Delta z') =$$
$$A \int_{u=0}^{\infty} J_0(u\omega|r - r'|)C(u)\{R^+ R^- e^{-i\omega b_{sc}(\Delta z + \Delta z')} + e^{i\omega b_{sc}(\Delta z + \Delta z')}\} du$$

and $$G_R(r - r', \Delta z/\Delta z') =$$
$$A \int_{u=0}^{\infty} J_0(u\omega|r - r'|)C(u)\{R^- e^{-i\omega b_{sc}(\Delta z + \Delta z')} + R^+ e^{i\omega b_{sc}(\Delta z + \Delta z')}\} du$$

These expressions can be combined into one equation by the judicious use of absolute values. The correlational part of the Green's operator can be transformed into a convolution by a suitable change of variables. The resulting Green's function for imaging inhomogeneities residing within Ambient Layered Media must be quantized by convolving with the sinc (really Jinc) basis functions described below. This is done analytically and the result is given below.

The same process is carried out as detailed above, in order to determine the P-SV total wavefield (the 2 by 2 matrix case), and is not repeated.

The matrix case is handled in exactly the same manner, with allowance for the differing algebra associated with matrices, the preservation of the convolution is preserved for the same reason as shown above in the scalar situation.

On avoiding convergence problems due to the presence of derivatives in the elastic Green's function (i.e. with shear wave motion)

One difficulty with this formulation is the presence of four derivatives acting upon the acoustic free space Green's function in the construction of the dyadic $G^{(LAY)}$. This problem we have overcome (see related code in Appendix E) by the following method:

Given an inhomogeneous distribution of isotropic density $\rho$ and Lame parameters $\lambda$ and $\mu$, imbedded in a homogeneous medium with density $\rho_0$ and Lame parameters $\lambda_0$ and $\mu_0$, the total infinitesimal displacement vector u satisfies the partial differential equation $$\omega^2 \rho u_i + (\pi u_{j,j})_{,i} + [\mu(u_{i,j} + u_{j,i})]_{,j} = 0 \qquad (1)$$

while the incident displacement field $u^i$ satisfies $$\omega^2 \rho u_i^i + (\lambda_0 u_{j,j}^i)_{,i} + [\mu_0(u_{i,j}^i + u_{j,i}^i)]_{,j} = 0 \qquad (2)$$

where $\rho_0$, $\lambda_0$, and $\mu_0$ are the homogeneous parameters of the imbedding medium. Subtracting (2) from (1) and rearranging results in $$u_i^s + \left(\frac{1}{k_{p2}} - \frac{2}{k_{s2}}\right)(u_{j,j}^s)_{,i} + \frac{1}{k_{s2}}\left[(u_{i,j}^s + u_{j,i}^s)\right]_{,j} = -fi \qquad (3)$$

for the scattered displacement field $u^s = u - u^i$. The inhomogeneous term f is given by $$fi = \qquad (4)$$
$$\left(\frac{\rho}{\rho_0} - 1\right)u_i - \left(\frac{1}{k_{p2}} - \frac{2}{k_{s2}}\right)\left\{\left(\frac{\lambda}{\lambda_0} - 1\right)u_{j,j}\right\}_{,i} + \frac{1}{k_{s2}}\left\{\left(\frac{\mu}{\mu_0} - 1\right)(u_{i,j} + u_{j,i})\right\}_{,j}$$

where the respective shear-wave and compression-wave velocities $c_s$ and $c_p$ and corresponding wave numbers $k_s$ and $k_p$ are given by $$c_s^2 = \frac{\mu_0}{\rho_0}; k_s^2 = \frac{\omega^2}{c_s^2}; c_p^2 = \frac{\lambda_0 + 2\mu_0}{\rho_0}; k_p^2 = \frac{\omega^2}{c_{p2}} \qquad (5)$$

for the imbedding medium. Introducing the scattering potentials $$\gamma_\rho = \frac{\rho}{\rho_0} - 1; \gamma\lambda = \left(\frac{1}{k_{p2}} - \frac{2}{k_{s2}}\right)\left(\frac{\lambda}{\lambda_0} - 1\right); \gamma_\mu = \left(\frac{1}{k_{s2}}\right)\left(\frac{\mu}{\mu_0} - 1\right) \qquad (6)$$

gives $$f_i = \gamma_\rho u_i + \{\gamma_\lambda u_{j,j}\}_{,i} + \{\gamma_\mu (u_{i,j} + u_{j,i})\}_{,j} \qquad (7)$$

Solution of (3) by the introduction of the free-space Green's function results $$u_i^s = G_{ij} * f_j = \int f_i(r') G_{ij}(\vec{r} - r') dv' \qquad (8)$$

where * denotes 3-D convolution, v is the support of the inhomogeneity, and the Green's function is given by [Aki and Richards, Quantitative Seismology, Freeman and Co., 1980, herein included as a reference]:

$$G_{ij}(r - r') = k_s^2 g(k_s|r - r'|)\delta_{ij} + \frac{\partial^2}{\partial x_i \partial x_j}\{g(k_s|r - r'|) - g(k_p|r - r'|)\} \qquad (9)$$

where g(kR) is the scalar Helmholtz Green's function $$g(kR) = \frac{e^{ikR}}{4\pi R} \qquad (10)$$

where $e^{-I\omega t}$ time dependence has been assumed. Inserting (7) into (8) and integrating by parts yields the following integral wave equation:

$$u_i^s = G_{ij} * \{\gamma_\rho u_j\} + G_{ij,j} * \{\gamma_\lambda u_{k,k}\} + G_{ij,k} * = \{\gamma_u (u_{j,k} + u_{kj})\} \qquad (11)$$

For now, consider the case where $\gamma_\mu = 0$ and note that:

$$G_{ij,j} = k_s^2 \frac{\partial}{\partial x_i} g(k_s R) + \frac{\partial}{\partial x_i}(\nabla^2 g(k_s R) - \nabla^2 g(k_p R)) \qquad (12)$$

using $$(\nabla^2 + k^2)g(kR) = -\delta(|r - r'|) \qquad (13)$$

reduces (12) to:

$$G_{ij,j} = k_p^2 \frac{\partial}{\partial x_i} g(k_p R) \qquad (14)$$

which will henceforth be denoted $C_i$. We have now arrived at the integral equation:

$$\begin{bmatrix} u_x^i \\ u_y^i \\ u_z^i \end{bmatrix} = \begin{bmatrix} u_x \\ u_y \\ u_z \end{bmatrix} - \begin{bmatrix} G_{xx} & G_{xy} & G_{xz} & C_x \\ G_{yx} & G_{yy} & G_{yz} & C_y \\ G_{zx} & G_{zy} & G_{zz} & C_z \end{bmatrix} * \begin{bmatrix} \gamma_\rho & 0 & 0 & 0 \\ 0 & \gamma_\rho & 0 & 0 \\ 0 & 0 & \gamma_\rho & 0 \\ 0 & 0 & 0 & \gamma_\rho \end{bmatrix} \begin{bmatrix} u_x \\ u_y \\ u_z \\ \nabla \cdot u \end{bmatrix} \quad (15)$$

since $u_{k,k} = \nabla \cdot u$

The integral equation (15) can be solved by application of the 3-D FFT to compute the indicated convolutions, coupled with the biconjugate gradient iteration, or similar conjugate gradient method. [Jacobs, 1981]. One problem with (15) is, however, the need to compute $\nabla \cdot u$ at each iteration. Various options for this include taking finite differences or the differentiation of the basis functions (sinc functions) by FFT. Our experience with the acoustic integral equation in the presence of density inhomogeneity indicates that it is best to avoid numerical differentiation. Instead, the system is augmented as:

$$\begin{bmatrix} u_x^i \\ u_y^i \\ u_z^i \\ \nabla \cdot u^i \end{bmatrix} = \begin{bmatrix} u_x \\ u_y \\ u_z \\ \nabla \cdot u \end{bmatrix} - \begin{bmatrix} G_{xx} & G_{xy} & G_{xz} & C_x \\ G_{xy} & G_{yy} & G_{yz} & C_y \\ G_{zx}0 & G_{zy} & G_{zz} & G_z \\ C_x & C_y & C_z & D \end{bmatrix} * \quad (16)$$

$$\begin{bmatrix} \gamma_\rho & 0 & 0 & 0 \\ 0 & \gamma_\rho & 0 & 0 \\ 0 & 0 & \gamma_\rho & 0 \\ 0 & 0 & 0 & \gamma_\rho \end{bmatrix} \begin{bmatrix} u_x \\ u_y \\ u_z \\ \nabla \cdot u \end{bmatrix}$$

where $$D = C_{XX} + C_{YY} + C_{ZZ} = k_p^2 \nabla^2 g(k_p R) = -k_p^2 \{k_p^2 g(k_i R) + \delta(R)\}. \quad (17)$$

Iterative solution of (16) for the four unknown fields $u_x$, $u_y$, $u_z$, and $\nabla \cdot u$ now involves no numerical differentiation of $u$, since all derivative operators have now been applied analytically to the Green's function. The incident component $\nabla \cdot u^i$ is assumed known. Equation (16) can be written symbolically as $$U^i = (I - G[\gamma]_{diag})U \quad (18)$$

where $U^i$ and $U$ are the augmented 4-vectors in Eq. (16), $[\gamma]_{diag}$ is the diagonal operator composed of $\gamma_\rho$ and $\gamma_\lambda$, and is the 4×4 dyadic Green's function in Eq. (16).

Inclusion of $\gamma_\mu$ Scattering to Give the General Elastic-wave Integral Equations We now give a method for solving integral equations in the general case for the inhomogeneous material properties $\rho$, $\lambda$, and $\mu$.

Because the inclusion of the more complicated term in $\gamma_\mu$ causes the matrix notation used above to require breaking the equations into parts on several lines, we elect for efficiency of space to use the more compact tensor notation. This should cause no difficulty because the translation is clear on comparing the special case of $\gamma_\mu = 0$ in the general tensor equations which follow with the previous matrix notation for this same case.

First we give again (see Eq (11)) the integral equations (which in practice have been discretized by sinc basis functions) for inhomogeneous $\rho$, $\lambda$, and $\mu$. Here * means convolution (the integration operation):

$$u_i^s = G_{ij} * \{\gamma_\rho u_j\} + G_{ij,j} * \{\gamma_\lambda u_{k,k}\} + G_{ij,k} * [\gamma_\mu(u_{j,k} + u_{kj})] \quad (19)$$

We note that the displacement field $u_j$ and its derivatives also $u_{j,k}$ appear. We choose not to compute derivatives of the fields numerically and avoid the associated numerical instability. Instead, we augment the above equation with additional equations to compute the derivatives in a more stable way by solving for them directly. Thus, solving for $(u_{i,1+u1,i})$ directly is more efficient and replaces computation of nine fields with only six. Forming the six unique symmetric-derivative pairs, we obtain an integral equation for these pairs.

$$u_{i,j}^s + u_{l,i}^s = (G_{ij,i} + G_{lj,i}) * [\gamma_\rho u_j] + (G_{ij,kl} + G_{lj,ki}) * [\gamma_\mu(u_{jk} - u_{kj})] + (G_{ij,jl} + G_{lj,ji}) * [\gamma \lambda^u k, k] \quad (20)$$

Note that $$G_{ij,jl} = k_p^2 \frac{\partial^2}{\partial x_i \partial x_l} g(k_p R) \quad (21)$$

We now augment the system Eq. (19) for the three components of $u_i^s$ with the system Eq. (20) which has six pairs of unique component derivatives.

These nine equations can also be placed in a matrix form similar to that of the augmented system given in Eq (16). The augmented system of nine components could be solved for $\gamma_\rho$, $\gamma_\lambda$, and $\gamma_\mu$, assuming knowledge of the fields $u^i$ and derivatives $u_{i,k}$. Since the fields and derivatives are also unknown, we must solve for them simultaneously with $\gamma_\rho$, $\gamma_\lambda$, and $\gamma_\mu$. This is done by adding these constraint equations. These nine equations are composed of the three equations for $u_i$ $$u_i^i = u_i - G_{ij} * (\gamma_\rho u_j) - G_{ij,j} * [\gamma_\lambda u_{k,k}] - G_{ij,k} * [\gamma_\mu(u_{j,k} + u_{kj})] \quad (22)$$

and the six equations for $u_{j,k} + u_{kj}$ $$u_{i,l}^i + u_{l,i}^i 32 (u_{i,l} - u_{l,i}) - (G_{ij,l} + G_{lj,i}) * [\gamma_\rho u_j] - (G_{ij,kl} + G_{lj,kl}) * [\gamma_\mu(u_{jk} + u_{kj})] - (G_{ij,jl} + G_{lj,ji}) * [\gamma_\lambda u_{k,k}] \quad (23)$$

These 9 equations can also be placed in a matrix form similar to that of the augmented system given in Eq (16).

Solving these twelve equations (Eq. (19, 22, 23)) for $(\gamma_\rho, \gamma_\lambda,$ and $\gamma_\mu)$, the fields, and their derivatives is accomplished using the Frechet derivative methods described next. As in Eq. (16) for the $\mu = \mu_0$ case, Eq. (23) can be written symbolically as $$U^i = (I - G[\gamma]_{diag})U \quad (24)$$

where the operators and $[\gamma]_{diag}$ are now 9×9, and the vectors $U$ and $U^i$ consist of the three components of $u$ and its six symmetric derivative sum-pairs.

EXAMPLE 7

Cylindrical Coordinate Methods for Numerical Solution of the SIE

The above examples all use the FFT-BCG algorithm for imaging. This method is one of three methods discussed in this patent. The other two methods are (1) The cylindrical coordinate recursion method (Cylindrical Recursion)

(2) Rectangular recursion of scattering matrix method (Rectangular Recursion for short reference)

We now discuss the cylindrical recursion method:

7.1 Cylindrical Coordinate SIE Formulation and Discretization

We begin with the acoustic scattering integral equation (SIE) for the constant density case:

$$f^i(\rho) = f(\rho) - \frac{k_0^2}{4i} \int\int \gamma(\rho')f(\rho')H_0^{(2)}(k_0|\rho-\rho'|)d^2\rho \quad (1.1)$$

Let each field be expanded in a Fourier series in the angular variable:

$$f(\rho) = \sum_n f_n(\rho)e^{in\phi}$$

Then using Graf's addition theorem:

$$H_0^{(2)}(k_0|\rho-\rho'|) = \begin{cases} \sum_n H_n^{(2)}(k_0\rho)J_n(k_0\rho')e^{in(\phi-\phi')} & \rho > \rho' \\ \sum_n H_n^{(2)}(k_0\rho')J_n(k_0\rho)e^{in(\phi-\phi')} & \rho > \rho' \end{cases} \quad (1.2)$$

results in the cylindrical coordinate form of (1.1):

$$f_n^i(\rho) = f_n(\rho) - \frac{\pi k_0^2}{2i}\int_0^a \left\{\sum_m \gamma_{n-m}(\rho')f_m(\rho')\right\}B_m(k_0\rho)C_m(k_0\rho')\rho'd\rho' \quad (1.3)$$

where the kernel is $$B_m(k_0\rho)C_m(k_0\rho') = \begin{cases} H_n^{(2)}(k_0\rho)J_n(k_0\rho') & \rho > \rho' \\ H_n^{(2)}(k_0\rho')J_n(k_0\rho) & \rho < \rho' \end{cases} \quad (1.4)$$

separably symmetric:

Henceforth assume that $k_0=1$. Discretizing the radial integral by trapezoidal rule using an increment of $\Delta$ results in:

$$f_{l,n} = f_{nl,n} - \left\{h_{l,n}\sum_{l'=l}^{l}(\gamma f)_{l,n,jl,n} + j_{l,n}\sum_{l'=l+1}^{L}(\gamma f)_{l',n}h_{l',n}\right\} \quad (1.5)$$

where $$f_{l,n} = f_n(l\Delta),\ h_{l,n} = \Delta\sqrt{\frac{\pi}{2i}}H_n^{(2)}(l\Delta),\ j_{l,h} = \Delta\sqrt{\frac{\pi}{2i}}J_n(l\Delta) \quad (1.6)$$

and $$(\gamma f)_{l',n} = 1'\sum_m \gamma_{l',n-m}f_{l',m} \quad (1.7)$$

Notice that the extra l' resulting from the $\rho'$ in the integral in (1.3) has been placed in the definition of $(\gamma f)_{l',n}$. Equation (1.5) is the final discrete linear system for the solution of the scattering integral equation in cylindrical coordinates. It can be rewritten as:

$$f_l^i = f_l - \left\{[h_l]\sum_{l'=7}^{l}[jr][\gamma_{1'}^*]f_{l'} + [jl]\sum_{l'=l+1}^{L}[h][\gamma r^*]f_{l'}\right\} \quad (1.8)$$

where the vector components are the Fourier coefficients:

$$f_i = \begin{bmatrix} f_{l,-N} \\ \vdots \\ f_{l,N} \end{bmatrix} \quad (1.9)$$

where, or, equivalently, $$\{f_l\}_n = f_{l,n}, n = -N, \ldots, N$$

where N is the range of the truncated Fourier series (The vectors are length 2N+1). The notation [x] denotes a diagonal matrix formed from the vector elements:

$$[x] = \begin{bmatrix} x_{-N} & 0 & \cdots & \cdots \\ 0 & \ddots & & \\ \vdots & & \ddots & \\ 0 & & & x_N \end{bmatrix} \quad (1.10)$$

and the notation $[\gamma_r^*]$ denotes a convolution (including the l' factor):

$$\{[\gamma_{1'}^*]f_{1'}\}_n = 1'\sum_{m=-N}^{N}\gamma_{1',n-m}f_{1',m}, n = -N \ldots, N. \quad (1.11)$$

Writing (1.8) out in full gives the matrix equation:

$$\begin{bmatrix} f_l^i \\ \vdots \\ f_L^i \end{bmatrix} = A\begin{bmatrix} f_l \\ \vdots \\ f_L \end{bmatrix} \quad (1.12)$$

where $$A = \begin{bmatrix} I & 0 & \cdots & \cdots & 0 \\ 0 & \ddots & & & \vdots \\ \vdots & & \ddots & & \vdots \\ \vdots & & & \ddots & 0 \\ 0 & \cdots & \cdots & 0 & I \end{bmatrix} - \quad (1.13)$$

$$\begin{bmatrix} [j_l][h_1] & [j_1][h_2] & \cdots & [j_l][h_L] \\ [h_l][j_1] & & & \vdots \\ \vdots & & \ddots & \vdots \\ [h_L][j_1] & [h_L][j_2] & \cdots & [j_L][h_L] \end{bmatrix} \cdot \begin{bmatrix} [\gamma_l] & 0 & \cdots & 0 \\ 0 & & & \vdots \\ \vdots & & & 0 \\ 0 & \cdots & 0 & [\gamma_L] \end{bmatrix}$$

Notice that the kernel is composed of a L×L block matrix with 2N+1×2N+1 diagonal matrix components and that the L×L block matrix is symmetric-separable, i.e.:

$$L_{nm} = \begin{cases} [j_n][h_m], & n \leq m \\ [h_n][j_m], & n > m \end{cases} \quad (1.14)$$

where $L_{nm}$ is one of the L×L component matrices.

For reference in the next section, we make the definitions:

$$s_l \equiv \sum_{l'}^{L} [h_{l'}][\gamma_{l'}^*]f_{l'} \quad (1.15)$$

$$p_l \equiv \sum_{l'=1}^{l-1} [h_{l'}][\gamma_{l'}^*]f_{l'} \quad (1.16)$$

7.2 Recursive Solution of the Cylindrical Coordinate SIE

The recursion for the 2-D cylindrical equation is:
Initialize:

$$p_L = 0 \quad (2.1)$$

$$\{s_L\}_n = f_{L,n}^s / h_{L,n}$$

For l=L, ..., 1

$$s_{l-1} = s_l - [j_l][\gamma_l^*]\{[h_l]s_l + [j_l]p_l\}$$

$$p_{l-1} = p_l - [h_l][\gamma_l]\{[h_l]s_l + [j_l]p_l\}$$

Next l.

Thus far, we have assumed that the number of angular coefficients is the same for each radius l. In fact, the number of angular coefficients should decrease as l decreases. We find that for $\Delta = \lambda/4$, an accurate interpolation is achieved with $N_l = 2l-1$, $n = -N_l, \ldots, N_l$ Fourier coefficients. To introduce this modification, we must slightly define the operators as:

$$\{[j_l]x\}_n = \begin{cases} jl_{,n}x_n, & |n| \leq N_l \\ 0, & |n| > N_l \end{cases} \quad (2.2)$$

$$\{[\gamma_l^*]x\}_n = \begin{cases} l\sum_{m=N_l}^{N_l} & |n| \leq N_l \\ 0, & |n| > N_l \end{cases} \quad (2.3)$$

where the vector operated on is always length N where N is now the maximum number of Fourier coefficients, $N=N_L$. The total field at each layer, l, is given by:

$$f_{l,n} = \begin{cases} h_{l,n}s_{l,n} + j_{l,n}p_{l,n} + f_{l,n}^i & |n| \leq N_l \\ 0, & |n| > N_l \end{cases} \quad (2.4)$$

In order to eliminate the need to know the starting values, $s_L$, we note that at each iteration, $s_l$ and $p_l$ are linear functions of $s_L$:

$$s_l = A_l s_L + b_l, p_l = C_l s_L + d_l \quad (2.5)$$

where the matrices $A_1$, $C_1$ (dimension 2N+1×2N+1) and the vectors $b_1$, $d_1$ (dimension 2N+1) have the initial values:

$$A_L = I, C_L = 0, b_1 = 0, d_1 = 0 \quad (2.6)$$

Using (2.5) and (2.6) in (1.1) and equating common terms leads a matrix and a vector recursion:
Initialize:

$$A_L = I, C_L = 0 \ b_L = 0, d_L = 0 \quad (2.7)$$

for l=L, ..., 1

$$A_{l-1} = A_l - [j_l][\gamma_l^*]\{[h_l]A_l + [j_l]C_l\}$$

$$b_{l-1} = b_l - [j_l][\gamma_l^*]\{[h_l]b_l + [j_l]d_l + f_l^i\}$$

$$C_{l-1} = C_l - [h_l][\gamma_l^*]\{[h_l]A_l + [j_l]C_l\}$$

$$d_{l-1} = d_l - [h_l][\gamma_l^*]\{[h_l]b_l + [j_l]d_l + f_l^i\}$$

Then using the fact that $s_L = 0$ leads to the solution:

$$A_o s_L + b_o = 0, s_L = -A_o^{-1} b_o, f_{L,n}^s = s_{L,n}/h_{L,n} \quad (2.8)$$

for the scattered field at the outer boundary. Iteration (1.1) with (1.4) can then be used to evaluate the total field internal to the object.

Notice that the LHS matrix recursion in (2.7) is independent of the incident field. Once it is used to compute A.sub.0, the RHS vector recursion can be done for any number of incident fields. Concurrent solution for any number of incident fields can be obtained by replacing the RHS vector recursion with the matrix recursion:

$$B_L = 0, D_L = 0 \quad (2.9)$$

$$B_{l-1} = B_l - [j_l][\gamma_l^*]\{[h_l]B_l + [j_l]D_l + F_l^i\}$$

$$D_{l-1} = D_l + [h_l][\gamma_l^*]\{[h_l]B_l + [j_l]D_l + F_l^i\}$$

where the matrices $B_l$, $D_{ll}$ are 2N+1×$N_v$ where $N_v$ is the number of views and the matrix of incident fields, $F_l^i$ is given by:

$$F_l^i = \begin{bmatrix} f_{l,-N}^{i1} & \cdots & f_{l,-N}^{iN_v} \\ \vdots & & \vdots \\ f_{l,N}^{i1} & \cdots & f_{l,N}^{i,N_v} \end{bmatrix} \quad (2.10)$$

where the superscript after i is the view number (note that although the incident matrix is written as 2N+1×$N_v$, the entries are zero for the row index $N_l < |n| \leq N$). A more compact recursion can be obtained by concatenating the two recursions to give:

$$G_L = [A_L, B_L] = [I, 0], H_L = [C_L, D_L] = [0, 0] \quad (2.11)$$

For l=L, ..., 1

$$G_{l-1} = G_l - [j_l][\gamma_l^*]\{[h_l]A_l + [j_l]C_l + [0, F_l^i]\}$$

$$H_{l-1} = H_l + [h_l][\gamma_l^*]\{[h_l]A_l + [j_l]C_l + [0, F_l^i]\}$$

where the matrices $G_l$, $H_l$ are 2N+1×2N+1+$N_v$ and in the notation [A,B] the first matrix is 2N+1×2N+1 and the second is 2N+1×$N_v$. Then $G_0 = [A_0, B_0]$ and the solution for all views is given by:

$$F_L^s = \begin{bmatrix} f_{L,-N}^{s1} & \cdots & f_{L,-N}^{sN_v} \\ \vdots & & \vdots \\ f_{L,N}^{s1} & \cdots & f_{L,N}^{s,N_v} \end{bmatrix} = [h_L]A_0^{-1}B_0 \quad (2.12)$$

A slightly modified recursion can be shown to yield the scattering matrix of the object. Recall that the total field is given by:

$$f_l = [h_l]s_l + [j_l]p_l + f^i \quad (2.13)$$

Any externally generated incident field can be expanded in a bessel series which implies that there exists a sequence, $g_{-N}^i, \ldots, g_N^i$ such that:

$$f^i(\rho, \phi) = \Delta \sqrt{\frac{\pi}{2i}} \sum_n g_n^i J_n(\rho) e^{in\phi} \quad (2.14)$$

(recall that we are assuming that $k_0=1$) which means that $$f_l^i = [j_l]g^i \quad (2.15)$$

Redefining $p_l \to p_l + g^i$ then gives $f_l = [h_l]s_l + [j_l]p_l$ and leads easily to the iteration:

$$G_L = [I,O], H_L = [0,I] \quad (2.16)$$

For $l = L, \ldots, 1$ $$G_{l-1} = G_l - [j_l][\gamma_l^*]\{[h_l]A_l + [j_l]C_l\}$$

$$H_{l-1} = H_l + [h_l][\gamma_l^*]\{[h_l]A_l + [j_l]C_l\}$$

where the matrices are now $2N+1 \times 2(2N+1)$. The last iterate $G_0 = [A_0, B_0]$ yields the scattering matrix:

$$S(\gamma) = A_0^{-1}B_0 \quad (2.17)$$

for the body $\gamma$ which relates the incident field coefficients to the scattering coefficients: $g^s = Sg^i$ where $$f^s(\rho, \phi) = \Delta \sqrt{\frac{\pi}{2i}} \sum_n g_n^s H_0^{(2)}(\rho) e^{in\phi} \quad (2.18)$$

for all incident field coefficient vectors, $g^i$. Notice that in the previous notation:

$$g_n^i = f_{L,n}^i / j_{L,n}, g_n^s = f_{L,n}^s / h_{L,n} \quad (2.19)$$

7.3 Computational Formulas for the Jacobian and its Adjoint

In order to apply the Gauss-Newton iteration to the solution of the imaging problem we must first derive recursive formulas for the application of the Jacobian and its adjoint. The Jacobian of the scattering coefficient vector, s.sub.L, operating on a perturbation in $\gamma$ is given by:

$$J\delta\gamma = \sum_{l'=1}^{L} \sum_{n'=N_l}^{N_{l'}} \delta\gamma_{1',n} \frac{\partial}{\partial \gamma_{1',n'}} s_L \quad (3.1)$$

From (2.8) we get:

$$s_L' = -A_0^{-1}(b_0' + A_0' s_L) \quad (3.2)$$

where the prime denotes differentiation followed by summation over the elements of $\delta\gamma$ $$s_L' = J\delta\gamma = \sum_{l'=1}^{L} \sum_{n'=-N_l}^{N_l} \delta\gamma_{1',n'} \frac{\partial}{\partial \gamma_{1',n}} s_L \quad (3.3a)$$

$$b_0' = \sum_{l'=1}^{L} \sum_{n'=N_l}^{N_l} \delta\gamma_{1',n'} \frac{\partial}{\partial \gamma_{1',n}} b_0 \quad (3.3b)$$

$$A_0' = \sum_{l'=1}^{L} \sum_{n'=-N_l}^{N_l} \delta\gamma_{1',n'} \frac{\partial}{\partial \gamma_{1',n}} A_0 \quad (3.3c)$$

Equation (3.2) provides the formula for computing J.delta.$\gamma$ is recursive formulas for $A'_0$ and $b'$ can be found. Define the notation:

$$A_l' = \sum_{l'=l+1}^{L} \sum_{n'=-N_l}^{N_l} \delta\gamma_{1',n'} \frac{\partial}{\partial \gamma_{1',n}} A_l \quad (3.4a)$$

$$C_l' = \sum_{l'=l+1}^{L} \sum_{n'=-N_l}^{N_l} \delta\gamma_{1',n'} \frac{\partial}{\partial \gamma_{1',n}} C_l \quad (3.4b)$$

(note the lower limit of the 1' summation). Then using the LHS recursion in (2.7), it is simple to show that:

$$A_{l-1}' = A_l' - [j_l]\{[\gamma_l^*]\{[h_l]A_l' + [j_l]C_l'\} + [\delta\gamma_l^*]\{[h_l]A_l + [j_l]C_l\}\} \quad (3.5a)$$

$$C_{l-1}' = C_l' + [h_l]\{[\gamma_l^*]\{[h_l]A_l' + [j_l]C_l'\} + [\delta\gamma_l^*]\{[h_l]A_l + [j_l]C_l\}\} \quad (3.5b)$$

A further reduction in computational requirements can be achieved by noting from (3.2) that we do not need $A'_0$ but rather $A'_0 S_L$ where $S_L$ is the matrix whose columns are the $s_L$s for each view. The matrix $A'_0$ is $2N+1 \times 2N+1$ while the matrix $A'_0 S_L$ is $2N+1 \times N_v$. Thus define:

$$A_l'^s = A_l'S_L, C_l'^s = C_l'S_L, A_l^s = A_lS_L, C_l^s \ne C_l S_L \quad (3.6)$$

Then we get the recursion:

$$A_L^s = A_L S_L = IS_L = S_L, C_L^s = 0, A_l'^s = 0 C_L'^s = 0 \quad (3.7a)$$

For $l = L, \ldots, 1$ $$A_{l-1}'^s = A_l'^s - [j_l]\{[\gamma_l^*]\{[h_l]A_l'^s + [j_l]C_l'^s\} + [\delta\gamma_l]\{[h_l]A_l^s + [j_l]C_l^s\}\} \quad (3.7b)$$

$$C_{l-1}'^s = C_l'^s + [h_l]\{[\gamma_l^*]\{[h_l]A_l'^s + [j_l]C_l'^s\} + [\delta\gamma_l^*]\{[h_l]A_l^s + [j_l]C_l^s\}\} \quad (3.7c)$$

$$A_{l-1}'^s = A_l^s - [j_l][\gamma_l^*]\{[h_l]A_l^s + [j_l]C_l^s\} \quad (3.7d)$$

$$C_{l-1}^s = C_l^s + [h_l][\gamma_l^*]\{[h_l]A_l^s + [j_l]C_l^s\} \quad (3.7e)$$

Similarly, for the b's and d's we get the recursion:

$$B_L = 0, D_L = 0, B_L' = 0, D_L' = 0 \quad (3.8a)$$

For $L = L, \ldots, 1$ $$B_{l-1}' = B_l' - [j_l]\{[\gamma_l^*]\{[h_l]B_l + [j_l]D_l'\} + [\delta\gamma_l^*]\{[h_l]B_l + [j_l]D_l + F_l^i\}\} \quad (3.8b)$$

$$D_{l-1}' = D_l' + [h_l]\{[\gamma_l^*]\{[h_l]B_l' + [j_l]D_l'\} + [\delta\gamma_l^*]\{[h_l]B_l + [j_l]D_l + F_l^i\}\} \quad (3.8c)$$

$$B_{l-1} = B_0 - [j_l][\gamma_l^*]\{[h_l]B_l + [j_l]D_l + F_l^i\} \quad (3.8d)$$

$$D_{l-1} = D_l + [h_l][\gamma_l^*]\{[h_l]B_l + [j_l]D_l + F_l^i\} \quad (3.8e)$$

where the matrices are all $2N+1 \times N_v$. The final Jacobian is then:

$$S'_L = -A_0^{-1}(B'_0 + A'^s_0) \quad (3.9)$$

where the columns of $S'_L$ are the vectors $J_n \delta\gamma$ for each view, $n=1, \ldots, N_v$.

We can of course concatenate these two recursions to give:

$$G_L = [S_L, 0], H_L = [0,0], G'^s_L = [0,0], H'_L = [0,0] \quad (3.10a)$$

For $l = L, \ldots, 1$ $$G'_{l-1} = G'_l - [j_l]\{[\gamma_l^*]\{[h_l]G'_l + [j_l]H'_l\} + [\delta\gamma_l^*]\{[h_l]G_l + [j_l]H_l + [0,F_l^i]\}\} \quad (3.10b)$$

$$H'_{l-1} = H'_l + [h_l]\{[\gamma_l^*]\{[g_l]G'_l + [j_l]H'_l\} + [\delta\gamma_l^*]\{[h_l]G_l + [j_l]H_l + [0,F_l^i]\}\} \quad (3.10c)$$

$$G_{l-1} = G_l - [j_l][\gamma_l^*]\{[g_l]G_l + [j_l]H_l + [0,F_l^i]\} \quad (3.10d)$$

$$H_{l-1} = H_l + [h_l][\gamma_l^*]\{[h_l]G_l + [j_l]H_l + [0,F_l^i]\} \quad (3.10e)$$

where, at the last iterate, $G'_0 = [A'^s_0, B'_0]$. The matrices (G's and H's) in this recursion are all $2N+1 \times 2N_v$. This is the form of the Jacobian recursion used in the imaging programs.

EXAMPLE 8

Rectangular Scattering Matrix Recursion

This section describes a new recursive algorithm the used scattering matrices for rectangular subregions. The idea for this approach is an extension and generalization of the cylindrical coordinate recursion method discussed in the previous section. The computational complexity is even further reduced over CCR. The CCR algorithm derives from the addition theorem for the Green's function expressed in cylindrical coordinates. The new approach generalizes this by using Green's theorem to construct propagation operators (a kind of addition theorem analogue) for arbitrarily shaped, closed regions. In the following, it is applied to the special case of rectangular subregions, although any disjoint set of subregions could be used.

Figure 16:
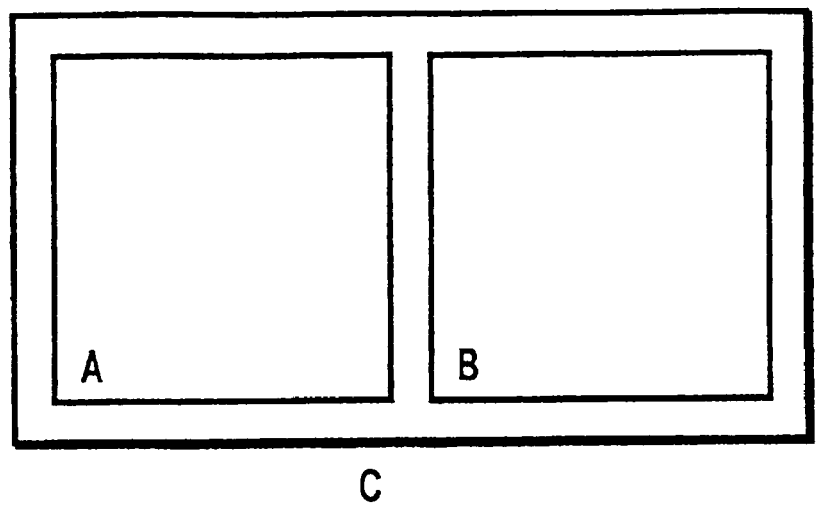
FIG. 16 illustrates a rectangular scattering matrix according to the present invention.
Figure 17:
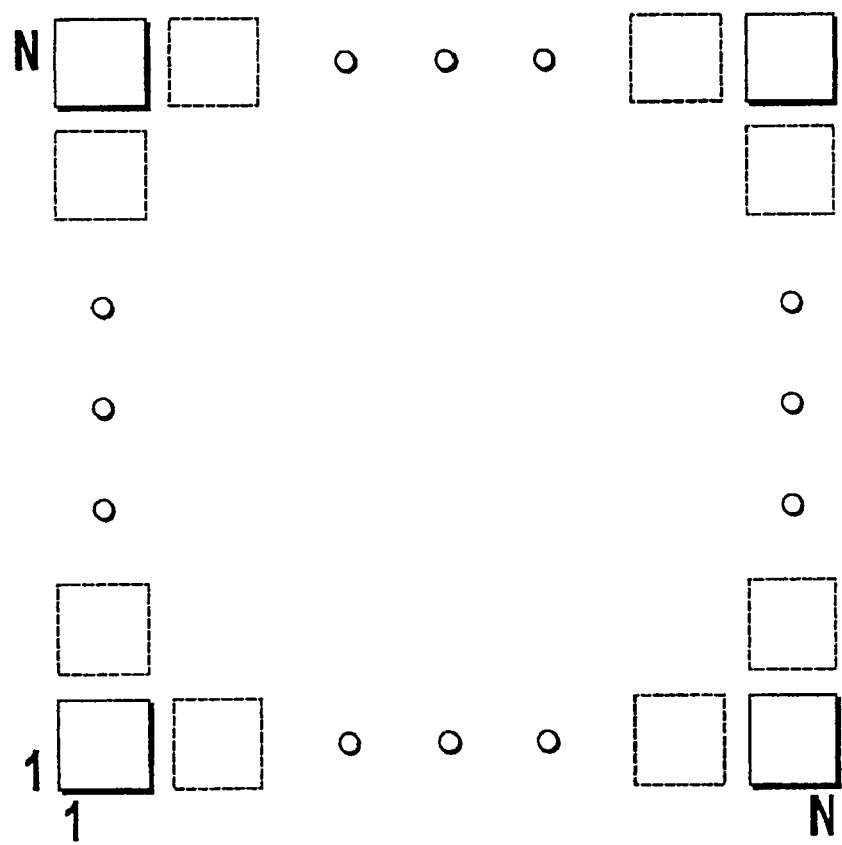
FIG. 17 illustrates a N-by-N scattering region according to the present invention.

Consider two rectangular subregions A and B of $R.^2$ as shown in FIG. 16 Although the regions are drawn as disjoint, assume that they touch at the center of the FIGURE Let C denote the external boundary of the union of A and B. Define the scattering operator, $S_A$, of region A as the operator that gives the outward moving scattered field on the boundary A, given the inward moving field, due to external sources, evaluated on the boundary A. Similarly, define the scattering matrix for boundary B. The goal is to find the scattering matrix for boundary C, given $S_A$ and $S_B$—the scattering matrices for A and B.

Let the incident field due to sources external to boundary C, evaluated on boundary A be denoted $f_A^i$ and similarly define $f_B^i$. For the total problem (A and B both containing scatterers) there exists a net, inward moving field at boundary A. Denote this field $f_A^{in}$ and similarly define $f_B^{in}$. total field leaving boundary $f_A^{out} = S_A f_A^{in}$. Knowledge of the radiated field on a closed boundary due to internal sources allows the field external to the boundary to be computed at any point. Let the operator that maps $f_A^{out}$ onto the boundary B be denoted $T_{BA}$ (rectangular translation operator from A to B). Similarly denote the operator mapping $f_B^{out}$ to boundary A be denoted $T_{AB}$.

The total, inward moving field at boundary A has two parts—that due to the incident field external to C and that due to sources internal to boundary B. From the forgoing definitions, it should be obvious that the inward moving fields satisfy:

$$f_A^{in} = F_A^i + T_{AB} S_B f_B^{in} \quad (1a)$$

$$f_B^{in} = F_B^i + T_{BA} S_A f_A^{in} \quad (1b)$$

Solving for the total inward moving fields gives:

$$\begin{bmatrix} f_A^{in} \\ f_B^{in} \end{bmatrix} = \begin{bmatrix} I & -T_{AB}S_B \\ -T_{BA}S_A & I \end{bmatrix}^{-1} \begin{bmatrix} f_A^i \\ f_B^i \end{bmatrix} \quad (2)$$

The total scattered field at boundary A has two components—one from inside A and one from inside B. It should be obvious that the total scattered fields at boundaries, A and B are given by:

$$f_A^s = S_A f_A^{in} + T_{AB} S_B f_B^{in} \quad (3a)$$

$$f_B^s = T_{BA} S_A f_A^{in} + S_B f_B^{in} \text{ or} \quad (3b)$$

$$\begin{bmatrix} f_A^s \\ f_B^s \end{bmatrix} = \begin{bmatrix} S_A & T_{AB}S_B \\ T_{BA}S_A & S_B \end{bmatrix} \begin{bmatrix} f_A^{in} \\ f_B^{in} \end{bmatrix} \quad (4)$$

Combining (2) and (4) gives:

$$\begin{bmatrix} f_A^s \\ f_B^s \end{bmatrix} = \begin{bmatrix} S_A & T_{AB}S_B \\ T_{BA}S_A & S_B \end{bmatrix} \begin{bmatrix} I & -T_{AB}S_B \\ -T_{BA}S_A & I \end{bmatrix}^{-1} \begin{bmatrix} f_A^i \\ f_B^i \end{bmatrix} \quad (5)$$

Assuming that the scattering operators are invertible, then we have the equivalent form:

$$\begin{bmatrix} f_A^s \\ f_B^s \end{bmatrix} = \begin{bmatrix} I & T_{AB} \\ T_{BA} & I \end{bmatrix} \begin{bmatrix} S_A^{-1} & -T_{AB} \\ -T_{BA} & S_B^{-1} \end{bmatrix}^{-1} \begin{bmatrix} f_A^i \\ f_B^i \end{bmatrix} \quad (6)$$

The scattered field on the boundary C can be obtained from $f_A^s$ and $f_B^s$ by simple truncation (and possible re-ordering depending on how the boundaries are parameterized). Let the operator that does this be denoted:

$$f_C^s = \begin{bmatrix} C_A & C_B \end{bmatrix} \begin{bmatrix} f_A^s \\ f_B^s \end{bmatrix} \quad (7)$$

Let the incident field on boundary C due to external sources be denoted $f_C^i$. There exist operators $D_A$ and $D_B$ that operate on $f_C^i$ to give $f_A^i$ and $f_B^i$ (similar to the external translation operators $T_{AB}$ and $T_{BA}$). Thus:

$$f_C^s = \begin{bmatrix} C_A & C_B \end{bmatrix} \begin{bmatrix} I & T_{AB} \\ T_{BA} & I \end{bmatrix} \begin{bmatrix} S_A^{-1} & -T_{AB} \\ -T_{BA} & S_B^{-1} \end{bmatrix}^{-1} \begin{bmatrix} D_A \\ D_B \end{bmatrix} f_C^i \quad (8)$$

from which we see that the scattering matrix for boundary C is given by:

$$S_C = \begin{bmatrix} C_A & C_B \end{bmatrix} \begin{bmatrix} I & T_{AB} \\ T_{BA} & I \end{bmatrix} \begin{bmatrix} S_A^{-1} & -T_{AB} \\ -T_{BA} & S_B^{-1} \end{bmatrix}^{-1} \begin{bmatrix} D_A \\ D_B \end{bmatrix} \quad (9)$$

Equation (9) then gives the core computation for our rectangular scattering matrix recursion algorithm. Technical details concerning the existence and discrete construction of the translation and other needed operators has been omitted in this write-up. We have, however written working first-cut programs that perform (9).

An $O(N^3)$ Algorithm for Computing all Scattering Views Based on Rectangular Scattering Matrix Recursion Consider a region containing scattering material covered by an N×N array of rectangular sub regions as shown in FIG. 16.

Again, although drawn as disjoint, assume that the subregions touch. Assume that the scattering matrix for each subregion is known (for example, if each subregion is only $\lambda/2$ on edge, the calculation of S is trivial given the material enclosed). Now coalesce 2×2 sets of these scattering matrices into larger scattering matrices (this coalesce of 4 subregions into one is similar to the algorithm defined above for coalescing two subregions). There are N/2×N/2 such 2×2 blocks to coalesce. When done, we have scattering matrices for the set of larger subregions shown in FIG. 18.

This process is continued until, at the final stage, the scattering matrix for the total region is computed. Note that the physical parameters of the scattering media (speed of sound, absorption, etc.) are used only in the first stage (computation of the N×N array of scattering matrices).

Assuming that N is a power of two, the algorithm will terminate after $\log_2(N)$ such stages with the scattering matrix for the whole region. A careful accounting of the computation required reveals that the total computation is $O(N^3)$. The end resulting scattering matrix then allows fast calculation of the scattered field anywhere external to the total region for any incident field (angle of view).

Although derived assuming that N is a power of 2, the algorithm can be generalized by including 3×3 (or any other sized) coalescing at a stage, allowing thereby algorithms for any N (preferably N should have only small, say 2,3,5, prime factors). Also, there is no reason that the starting array of subregions cannot be N×M (by using more general nxm coalescing at some stages).

In addition, the existence of layering can be included. If layering occurs above and below the total region so that the total inhomogeneity resides in a single layer, then the algorithm proceeds as before. Once the total region scattering matrix has been obtained, its interaction with the external layering can be computed. If inhomogeneous layer boundaries lie along horizontal borders between row of subscatterers, then the translation matrices can be modified when coalescing across such boundaries, properly including the layer effects. This is an advantage over our present layered Green's function algorithms which require that the inhomogeneity lie entirely within a single layer (This can be fixed in our present algorithms but at the expense of increased computation).

The $O(N^3)$ computation of this approach is superior to the $O(N^4 \log_2(N))$ computation of our original FFT-BCG approach and our present recursion based on cylindrical coordinates which is O $O(N^3 \log_2(N))$.

EXAMPLE 9

Modeling System Transfer Function Including Driving Voltage, Transmitting Transducers Receiving Transducers, Preamplifiers, Analog to Digital Converter etc.

Let the transfer function of the transmitting waveform generator, power amplifier, transmitting multiplexer, transmitting transducer, ocean/sediment, receiving transducers, preamplifiers, differential amplifier, differential waveform generator, and analog to digital converter be, respectively, $T_{TWG}$, $T_{PA}$, $T_{TM}$, $T_{TT}$, $T_{O/S}$, $T_{RT}$, $T_{RM}$, $T_{DA}$, $T_{DWG}$, and $T_{DAC}$. These separate transfer function can be identified with the system hardware. Then the total transfer function is:

$$T_{total} = T_{DAC}(T_{DA1} T_{RM} T_{RT} T_{O/S} T_{TT} T_{TM} T_{PA} T_{TWG} - T_{DA2} T_{DWG})$$

Note that the term $T_{DA2} T_{DWG}$ is subtracted in order to remove direct path energy and to remove reverberations in the transducers and the platform; this subtraction effectively increases the analog to digital converter dynamic range. The signal in the differential waveform generator is programmed to produce a net zero signal output from the analog to digital converter for the case of no sediment present.

Recall that the equation for the scattered field $f^{(sc)}$ (from the sediment) at a transducer (not the output voltage) at a given temporal frequency is given in terms of the transducer-to-sediment Green's function D, the sediment's acoustic properties γ and the internal field in the sediment f by $f^{(sc)} = D\gamma f$ The field (at a given temporal frequency) within the sediment itself f is given in terms of the incident field $f^{(inc)}$, the sediment's acoustic properties γ, and the sediment-to-sediment Green's function C by $$f^{(inc)} = (I - C\gamma)f.$$

On combining these two equations we eliminate the internal field and find the scattered field in terms of the incinet field and the sediment properties $$f^{(sc)} = D\gamma(I - C\gamma)^{-1} f^{(inc)}$$

These equations involving C and D are true for both the free space Green's function ["Nonperturbative Diffraction Tomography Via Gauss-Newton Iteration Applied to the Scattering Integral Equation, Borup, D. T. et al., Ultrasonic Imaging] and our newly developed layered Green's functions [Johnson, S. A., D. T. Borup, M J. Berggren, Wiskin, J. W., and R. S. Eidens, 1992, "Modelling of inverse scattering and other tomographic algorithms in conjunction with wide bandwidth acoustic transducer arrays for towed or autonomous sub-bottom imaging systems," Proc. of Mastering the Oceans through Technology (Oceans 92), 1992, pp 294-299.]. We now combine the scattering equations with the transfer functions. First, identify $f^{(sc)}$ with $T_{O/S} T_{TT} T_{TM} T_{PA} T_{TWG}$ and $f^{(inc)}$ with $T_{TT} T_{TM} T_{PA} T_{TWG}$. Next we note that measuring $f^{(inc)}$ is a direct way of finding the product $T_{TT} T_{TM} T_{PA} T_{TWG}$. We also note that $T_{total}$ can be written as $$T_{total}(\gamma, T_{TWG}) = T_{DAC}(T_{DA1} T_{RM} T_{RT} D\gamma(I - C\gamma)^{-1} T_{TT} T_{TM} T_{PA} T_{TWG} - T_{DA2} T_{DWG}).$$

Then $T_{total}(\gamma, T_{TWG})$ is a nonlinear operator that transforms $(\gamma, T_{TWG})$ into recorded signals $T_{total\text{-}measured}$. Thus, for a given set of $T_{total\text{-}measured}$ measurements and for a given $T_{TWG}$, we may in principal find γ by a nonlinear inverse operator $$\gamma = T_{total}^{-1}(T_{total\text{-}measured}(\gamma, T_{TWG}))$$

Since the exact form of Tiotal $(\gamma, T_{TWG})$ is not known, we find γ by a Gauss-Newton iteration method. This requires that the Jacobian of $T_{total}(\gamma, T_{TWG})$ be computed. The Jacobian is readily computed in closed form [Borup, 1992] and is given by $$J(\gamma) = -\partial T_{total}(\gamma^{(n)}, T_{TWG})/\partial j(\gamma).$$

Then the Gauss-Newton iteration for computing γ is given by: (1) set n=1, estimate a value for $\gamma^{(n)}$; (2) compute $J(\gamma^{(n)})$; (3) solve $$J^T(\gamma^{(n)})J(\gamma^{(n)})\delta\gamma^{(n)} = -J^T(\gamma^{(n)})(\gamma^{(n)})[T_{total\text{-}measured} - T_{total}(\gamma^{(n)}, T_{TWG})]$$

for $\delta\gamma^{(n)}$; (4) update $\gamma^{(n)}$ by the formula $\gamma^{(n+1)} = \gamma^{(n)} + \delta\gamma^{(n)}$; (5) if $$|T_{total\text{-}measured} - T_{total}(\gamma^{(n)}, T_{TWG})| < \epsilon$$

then set $\gamma = \gamma^{(n+1)}$ and quite, else go to step 2.

The extra dynamic range provided by the differential waveform generator/analog to digital converter circuit raises questions as to the optimal setup procedure (e.g. how many bits to span the noise present with no signal). We have modeled the signal to noise ratio that can be achieved by a beamformer which delays and sums multiple channel signals, each channel being such a circuit. We find as a rule of thumb, that the lowest order one or two bits should span either the noise or the signal, depending which ever is smaller (i.e., for signal to noise ratios greater than unity the noise should be spanned, but for signal to noise ratios less than unity the signal should be spanned). Upon using commercial 16 or 18 bit analog to digital converters this method may well extend their range to 20 bits or more.

2. Model Electrical Crosstalk, Acoustic Crosstalk

Electrical cross talk can be removed by use of knowledge of the cross coupling matrix M. Let $V_n^{(true)}$ be true electrical signal at transducer n and let $Vm^{(meas)}$ be the measured signal at transducer m. Then $V_n^{(meas)} = M_{nm} V_m^{(true)}$. We observe for small cross talk that matrix M has the form $M = D_2(I + \epsilon)D_1$, where I is the identity matrix, $D_1$ and $D_2$ are diagonal matrices and $\epsilon$ is the differential cross talk matrix whose elements are small in value. We seek $V_n^{(true)} = M^{-1}V_n^{(meas)}$. By the binomial theorem $(I+\epsilon)^{-1} \approx (I-\epsilon)$. Thus, $M^{-1} \approx D_1^{-1}(I-\epsilon)D_2^{-1}$. Once $D_1$, $D_2$, and M are measured the problem of removing cross talk is quite inexpensive numerically (even if $\epsilon$ is not small the exact inverse $M^{-1}$ can be computed once and stored). If the matrix M turns out to be noninvertible (as can be the case for large magnitude coupling) then we can alternatively concatenate M onto the inverse scattering equation to give:

$$v_{\omega\phi}^{(meas)} = M_\omega P_\omega G_\omega [f_{107\,\phi}]\gamma$$

to which the inverse scattering algorithm can be directly applied.

We believe that cross talk can be removed by good fabrication techniques including careful shielding. Nevertheless, the above numerical method can be used if necessary.

Acoustic cross talk can be removed by several methods: (1) acoustic baffling of each transducers; (2) calibration of individual (isolated) transducers, computing the acoustic coupling in the array from wave equations methods, then inverting the model by a cross talk matrix as above; (3) direct measurement of the coupling in a finished array to find the cross talk matrix and then inverting as shown above.

A more difficult type of cross talk to remove is the direct mechanical coupling between transducers. This problem will be attacked by using vibration damping techniques in mounting each transducer on the frame. We believe that such damping methods will eliminate direct mechanical coupling. As a backup we note that modeling of the coupled system are theoretically possible and has been successfully accomplished by the university's AIM Lab for circular mounting geometries (by derivation of a new "total system Green's function" for the imaging system that that includes cross coupling between elements).

EXAMPLE 10

Inclusion of Transducer Coupling

In the event that significant coupling exists between the object to be imaged and the transducers (and/or coupling between transducers is not negligible), a computationally efficient means of incorporating this coupling into the inverse scattering algorithm is needed. Equivalently, the transducers must be included as part of the scattering problem This section details a computational algorithm for achieving this incorporation.

Figure 24:
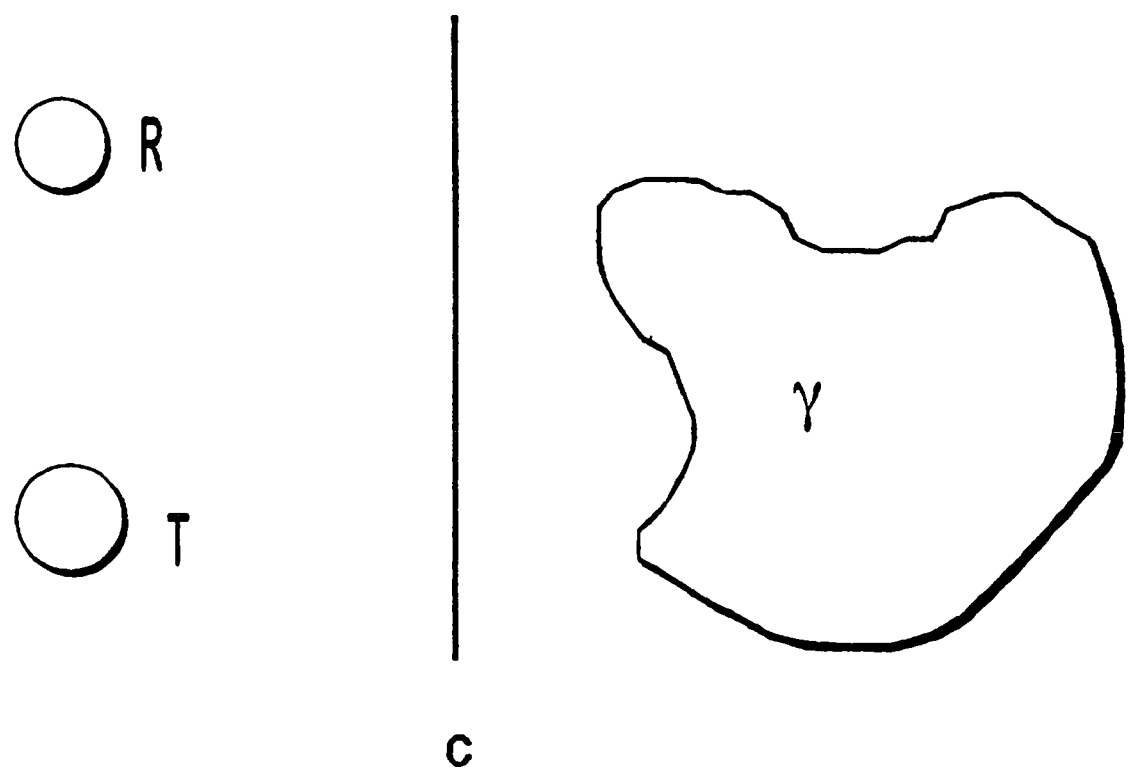
FIG. 24 shows a transducer coupling according to the present invention.
Figure 25A:
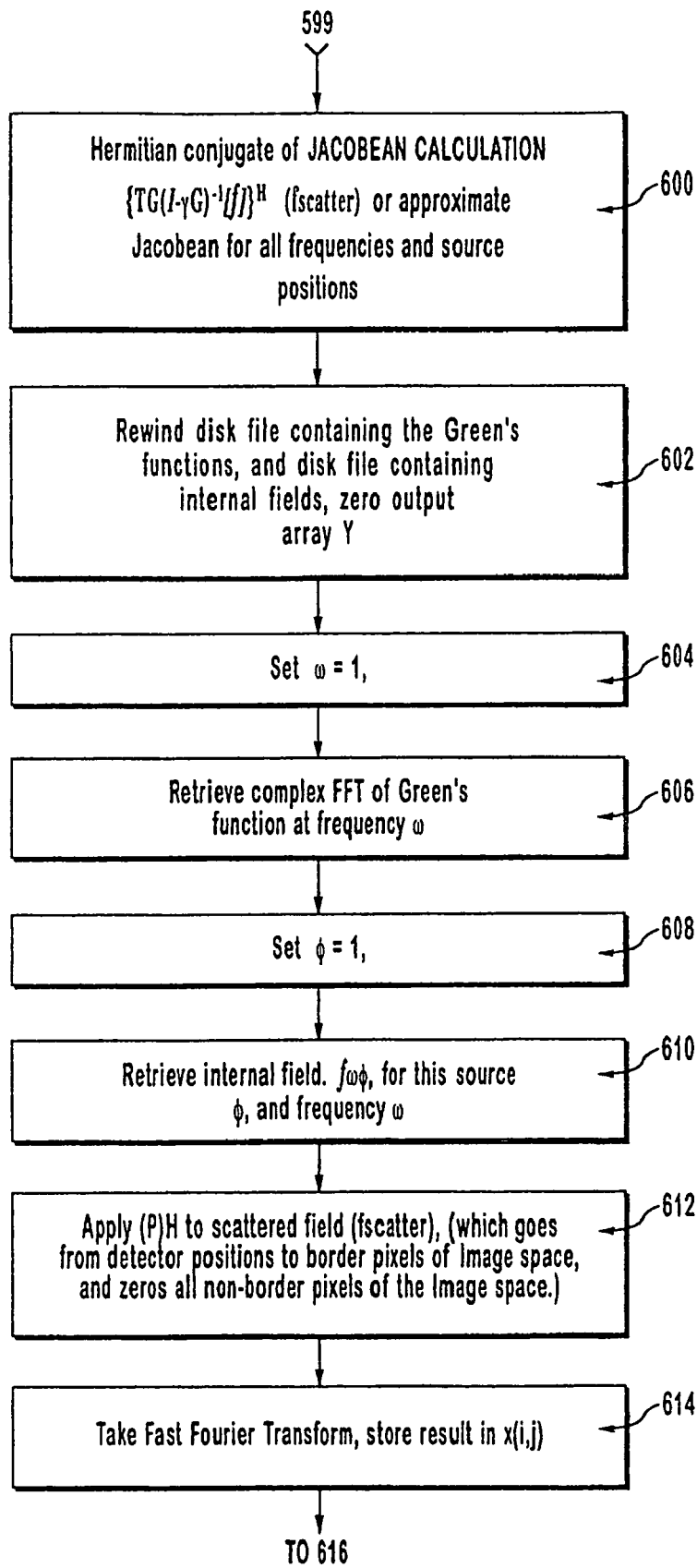
FIGS. 25A, B. and C illustrates application of the Hermitian Jacobian Matrix in the generic case according to the present invention.
Figure 25B:
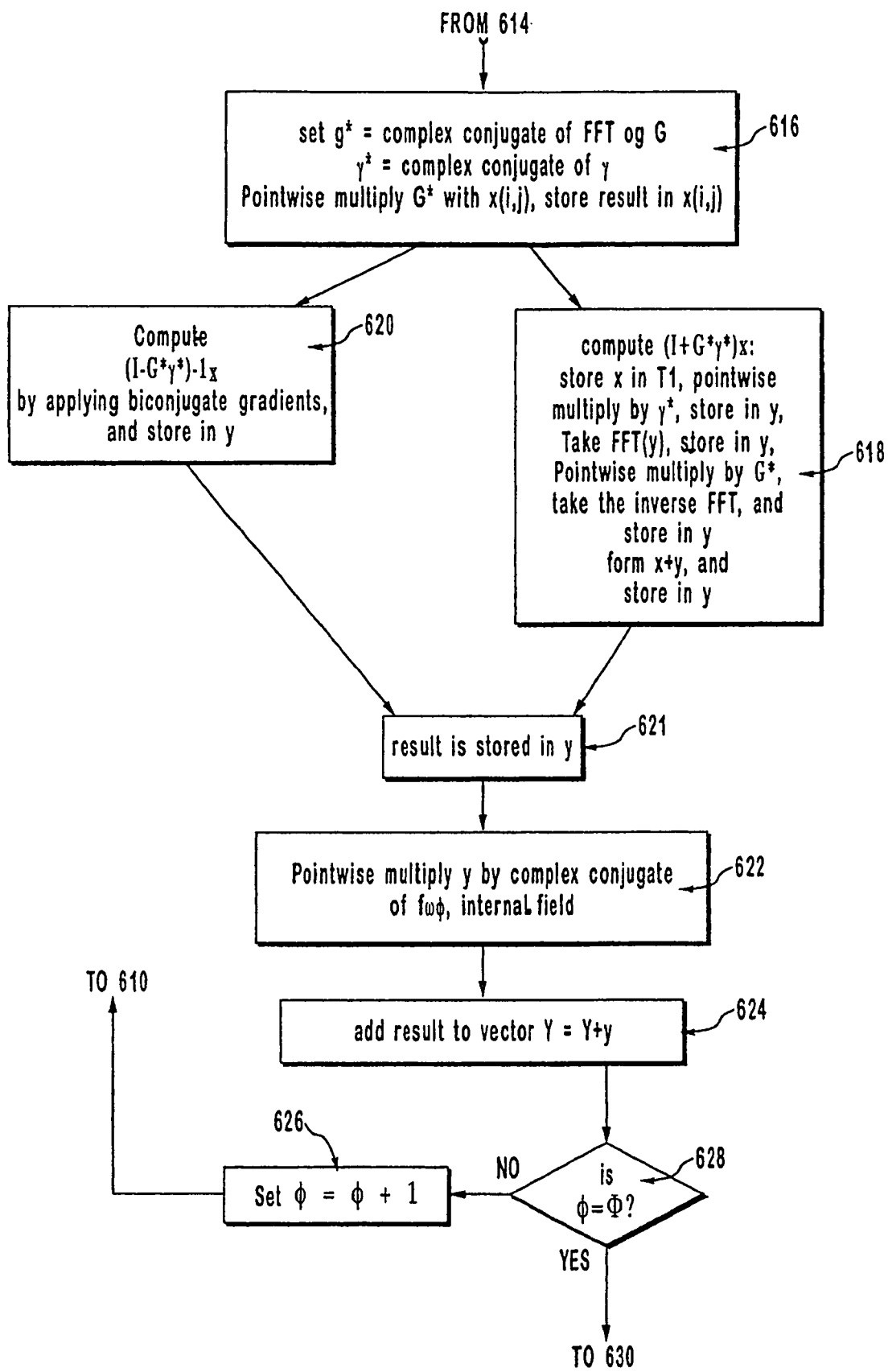
Figure 25C:
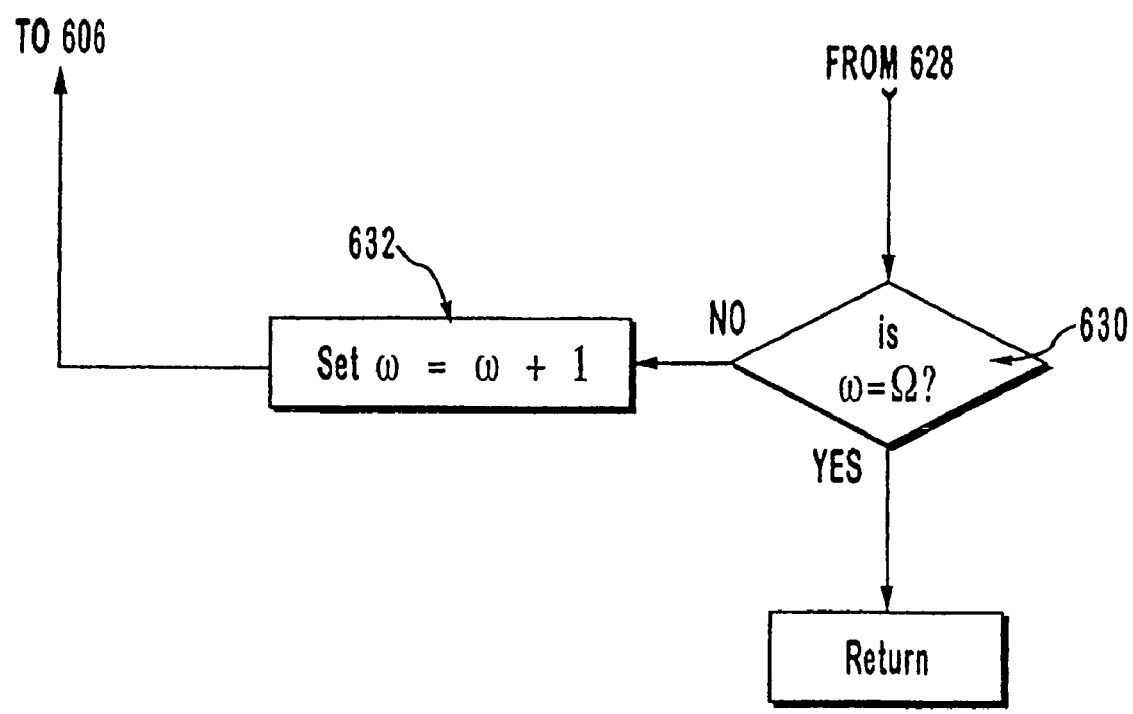

Consider an object to be imaged, γ, illuminated by a transmitter, T, with the scattering received by a receiver, R, as shown in FIG. 24 Let C denote a closed surface separating γ from the transceivers.

Let S be the scattering matrix of γ which, given the incident field generated from sources outside of C, gives the outward moving scattered field evaluated on C. This operator can be computed by solving a sufficient number of forward scattering problems for the object γ.

Let $P_R$ denote the operator that computes the field impinging on R due to sources inside of C from the scattered field evaluated on C. This is a simple propagation operator computable by an angular spectrum technique.

Let $P_T$ denote the operator that computes the field impinging on T due to sources inside of C from the scattered field evaluated on C. This is a simple propagation operator computable by an angular spectrum technique.

Let $A_{RT}$ denote the operator that computes the field impinging on R due to scattering from T (it operates on the net total field incident on T). This operator is computed by a moment method analysis of the transmitter structure.

Let $A_{TR}$ denote the operator that computes the field impinging on T due to scattering from R (it operates on the net total field incident on R). This operator is computed by a moment method analysis of the receiver structure.

Let $B_T$ denote the operator that computes the field on C due to scattering from T (it operates on the net total field incident on T). This operator can be computed by a moment method analysis of the transmitter structure.

Let $B_R$ denote the operator that computes the field on C due to scattering from R (it operates on the net total field incident on R). This operator can be computed by a moment method analysis of the receiver structure.

Assume that the transmitter T also produces a field, $f^i$, due to eternally applied excitation (electrical). Denote by $f_c^i$ the values of this field on C. Denote by $f_R^i$ the values of this field on the receiver surface. We assume that these field values are known (i.e., we know the free-space radiation characteristics of the transmitter).

Given these definitions, the total field incident from outside of C evaluated on C is given by:

$$f_C^{tot} = f_C^i + B_T f_T^{tot} + B_R f_R^{tot} \qquad 1$$

where the superscript tot indicates the field incident on the particular element due to all other sources. For T and R we have:

$$f_T^{tot} = P_T S f_C^{tot} + A_{TR} f_R^{tot} \qquad 2$$

$$f_R^{tot} = f_R^i + P_T S f_C^{tot} + A_{RT} f_T^{tot} \qquad 3$$

Note that the formula for $f_T^{tot}$ has no superscript i term since the incident field emanates from its interior. Solving 1-3 for the tot fields gives:

$$\begin{bmatrix} f_C^{tot} \\ f_T^{tot} \\ f_R^{tot} \end{bmatrix} = \begin{bmatrix} I & -B_r & -B_R \\ P_T S & I & -A_{RT} \\ P_R S & -A_{RT} & I \end{bmatrix}^{-1} \begin{bmatrix} f_C^o \\ 0 \\ f_R^i \end{bmatrix} = \begin{bmatrix} f_C^{tot} \\ f_T^{tot} \\ f_R^{tot} \end{bmatrix} \quad (4)$$

The size of this matrix operator is O(N×N) and so computation of its inverse does not require much CPU time (mere seconds). In order to compute the signal received by the receiver transducer, we take $f_R^{tot}$ computed in 4 and compute the surface currents (EM case) or surface velocities (acoustic case) from which the signal from the receiver can be computed.

This procedure for analyzing a scatterer in the presence of coupling between the T/R pair includes all orders of multiple interaction allowing transducers with complex geometries to be incorporated into our inverse scattering algorithms.

EXAMPLE 11

Frequency Dependent Scattering Parameters

Throughout the previous sections it has been assumed that $\gamma$ is independent of frequency. Suppose now that $\gamma$ is a function of frequency. In the event that only a single frequency is needed (transmission mode with encircling transducers and only one complex parameter to be imaged) this is not a problem—the algorithm will simply image 2 or 3-D distribution of $\gamma$ evaluated at that frequency. However, in reflection mode or when imaging multiple parameters, multiple frequencies are needed. This increases the number of unknowns to $\Omega^* N_x^* N_y$ if we naively seek a separate image at each frequency. Since multiple frequencies were already needed to complete the data for a frequency independent unknown, we have no way of correspondingly increasing the number of equations by a factor of $\Omega$. Instead, consider approximating the frequency variation with a set of parameters at each pixel:

$$\gamma_{nm}(\omega) \approx \gamma_{nm}^{(0)} \Psi^{(0)}(\omega) + \gamma_{nm}^{(1)} \Psi^{(1)}(\omega) + \ldots + \gamma_{nm}^{(q-1)} \Psi^{(q-1)}$$

where the basis functions $\Psi$ are selected based on the physics of the frequency dependence (we may, for example, simply use the monomial basis: $\Psi^{(n)}(\omega) \equiv \omega^n$, perhaps a rational function basis might be chosen since simple relaxation dispersion is a rational function). The formula for the GN update for this case is:

$$P_\omega G_\omega ((I - [\gamma_\omega] G_\omega)^{-1} [f \omega \phi] M_{\omega j} \delta \gamma^{(i)} = -T_{\omega \phi})$$

where summation over j is assumed and the matrix M is given by:

$$M = \begin{bmatrix} \Psi^{(1)}(\omega_1) & \Psi^{(2)}(\omega_1) & \ldots & \Psi^{(q-1)}(\omega_1) \\ \Psi^{(1)}(\omega_2) & \Psi^{(2)}(\omega_2) & \ldots & \Psi^{(q-1)}(\omega_2) \\ \Psi^{(1)}(\omega_\Omega) & \Psi^{(2)}(\omega_\Omega) & \ldots & \Psi^{(q-1)}(\omega_\Omega) \end{bmatrix}$$

Solution for the $q \times N_x \times N_y$ unknowns, assuming that q is sufficiently smaller than $\Omega$ can then carried out via the GN-MRCG or RP algorithms. We have already verified the success of this approach using quadratic polynomial models of the frequency variation $(q=3, \Psi^{(n)}(\omega) \equiv \omega^n)$.

We have discussed 3 separate algorithms for imaging:
(1) FFT-BCG
(2) Cylindrical Recursion
(3) Rectangular Recursion We have given examples of how this technology is used in various scenarios. We have shown how various modalities of wave propagation are amenable to the imaging algorithm. Any propagating substance or energy that can be successfully modelled with the wave equation is suitable. We have also included examples of simulated and actual data, thereby establishing the concept as workable.

The apparatus and method of the present invention holds promise for many useful applications in various fields, including seismic surveying, nondestructive testing, sonar, radar, ground penetrating radar, optical microscopes, x-ray microscopes, and medical ultrasound imaging, to name just a few. For purposes of illustrating the utility of the present invention, the detailed description which follows will emphasize the apparatus and method of the invention in the context of a system for use in performing ultrasound imaging of human organs, such as the breast. However, it will be appreciated that the present invention as claimed herein may employ other forms of energy such as microwaves, light or elastic waves and furthermore may be used in other fields and is not intended to be limited solely to medical acoustic imaging.

1. The Scanner and Transducer Configuration

Reference is first made to FIG. 1 which generally illustrates one type of scanner which may be used to implement the apparatus and method of the present invention for purposes of medical ultrasound imaging of a human breast or other organs. As shown in FIG. 1, the scanning apparatus generally designated at 30 includes fixed base 32. Wheels 38 and 40 are attached to the underside of a movable carriage base 34. Small shoulders 42-45 formed on the upper surface of cylindrical pedestal 36 define a track along which the wheels 38 and 40 are guided.

A stepping motor 46 mounted within the fixed base 32 is joined by a shaft 48 to a small pinion gear 50. Pinion gear 50 engages a large drive gear 52. Pillars 54-57 are rigidly ioined at one end to the top of drive gear 52 and at the opposite end to the underside of movable carriage base 34. Bearing block 58 supports drive gear 52 and movable carriage base 34.

Stepping motor 46 may be operated to turn the drive gear 52 which in turn will cause the movable carriage base 34 to rotate on top of the cylindrical pillar 36 within the tracks defined by shoulders 42-45. As hereinafter more fully described, rotation of the movable carriage base 34 may be employed to insure that an object is fully scanned from every possible angle.

With continued reference to FIG. 1, it will be seen that movable carriage base 34 has an inner cylindrical wall 60 and an outer cylindrical wall 62. The outer wall 62 and inner cylindrical wall 60 of movable carriage base 34 define a generally cylindrical chamber 64. Vertical drive motor 66 is mounted within chamber 64 and is connected by a shaft 68 to a circular ring of transducer arrays generally designated at 70. Vertical drive motor 66 permits the circular ring of transducer arrays 70 to be vertically adjusted. Slide bracket 72 is mounted within the chamber 64 and serves to guide in a sliding manner, the ring of transducer arrays 70 when it is vertically adiusted.

The ring of transducer arrays 70 is electrically connected through line 74 to components of an electronic system which may be housed in part within the chamber 64, as schematically indicated at 76. As hereinafter more fully described, the electronic system is used to control transmission and reception of acoustic signals so as to enable reconstruction therefrom of an image of the object being scanned.

Circular bracket 78 is attached to the top of the outer wall 62 of movable carriage base 34. A flexible, transparent window 80 extends between circular bracket 78 and the inner cylindrical wall 60 so as to enclose the transducer arrays 70 and stepping motor 66 within the chamber 64. The length of flexible window 80 is greater than the distance between bracket 78 and inner cylindrical wall 60. Window 80 thus serves as a flexible yet water-tight seal which permits vertical motion of the transducer arrays 70 for purposes of vertical focusing. Acoustically transparent window 80 may be made of any suitable material, such as plastic or rubber.

A stationary water tank generally designated 86 is adapted to fit within the movable carriage base 34. Water tank 86 consists of a fixed top plate 88 rigidly attached to vertical support bars 82 and 84. Support bars 82 and 84 are mounted on the fixed base 32. The length of support bars 82 and 84 is chosen such that the fixed top plate 88 of water tank 86 will be slightly suspended above the bracket 78 of movable carriage 34. Thus, a space 87 is provided between bracket 78 and fixed top plate 88. Additionally, a space 89 will be provided between side 94 and bottom 95 of water tank 86 and cylindrical wall 60 and bottom 61 of movable carriage 34. A third support bar 83 extends through a central hole (not shown) provided in block 58 and drive gear 52. Support bar 83 also extends through a watertight opening 85 provided in the bottom 61 of movable carriage 34. Support bar 83 thus helps to support water tank 86 in spaced relation from movable carriage 34. Since water tank 86 is suspended in spaced relation from movable carriage base 34, water tank 86 will remain stationary as movable carriage 34 is rotated. As hereinafter more fully described, rotation of the carriage 34 permits the transducer arrays 70 to scan the object 98 from every possible position around the object 98.

Fixed top plate 88 has a short downwardly extending lip 90 which extends over the end of circular bracket 78. A rubber-covered window 92 extends between the lip 90 and side 94 of the water tank. Window 92 encloses within space 89, water 97, or some other suitable acoustic medium so as to acoustically couple the transducer array 70 to the water 96 contained in tank 86. The rubber-covered window 92 also permits acoustic energy signals to be transmitted therethrough by the transducer arrays 70 and insures that the patient will be protected in the event window 92 should be broken.

The scanning apparatus generally described above may be employed to scan various parts of the human anatomy as, for example, a patient's breast, as schematically illustrated at 98. The scanning apparatus generally described above may be used for nonmedical applications and may employ acoustic or electromagnetic energy wavefields. For example, the same scheme may be used with acoustic transducers for scanning nonbiological specimens such as plastic parts. As further example, the same scheme may be used with microwave wavefields. In this latter case, the use of a coupling medium such as water 96 and water 97 is optional. Indeed, at frequencies over one GH.sub.z, the microwave absorption of water limits the size of the apparatus to a few centimeters. However, the use of air permits the use of electromagnetic energy over the spectrum from DC to far ultraviolet and soft x-rays. For microwave imaging, the ring of acoustic transducer arrays 70 is replaced with a corresponding ring of microwave transducer (i.e. antennas).

Figure 2:
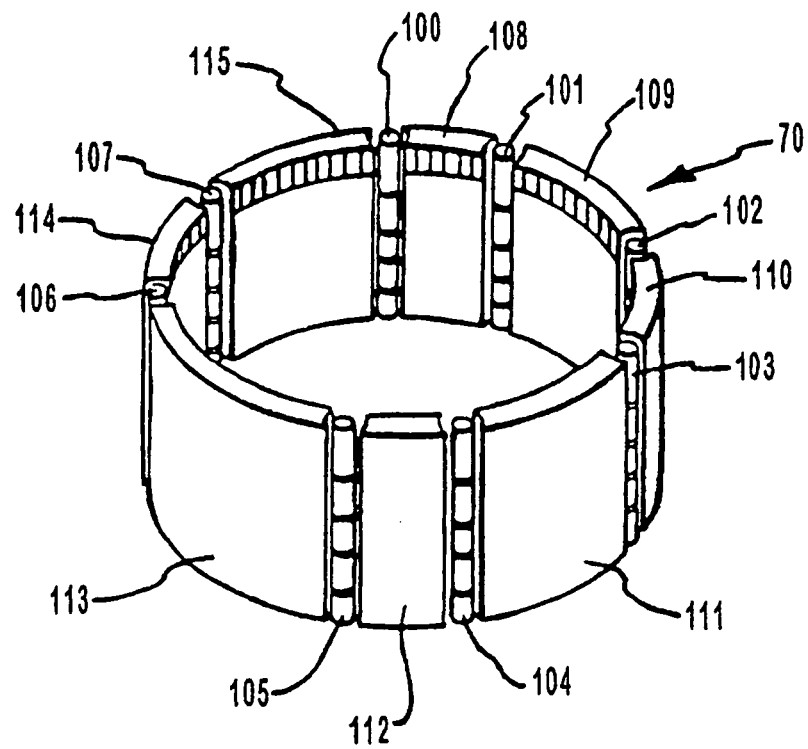
FIG. 2 is a perspective view illustrating one type of configuration which may be used for the transducer arrays employed in the scanner of FIG. 1.
Figure 3:
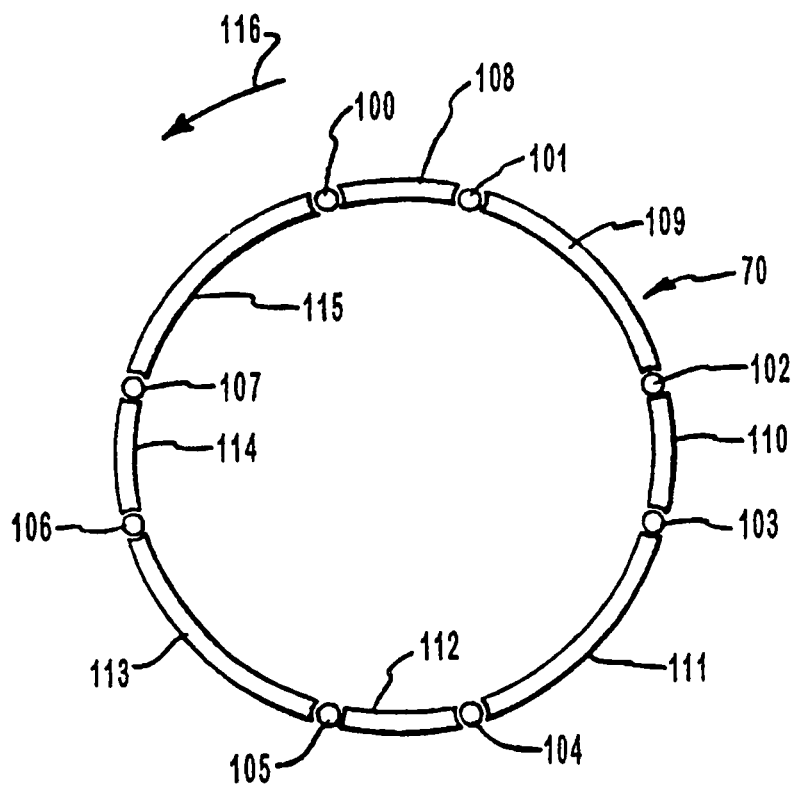
FIG. 3 is a top view of the transducer arrays shown in FIG. 2.

Reference is next made to FIGS. 2-3. FIG. 2 generally illustrates one suitable type of transducer configuration for the transducer arrays of FIG. 1. As shown in FIG. 2, the transducer configuration consists of eight transmitter arrays 100-107 and eight corresponding receiver arrays 108-115. The transmitter array 100-107 are thin, cylindrically-shaped transducer arrays which provide point-source or line-source segment transmission of acoustic energy. The receiver arrays 108-115 are arc-wise shaped arrays which are interposed between each pair of transmitter arrays 100-107. For purposes hereinafter more fully described, every other receiver array (e.g., receiver arrays 108, 110, 112 and 114) has a shortened arc-wise length.

Each of the transducer arrays 100-115 may be any of several well-known types of transducers. For example, transducers 100-115 may be piezoelectric transducers which produce ultrasound energy signals directly from high-frequency voltages applied to the transducer. Alternatively, the transducer arrays 100-115 may be magnetostrictive transducers having a magnetic coil (not shown) which receives the electrical oscillations and converts them into magnetic oscillations which are then applied to the magnetostrictive material to produce ultrasound energy signals.

With continued reference to FIG. 1, it will be seen that the transducer arrays 100-115 are arranged so as to form a cylindrical ring of arrays which encircles the object 98. By encircling the object with the transducer arrays 100-115, the arrays 110-115 may be quickly commutated by either mechanical methods, electronic methods or by a combination of both methods so as to completely scan the object in a much shorter time. In the illustrated embodiment, commutation is achieved by both mechanical rotation by stepping motor 46 and by electronic triggering of transmitter arrays 100-117 in sequence, as described more fully below.

Commutation of the transmitter arrays 100-107 permits acoustic energy to be transmitted from every possible position about the object, thus insuring that the data received (i.e. scattered acoustic energy) is complete. Commutation of the receiver arrays 108-115 insures that all spaces between receiver arrays 108-115 (known as "sound holes") will be covered, thus providing for accurate collection of all acoustic energy that is transmitted through or scattered by the object 98. However, commutation of the receiver arrays 108-115 is not necessary where transmitter arrays 100-107 are also used to receive acoustic signals. The circular configuration of transducer arrays 100-115 permits certain parts of the body to be scanned which would otherwise be inaccessible because of bones or other obstructions of the tissue.

The method for commuting the arrays 100-115 is best understood by reference to FIG. 3. First, each of the transmitter arrays 100-107 is sequentially triggered so as to transmit acoustic energy. Immediately after each transmitter array 100-107 is triggered, arrays 108-115 receive acoustic energy signals that have been either transmitted through or scattered by the object being scanned. Once this procedure has been followed for each of the transmitter arrays 100-107, the ring of arrays 70 is then mechanically rotated counterclockwise through a small angle, as schematically represented by arrow 116. The mechanical rotation is achieved by the stepping motor 46 (see FIG. 1) which rotates the movable carriage base 34, as described above.

After rotation of the arrays 100-115 to a second position, each of the transmitter arrays 100-107 is again sequentially triggered and data are again collected through receiver arrays 108-115. This procedure is repeated until acoustic energy has been transmitted at each possible point about the object.

Where the arrays 100-107 are used only for transmitting acoustic energy, a second series of rotations must then be effected to cover the sound holes between each pair of receiver arrays 108-115. For example, by rotating transmitter array 101 to the position occupied by the transmitter array 100, receiver arrays 109, 111, 113 and 115 will, because of their longer arcuate (arcwise measured) length, cover the spaces previously occupied by transmitter arrays 101, 103, 105 and 107. This procedure is repeated until all sound holes have been covered.

It should be noted that for a fixed circumference by decreasing the length of each array and increasing the number of arrays, electronic commutation may be used to reduce the angle through which the ring of transducer arrays must be rotated to achieve complete collection of both echo and transmission data.

It should also be noted that, in principle, no mechanical rotation of the array of detectors is necessary if every element is small enough and can be made to act as either a receiver or transmitter. Such an arrangement is more expensive than the technique illustrated in FIGS. 1, 2, and 3.

The transducer array 70 generally describes an implementation for an acoustic scanner and, in particular, of a breast scanner. In this case, the transducer elements generate and detect acoustic energy wavefields. However, can be seen that the acoustic transducers can be replaced with microwave transducers (antennas). The functions of interleaving, rotation, commutation are identical, for either microwave or acoustic transducers.

2. The Electronic System

Figure 4A:
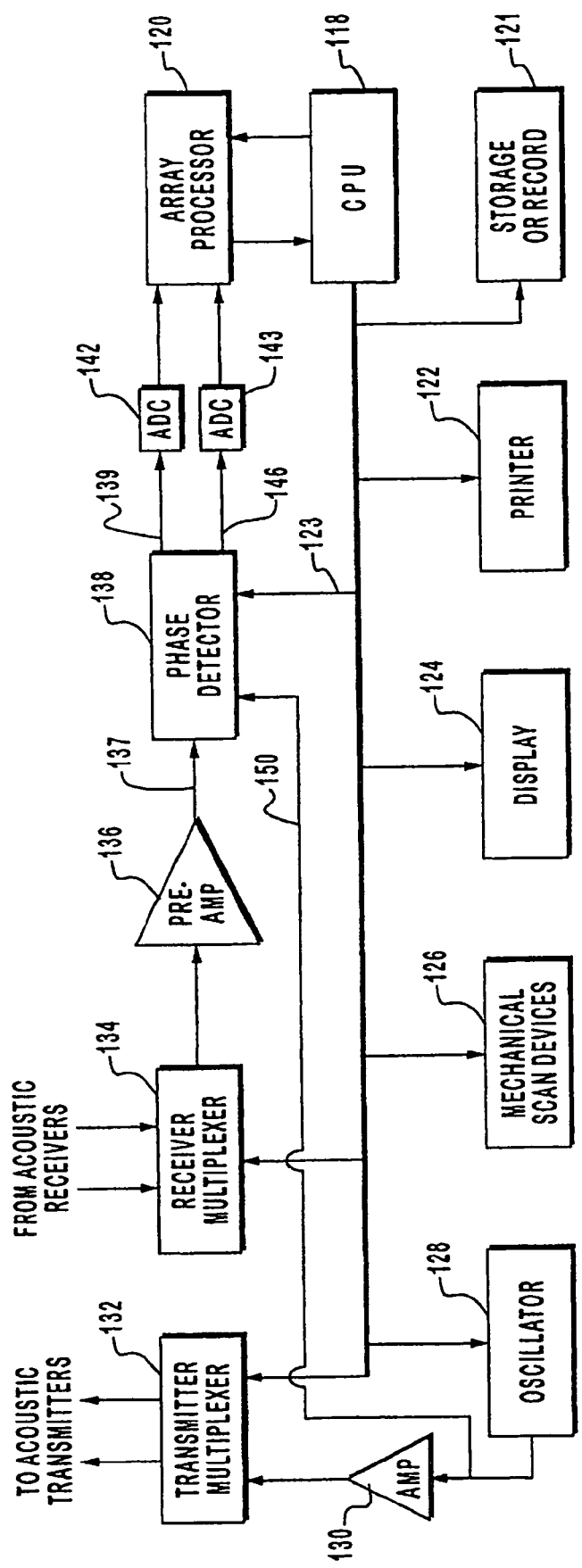
FIGS. 4A-4B are schematic diagrams illustrating one embodiment of an electronic system that may be used to implement the apparatus and method of the present invention, generally illustrate the invention in both the acoustic and electromagnetic wavefield case.
Figure 4B:
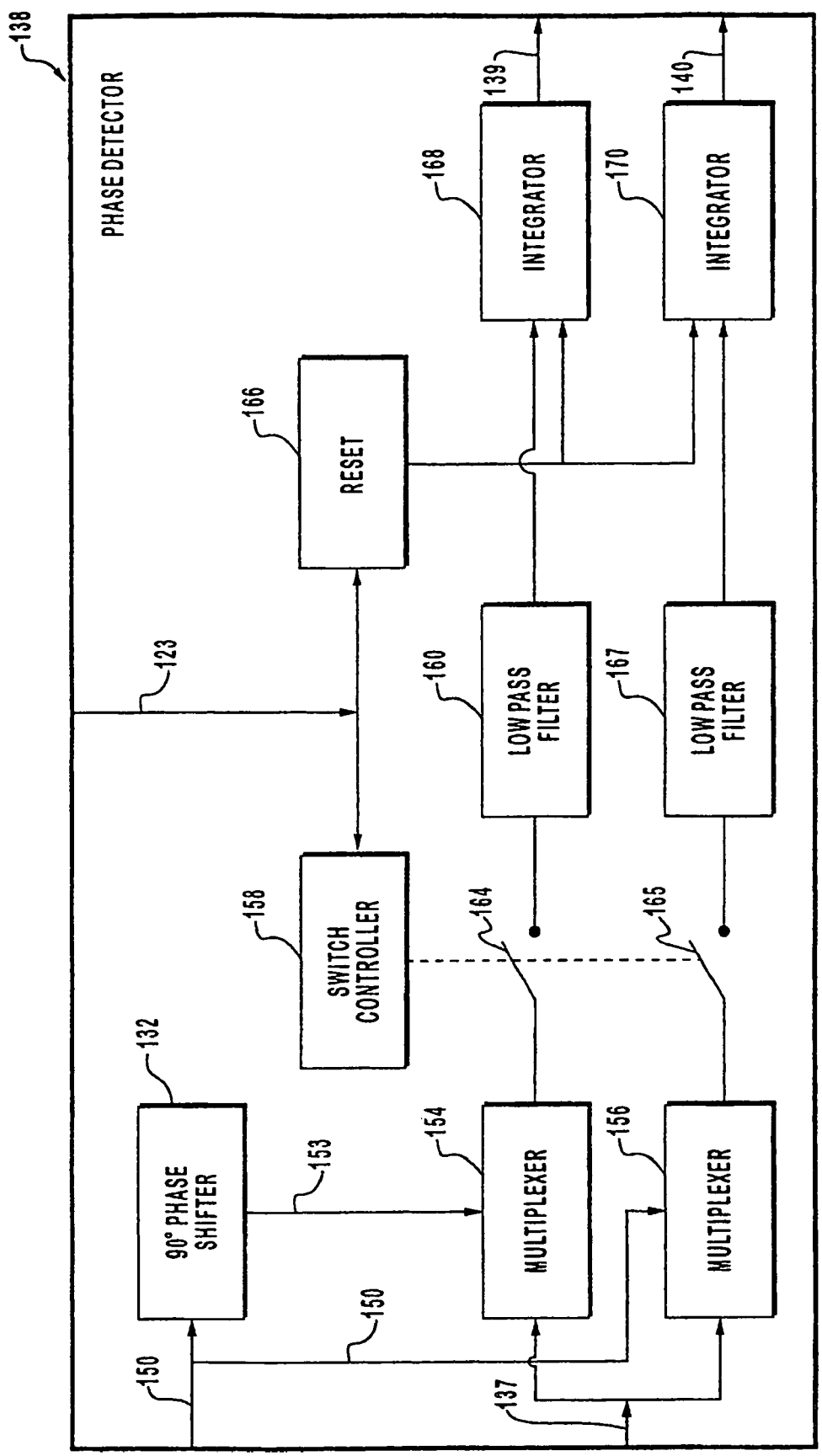

Reference is next made to FIGS. 4A-4B which schematically illustrate an electronic system which may be used to implement the apparatus and method of the present invention. It is clear from present practices in acoustics and radar technology that in both disciplines quadrature detection and analog to digital conversion are well known and widely used. Therefore, FIGS. 4A-4B generally illustrate the invention in both the acoustic and electromagnetic wavefield case. For clarity and simplicity, the electronic system is described in the context of acoustic wavefields. Following this acoustic description additional discussion on the applicability of FIGS. 4A-4B to microwave energy wavefields is made.

As hereinafter more fully described, the electronic system generates the acoustic energy that is propagated through and scattered by the object 98. The electronic system thereafter detects and processes the acoustic energy signals that are scattered by and transmitted through the object 98, and then communicates the processed signals to a computer (CPU) which interprets the signals and outputs the result in the form of a visual display or printed output.

In the transmission mode, CPU 118 causes an oscillator 128 to output a waveform which is amplified by a power amplifier 130 before being sent through multiplexer 132 to one of the transmitters. CPU 118 controls the multiplexer 132 so as to sequence each transmitter array 100-107 used to generate the acoustic energy propagated through the acoustic medium and object. If desired, after it is amplified, the waveform can also be input to an impedance matching transformer (not shown) and to a series of RC or RLC networks connected in parallel across the transmitter arrays 100-107 as illustrated and described in U.S. Pat. No. 4,222,274 (hereinafter the Johnson '274 patent), which is incorporated herein by reference. The impedance matching transformer may be used to achieve maximum power transfer while the RC or RLD networks may be used to distribute power across each transmitter array 100-107 in a way that deceases the side lobes in the transmitted signal.

Each of the acoustic receivers 108-115 (FIG. 2) are connected through a multiplexer 134 which is also controlled by CPU 118. In the receive mode, the detected signals may also be input through a delay line (not shown) to an analog adder and time variable gain circuit (not shown) to vertically focus the signals and to compensate for signal attenuation, as shown and described in the Johnson '274 patent. CPU 118 causes multiplexer 134 to sequence in turn each of the acoustic receivers 108-115 so as to gather transmitted or scattered acoustic energy around the entire circumference of the object. From receiver multiplexer 134, detected acoustic energy signals are amplified by a preamplifier 136 which may be used to logarithmically amplify the detected signal to reduce storage space required for each signal after it is digitized. The amplified signal is then processed by a phase detector 138.

The operation and components of phase detector 138 are best illustrated in FIG. 4B. As there shown, phase detector 138 receives the amplified signal as schematically represented by line 137 on which the signal is input to multipliers 154 and 156. The signal generated by oscillator 128 is input as shown at line 150 to one of the multipliers 156, and the signal from oscillator 128 is also shifted 90 degrees by the phase shifter 152 and then input as shown at line 153 to the other multiplier 154. Thus, each signal detected at the acoustic receivers is multiplied at multiplier 154 by a signal which is 90 degrees out of phase with the signal which is used to multiply the detected signal at the other multiplier 156. During the receive mode, the switch controller 158 and reset 166 are controlled as shown at line 123 by CPU 118 so that controller 158 closes each switch 164 and 165 after integrators 168 and 170 are reset. The resulting signals from multipliers 154 and 156 are then filtered by low-pass filters 160 and 162 and integrated by integrators 168 and 170. The integrated signals are then output, as shown at lines 139 and 140 to the analog to digital converters (ADCs) 142 and 143 (see FIG. 4A). The two signals which are output by phase detector 138 electronically represent the real and imaginary mathematical components of the acoustic signals which are detected at the acoustic receivers 108-115.

Once the received signals have been digitized, they are input and stored in the memory of an array processor 120. Alternately, a parallel processor or other special purpose high-speed computational device may be used for even higher computational speed. As hereinafter more fully described, CPU 118 in combination with the array processor 120 are programmed to then reconstruct the acoustic image using inverse scattering techniques, several alternatives of which are described more fully in Examples 1-3 of section 3 below. Once the acoustic image is reconstructed, it may be output either visually at a display 124 or in printed form at printer 122, or stored on a disc or other storage medium 123. Mechanical scan devices represented at 126 correspond to the motors 46 and 66 (FIG. 1) for controlling commutation and vertical positioning at the transmitter and receiver arrays 100-107 and 108-115, and are controlled by CPU 118. Other configurations of transducers can be scanned by mechanical means through use of mechanical scanning device 126.

The electronic circuits of FIGS. 4A-4B are effective over the frequency ranges of fractions of $H_z$ to hundreds of $GH_z$. The transmitter multiplexer 132 can drive signals to either acoustic or electromagnetic energy transmitting transducers. Likewise, receiving multiplexer 134 can receive signals from either acoustic or electromagnetic energy transducers. The operation of the circuit in FIG. 4A is independent of the source of the received signal at receiver multiplexer 134 or the destination of signal from transmitter multiplexer 132. The operation of the phase detector of FIG. 4B is independent of the type of wavefield used.

Figure 4C:
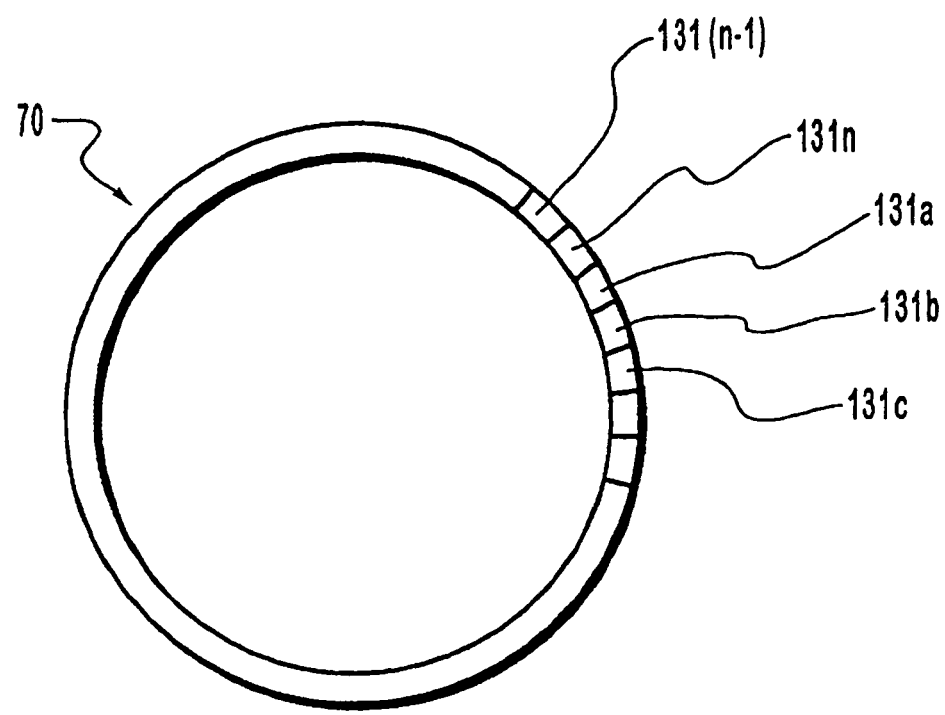
FIGS. 4C-4F schematically illustrate how electronic multiplexing may be used to eliminate the need for mechanical rotation, thus further enhancing system performance.
Figure 4D:
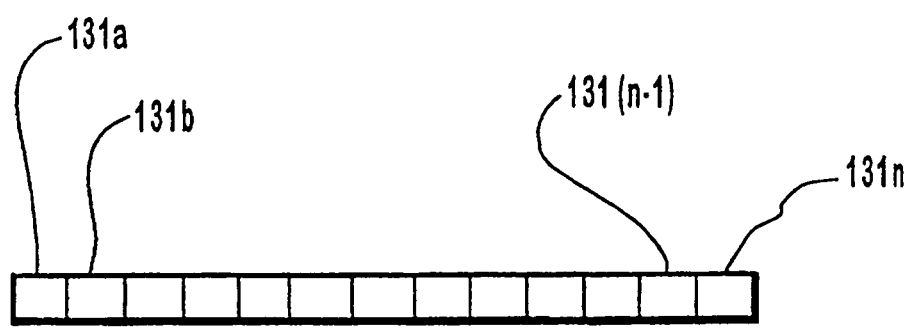

Reference is next made to FIGS. 4C-4F which schematically illustrate how electronic multiplexing may be used to eliminate the need for mechanical rotation, thus further enhancing system performance. In the following description, the term transducer applies equally well to both acoustic and electromagnetic energy types. In particular, FIG. 4C shows n transducer elements 131a through 131n of a circular array closely spaced to form a continuous array surrounding the body. The array is shown as a one-dimensional structure, but clearly could be a two-dimensional structure as in FIG. 2. FIG. 4D illustrates the n elements 131a through 131n arranged in a linear fashion. It is also clear that a planar or checkerboard two-dimensional array of element could be used.

Figure 4E:
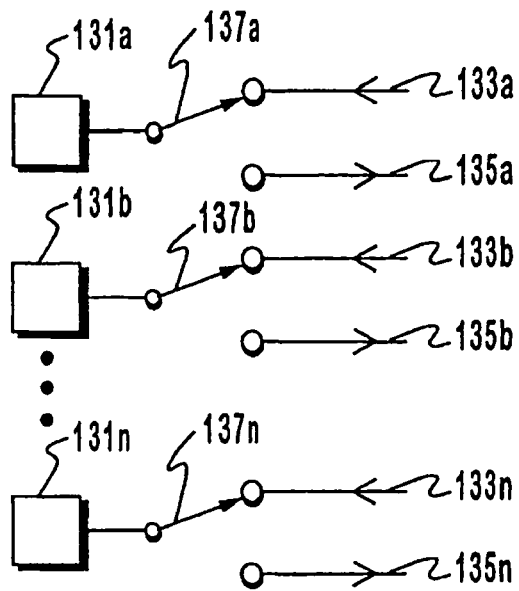
Figure 4F:
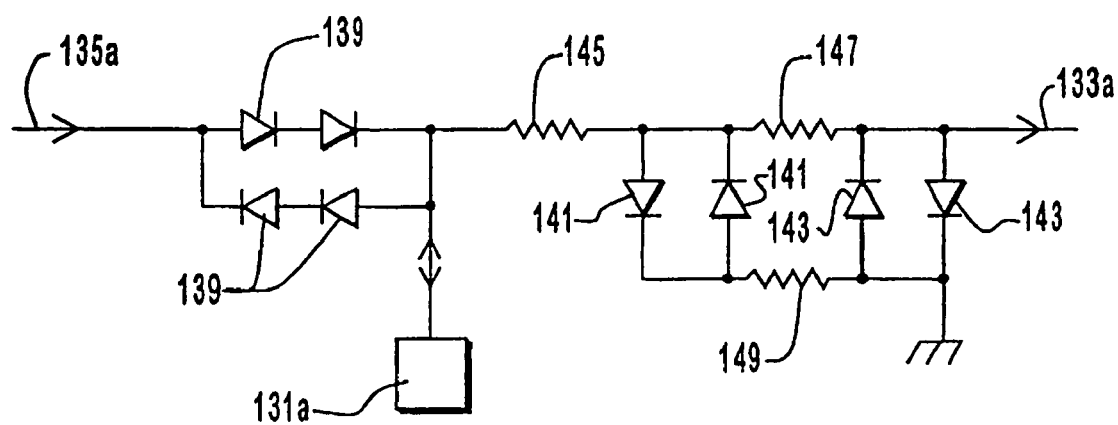
Figure 4G:
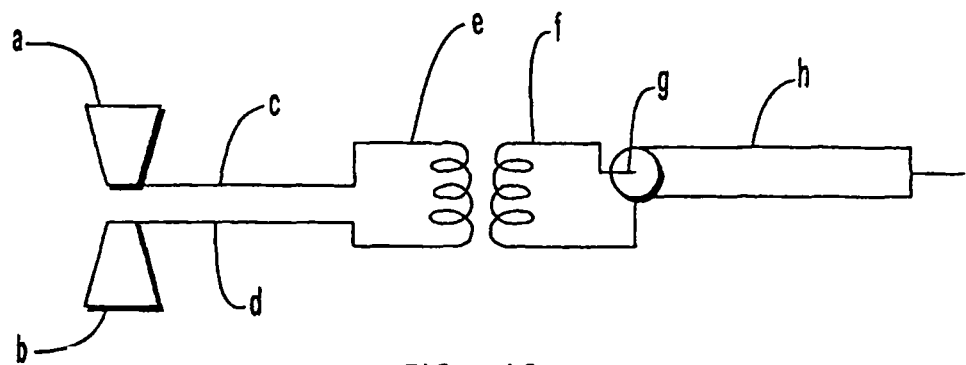
FIG. 4G is an electrical schematic illustration of a Bow-Tie Antennae used with the apparatus and method of the present invention.
Figure 4H:
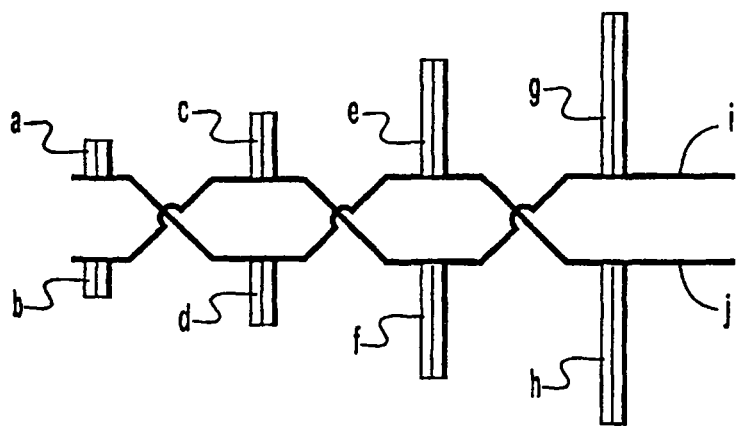
FIG. 4H is an electrical schematic illustration of a Log-Periodic Antennae used with the apparatus and method of the present invention.
Figure 4I:
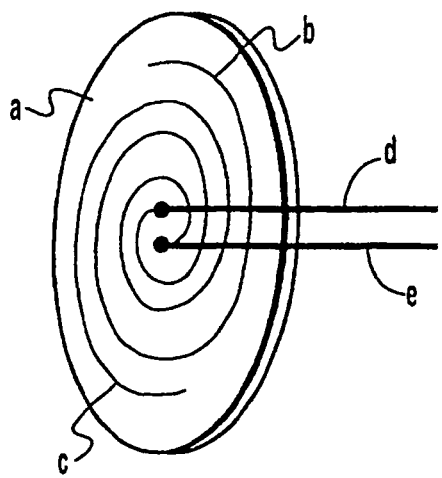
FIG. 4I is an electrical schematic illustration of a Spiral Antennae used with the apparatus and method of the present invention.

Such one-dimensional and two-dimensional arrays of receivers and transmitters have a direct application to advanced medical imaging instruments where motion of the array is undesirable or in seismic exploration in which such movements are difficult. FIG. 4E illustrates how each element 131a through 131n may be switched to either a transmitter circuit or a receiver circuit. Here, for example, element 131a is switched by switch 137a to either a receiver circuit 133a or a transmitter circuit 135a. FIG. 4F shows how a passive network of diodes and resistors may be used to allow a single element to act as either a transmitter or a receiver, or in both capacities. For example, in the transmit mode, diodes 139 are driven into conduction by transmit signal on line 135a. With two silicon diodes in series in each parallel leg, the voltage drop is a few volts. Thus, for an applied transmit signal of 20 volt or more, only a small percentage of signal power is lost across diodes 139. Diodes 139 are arranged in a series parallel network so that either polarity of signal is passed to transducer element 131a with negligible loss. In the transmit mode, resistors 145, 147, and 149 and diodes 141 and 143 prevent excessive and harmful voltage from appearing at output 133a that leads to the preamplifier multiplexer, or analog-to-digital circuits that follow. In operation, resistor 145, diode 141, and resistor 149 act as a voltage divider for the large transmit voltage present at the transducer element 131a. Diodes 141 are arranged with opposing polarity to provide a path for any polarity of signal above their turn on voltage of about 0.7 to 1.0 volts. The values of resistors 145 and 149 are typically so that the impedance of resistor 145 is greater than or equal to that of the internal impedance of transducer element 131a. Resistor 149 is chosen to be some fraction of resistor 145, such as one-fifth. Resistor (resistor 147) typically is chosen to be about equal to the resistance of resistor 149. Thus, during transmission, the voltage appearing at output 133a is only the conduction voltage drop across diodes 143.

In the receiving mode, signals received at transducer element 131a are typically less than one diode voltage drop (about 0.7 volt) and thus are isolated from transmitter 135a, since point 135a is a ground and diodes 139 are not conducting. Diodes 141 and 143 are not conducting and therefore output 133a is not shunted. Thus, the preamplifier following 133a would only see an impedance of resistor 145 plus resistor 147 plus that of the transducer element 131a. In practice, resistor 145 plus resistor 147 can be made about equal to or less than the impedance of transducer element 131a to minimize signal loss. It is clear that the principles illustrated in FIGS. 4C-4F may also be applied in the case of wide bandwidth signal transmission as described further below in connection with FIGS. 5A-5B.

FIG. 4F describing the use of diode networks to isolate the transmitter from the receiver circuits is commonly used in ultrasound scanners and sonar systems. Similar circuits are used in some radar systems. At radar frequencies other methods of isolation such as gas diodes, directional couplers, active diode switches, etc. are also used.

Figure 5A:
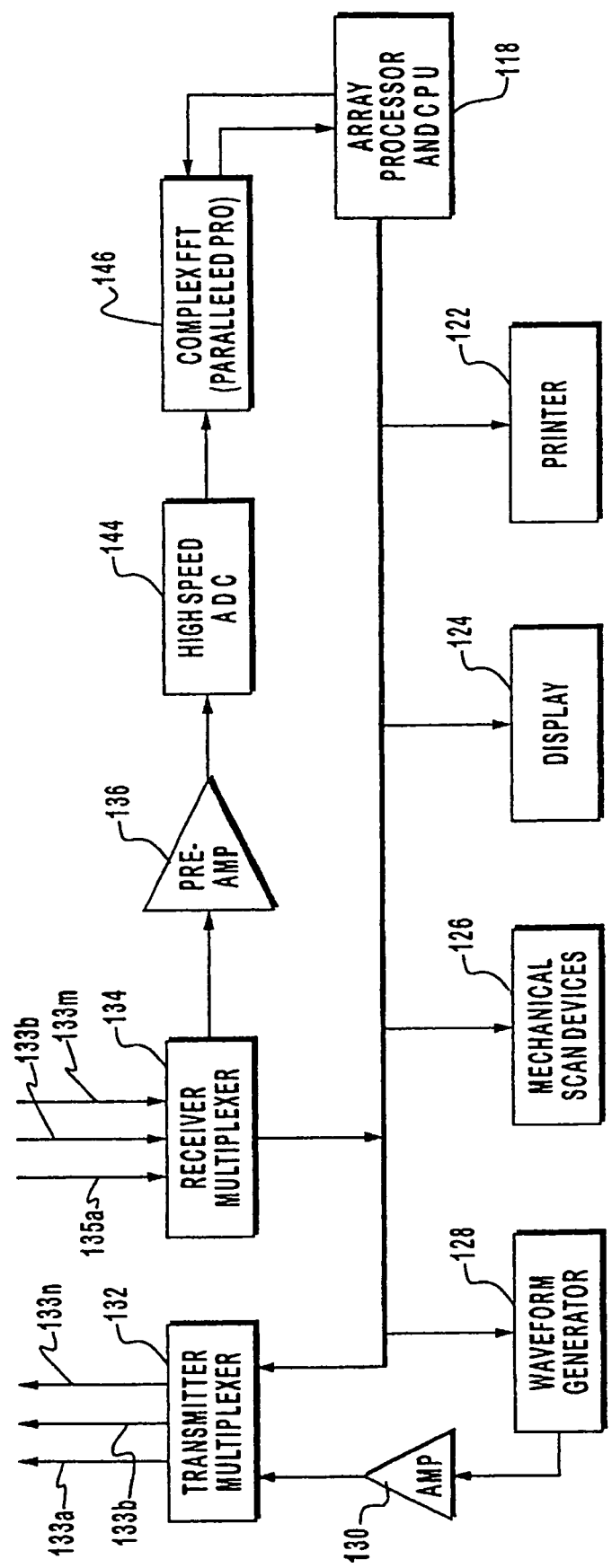
FIGS. 5A and 5B schematically illustrate another electronic system which can be used to implement the apparatus and method of the present invention.
Figure 5B:
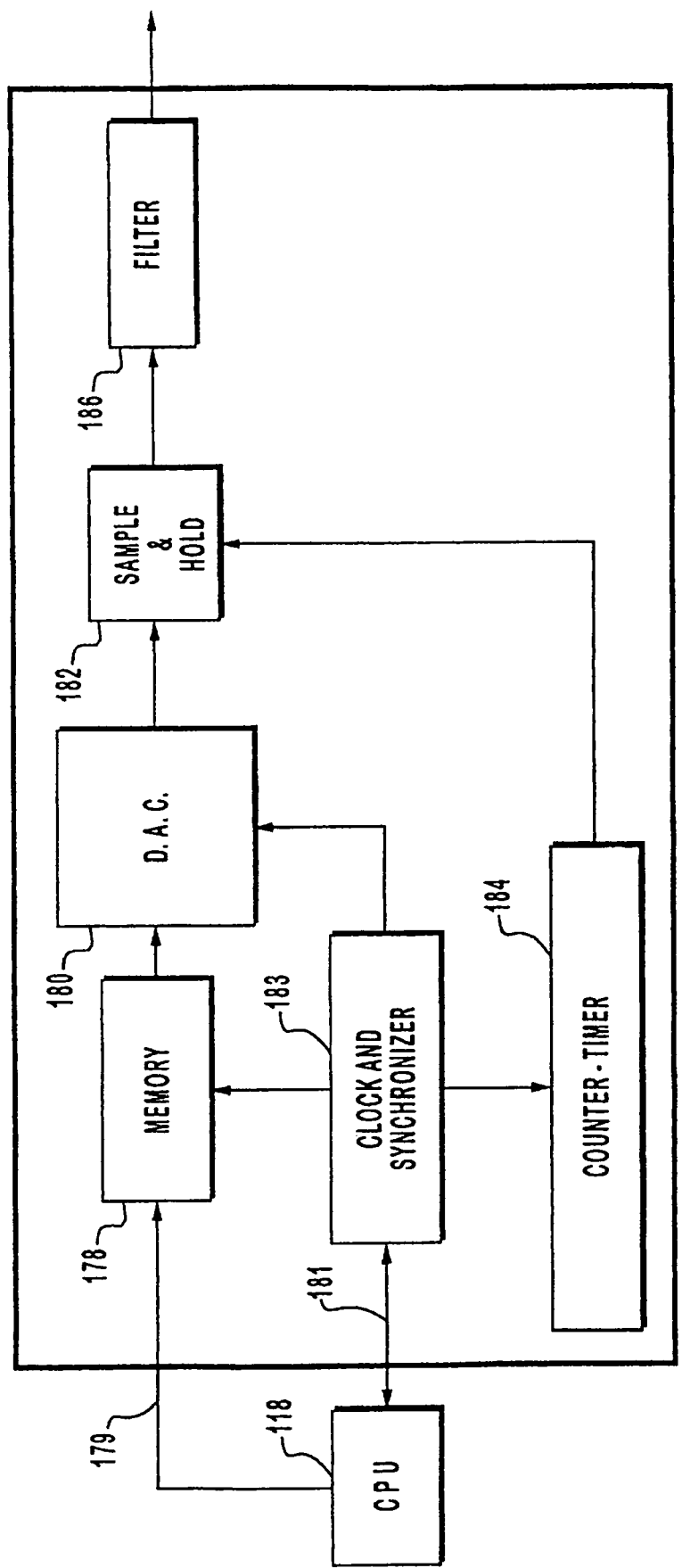

FIGS. 5A and 5B schematically illustrate another electronic system which can be used to implement the apparatus and method of the present invention. In the description that follows, the circuit is specifically designed for driving acoustic transmitting transducers and for digitizing signals from acoustic transducers, but the same circuit also applies to electromagnetic transducers (antennae) as well. In FIG. 5A, oscillator 128 has been replaced by waveform generator 129 that can produce repetitive narrow bandwidth signals or a wide bandwidth signal. The advantages of using a suitable wide bandwidth signal is that in one transmit-receive event, information at all frequencies of interest may be collected. Typically, it will be preferable to scan the object under consideration with signals having several different frequencies. This may be especially true in cases where it is not possible to encircle the object with a ring of transducer arrays, as in the case of seismic imaging. Moreover, by using multiple frequencies, it will typically be possible to obtain more data for use in reconstructing the image. The lowest frequency used for the signal must be such that the wavelength of the signal is not significantly larger than the object to be imaged. The highest frequency must be such that the acoustic signal may be propagated through the object without being absorbed to such an extent as to render detection of the scattered signal impossible or impractical. Thus, depending upon the absorption properties and size of the object which is to be scanned, use of multiple frequencies within the range indicated will typically enhance the ability to more accurately reconstruct the image of the object.

The use of multiple frequencies or signals containing many frequencies also has the advantage of obtaining data that may be used to accurately reconstruct frequency dependent material properties.

In the electronic system of FIG. 4A, in order to scan the object using multiple frequencies, the frequency of oscillator 128 must be change several times at each transmitter position. This increases the time involved in transmitting and detecting the scattered acoustic energy from which the image is reconstructed. In the electronic system of FIG. 5, a special waveform is used which inherently includes multiple frequencies within it. The type of waveform generated by waveform generator 129 may be the well-known Tanaka-linuma kernel or the Ramachandran and Lakshiminaraynan kernel, as illustrated and described in the Johnson '274 patent. Swept frequency signals such as the well-known frequency modulated chirp or other types of waveforms could also be used to provide acceptable results.

As shown in FIG. 5B, the waveform generator 129 basically comprises five elements. An electronic memory device 178 is connected to the CPU 118 through read-and-write lines 179 and 181. CPU 118 determines the numerical value for a series of discrete points on the selected waveform. These numerical values are stored in binary form in memory device 178. Each of the discrete values stored in the memory device 178 is then sent to a digital to analog converter (DAC) 180. DAC 180 then transforms each of these digital values into a corresponding analog pulse which is then input to a sample and hold circuit 182. Sample and hold circuits, such as that schematically illustrated at 182, are well-known in the art and operate to hold each analog signal for a predetermined period of time. Counter-timer 184 is used to control the amount of time that each signal is held by the sample and hold circuit 182. Clock and synchronizer 183 is triggered by computer 118 and advances the memory address in memory 178, synchronizes the DAC 180, and controls the sample and hold 182.

With each clock pulse from counter-timer 184, the sample and hold circuit 182 retrieves one of the analog signals from DAC 180 and then holds the value of that signal for the duration of the clock pulse. Sample and hold circuit 182 thus outputs the approximate shape of the desired waveform which is then input to a low pass filter circuit 186 which is used to smooth the shape of the waveform before amplification and transmission through multiplexer 132 to one of the transmitters.

The electronic system of FIG. 5A also differs from the system shown in FIG. 4A in that the amplified analog signals output by the preamplifier 136 are digitized by a high-speed analog-to-digital converter 144 rather than being input to a phase detector. The digitized signals are then transformed by a complex fast Fourier transform (hereinafter "FFT") operation provided by a parallel processor 146 prior to being input and stored in the memory of the CPU 118. As described further in section 3 below, CPU 118 then reconstructs the image using a novel inverse scattering technique. Use of array processor 120 with CPU 118 in FIG. 4A and parallel processor 146 with CPU 118 in FIG. 5A is arbitrary and in principle either array processor 120 or parallel processor 146 or special purpose hard wired computational hardware could also be used in either FIG. 4A or 5A to accomplish the image reconstruction, as described further in section 3.

Optical Microscope

The operation of the inverse scattering microscope can be seen in block diagram form in FIG. 6A. This figure explains the operation of a specially modified Mach Zehnder interferometer based detection system. This detection system produces the information from which phase and modulus information is produced that is needed by an inverse scattering algorithm. A monochromatic, coherent light source such as laser 500 produces an approximately parallel beam of light 501 that passes through polarizer 502 and passes into beam expander and spatial filter 504. Such beam expanders are well known and a representative form is shown wherein the input beam enters a positive lens 506 with focal length $L_1$. A pin hole is placed at a distance of $L_1$ from lens 506 to remove unwanted spatial frequency spectral components. Light from pin hole 508 is reconverted into output parallel beam 509 by lens 508 with focal length L.sub.2. The pinhole 508 is placed at a distance L.sub.2 from lens 508. Output of beam expander 504 is beam 509 which passes to beam splitter 510 and split into two beams: beam 511 and beam 513. Beam 511 is the precursor of the main beams 515 and 516. Beam 513 is the precursor of stabilizing beams 517 and 518.

The operation of main beams 515 and 516 is now described. Beam 515 is the precursor of a beam that will pass through the interferometer in a clockwise direction and will pass through and scatter from the sample and will act as a probing beam. Main beam 516 is the precursor of a beam that will not pass through the sample, but will act as a reference beam as it traverses the interferometer in a counterclockwise direction. The probing beam and the reference beam will be combined to produce various interference patterns from which phase and modulus information can be obtained. Beam 515 passes through shutter 520 and then is reflected by mirror 522 to become beam 519. Beam 519 passes through objective lens 523 into sample holder 525. The light that is scattered by the sample and the sample holder is collected by objective lens 526 and passed as beam 527 to beam splitter 528. Companion main beam 516 passes from beam splitter 514 through shutter 530 to phase shifter 532. Phase shifter 532 can be set to introduce either a 0 degree phase shift or a 90 degree phase shift. Beam 533 is the output of phase shifter 532.

The purpose of objective lens 526 is to collect as large an angle of scattered light as possible. Objective lens 523 serves several purposes including: (1) that of focusing a small spot of light onto the sample holder of higher intensity than normally would be present in beam 519 in order to improve the signal to noise ratio; and (2) that of restricting the illumination to a narrow, focal spot region with desirable, plane-wave-like phase fronts with lateral amplitude anodizing.

Light beam 531 from shutter 530 passes through transmission-type phase shifter 532 where its phase is shifted either 0 degrees or 90 degrees. Beam 533 exits transmission-type phase shifter 532 and passes to mirror 536. At mirror 536 beam 533 is reflected to become light beam 539. Mirror 536 is driven by optional mirror driver 538 in small amplitude, periodic motion at frequency ω and in a direction perpendicular to the mirror face in its resting position. As mirror 538 vibrates it introduces a small periodic phase shift modulation to beam 537, but this phase shift is negligible. The purpose of either transmission-type phase shifter 534 or reflection phase shifter 538 is to impart a small periodic phase shift, typically from 1 degree to 10 degrees at frequency ω into beam 518 in order to stabilize the main beams 527 and 541 as combined to form beam 543. Either of these phase modulation methods is workable either separately or in combination. Usually, for cost reasons, only one of these phase modulation methods will be implemented in hardware.

Beam 539 emerges from mirror 538 and passes through beam transformer 540 and thence to beam splitter 528. Beam transformer 540 serves the purpose of adjusting the phase fronts and lateral amplitude of beam 541 to match those of beam 527 at the mirror 528 and at camera 544. While such matching may not be strictly necessary it does provide a more simple interference pattern that is mostly a function of the inserted object and not a function of the interferometer itself. Beam transformer 540 could be constructed in a number of ways, but one obvious way would be to replicate objective lens pair 523 and 526, however with the following modifications: (1) the sample holder and object is omitted; or (2) the sample holder is present but no object is present.

Beams 541 and 527 are combined by beam splitter 528, now acting as a beam combiner, and produce an interference pattern on the sensitive one-dimensional or two-dimensional solid state array of detector cells in camera 544. The intensity pattern on the array of detector cells is then converted into an electrical signal that is sent to the digitizer and computer 545 where this signal is digitized and stored in memory. Computer 545 controls the angular position of sample holder 525 by means of rotation device 524. Rotation device 524 also serves the function, under direction of computer 545, of inserting or removing the object from the beam. Rotation device 524 may be a stepping motor or a worm gear driven rotation stage as is common in optical technology. Computer 545 also controls the transmission of shutters 520 and 530, controls the phase of phase shifter 532, and controls the digitizing of camera 544. Computer 545 performs the important role of creating different diffraction patterns by changing the combinations of: (1) sample in or sample out; (2) main beam A only or main beam B only or their sum; or (3) phase sifter in main beam set at 0 degrees or at 90 degrees. From these different diffraction patterns, as described by the eight measurements and equations in the summary of invention section, computer 545 can compute the scattered detected field from the object. By including various test objects of know properties the incident field present at object 526 can be calculated. The set of scattered fields calculated for each of the various respective adjusted angular position of the object holder 525 is used as the detected scattered fields in the inverse scattering algorithms. Likewise, the incident field in and around the sample holder is taken as the incident fields in the inverse scattering algorithms.

Returning to FIG. 6A, note that a second set of beams defined as stabilizing beams is shown and these beams also are caused to interfere by the same mirrors and beam splitters as is traversed by the main beams. The function and justification for using these stabilizing beams is described in the summary of invention section. Note beam 513 is reflected by mirror 512 into beam splitter 514 to become beams 517 and 518. Beam 517 is reflected by mirror 522 to become beam 521 which then passes to beam splitter 528 where it is reflected into detector 542a and transmitted into detector 542b. Beam 518 passes through phase modulator 534 to mirror 536 where it is reflected and becomes beam 537. A fraction of beam 537 then passed through beam splitter 528 to detector 542a where it interferes with reflected version of beam 521. A fraction of beam 537 is also reflected into detector 542b where it combined with a fraction of beam 521. Detector 542a typically would be a semiconductor pn diode or pin diode. The output of detectors 542a and 542b passes to locking amplifier system 546 which adjusts the mean phase shift imposed by mirror 536.

Locking amplifier system 546 functions in the following manner. The signal from detector 542a passes into locking amplifier system to amplifier 547. Output of amplifier is the input of multiplier 548. Multiplier has a second input 550a. The product of the output of amplifier 547 and input 550a passes through low pass filter 549 thence both to non inverting amplifier 550h and to inverting amplifier 550i. Switch 550j selects either the output of noninverting amplifier 550h or that of inverting amplifier 550i. The output of switch 550j passes to switch 550s and thence to summing amplifier 550g. Input 550a to multiplier 548 originates in oscillator 550f at frequency ω. The output of oscillator 550f is shown as signal 550l and is split into two parts: one part, signal 552n, is an input to summing amplifier 550g; the other part, signal 550p, is in turn split into two signals 550c and signal 552q. Signal 550c is one input to switch 550b. Signal 552q is imposed on both inputs of multiplier 550e. The effect of multiplying a signal by itself is to produce sum and difference signal. The difference signal is at zero frequency while the sum frequency is at double the input frequency. The output of multiplier 550e passed through high pass filter 550d to switch 550b. High pass filter 550d rejects the zero frequency signal but passes the doubled frequency. An offset constant voltage 550m is also an input of the summing amplifier 550g. Summing amplifier 550g sums signals 550m, 550k and 552n. The output of summing amplifier 550g is then sent to a phase modulator which may be mirror driver 538 or phase modulator 534. If output of summing amplifier 550g is sent to mirror driver 538 then this signal is first amplified by amplifier 507. If output of summing amplifier 550g is sent to phase modulator 534 then this signal is first amplified by amplifier 505.

The phase locking circuits can function in several modes. In a first mode, heterodyning techniques are used. In the summary of the invention section four different heterodyning methods are described. The hetrodyning mode is now described. One of two heterodyne methods to lock the two component beams at the same phase is now described. The output of amplifier 547 is multiplied by signal of frequency ω at multiplier 548 and the resulting signal is low pass filtered in low pass filter 549. The output is then passed through inverting amplifier 550i or noninverting amplifier 550h and thence through switches 550j and 550s to summing amplifier 550g and thence to phase modular 534 or phase modulator 538. The feedback loop adjusts the phase shifters 534 or 538 to minimize the signal component at (o present in the signal output of amplifier 547.

One of two heterodyne methods to lock the two component beams in quadrature (i.e. 90 degree phase difference) is now described. The output of amplifier 547 is multiplied by signal of frequency 2ω from high pass filter 550d. The signal from high pass filter 550d passes through switch 550b to multiplier 548 and thence to low pass filter 549. From low pass filter 549 the signal passes through either inverting amplifier 550i or noninverting amplifier 550h to switch 550j and thence to switch 550s and thence to input 550k to summing amplifier 550g. Output from summing amplifier 550g then drives either phase modulator 534 or mirror driven 538 to maximize the signal component at 2ω present in the signal output of amplifier 547.

The phase locking circuit can operate in a second mode where no heterodyning techniques are used. In this mode, output signal from detector 542a and output signal from detector 542b are passed to differential amplifier 552q, whose output is proportional to the difference in voltage between these two input signals. The output of differential amplifier is low pass filtered by low pass filter 550r to remove high frequency noise and passed to switch 550s and thence to summing amplifier 550g. The output of summing amplifier is then sent to either mirror driver 538, or phase modular 534. The advantage of this method is a reduction in parts, since no heterodyning circuits are required. Also significant is the elimination of phase modulators. Only the mirror driver for zero frequency baseband stabilization adjustments is necessary. A possible disadvantage may be an insensitivity to systematic errors.

Figure 6B:
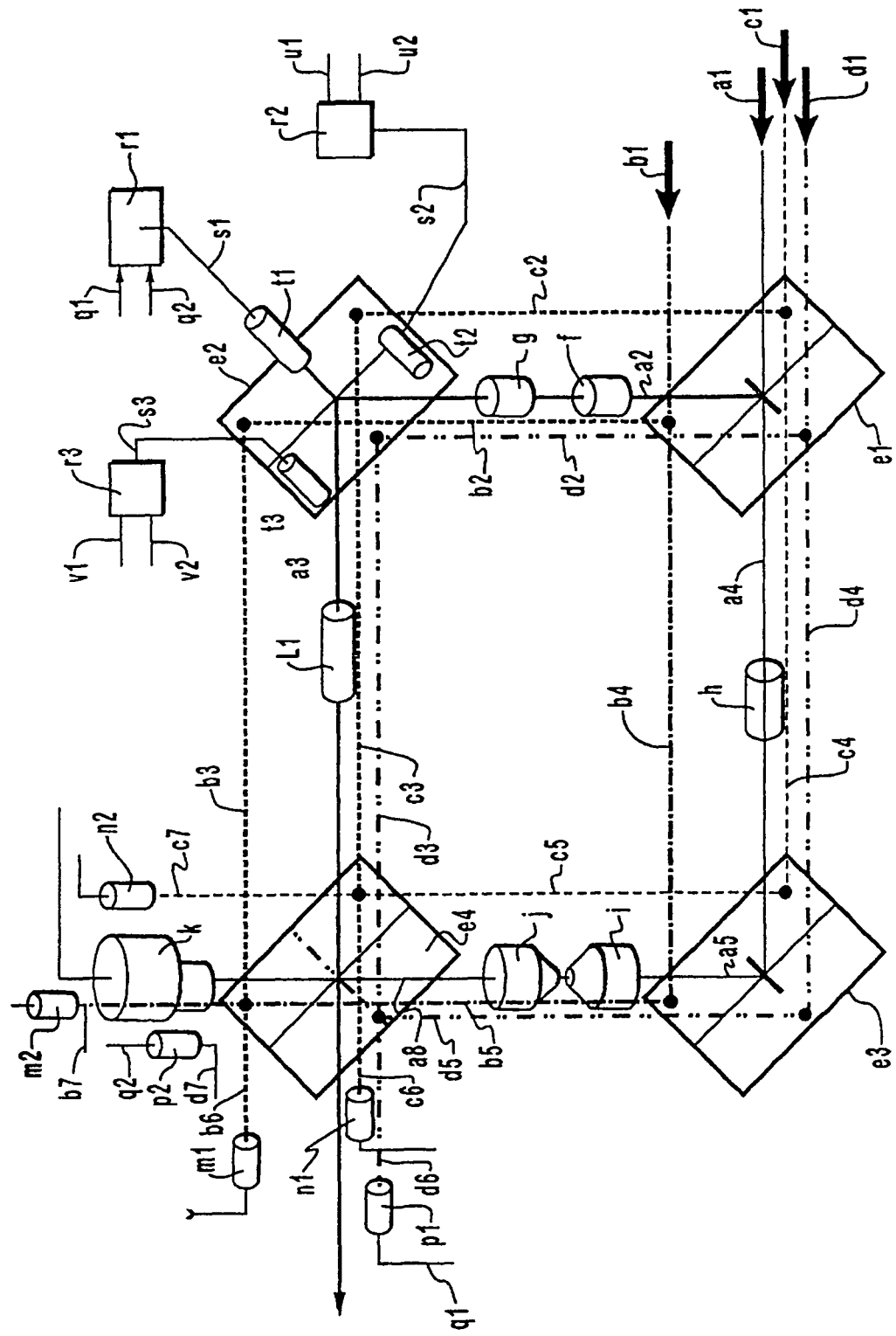
FIG. 6B is a perspective view which schematically illustrates an interferometer used with the apparatus and method of the present invention.

Referring to FIG. 6B, a perspective drawing of the interferometer section of the optical microscope of FIG. 6A is shown. This drawing is useful for visualizing the spatial relationships between the main imaging beam (located in the center of the mirrors and beam splitters) and the stabilizing beams (located at the edges of the mirrors and beam splitters). The main beam passes through the sample and objective lenses. The stabilizing beam passes around and misses the objective lenses and sample. The main beam is collected by solid state camera k, but stabilizing beams are collected by photodetectors m1, m2, n1, n2, p1 and p2. The normals to mirrors e2 and e3 and the normals to beam splitters e1 and e4 are mutually parallel. Main beam a1 enters the interferometer and is split by beam splitter e1 into beams a2 and a4. Beam a2 passes through shutter f and through phase shifter g to mirror e2. From mirror e2 the reflected version of beam a3 passes through wave front transformer L.sub.1 to mirror e4 where it combines with beam a8 and passes to the solid state camera k. Main beam a4 passes through shutter h to mirror e3 where it is reflected and becomes beam a5. Beam a5 passes through objective lens i and lens j and becomes beam a8. The sample is placed between objective lens i and objective lens j as shown in FIG. 6A.

The paths of the stabilization beams are now described. The stabilization beams are comprised of three parallel beams. These beams enter mirror e1, as respective beams b1, c1, and d1. They leave in the clockwise direction as respective beams b4, c4, and d4 and reach mirror e3. They leave mirror e3 as respective beams b5, c5, and d5 and reach beam splitter e4. Beams b1, c1, and d1 also incident at beam splitter e1 produce respective counterclockwise directed beams b2, c2 and d2 which leave beam splitter e1 and are reflected from mirror e2 to become respective beams b3, c3, d3. Beams b3, c3 and d3 reach beam splitter e4 where they combine with respective beams b5, c5 and d5. This combination then exits beam splitter e4 as respective pairs b6, c6 and d6 to the right, and as respective pairs b7, c7, and d7 to the top. Beams b6, c6, and d6 are detected by respective detectors m1, n1 and p1. Beams b7, c7 and d7 are detected by detectors m2, n2, and p2, respectively. Outputs of m1 and m2 are combined to form a first feedback signal for mirror and beam splitter alignment. Outputs of n1 and n2 are combined to form a second feedback signal for mirror and beam splitter alignment. Outputs of p1 and p2 are combined to form a third feedback signal for mirror and beam splitter alignment. The stabilization scheme show in FIG. 6B is the nonheterodyne method described in the brief summary and object of the invention section. Clearly, the heterodyne methods may also be used.

The function of the feedback signals is now described. The signal outputs of detectors p1 and p2 are respectively q1 and q2 and these pass into differential amplifier r1. The output of differential amplifier V1 passes to linear actuator t1 that moves mirror e2. A solid frame is not shown on which linear actuators t1, t2 and t3 are mounted as well as components e1, e3, e4, i, j, m1, n1, p1, m2, n2, p2, and h. Differential actuator provides motion parallel to normal of mirror e2. Detectors m1 and m2 produce respective signals U1 and U2 that pass to differential amplifier r2 and thence becomes signal S2 that drives linear actuator t2 at mirror e2. Detectors n1 and n2 produce respective signals v1 and v2 that pass to differential amplifier r3 and thence as signal s3 to linear activator t3 on mirror e2. Once mirrors e2 and e3 and beam splitters e1 and e4 are aligned, the stabilizing feedback loops just described will maintain alignment.

Figure 28A:
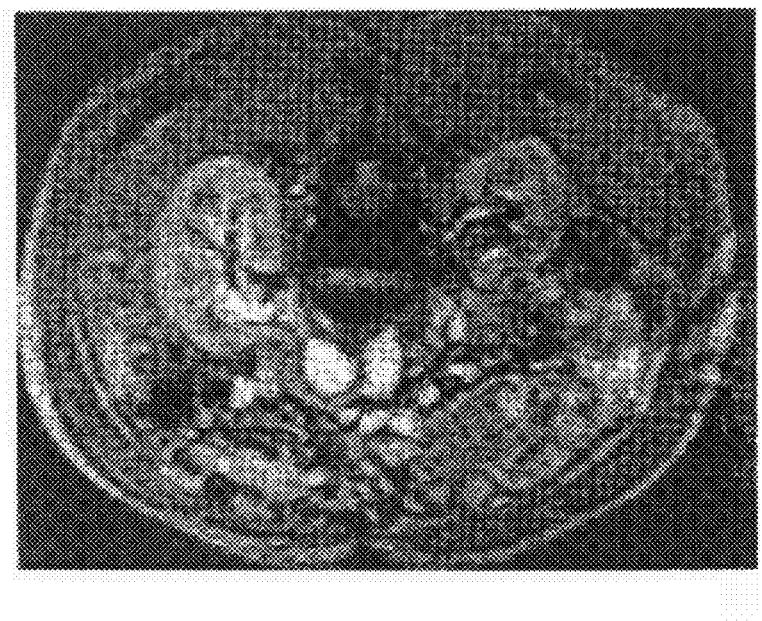
FIG. 28A through 30C are photographs of computer renderings of computer models and their reconstructions using inverse scattering.
Figure 28B:
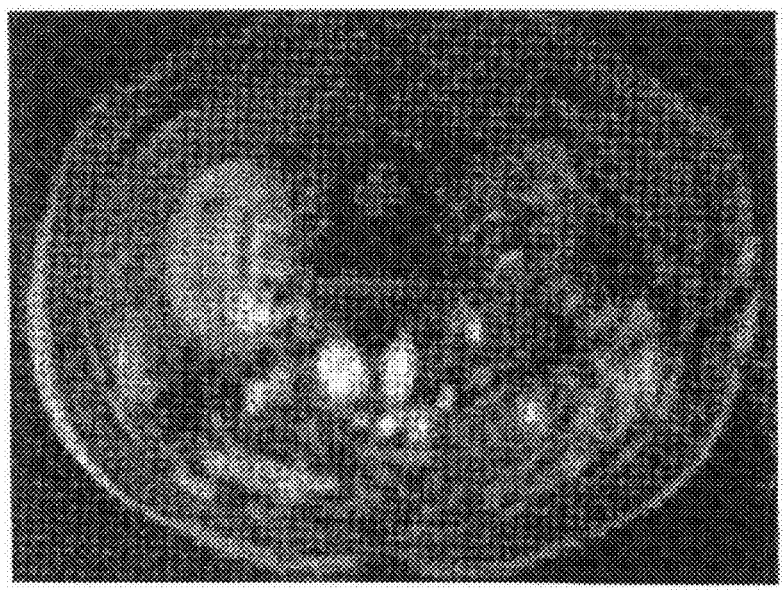

FIGS. 28A and 28B show an example of the application of inverse scattering to medical imaging through the use of computer simulation. FIGS. 28A and 28B also illustrate the powerful impact of a large inverse scattering image. FIG. 28A is a photograph of a cross section of a human through the abdomen that could appear in an anatomy atlas. The image was actually made on a magnetic resonance clinical scanner. This image is 200 by 200 pixels, each pixel being ¼ wave length square. It was used a the starting image in the process of creating synthetic scattering data. The pixel values in this image were assigned to a set of speed of sound values in a range that is typical for soft tissue. This range is typically plus or minus 5 percent of the speed of sound of water. Using this image of speed of sound the forward scattering algorithm then computed the scattered field at a set of detectors on the perimeter of the image for the case of incident plane waves for 200 source directions equally spaced in angle around 360 degrees. The detectors enclosed the cross section on all sides and numbered 4(200)×4=796. This set of synthetic scattering data was used to compute the inverse scattering image of FIG. 28B.

FIG. 28B shows the inverse scattering image computed from the synthetic data generated from the image in FIG. 28A. Note that the quantitative values in each pixel are preserved and that the spatial resolution is only slightly degraded.

Figure 29A:
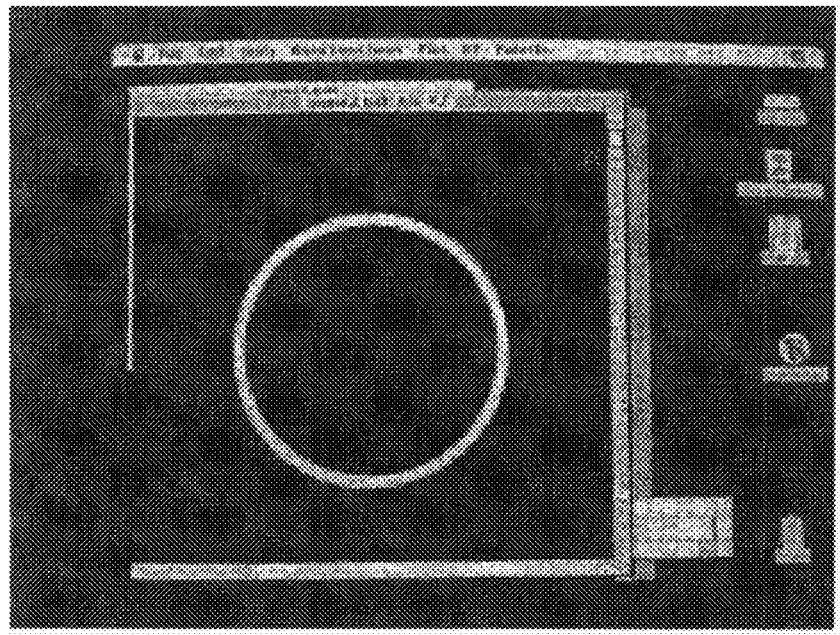
Figure 29B:
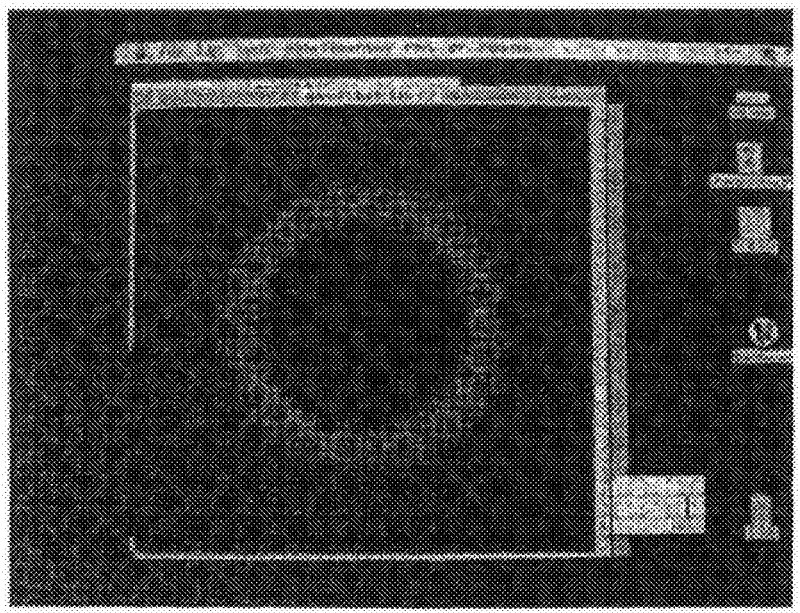

FIGS. 29A and 29B show that the quality of inverse scattering images of a test object computed from real data collected in the laboratory is excellent. The laboratory data was collected using microwave energy at 10 GHz. FIG. 29A is the image of the cross section of a test object that is a thin walled plastic pipe with an outside diameter of 6 cm and a wall thickness of 4 mm. This pipe was illuminated by microwaves at 10 GHz from a horn antenna. A second receiver horn antenna was rotated 120 degrees in both clock wise and counter clock wise directions from the forward propagation direction, about the sample to pick up the scattered field. The receiving antenna rotates around an axis that is parallel to the axis of the pipe. The transmitting antenna and the receiving antenna lie in a common plane that is perpendicular to the axis of the pipe. FIG. 29B is the inverse scattering image made from the data collected by the receiving antennas. The thickness of the pipe wall has been broadened because the true pipe wall thickness is less than one half-wave length at 10 GHz. The reconstructed wall thickness is about 0.6 wavelength.

Figure 29C:
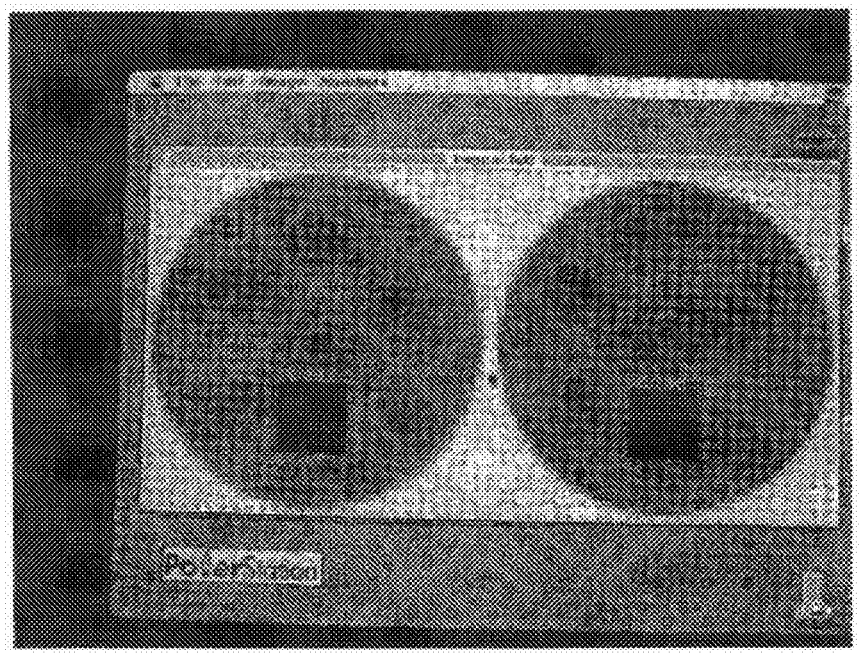
Figure 29D:
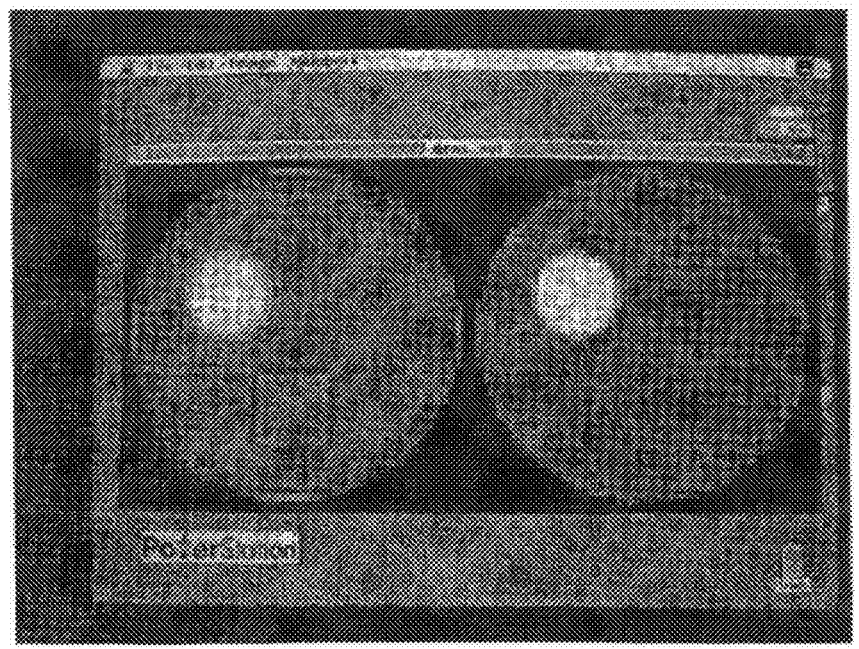
Figure 29E:
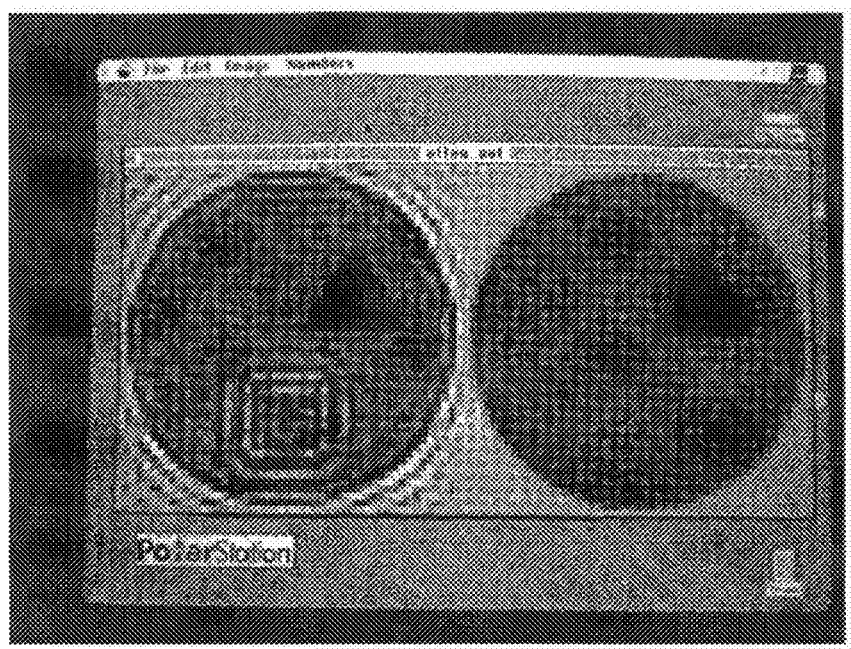

FIGS. 29C, 29D and 29E demonstrate through computer simulation that three different and independent acoustic parameters can be imaged accurately by inverse scattering. FIGS. 29C, 29D and 29E show respective images of compressibility, density and acoustic absorption. The images are 50 by 50 pixels, each pixel being ¼ wavelength square, and were reconstructed from frequencies in the range from f.sub.max to $f_{max}$/50. The sources were 8 plane waves equally distributed around 360 degrees. The receivers surrounded the object and were placed on the perimeter of the image space. In FIG. 29C an image of true compressibility in the test object is on the right while the reconstructed compressibility is shown on the left. The compressibility scattering potential component has a range of values spanning 0.2 for black, 0.1 for gray and 0 for white. The compressibility region is square in shape. Note that little cross coupling from density and absorption is present. FIG. 29D shows on the right an images of true density in the test object, while the reconstructed density is shown on the left. The density scattering potential component has a range of values spanning 0 for black, −0 025 for gray and −0.05 for white. The density region is circular in shape. Note that little cross coupling from absorption is present and a small amount from compressibility is present. FIG. 29E shows on the right an image of true acoustic absorption in the test object, while the reconstructed acoustic absorption is shown on the left. The attenuation scattering potential component has a range of values spanning 0 for white, 0.01 for gray and 0.02 for black. The absorption region is triangular in shape. Note that little cross coupling from density is present but a little cross coupling from compressibility is present.

Figure 30A:
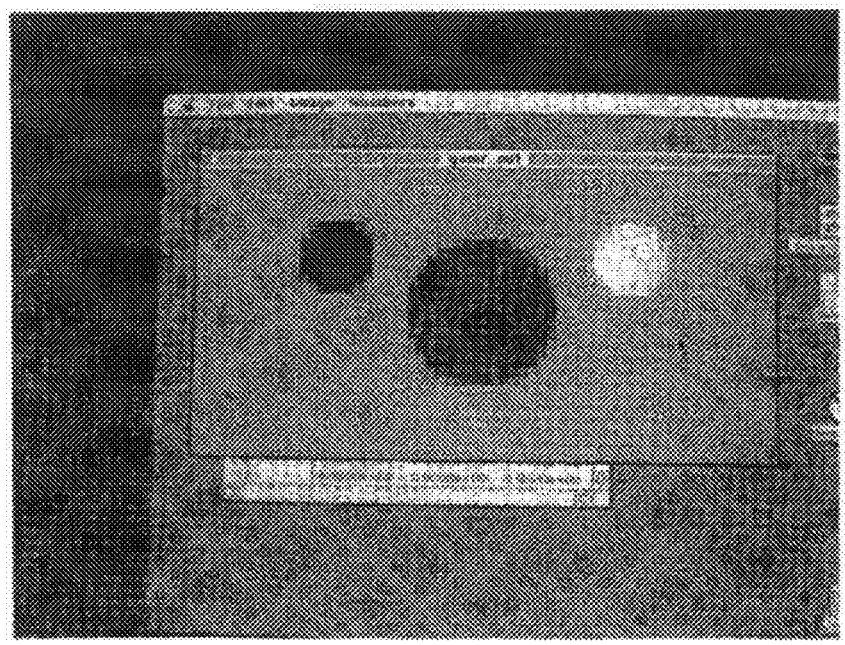
Figure 30B:
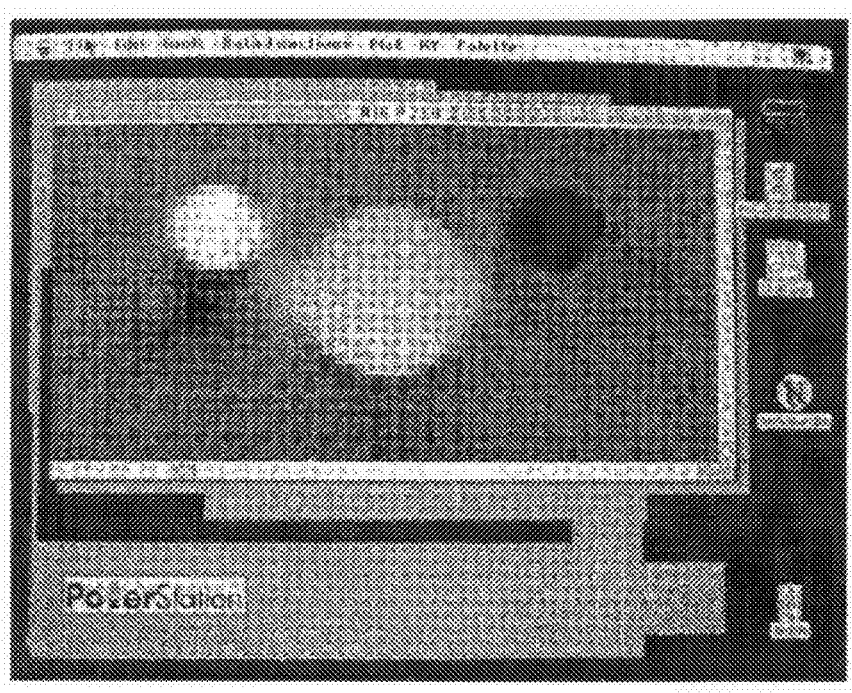
Figure 30C:
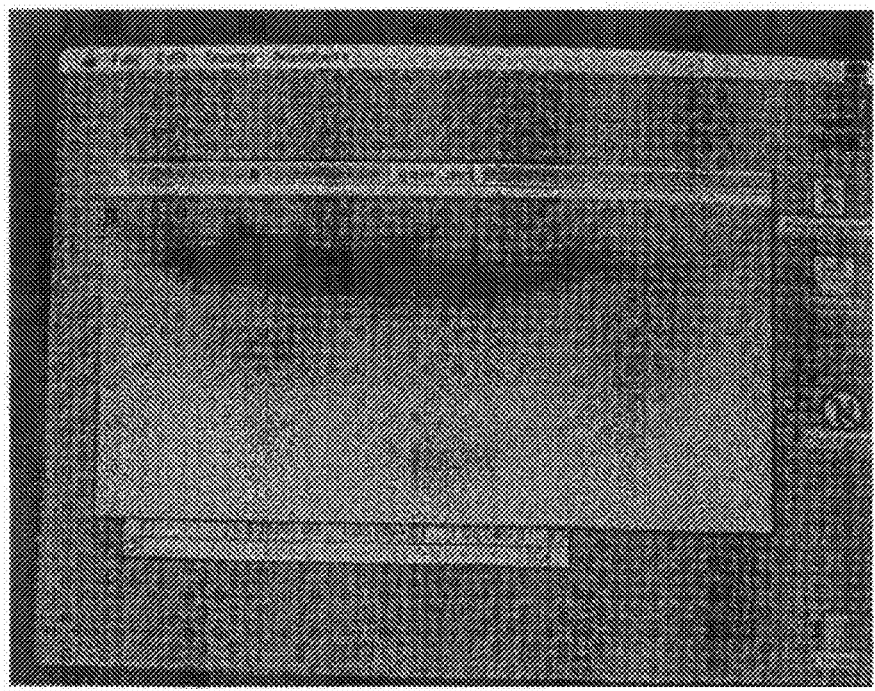
Figure 31A:
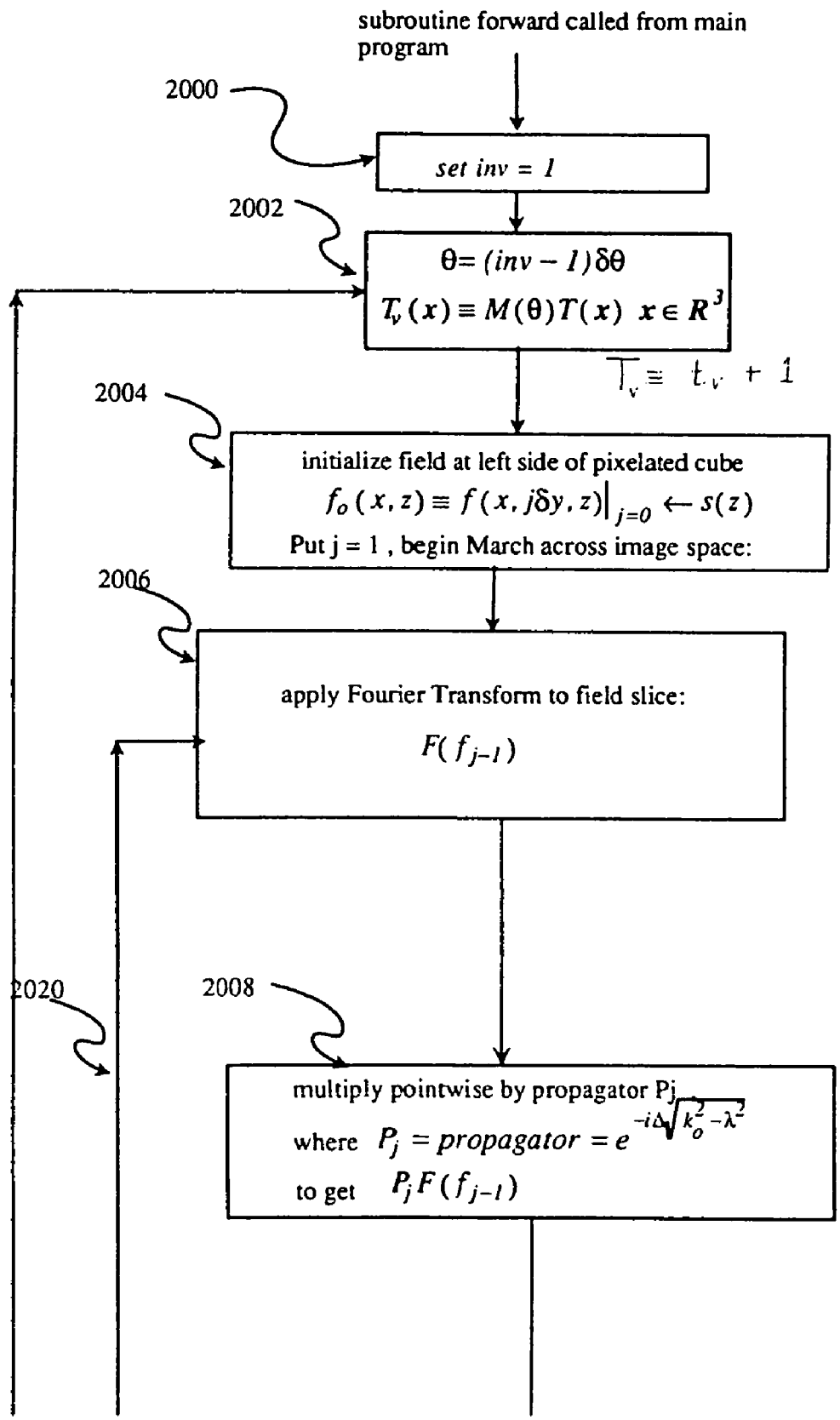
FIG. 31A. Example of subroutine forward called from main program.
Figure 31B:
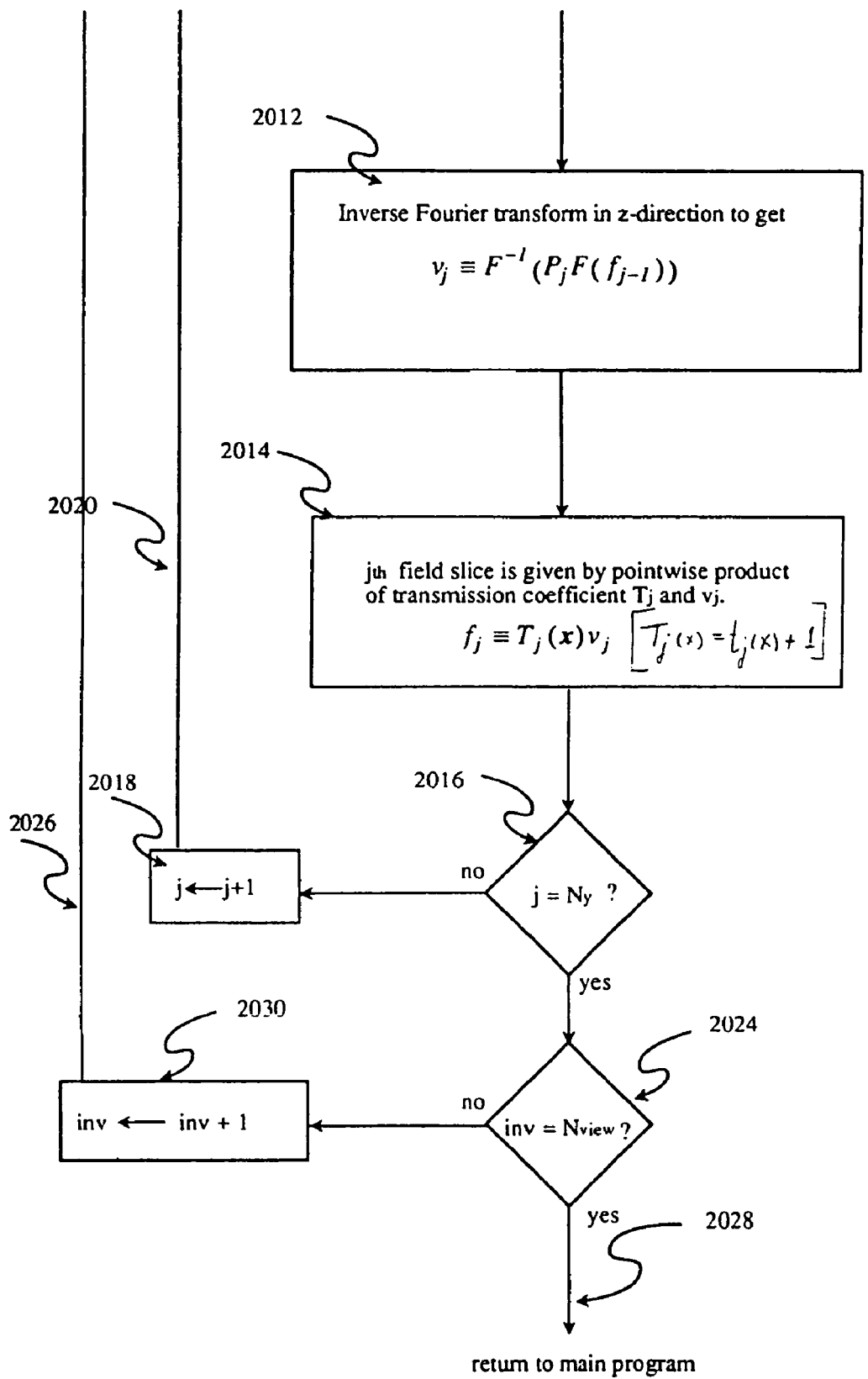
FIG. 31B. Example of subroutine forward called from main program continued.

FIGS. 30A, 30B and 30C describe the application of inverse scattering to the case where sources and detectors are limited to a single line (as in the case of 2-D scattering) or a single plane (as in the case of 3-D scattering). FIG. 30A shows the true scattering potential values for a test object. In this example, the scattering potential variation corresponds to different dielectric constants. The background dielectric constant corresponds to earth with a dielectric constant of 18 and extends to infinity on both sides and below the image space. Air, with a dielectric constant of unity lies above and next to the top of the image. The small black circle has a dielectric constant of 21.6; the small white circle on the right has a dielectric constant of 16.2; and the larger gray circle in the center has a dielectric constant of 19.8. The pixels are ¼ wave length on a side at the highest frequency. A set of 32 frequencies uniformly distributed between the highest to 1/32 of the highest are used. The image space is 64 pixels horizontally and 32 pixels vertically. 64 detectors and 5 sources are uniformly placed across the top of the image space. The scattering potential values, relative to the background dielectric constant of 18, (scattering potential=.∈/∈$_{background}$−1 span the range of 0.1 for black to −0.1 for white. A dielectric constant of 18 therefore corresponds to a scattering potential of zero.

FIG. 30B shows the inverse scattering reconstruction generated by imaging data synthesized from the model in FIG. 30A (please note that the image in this figure was accidentally video reversed). The synthesized data was inverted using a layered Green's function. Note the excellent spatial resolution and excellent quantitative accuracy of the reconstruction. FIG. 30C shows an image generated by using conventional radar beam forming methods. This conventional method places echoes at a given range and angle by processing the transmitted signals.into transmit beams and the received signals into receiver beams. This conventional method is mathematically equivalent to seismic migration imaging. Such methods are linear, not nonlinear as is inverse scattering. As such, linear methods do not accurately model multiple scattering, reverberation from the air-soil interface, and refraction. Such images are not quantitative. Note the inferior quality of this image relative to the inverse scattering image in FIG. 30B.

Inverse Scattering Scenarios

FIG. 1-A shows a typical imaging scenario, such as might be encountered in the geophysical applications. Half space 1300 represents air, with a speed of sound equal to about 344 meters/sec. The image space 1312 is divided up into "pixels" (1320), which cover the region to be imaged. The object to be imaged, 1310, is located within this pixel grid. The term "pixel" is usually associated with two dimensions, however, we apply the same discretization procedure in 3-D (voxels), and higher dimensions (or lower) are certainly possible. For the sake of brevity and clarity, we refer throughout this patent to "pixels", even though their n-dimensional counterpart is meant.

The layers 1302, 1304, 1306, and 1316 are arbitrary both in vertical dimension, as well as speed of sound associated with them. The sources 1314, and receivers 1298, are in both boreholes 1308.

FIG. 1-B shows a typical scenario such as might be encountered in nondestructive evaluation, or in geophysical imaging. The source positions 1314 are located along the top of the image space at the interface of half space 1340 (sea-water), and layer 1342. Layer 1344 is basement sediment, and the image space 1312 is divided up into pixels, 1320. The detectors, 1348 are also located at the sea-water interface. Notice that the sources and receivers in this case, and the previous case, are juxtaposed to the image space 1312, which contains 1350, the object to be imaged.

FIG. 1-C shows the reflection scenario, as in FIG. 1-B, with the twist that the sources and receivers (1314 and 1308 respectively) are located at some finite distance from the image space. This remote source/receiver geometry is also implementable with the cross-borehole geometry of FIG. 1A. The layers 1302, and target to be imaged 1310 are as before in FIG. 1A. The pixels 1320 are as before. The speeds of sound are such as to be appropriate to the geophysical case.

Software Description

Figure 8:
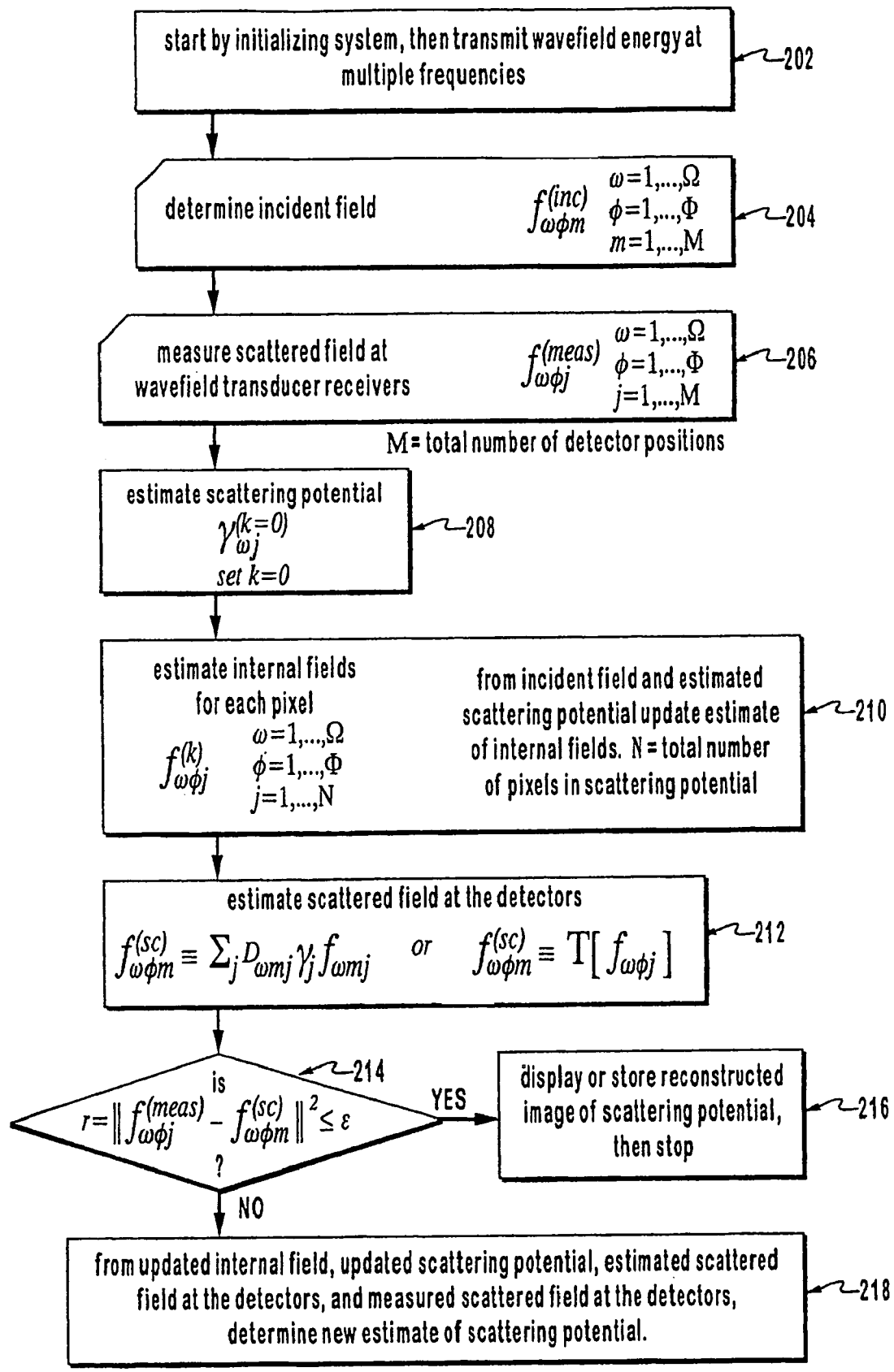
FIG. 8 illustrates a generic imaging algorithm, according to the present invention.

Having described some examples in the previous section which illustrate mathematical and physical models which may be used to model scattered wavefield energy and to process data so as to reconstruct an image of material parameters using inverse scattering, theory, reference is next made to FIG. 8.

Figure 1A:
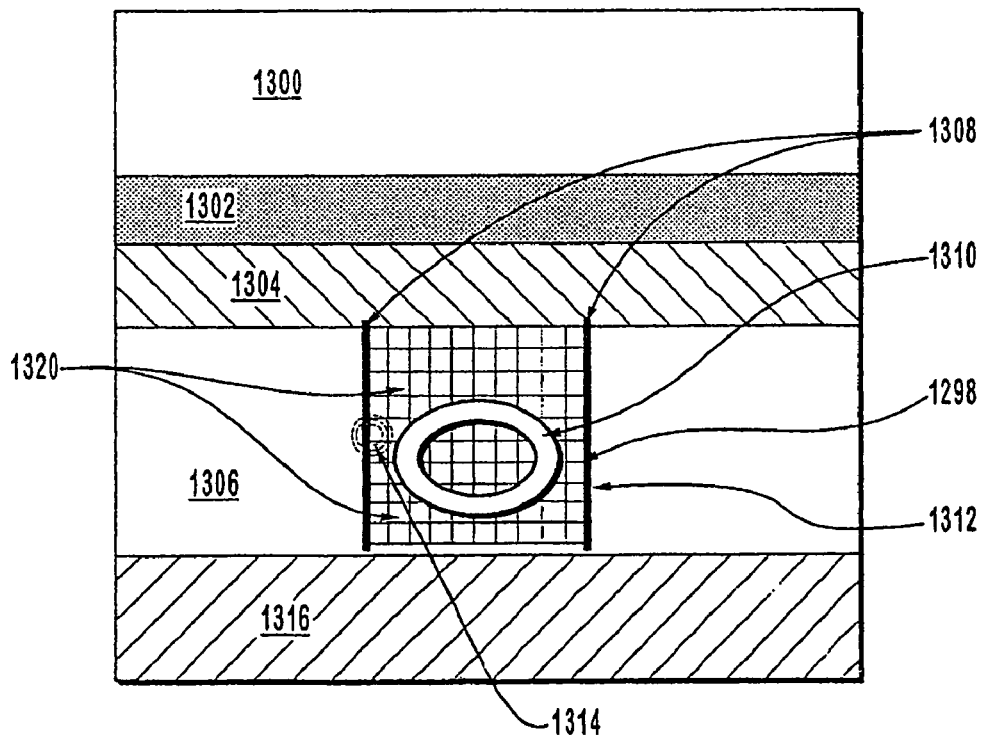
FIG. 1A is a two dimensional view of a cross-borehole geometry imaging method, according to the present invention, using inverse scattering.

This figure schematically illustrates a flow diagram for programming the CPU No. 118 or combination of CPU 118 and array processor 120 or parallel processor 146 in order to enable CPU 118 or said combination to control the electronic system of FIGS. 4 and 5 and the apparatus of FIGS. 1, 2, and 3 in accordance with one presently preferred method of the invention. It should also be understood that special purpose computational hardware should be constructed to incorporate the flow diagrams including FIGS. 8-26 and also explicitly encoded in Appendices A-J. These flow diagrams of FIGS. 8-26 are merely illustrative of one presently preferred method for programming CPU 118 using the scalar Helmholtz wave equation or vector wave equation or similar wave equation for modeling scattered wavefield energy as described in Example 1 in the Summary of the Invention section. Any suitable computer language which is compatible with the type of CPU 118 that is used in the electronic system can be used to implement the program illustrated in the diagrams and flowcharts. As shown in FIG. 8, the CPU 118 is programmed so that it will first cause the transmitter multiplexer 132 to sequence in turn each transducer or antenna so that each transmitter or antenna will in turn propagate a signal at a selected frequency. In the case of FIG. 4A, for each transmitter position sequential multiple frequencies may be transmitted by changing the frequency of the oscillator 128. On the other hand, in the system of FIG. 5A multiple frequency signals are transmitted by selecting and generating a type of waveform which inherently includes multiple frequencies. As schematically illustrated in Step 202, for each transmitter from which a signal is sent CPU 118 next causes a receiver multiplexer 134 to sequence each receiver array 108-115 so as to detect the scattered wavefield energy at each position around the ring of transducers 70. The source receiver geometry represented by Step 202 is not restricted to the ring of transducers 70. One alternative source receiver geometry is depicted in FIG. 1A. This figure depicts inverse scattering in a cross-borehole geometry relevant to geophysical imaging. This FIG. 1A shows four layers representing sedimentation sandwiched between two half spaces which represent, respectively, the ocean and the basement sediment. The image space is depicted and an object to be imaged, 1310 is shown. The sources and receivers are located down two boreholes which exist on either side of the image space. The receiver arrays 1308 detect scattered wavefield energy for each frequency that is transmitted. As described previously, the electronic system then amplifies the detected signals and processes the signals in order to develop the electronic analog of the real and imaginary components of each signal and in order to digitize each detected signal.

Once the scattered wavefield energy has been detected, processed, and digitized, CPU 118 next determines the incident field $f_{\omega\phi}^{inc}$, as indicated at step 204. The incident field is determined from the wavefield energy [i.e., frequency and amplitude components of the transmitted waveform] and transducer geometry from which the incident field is transmitted. The process of determining this incident field may involve direct measurement of the incident field or calculation of the incident field using the appropriate Green's function whether it be Biot, elastic, electromagnetic, scalar, vector, free space or some combination or permutation of these. The incident field is determined at each pixel in the imaged space for each source position $\phi=1, \ldots, \Phi$ and for each frequency $\omega$, which varies from 1 to $\Omega$. In step 206, the scattered wavefield is measured, recorded and stored at the wavefield transducer receivers for each $\omega$, varying from 1 to $\Omega$ each source position $1-\Phi$, and each pixel element at each wavefield transducer receiver position. As described in step 208, the initial estimate for the scattering potential is input directly into CPU 118 or estimated within CPU 118 from data input to it from some outside source. The initial estimate for the scattering potential can be set at either 0 or at an average value which is derived from the average material parameters estimated a priori for the object. When applicable, a lower resolution image of $\gamma$, such as produced by a more approximate method such as the time of flight method described in U.S. Pat. No. 4,105,018 (Johnson) may also be used to advantage (in the acoustic case) to help minimize the number of iterations. Similar approximations for other forms of wavefield energy may be used to advantage to help minimize the number of iterations.

Figure 7:
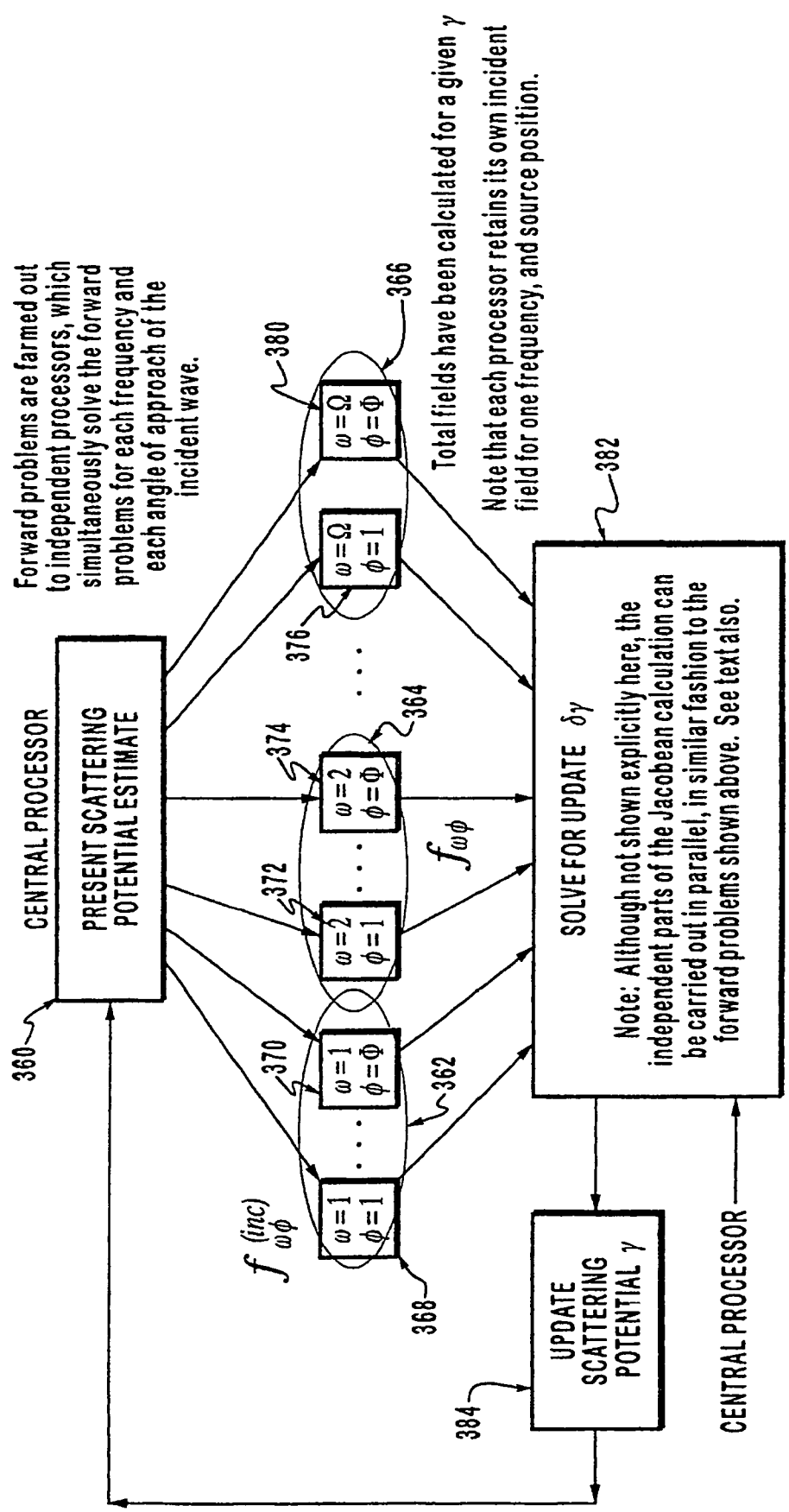
FIG. 7 shows parallelization of the forward problem according to the present invention.

CPU 118 next determines in step 210 an estimate of the internal fields for each pixel in the image space and for each frequency ω, and each source position Ω This estimate is derived from the incident field and the estimated scattering potential. This step corresponds to step 222 in FIG. 9A as well as to step 210 in FIG. 8. FIG. 7 is also relevant here. As is indicated in step 360 of FIG. 7, the present scattering potential estimate is used simultaneously in several independent processors so that the forward problems are farmed out to these independent processors which simultaneously solve the forward problems for each frequency and for each source position of the incident wavefield. These independent processors are labeled 368-380 in FIG. 7. It may be that there are not enough parallel processors available to farm out each incident field for each frequency and source position. However, effort should be made to delegate and solve as many forward problems independently and in parallel as possible. Ovals 362, 364 and 366 indicate that the forward problems for all possible source positions and a given fixed frequency can be calculated in one processor and simultaneously a second frequency forward problem can be calculated simultaneously in a second parallel independent processor. There is great flexibility in this approach and this example is not meant to be restrictive; for example, it is not difficult to see that the multiple frequency and source position parts of the Jacobian calculation can also be done in parallel in the same manner.

The total fields are then stored in central processor 382 of FIG. 7. For a given and fixed frequency ω, and fixed source position φ, the forward problem consists of using equation 1 or 17 of the Summary of Invention section to determine the total field $f_{\omega\phi}$ given the scattering potential γ and the incident field $f^{inc}_{\omega\phi}$ and the appropriate Green's function. This Green's function could be the scalar Green's function which is essentially the Hankel function of the second kind of zero order, or it could be the elastic Green's functions which is from the scalar Helmholtz Green's function, or it could be the Biot Green's function, or it could be the electromagnetic vector or scalar Green's function as well as a layered Green's function derived from one of the preceding green's function in the manner described in the Summary of the Invention section. The process whereby this is done is elucidated in FIGS. 11A-1, 11A-2.

Figure 1B:
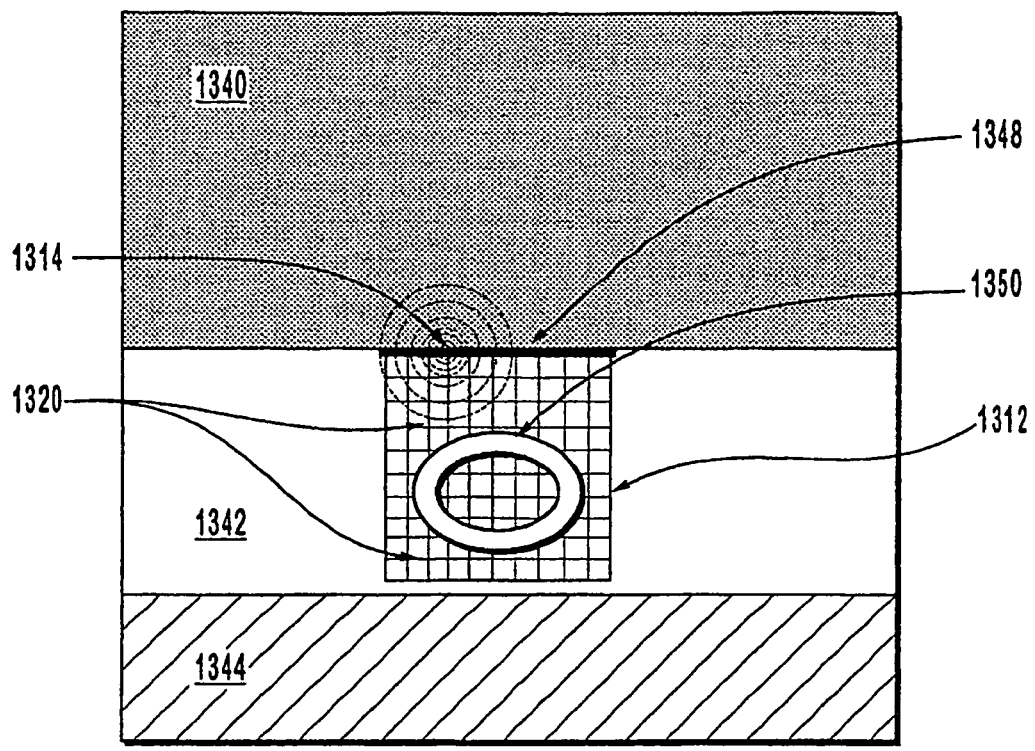
FIG. 1B is a two dimensional view of a reflection geometry imaging method, according to the present invention, using inverse scattering with both a wave energy source means and wave energy detection means juxtaposed to the image field.

Before applying this algorithm, it is required to discretize equation 1 or 17 of the Summary of Invention section so that it may be input into the CPU. This process is described in detail in the Summary of the Invention. The subroutine that solves the forward problem is given explicitly in Appendix B for the two-dimensional case and in Appendix F for the three-dimensional forward problem solution. Our algorithm uses the Whittaker sinc function which is defined on page 18, equation E of the Summary of the Invention. We use the sinc function because of its optimal approximating qualities. However, the infinite support of the sinc function precludes its use in certain situations. More specifically in the presence of layering, one-dimensional "hat" functions are required. This is outlined in detail after eqn (41) in the Summary of the Invention. The number of frequencies that are used in the inverse scattering problem is a function of the source receiver geometry, among other things. FIG. 1B shows the reflection-only source-receiver geometry prevalent in geophysics. In this scenario it is imperative to use multiple frequencies which distinguishes this case from FIG. 1A where, because the source receiver geometry allows transmission mode imaging only a small number of frequencies may be used. An example of such code using transmission mode imaging is given in Appendix H.

Figure 10:
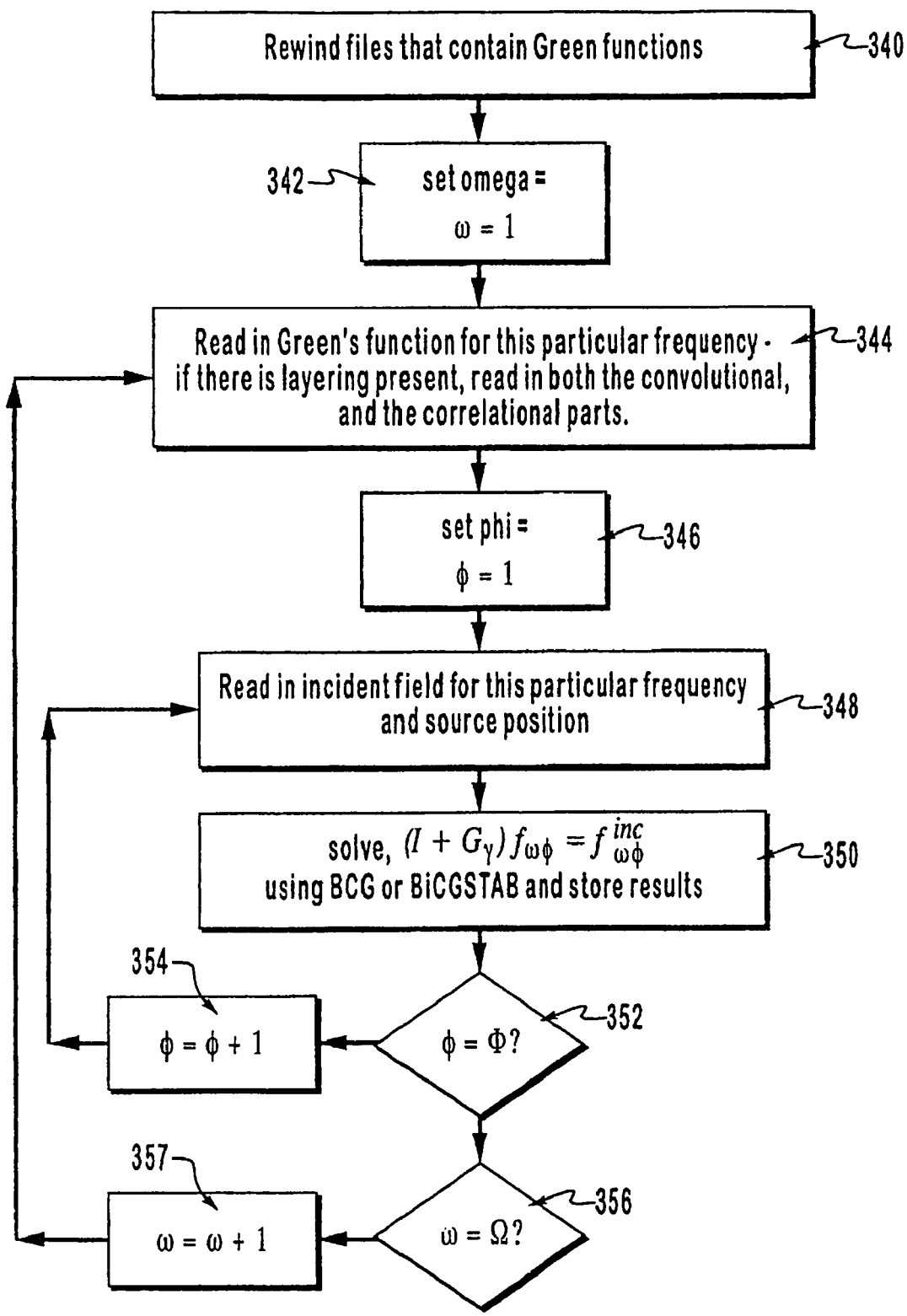
FIG. 10 shows the generic solution to the forward problem according to the present invention.
Figures 1, 11A:
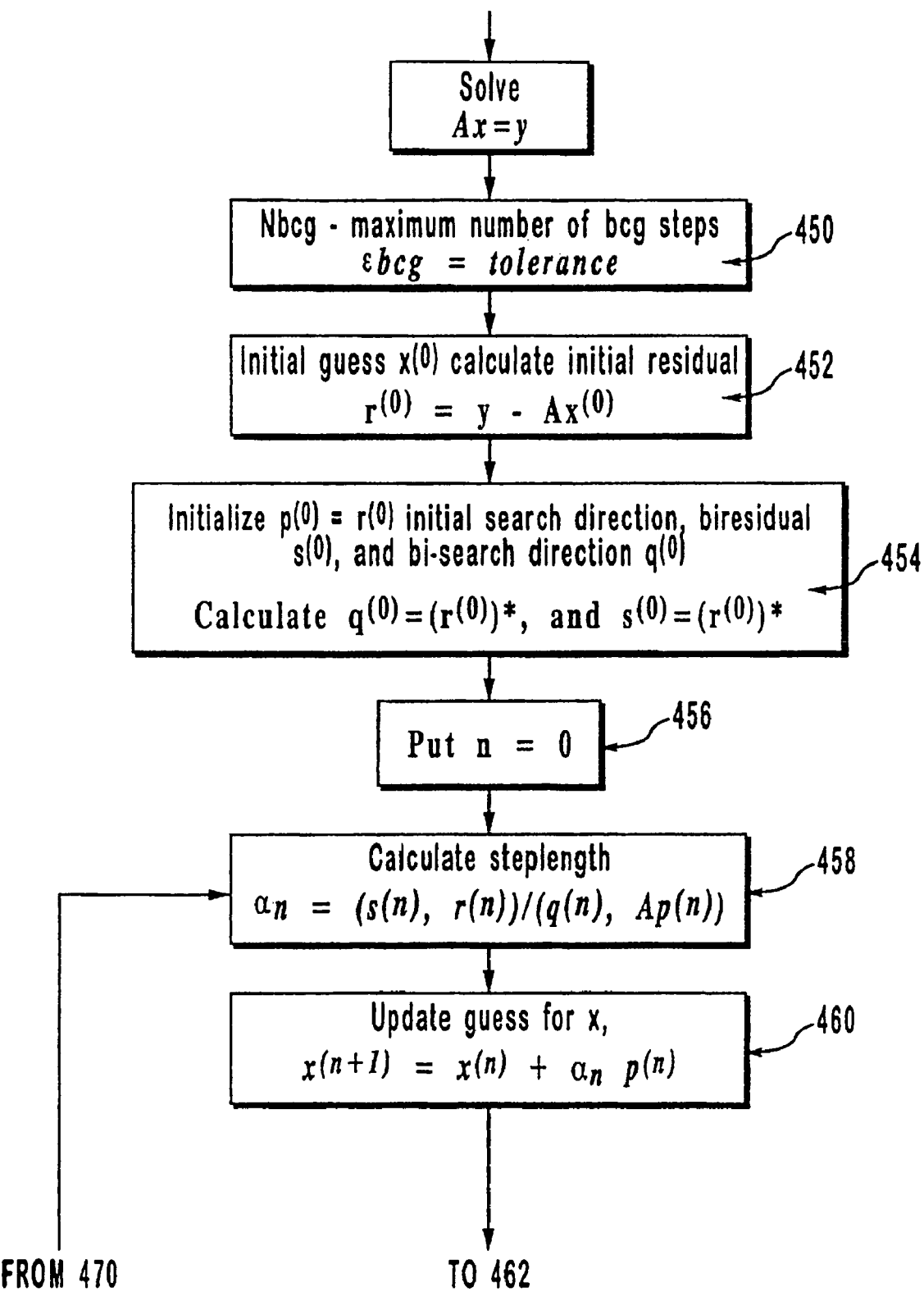
Figures 2, 11A:
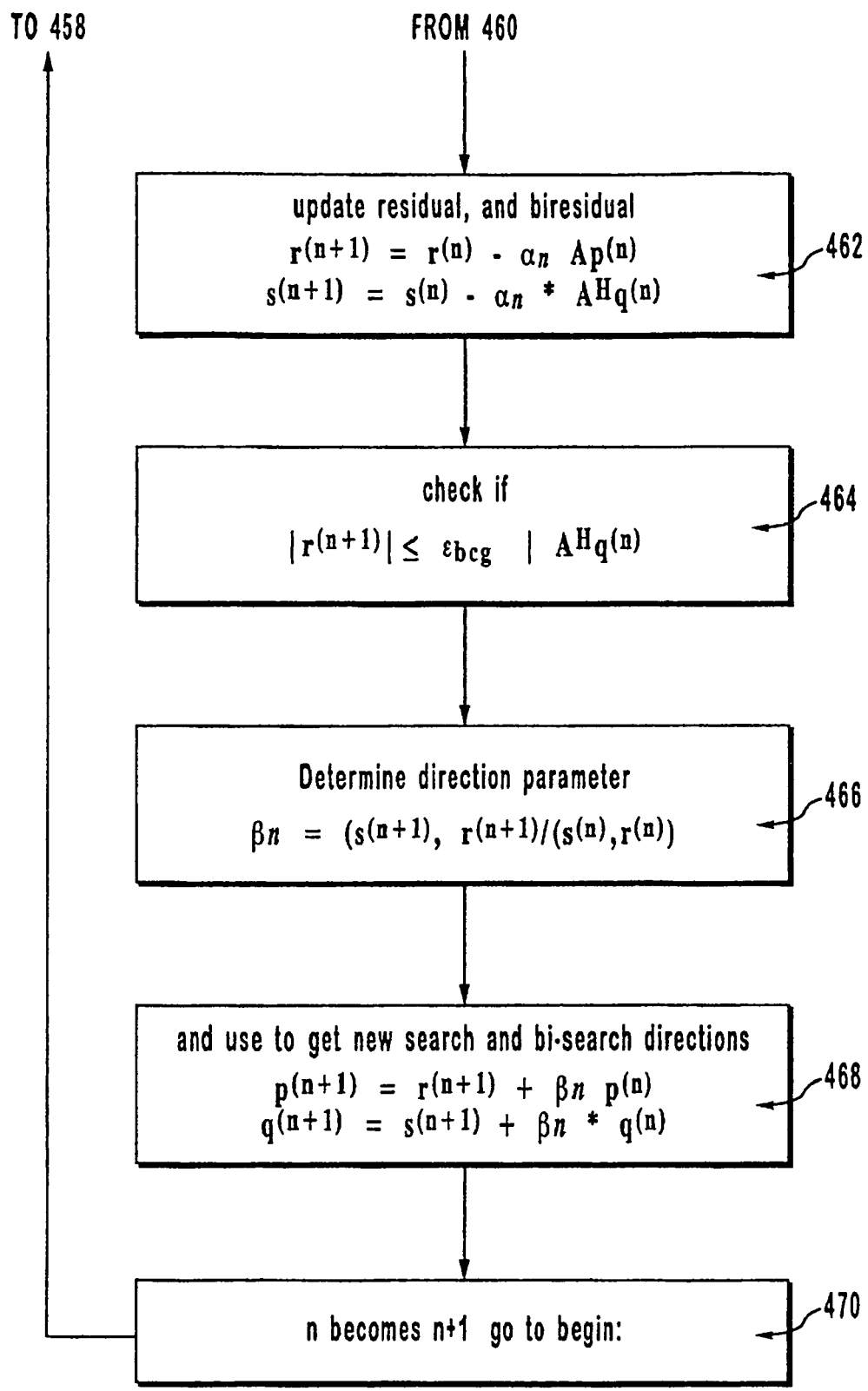

All forward problems for all possible frequencies, and all possible source positions are solved with one call of the subroutine in Appendix B for the two-dimensional case, and Appendix F for the three-dimensional case, whichever is relevant. FIG. 10 gives in detail the procedure for solving for the internal fields at all possible source positions and all possible frequencies. From step 222 in FIG. 9A we enter step 340 on FIG. 10. In step 340 of FIG. 10, all of the files that contain all of the Green's functions for all possible frequencies and the files that contain the incident fields for all possible frequencies and all possible source-positions are rewound. In step 342 of FIG. 10, ω is set equal to 1, i.e., we indicate that we are about to calculate the forward problem for the first frequency. In step 344 of FIG. 10, the Green's function for this particular frequency is read into memory. In step 346 of FIG. 10, the source position index φ, is set equal to 1 indicating that we are solving the forward problem for the first source position. In step 348, the incident field for this particular φ, i.e., source position, and this particular ω, i.e., frequency, is read into memory. In step 350, the forward problem for this particular frequency and this particular source position is solved using either biconjugate gradients or BiSTAB. This process is detailed in FIG. 11A-1/2 for the biconjugate gradient or BCG algorithm and FIGS. 11B-1/11B-2 for the BiSTAB or biconjugate gradient stabilized algorithm. In FIG. 11A-1, in step 450 which follows step 350 in FIG. 10, the predetermined maximum number of biconjugate steps and tolerance are read into memory, and the forward problem, which in discrete form reads $(I-G_\omega)f=f^{inc}$, is solved. For purposes of generality, we consider the BCG or biconjugate gradient algorithm applied to the system Ax=y. A is a matrix which is square, x and y is a vector of suitable dimension. Step 452 consists of reading in an initial guess $X^0$ and calculating an initial residual which is calculated by applying A to the initial guess $X^0$ and subtracting from the right-hand side Y. In step 454, the initial search direction $P^0$, bi-search direction Q, bi-residual S are calculated and stored. In step 456, we put N equal to 0. In step 458, we calculate the step length $\alpha_n$ by taking the inner product of the two vectors s and r, the bi-residual and residual respectively, and dividing by a quantity which is the inner product of two vectors. These two vectors are 1) q, the bi-search direction, and 2) the result of the application of the operator A to the present search direction P. In step 460 of FIG. 11A-1, the guess for x is updated as per the equation that is shown there. In Step 462, the residual R is updated as per the formula given, and the bi-residual S is updated as per the formula given. (H indicates Hermitian conjugate.) In particular, the bi-residual is given by the previous bi-residual $S^n$ minus a quantity which is given as $\alpha^*_n$, which is the complex conjugate of $\alpha_n$, multiplied by a vector, which is the result of the operation of the Hermitian conjugate of the operator A, applied to the vector q, the bi-search direction. This is carried out by a call to FIG. 13, which we discuss below. In step 464, check to see if the stop condition has been satisfied, i.e, is the present updated residual less than or equal to ε (which is given a priori) multiplied by the initial residual in absolute value. Step 466 consists of the determination of β, the direction parameter, which is given as the ratio of two numbers. The first number in this ratio is the inner product of the new updated bi-residual with the updated residual and the denominator is the inner product of the previous residual with the previous bi-residual, which has already been calculated in box 458. In step 468, use the calculated β to update and get a new bi-search direction, and a new search direction given by the formulas shown. In step 470, N is incremented by 1 and control is taken back to step 458. In step 458, a new step length is calculated, etc. This loop is repeated until the condition in step 464 is satisfied, at which time control is returned to step 350 in FIG. 10. The forward problem for this particular frequency and this particular source position has now been solved and the result, i.e. the internal field, is now stored.

Figures 1, 11B:
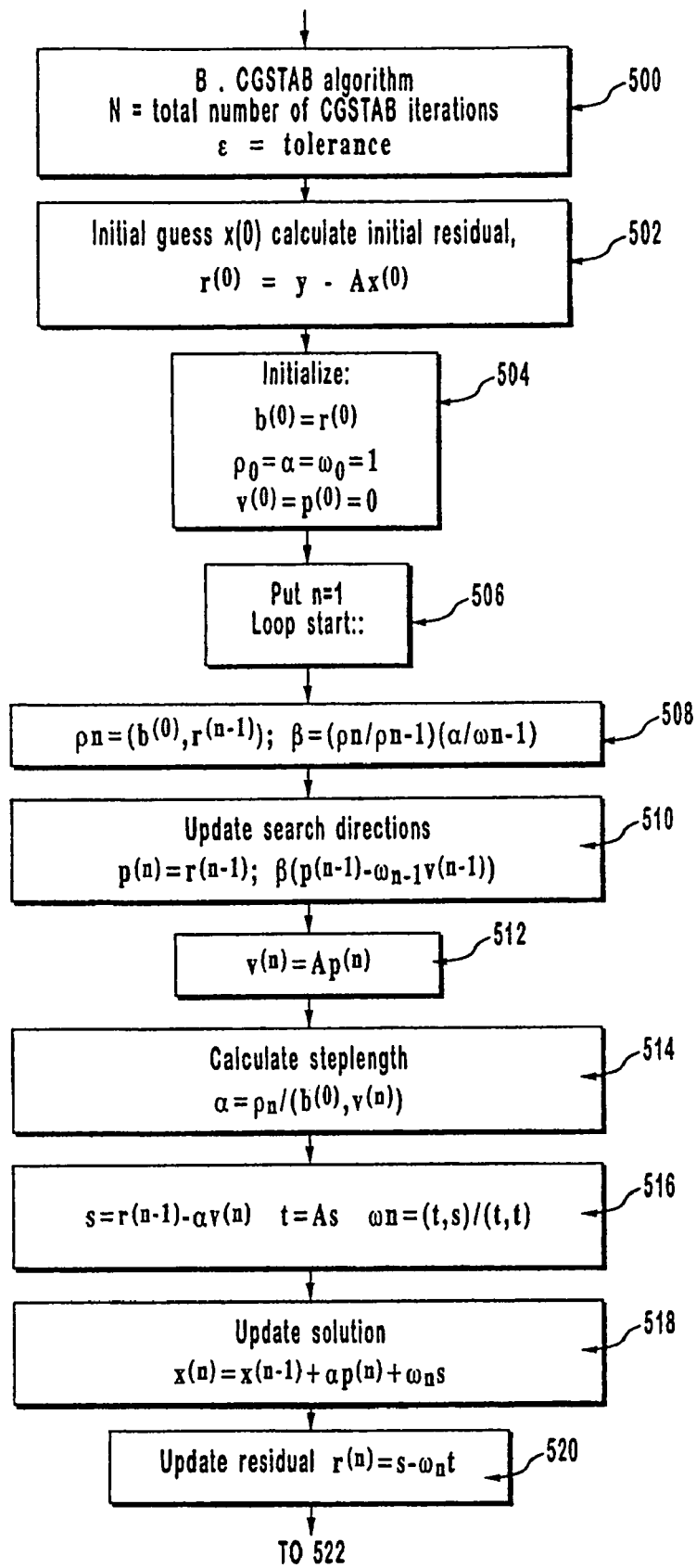
Figures 2, 11B:
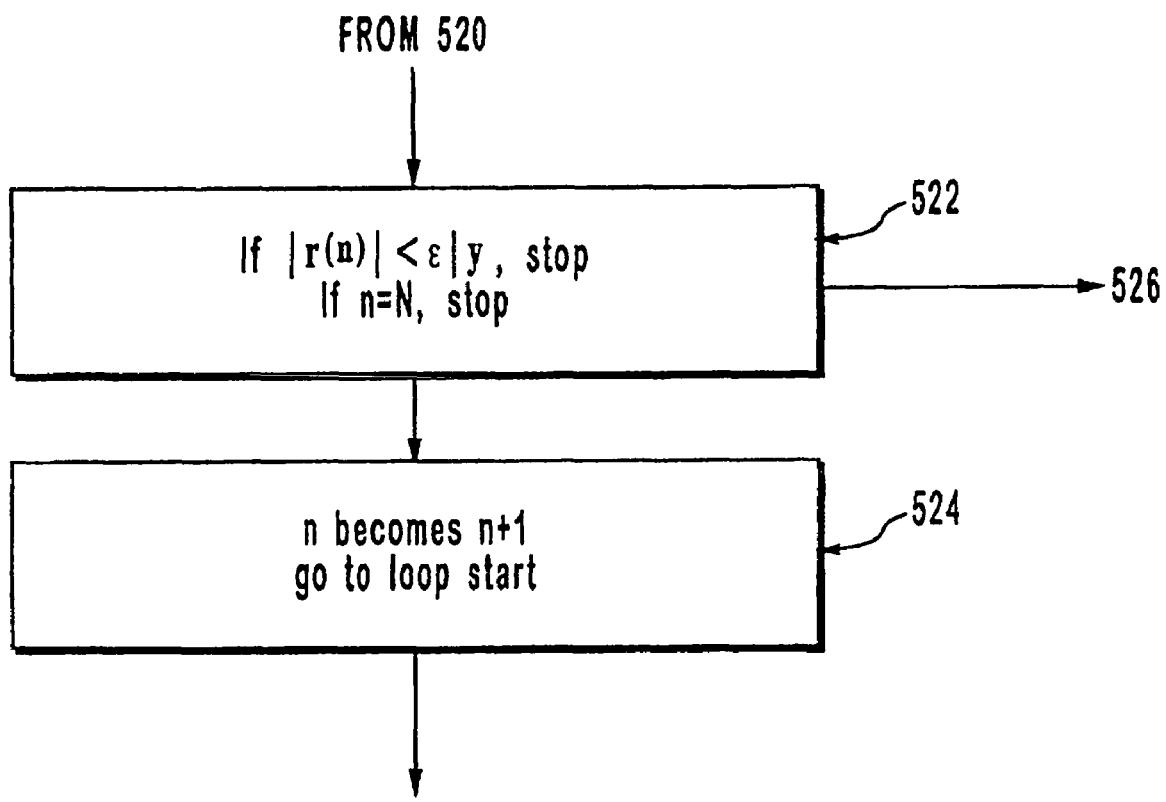
Figure 11C:
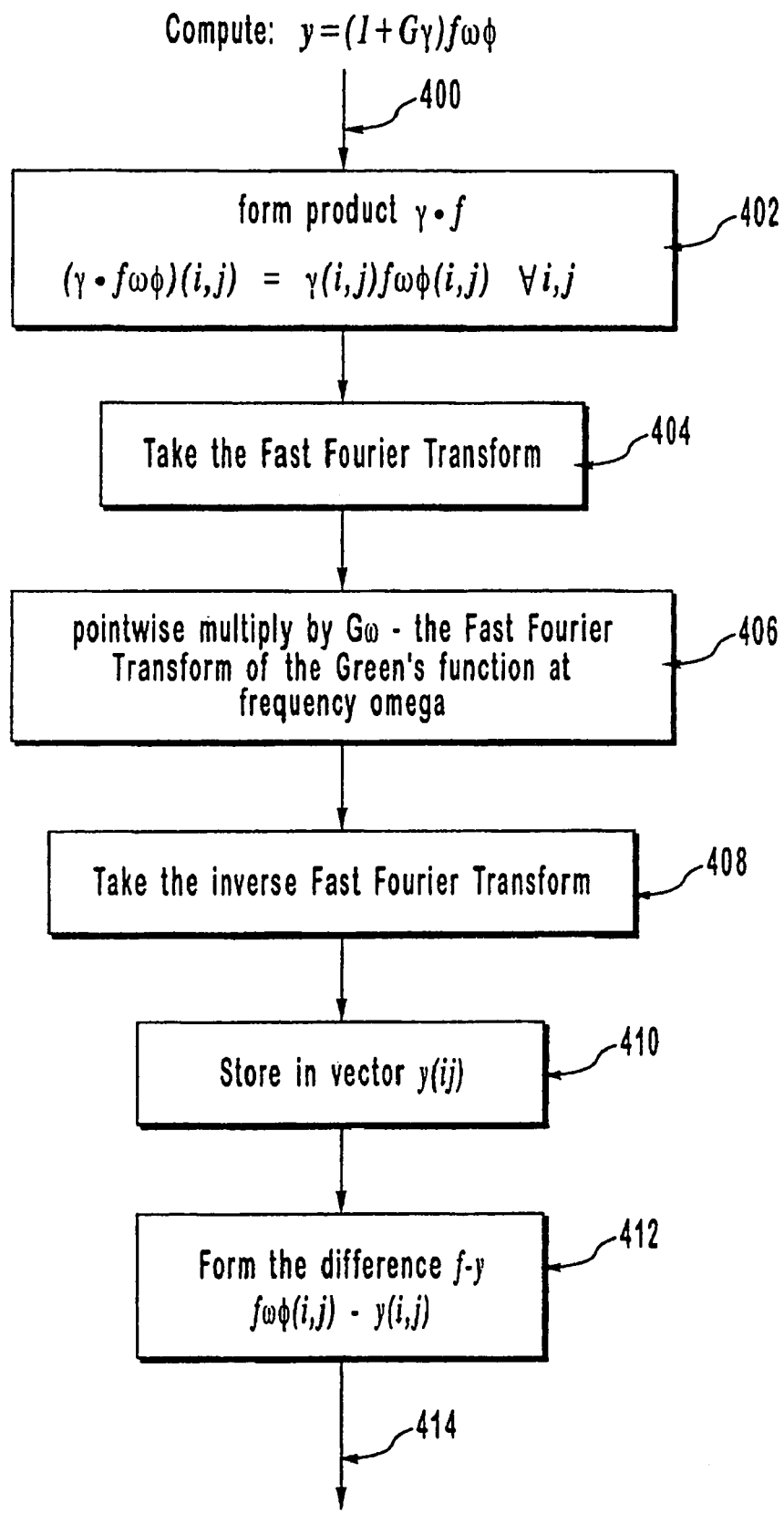
FIG. 11C illustrates the application of the Lippmann-Schwinger Operator to the internal field estimate according to the present invention.
Figure 13:
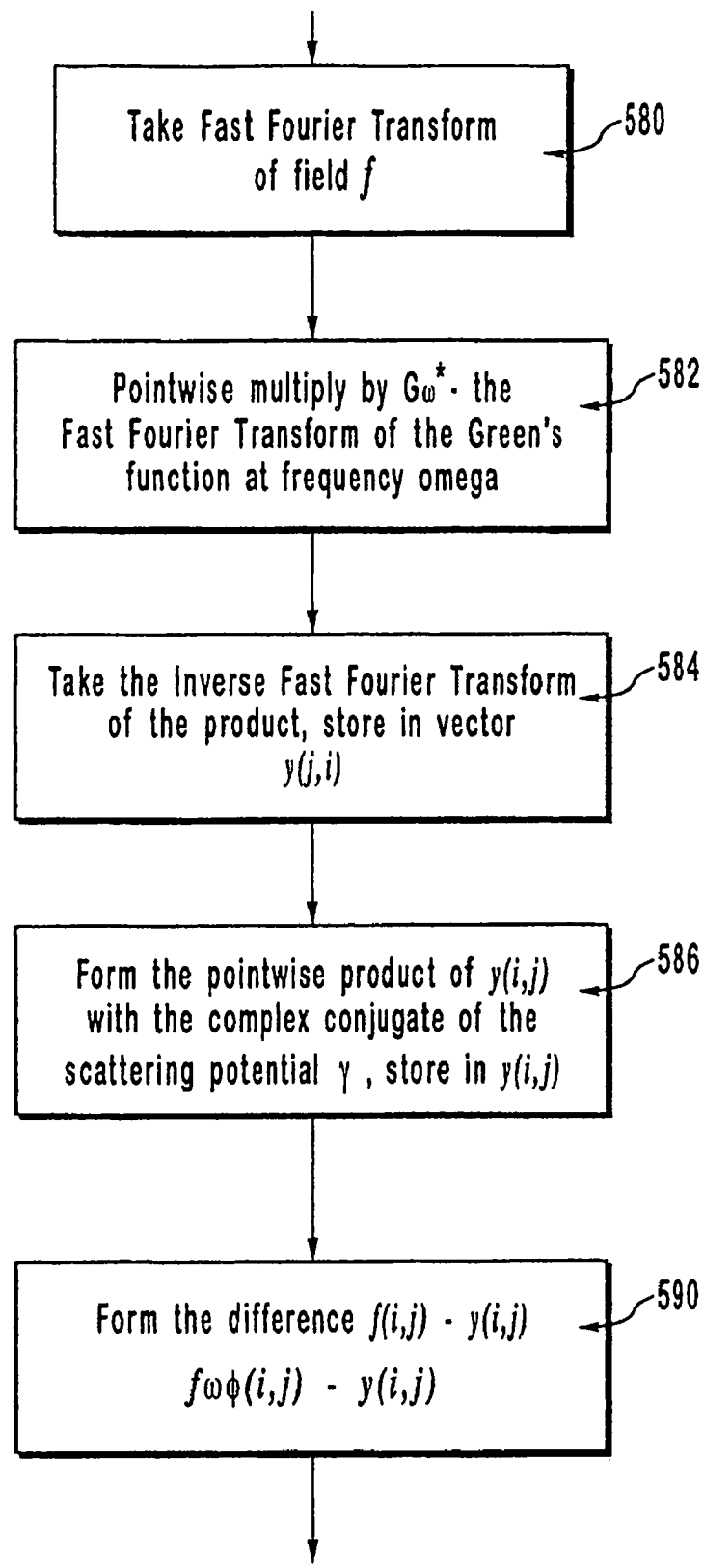
FIG. 13 illustrates the application of the Hermitian conjugate of the Lippmann-Schwinger operator.

In step 352, back in FIG. 10, it is determined if φ is equal to Φ, i.e. have we computed all the forward problems for this particular frequency for all possible source positions. If not, then φ is incremented by 1 in step 354 and control is returned to step 348 of FIG. 10. If so, we have calculated the forward problem for all possible source positions φ and control is transferred to step 356 where it is determined if ω is equal to Ω, i.e. have we calculated the forward problem for all possible frequencies ω?" If not, ω is incremented by 1 in box 357 and control is returned to step 344. If so, we have completed the computation of the internal fields for all possible source positions and all possible frequencies and have stored the results, i.e. we have finished the subroutine in Appendix B and Appendix F for the two-dimensional or three-dimensional problem, respectively. Control is now transferred to the main program which is in Appendix A for the two-dimensional case, and in Appendix E for the three-dimensional case. This corresponds to step 224 in FIG. 9A. This also corresponds to step 212 of FIG. 8. FIGS. 9A, 9B, 9C, 9D together comprise an expanded version of the inverse scattering algorithm in its entirety, which is given in compressed form by FIG. 8. Before proceeding further to describe in detail step 212 of FIG. 8, i.e. also FIG. 226 of FIG. 9A, we mention that the BCG algorithm just described may be replaced by the BiSTAB (biconjugate gradient stabilized algorithm) of FIGS. 11B-1/11B-2. Furthermore, in the calculation of both the BiSTAB algorithm or the biconjugate gradient algorithm, the implementation of the operation of the operator A acting on the vector x is carried out in a very specific manner which is described in FIG. 11C. Furthermore, in FIG. 13, the hermitian conjugate of the operator A, denoted $A^H$, is applied to vectors in its domain. Specifically, in step 400 of FIG. 11C, we come in from any step in FIG. 11B-1/11B-2 or 11A-1/11A-2, respectively, the conjugate gradient stabilized algorithm or the bi-conjugate gradient algorithm which requires the calculation of the operation of the operator A acting on the vector "x". In step 402, the pointwise product of the scattering potential γ and the present estimate of the internal field at frequency ω and source position φ is formed and stored. Step 404, the Fast Fourier Transform (FFT) of this pointwise product is taken. In step 406, the result of the Fast Fourier Transform (FFT) taken in step 404 is pointwise multiplied by $G_\omega$ which is the Fast Fourier Transform (FFT) of the Green's function at frequency ω, which has been stored and retrieved. In step 408, the inverse Fast Fourier Transform (FFT) is taken the pointwise multiplication that was formed in the previous step. In step 410 this result is stored in vector y. In step 412 the difference, taken pointwise, of the $f_{\omega\phi}$, the present value for the internal field at frequency ω, and source position φ, and the constructed vector y is taken. Step 414 returns control to either the BCG or the BiSTAB algorithm, whichever has been called by step 350 of 10. The application of the operator which is described in FIG. 11C is carried out multiple times for a given call of the biconjugate gradient or the BiSTAB algorithm, it is imperative, therefore, that this step be computed extremely quickly. This explains the presence of the fast Fourier transforms to compute the convolutions that are required. This operator, (I–Gγ) symbolically written, we refer to as the Lippmann-Schwinger operator. FIG. 13 calculates the adjoint or hermitian conjugate of the given Lippman-Schwinger operator and applies this to a given vector. Step 580 of FIG. 13 takes control from the appropriate step in the biconjugate gradient algorithm. It is important to note that the BiSTAB algorithm does not need to compute the adjoint of the Lippmann-Schwinger operator. Therefore, FIG. 13 is relevant only to FIGS. 11A-1 and 11A-2, i.e. the biconjugate gradient algorithm. In step 580 of FIG. 13 the Fast Fourier Transform (FFT) of the field f to which the adjoint of the Lippmann-Schwinger operator is being applied, is taken. In step 582 of FIG. 13, the Fast Fourier Transform (FFT) computed above is pointwise multiplied by $G^*_{\omega}$, the complex conjugate of the Fast Fourier Transform (FFT) of the Green's function at frequency ω. In step 584, the inverse Fast Fourier Transform (FFT) of this pointwise product is taken and stored in vector y. In step 586, the pointwise product of the complex conjugate of γ, the present estimate of the scattering potential is taken with the vector y. The result is stored in vector y. In step 590, the difference is formed between the original field to which the adjoint of the Lippmann-Schwinger operator is being applied, and the vector y just calculated. Now $(I-G\gamma)^{H f_{\omega\phi}}$ has been calculated and control is now returned to box 462 of FIG. 11A-1/11A-2, the biconjugate gradient algorithm, where use is made of the newly created vector, $A^H q$. Next the stop condition is checked at step 464.

Figure 9A:
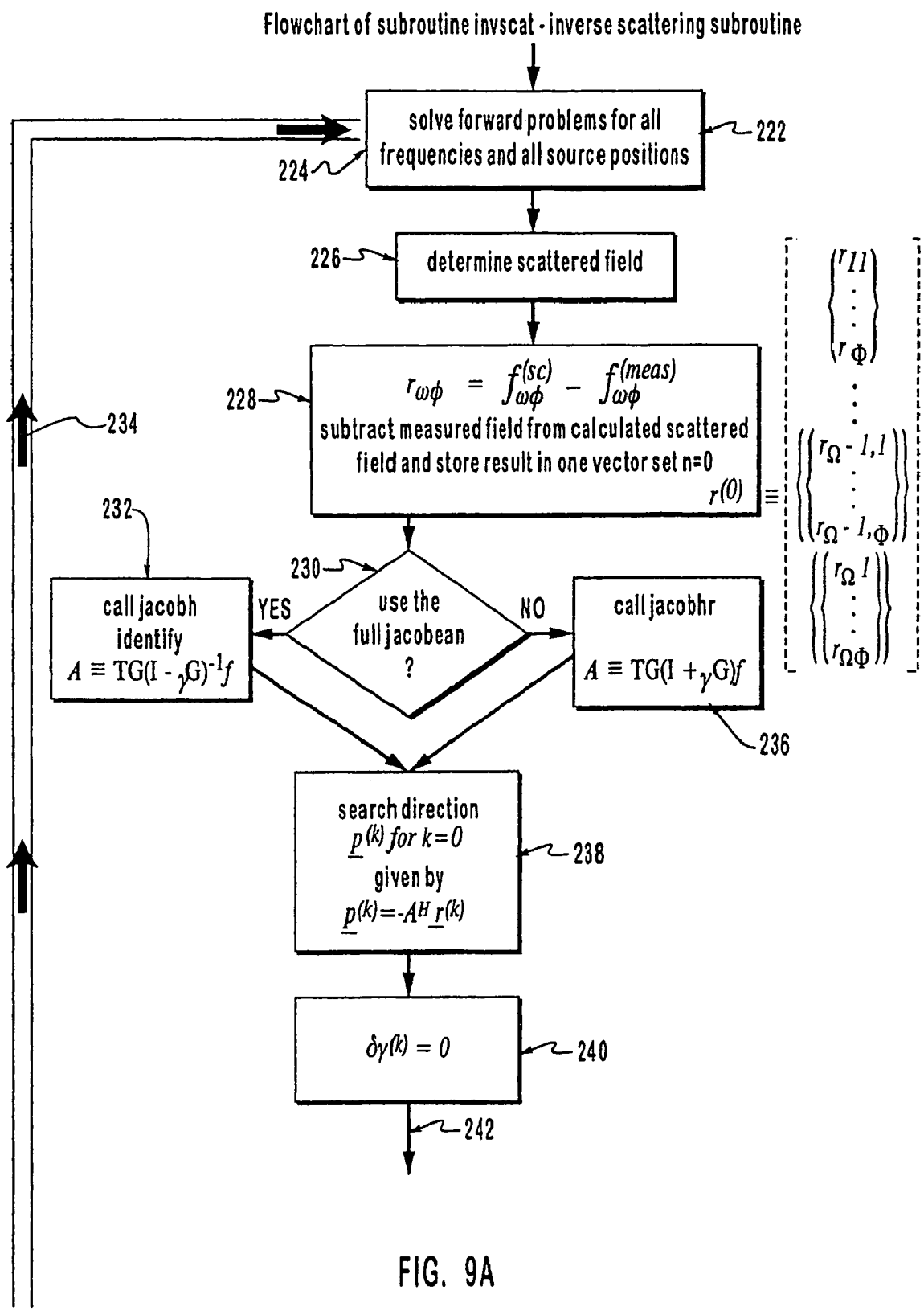
FIGS. 9A through 9D detail an expanded imaging algorithm with respect to that shown in FIG. 8 which schematically illustrates a flow diagram for programming a computer or combination of computer and array processor or parallel processor to enable the computer or combination mentioned to control the electronic system of FIG. 4 or 5 and the apparatus of FIGS. 1-3 so as to rapidly develop a reconstruction of the image of an object from scattered acoustic energy using inventive scattering techniques, in accordance with one presently preferred method of the invention.
Figure 9B:
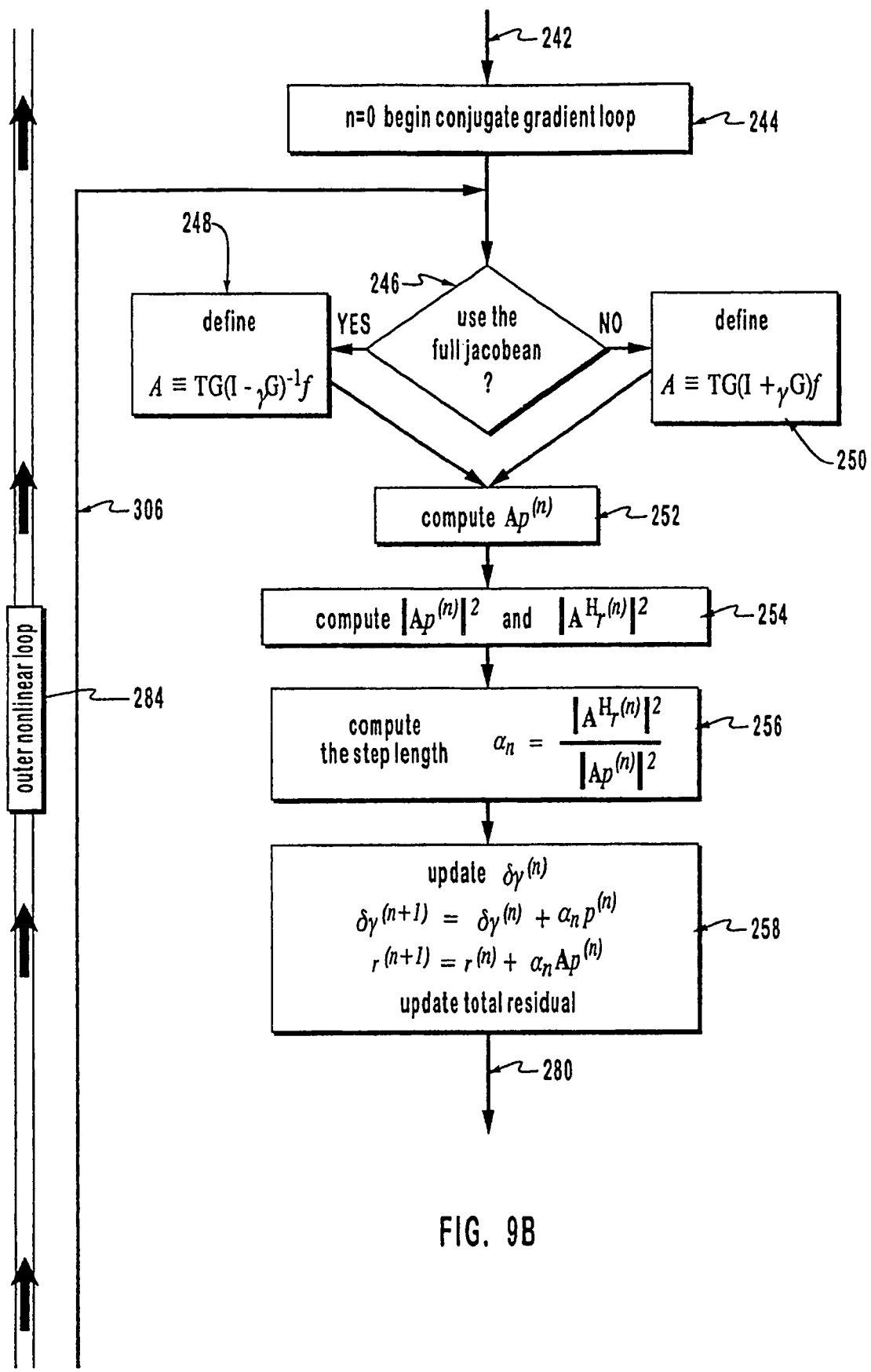
Figure 9C:
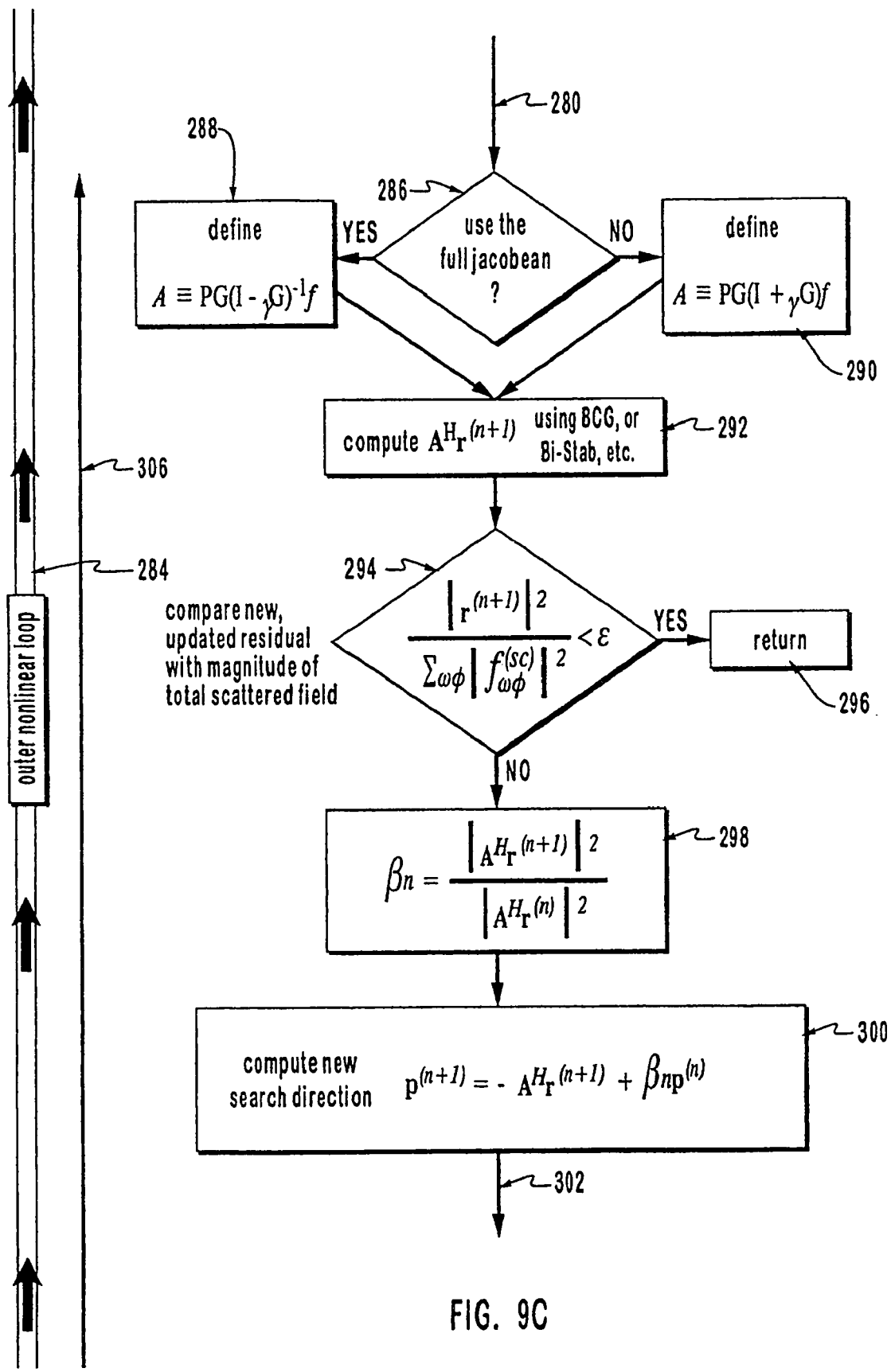
Figure 9D:
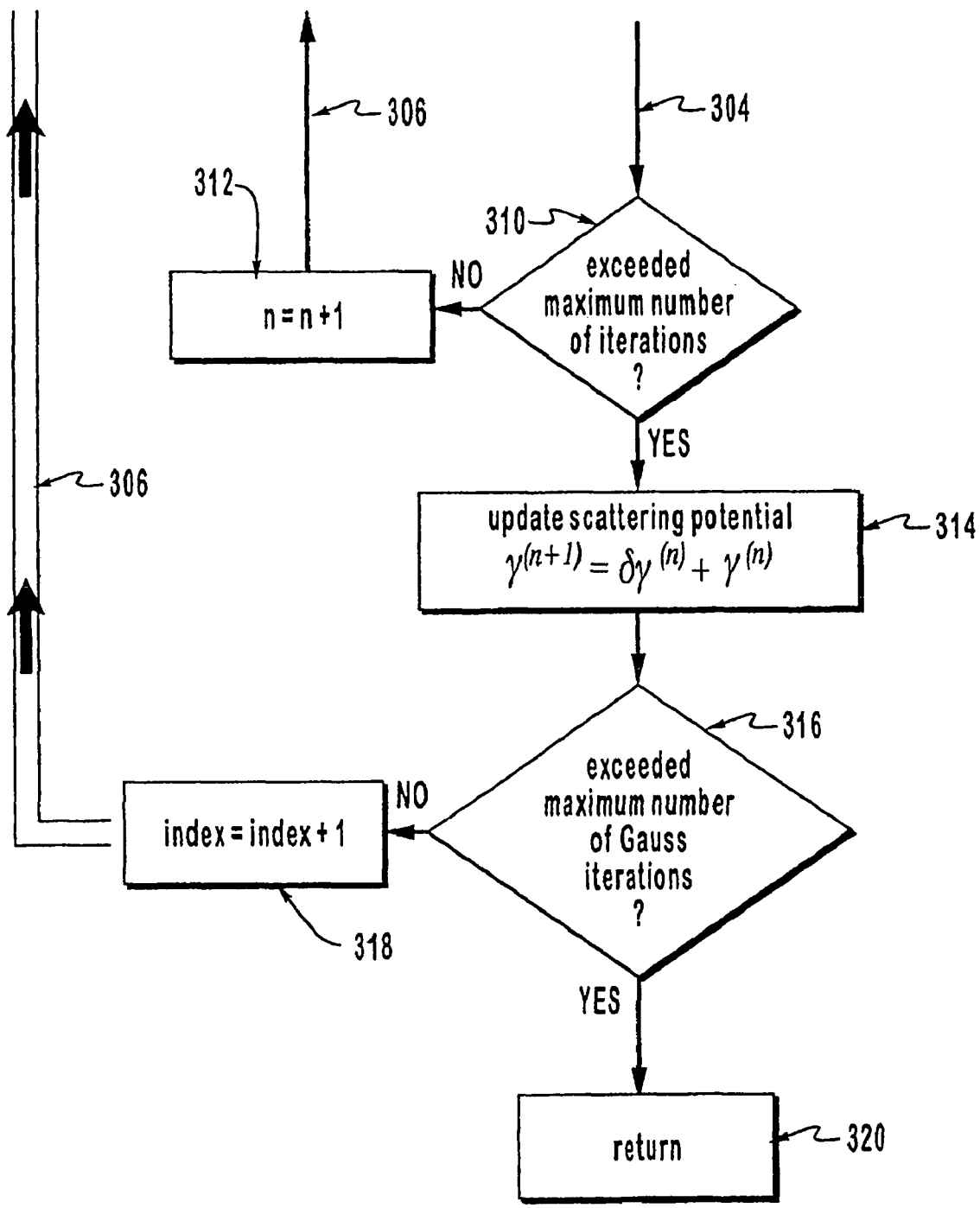

We now return to step 224 of FIG. 9A, i.e. step 212 of FIG. 8 where we determine the scattered field at the detector locations for all possible source positions, i.e. incident fields and also all possible frequencies ω. This process is carried out in FIG. 26, to which we now turn.

Figure 21:
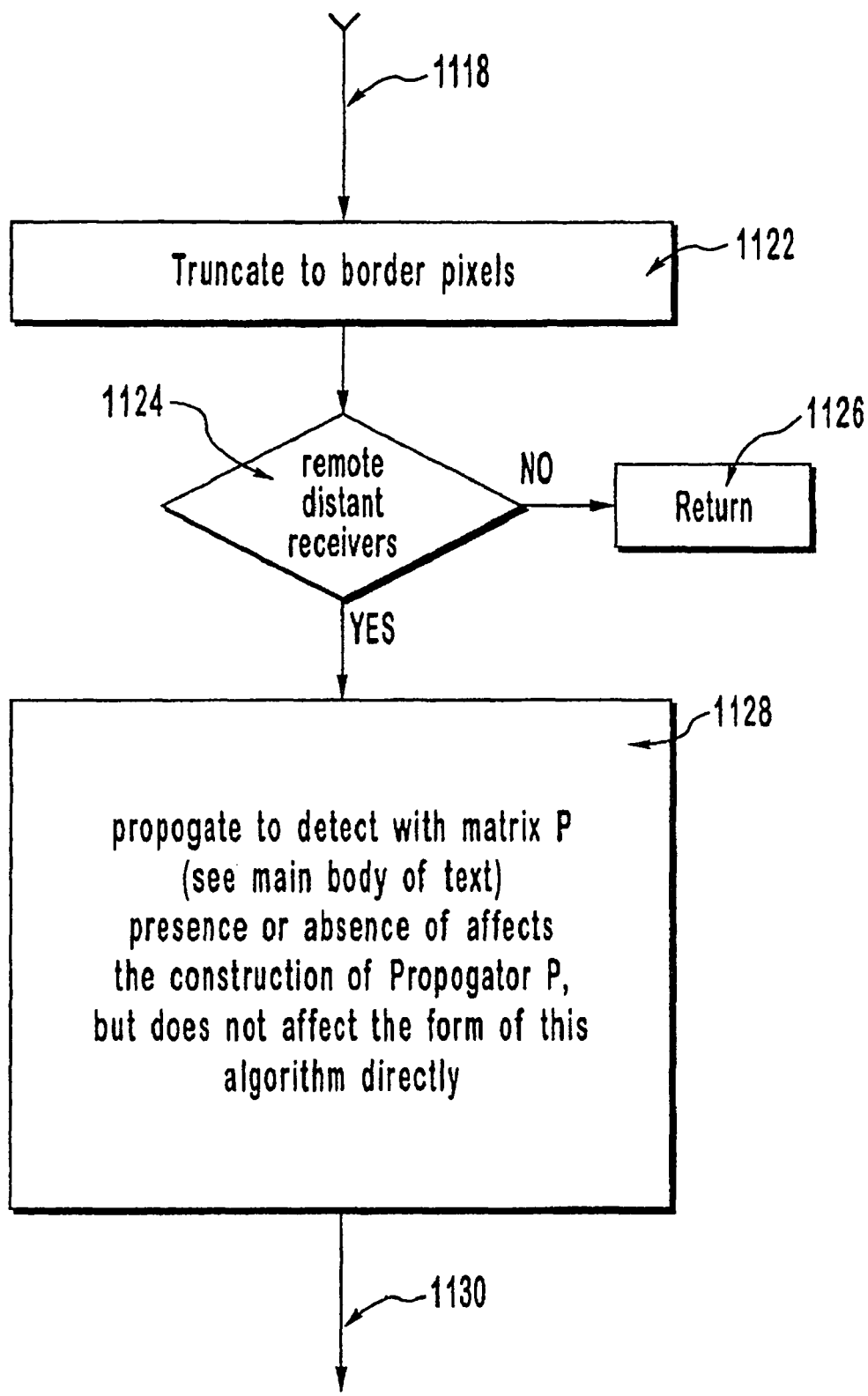
FIG. 21 illustrates the propagation or transportation of fields from image space to detector position.
Figure 26:
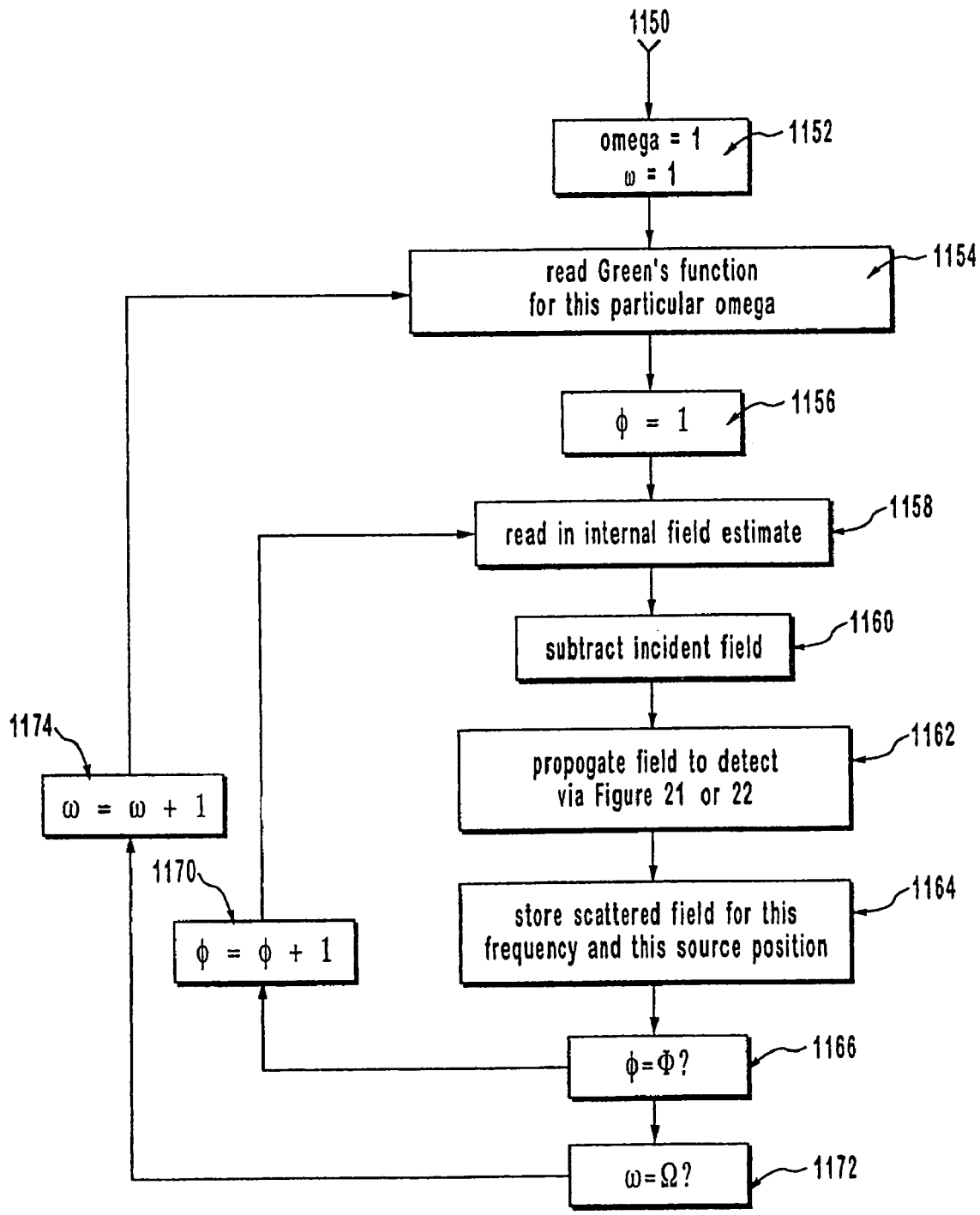
FIG. 26 illustrates the scattering subroutine, according to the present invention.

Step 1150 of FIG. 26 transfers control to step 1152 of FIG. 26 where ω is set equal to 1. Control is then transferred to step 1154 where the Green's function for this particular ω is read into memory. Control is then transferred to step 1156 where φ is set equal to 1. Control is then transferred to step 1158 where the internal estimate for this source and this frequency is read into memory. Control is then transferred to step 1160 where the incident field is subtracted from estimated total internal field. In step 1162 the truncation or propagation operator shown FIG. 21 is performed. When the truncation or propagation has been performed, control is transferred back to FIG. 26 and in step 1164 the calculated scattered field is stored. In step 1166 it is determined if φ is equal to Φ, if it is not, then φ is incremented by one, in step 1170, and control is returned to step 158 of FIG. 26. If φ is equal to Φ, then control is transferred to step 1172 where it is determined if ω is equal to Ω. If it is not, ω is incremented by one in step 1174, and control is returned to step 1154 of FIG. 26. If ω is equal to Ω, then control is returned to step 226 of FIG. 9A, the inverse scattering subroutine.

Now consider FIG. 21, which was called by FIG. 26 above.

Figure 1C:
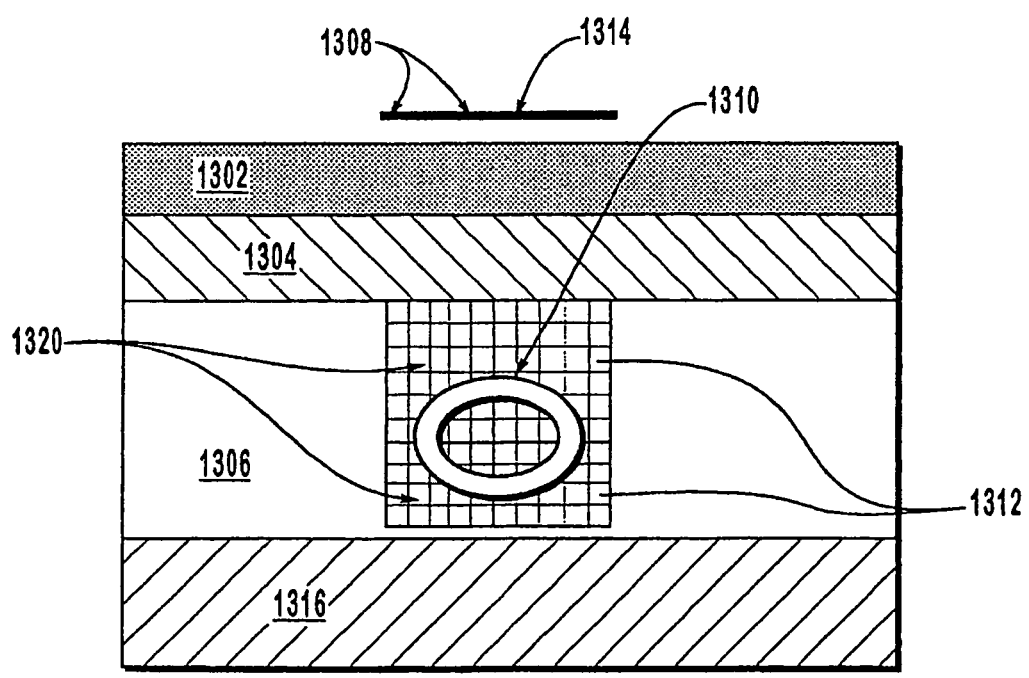
FIG. 1C is a two dimensional view of a reflection geometry imaging method, according to the present invention, using inverse scattering with a remote wave energy source means and remote wave energy detection means.

Step 1118 of FIG. 21 transfers control to step 1122 where the input is truncated to the border pixels. Control is passed to step 1124 which determines if the receivers are distant from the image space as in FIG. 1C or whether the receivers are juxtaposed to the image space as in FIG. 1A or 1B. If the detectors are in fact juxtaposed to the image space, then control is transferred to step 1126 and from there to the calling subroutine. If the detectors are not juxtaposed to the image space, the fields are propagated to the detector positions. The details of this propagation are given in the "EXTENSION OF THE METHOD TO REMOTE RECEIVERS WITH ARBITRARY CHARACTERISTICS" section of this patent. Actually, there are several methods which could be used to accomplish this. For example, an application of Green's theorem is one possibility. The beauty and utility of the method shown in the "EXTENSION OF THE METHOD TO REMOTE RECEIVERS WITH ARBITRARY CHARACTERISTICS"

section however, is that the normal derivatives of the Green's function, or the fields themselves, do not need to be known or estimated.

The input to FIG. 21 is a vector of length $N_xN_y$. FIG. 21 represents the subroutine that is called by the Jacobian calculation or following immediately after the calculation of the internal fields. The input in the first case of the Jacobian calculation consists of box 720 of FIG. 20B. The input in the second case is the scattered field calculated for a particular frequency ω and a particular source position φ. The purpose of FIG. 21 is to propagate the input (scattered field in the image space) to the detector positions. In step 1124 it is determined whether the receivers are distant. If the detector positions are located at some distance from the image space, the subroutine passes control from step 1124 to step 1128.

In step 1128, the matrix P, constructed earlier is used to propagate the field to remote detectors. In step 1130 of 21, control is returned to the program which called the subroutine. The matrix P will change when correlation is present; the fundamental form of the propagation algorithm remains unchanged, however.

These scattered fields are stored in vector $d^{\omega,\phi}$. Control is then transferred to step 228 in FIG. 9A which subtracts the measured scattered field from the calculated scattered field and stores the result in one vector $r^{\omega,\phi}$ which is the residual vector for frequency ω and source position φ. This step is repeated until all possible frequencies and all possible source positions have been accounted for, whereupon the residual vectors $r^{\omega,\phi}$ for all possible ω's and φ's are stored in one large residual vector shown in FIG. 9A as step 228. We now apply the Hermitian conjugate of the Jacobian to the residual vector r just calculated in order to establish the search direction $P^n$ where n=0, i.e. the initial search direction. The search direction is given explicitly by the negative of the action of the hermitian conjugate of the Jacobian acting upon the residual vector r, in step 238.

There are in effect at least two possibilities regarding the use of the Jacobian. First, the full Jacobian could be used or, secondly, an approximation to the Jacobian could be used. The determinator of which path to follow is the programmer, who bases his decision on the magnitude of the γ which is to be solved in the full inverse scattering problem. If the γ is large, the exact Jacobian must be used. On the other hand, if the γ is reasonably small, although still larger than required for the Born or Rytov approximation, the approximation to the full exact Jacobian which is shown on FIG. 9A, step 236 may be used. The application of the exact or approximate Jacobjan will be discussed later.

Now we step through FIGS. 9A to 9D to get an overall view of how the algorithm works.

Step 238 computes the initial search direction $P^{(0)}$ Step 240 of FIG. 9A zeros the initial guess for δγ, which is the Gauss-Newton (or Ribiere-Polak, or other) update to γ, the scattering potential. γ can be initially set=0. A large portion of the rest of FIG. 9A, 9B, 9C, 9D is concerned with the calculation of δγ. This is used in FIG. 8 also, of course.

Step 212 of FIG. 8 has estimated the scattered field at the detector positions. Step 214 of FIG. 8 now determines if the residual (which is given by the magnitude squared of the difference between the measured scattered field and the calculated scattered field, for each possible source position and each possible frequency) is less than some predetermined e tolerance. If the condition is satisfied then control is transferred to Step 216 where the reconstructed image of the scattering potential is either displayed or stored. If the condition is not met, then from the updated internal field calculated in Step 210 of FIG. 8 and also from the most recent estimate of the scattering potential and also from the estimated scattered field at the detectors calculated in Step 212 of FIG. 8 and also from the measured scattered field at the detectors, a new estimate of the scattering potential γ is calculated in a manner to be made explicit below. This updated scattering potential estimate is derived in Step 218, and is now used in Step 210 of FIG. 8 to calculate a new update of the estimate of the internal fields, for each possible frequency ω and each possible source position φ. Then in Step 212 of FIG. 8 a new estimated scattered field at the detectors is calculated by means of Green's theorem as shown in FIG. 26. This new estimate of the scattered field is then used in Step 214 as before, to estimate the magnitude of the residual vector between the measured scattered field and the calculated scattered field to determine if this quantity is less than ε, the predetermined tolerance. As before if this tolerance is exceeded the loop just described, is repeated until such time as either the tolerance is satisfied or the maximum number of iterations of this loop has been exceeded. This maximum number is predetermined by the operator.

We have just concluded a general description of the overall inverse scattering algorithm leaving out many important details. We now look at each of the steps in more detail. First, we explain how the $\delta\gamma^0$ shown in Step 240 of FIG. 9A is related to Step 218 of FIG. 8. $\delta\gamma^0$ in FIG. 8 is the first estimate of δγ in Step 314, which is the vector which is solved for, in Steps 244 through to Step 314 in FIGS. 9B through 9D. This δγ is the correction term to the scattering potential which is applied to the present estimated scattering potential $\gamma^{(n)}$ in Step 314 of FIG. 9D in order to get the updated scattering potential $\gamma^{(n+1)}$. Once this new updated scattering potential has been determined, transfer to Step 316 of FIG. 9D where it is determined if the maximum number of Gauss-Newton corrections have been exceeded. Each pass through Steps 244 through 314, to calculate δγ is one Gauss-Newton step. These Gauss-Newton steps are repeated until one of two things occurs. Either the maximum number of Gauss-Newton corrections is exceeded, or the tolerance condition of Step 294 is satisfied. It is important to reiterate that which was noted earlier, namely, that the description of the Gauss-Newton algorithm here, does not preclude the use of a suitable Ribiere-Polak, or Fletcher-Reeves non-linear algorithm, or other non-linear system solver. The changes in detail do not change the overall character of the minimization algorithm.

The appendix A contains the main program for imaging in two dimensions, which represents the code associated with the FIGS. 9A through 9D. More specifically Appendix A deals with the two-dimensional situation whereas Appendix E deals with the three-dimensional imaging situation.

It is important to note that the code in Appendices A, B, C, F, and G, deal with the most general case. This means that they can account for layering as is discussed in the Summary of the Invention Example 2. This means that the Lippman-Schwinger operator described earlier incorporates a convolution and correlation part. If it is known a priori that there is negligible layering in the geophysical or non-destructive testing or other scenario envisioned then it is appropriate to use the code given in Appendix H and Appendix I which deals with the case of no correlation part in the Green's function. The great simplification of the code that results from this omission and specialization is reflected in the fact that the code in Appendix H contains both the main imaging program and the forward problem solution. Furthermore, this code also computes the two-dimensional free space Green's function from scratch. This is in contradistinction to the codes in Appendix A or B or C where in the two-dimensional case in the presence of layering, three separate programs are used to solve the inverse scattering problem, the forward problem and the construction of the layered Green's function. The construction of this layered Green's function which is discussed in Example 2 for the acoustic scalar case, requires substantial amount of time for its computation. However, it is important to note that once the Green's function has been constructed for a given layered scenario, in a geophysical context, for example, it is not necessary to recalculate this Green's function iteratively. Rather the Green's function once it has been determined by methods discussed in the literature, see for example [Johnson et al. 1992, or Wiskin et al, 1993], is used in the code in Appendix A and Appendix B to complete the imaging problem. To display the versatility of this inverse imaging code note that the code in Appendix H deals with the transmission mode imaging problem with the particular modality being electromagnetic wave propagation in particular in the microwave frequency range. Note also that Appendix H incorporates within it the situation where the detectors are at some finite distance away from the image space, i.e. they are not juxtaposed to the image space. The implication being that Green's theorem or some type of "scattering matrix" is required to propagate the field from the border pixels of the image space to the detector positions at some finite distance away from the image space. Such a scattering matrix is constructed earlier.

It is important to note that all of the Appendices deal with the rectangular iterative method. It is also important to recognize that the construction of the layered Green's function as shown in Summary of the Invention, Example 2 shows explicitly how the convolution and correlation are preserved even though the distribution of the layers above and below the layer containing the image space are arbitrarily distributed. The preservation of convolution and correlation is a critical element of the ability to image objects in a layered or Biot environment (Biot referring to the Biot theory of wave propagation in porous media) in real time. The reflection coefficients which are used in the construction of the layered Green's function in the acoustic, elastic and the electromagnetic case are well known in the literature. See, for example [Muller, 1985] or Aki and Richards, 1980. The incorporation of this Green's function for layered media in the acoustic, elastic and electromagnetic case for the express purpose of imaging objects buried within such a layered medium is novel. The ability to image in real time is critical to practical application of this technology in the medical, geophysical, non-destructive and testing microscopic environments.

We now elucidate the steps shown in FIG. 9A. We have already discussed in detail, steps up to 240, Step 242 of FIG. 9A begins the conjugate gradient loop. Step 244 of FIG. 9A sets n equal to 0.

Figure 20A:
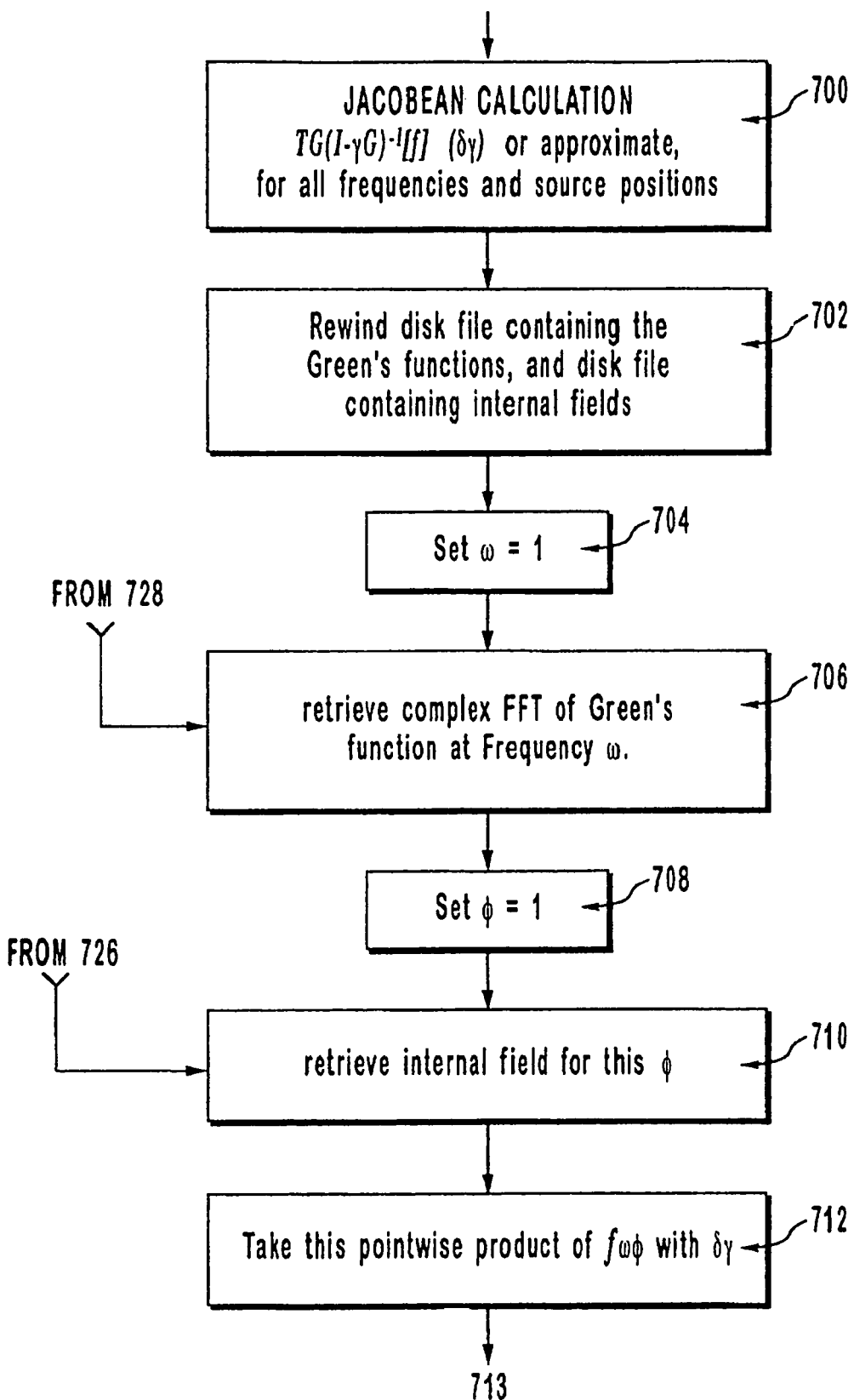
FIG. 20A through 20C illustrate application of the Jacobian Matrix in the generic case (free space—or no layering), according to the present invention.

This n is the counter that keeps track of the number of conjugate, gradient steps that have been performed in the pursuit of $\delta\gamma$, the update to the scattering potential estimate. Step 246 of FIG. 9A again determines if the full Jacobian will be used. As in previous step 230 of FIG. 9A the answer depends on the magnitude of $\gamma$. In the case that the $\gamma$ is large, the approximation given in Step 250 is not appropriate. Furthermore the actual implementation of the algorithm depends on whether there is correlation present. They are sufficiently different to warrant separate flow charts. FIGS. 20A/B/C deal with the free space case. Considering this case first, JACFLAG is set to one and Step 252 is computed via FIG. 20A/B/C. Step 700 of FIG. 20A transfers the algorithm control to Step 702 where the disk file containing the Green's functions and the disk file containing the internal fields for all possible $\omega$ and all possible $\phi$ source positions are rewound. Control is then transferred to Step 704 where $\omega$, the index for the frequency, is set equal to 1. In Step 706 thereafter, the complex Fast Fourier Transform (FFT) of the Green's function, at this particular frequency, is retrieved. In Step 708, $\omega$, the counter corresponding to the source positions, is set equal to 1. The Step 710 in FIG. 20A/B/C retrieves the internal field for this particular source position $\phi$, the Step 712 takes the point-wise product of this internal field which was retrieved in Step 710, with the $\delta\gamma$ which is the input to FIG. 20A/B/C and is also the same $\delta\gamma$ which is being sought after in the main program in FIG. 9A through 9D. In Step 252 of FIG. 9B which is where we have come from in FIG. 20A/B/C, the Jacobjan is applied to p, which is the search direction for $\delta\gamma$. That is p is the input to FIG. 20A/B/C, i.e. $\delta\gamma$ $\gamma$ in this call of FIG. 20A/B/C is p of Step 252 in FIG. 9B. In Step 714 of FIG. 20A/B/C either the inverse of a certain operator or the first order binomial approximation of the inverse, is applied to the point-wise product produced in Step 712. This operator, $(I-\gamma G)$, is similar to, but not the same, as the Lippmann-Schwinger operator which is represented as $(I-G\gamma)$. Note, the determinator of which operator $(I-G\gamma)^{-1}$ or $(I+G\gamma)$ is applied is the JACFLAG variable defined in FIG. 9B JACFLAG=1 corresponds to application of $(I-G\gamma)^{-1}$ It is important to note that the inverse of this operator, $(I-\gamma G)^{-1}$, is never explicitly calculated in Step 714. The actual computation of the inverse of this operator, which in discrete form is represented as a matrix would be computationally very expensive. Therefore, the inverse action of the operator $(I-\gamma G)^{)-1}$ acting on the point-wise product calculated in Step 712 is calculated by using bi-conjugate gradients or BiCGStab as indicated in Step 714 of FIG. 20A/B/C. This bi-conjugate gradient algorithm is the same bi-conjugate algorithm shown in FIG. 11A-1/11A-2 and was used to calculate the application of the Lippman-Schwinger operator $[I-G\gamma]$ on a vector f. However, it is important to note that the operator represented by the matrix A in Step 450 of FIG. 11A-1 is not the Lippman-Schwinger operator, rather it is the above $(I-\gamma G)$ operator in this case. As before, the BiCGStab or Biconjugate gradient stabilized algorithm may be used in place of the bi-conjugate gradient algorithm. This BiCGStab or conjugate gradient stabilized algorithm is shown in FIG. 11B-1/11B-2. The application of the algorithm shown in FIG. 11C for the actual application of the operator A in BiCGStab, FIG. 11B-1/11B-2, or BCG, FIG. 11A-1/11A-2, will of course, differ, in that the point-wise multiplication by $\gamma$ will be performed after the convolution with the Green's function G appropriate to this frequency $\omega$, in this case. However, the changes that must be made to FIG. 11C are clear in this case. Namely, the point-wise product shown in Step 402 is taken after the computation of the inverse Fast Fourier Transform (FFT) in Step 408 instead of before. A similar comment applies to FIG. 13 where the Hermitian conjugate of I–$\gamma$G is computed. In this case the Hermitian conjugate of the operator I–$\gamma$G requires that the pointwise product of the conjugate of $\gamma$ which is carried out in Step 586 of FIG. 13 be calculated before the Fast Fourier Transform (FFT) is taken in Step 580 of FIG. 13. Step 254 of FIG. 9B now calculates the magnitude of the vector computed in Step 252 namely, the application of the vector A to the search direction p. Step 254 of FIG. 9B also computes the magnitude of the vector which is the result of the application of the Hermitian conjugate of the vector A to the residual vector r. Again, A is either the exact Jacobian or the approximation to the Jacobian shown in Step 250. The Step 256 computes the square of the ratio of the two magnitudes computed in Step 254, this ratio is denoted by $\alpha$. Step 258 of FIG. 9B now updates $\delta\gamma$ which is the Gauss-Newton correction sought after in the loop from Step 244 to 314 of FIGS. 9B through 9D. The update is given explicitly in Step 258 of FIG. 9B. Also at the same time the residual is updated via the formula shown explicitly in Step 258 of FIG. 9B. Step 260 transfers control to the Step 286 in FIG. 9C which determines if the full, exact Jacobian will be used or the approximation shown explicitly in Step 290. Depending upon which A is defined i.e. either the exact Jacobian or the approximation, JACFLAG is set to 1 or 0 and Step 292 is carried out. It is the application of the Hermitian conjugate of the matrix A which is defined in either Step 290 or 288, depending upon whether the exact Jacobian is used. The Hermitian conjugate of A is applied to the updated residual vector r. Step 294 calculates the ratio of two numbers. The first number is the magnitude of the updated residual calculated in Step 292, the second number is the magnitude of the scattered field for all possible ω's, i.e. source positions, and φ's i.e. frequencies, and compares this ratio to ϵ the pre-determined tolerance. If the tolerance is larger than this calculated number, control is transferred to Step 296 which effectively stores the image of the scattering potential and/or displays this image. If the tolerance is not satisfied, control is transferred to Step 298 where β is calculated as shown explicitly in Step 298. Step 300 calculates the new search direction which is given by the explicit formula shown. Note that the Hermitian conjugate applied to the residual vector r has already been calculated in previous Step 298. Now transfer to Step 304 of FIG. 9D and it is determined in Step 310 if the maximum number of iterations allowed for the conjugate gradient solution have been exceeded. If no, then n, the counter for the conjugate gradient steps is incremented by one, and control is transferred to Step 246 of FIG. 9B. If, however, the maximum number of conjugate gradient iterations has been in fact exceeded, control is transferred to Step 314 of FIG. 9D. This is the step that has been discussed previously in which the scattering potential is updated by the δγ vector which has been computed by the conjugate gradient iterations. Control is then transferred to Step 316 of FIG. 9D where it is determined if the maximum number of Gauss-Newton corrections, specifically the δγ's, have been calculated. If the maximum number of Gauss-Newton (see earlier note regarding Gauss Newton vs Ribiere Polak) steps has been exceeded then the control is transferred to Step 320 where the present scattering potential estimate is stored and/or displayed. If the maximum number of Gauss-Newton corrections has not been exceeded then the index parameter that counts the number of Gauss-Newton corrections that have been computed, is incremented by 1 and control is transferred to Step 308 which transfers to Step 284 (arrow) of FIG. 9C which transfers control to Step 244 (arrow) of FIG. 9B which transfers control to Step 236 (arrow) of FIG. 9A which transfers control to Step 222 of FIG. 9A. Again as before, in Step 222 the forward problems for all possible ω's and all possible φ's are calculated. More specifically control is transferred to Step 340 of FIG. 10. This FIGUREure has been discussed in detail above.

The loop just described and displayed in FIG. 9A through 9D is now reiterated as many times as necessary to satisfy the tolerance condition shown in Step 294 of 9C or until the maximum of Gauss-Newton iteration steps has been performed.

It is appropriate to study in detail the application of the Lippman-Schwinger operator and the Jacobian in the situation where layering is present. It is important to note that the discussion heretofore, has emphasized the special situation where layering is not present so that the free space or similar Green's function not involving any correlation calculation, has been used. This specialization is appropriate for pedagogical reasons, however, the importance of the layered Green's function makes it necessary to discuss in detail the application of the Lippman-Schwinger operator in this case. Before doing this however, we look at FIG. 25A/B/C where the Hermitian conjugate of the Jacobian calculation is considered in the free space case. Just as in the calculation of the Jacobian itself (or its approximation) the variable JACFLAG determines whether BCG (or variant thereof) is applied or whether the binomial approximation shown is used.

In Step 600 the full Hermitian conjugate of the Jacobian calculation is undertaken with the disk files containing the Green's functions and the disk files containing the internal fields for each ω and each φ being rewound. In Step 604 ω is set equal to 1, i.e. the first frequency is considered. In Step 606 the complex Fast Fourier Transform (FFT) of the Green's function at this particular frequency ω is retrieved from disk where it has been stored previously. In Step 608 φ is set equal to 1 indicating we are dealing with the first source position. Step 610 retrieves the internal-field fωφ, for this source position φ at frequency ω. Step 612 propagates the scattered field from the detector positions to the border pixels of the image space. Also in Step 612 the field values at the non-border pixels of the image space are equated to 0. In Step 614 the Fast Fourier Transform (FFT) of the field resulting from Step 612 is computed and stored in vector x. In Step 616 the complex conjugate of the Fast Fourier Transform (FFT) of the Green's function G is point-wise multiplied by x, the vector computed in Step 614. As before the actual computation of this inverse operator is computationally prohibitive. Therefore, the application of the inverse of I−G*γ* to the vector x is carried out by using bi-conjugate gradients or BiCGStab as discussed above. In Step 620 either the inverse of the operator I−G*γ* or the approximation (I+G*γ*) is applied to this result. The system [I−G*γ*]y=x is solved for y using BCG. See FIGS. 11A-1/11A-2. In Step 622 of FIGURE FOI the point-wise multiplication by the complex conjugate of $f_{ωφ}$, the internal field for this frequency and source position, is carried out. This point-wise multiplication is the product with the result of Step 620. The Step 624 stores the result of this point-wise multiplication. Step 626 determines if φ is equal to Φ, the maximum number of source positions. If the maximum number of source positions has not yet been achieved, then the φ is incremented by 1 to indicate movement to the next source position. Transfer of control is now made to Step 610, where the internal field for this particular source position is retrieved. The loop from Step 610 to Step 626 is performed iteratively until the maximum number of source positions has been achieved. When this occurs, it is determined if ω is equal to Ω, the maximum number of frequencies, in Step 630. If the maximum number of frequencies has been achieved then control is transferred to Step 634 which transfers control back to FIG. 9A where the Hermitian conjugate of the Jacobian, or its approximation, was being applied. If, however, the maximum number of frequencies has not been achieved then transfer is made to Step 632 where the frequency index is incremented by 1 and control is transferred to Step 606 of FIGURE F01 which is the retrieval of the complex Fast Fourier Transform (FFT) of the Green's function at new frequency ω. This loop is now repeated until all possible frequencies and all possible source positions have been exhausted. At this time control is transferred to the inverse scattering routine in FIG. 9A through 9D.

Figure 20B:
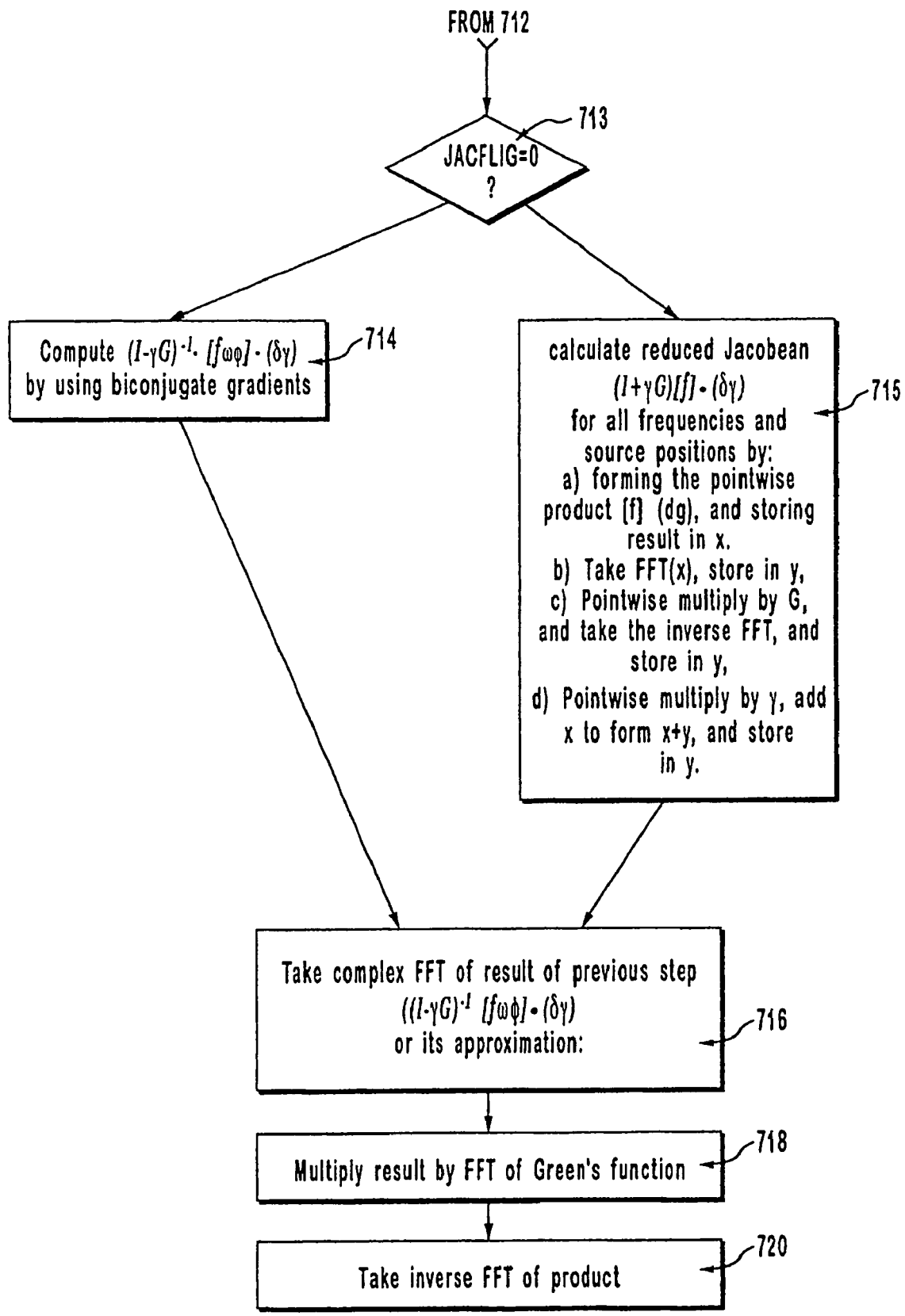
Figure 20C:
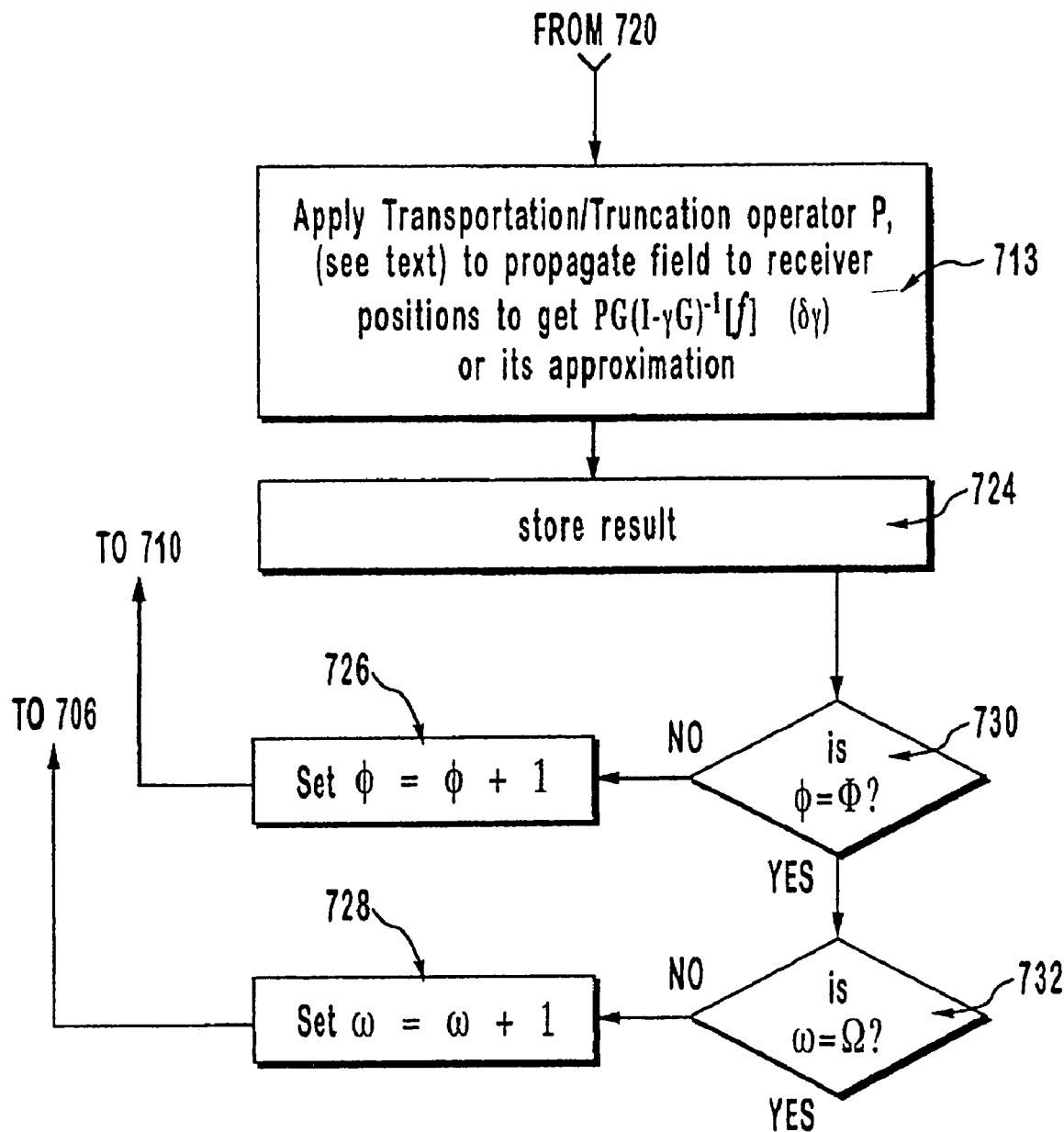

It is appropriate now to turn to that part of FIG. 20A/B/C which details the application of the reduced Jacobian calculation which is used by FIG. 9A through 9D, i.e. the Gauss-Newton iteration in the situation where it is permissible to use the approximation to the Jacobian in place of the exact Jacobian. This calculation is called the reduced Jacobian calculation by virtue of the fact that no inverse operator is required to be calculated in this FIGURE Therefore, the total computational complexity of this part of FIGS. 20A through 20C (ie.Step 715) is less than the corresponding Step 714 of FIGS. 20A 20C, in which the full exact Jacobian calculation is carried out. When the Jacobian calculation in FIG. 20A through 20C is being carried out to compute Step 252 in FIG. 9B $\delta\gamma$ is in fact $p''$, the search direction for the conjugate gradient step in determining $\delta\gamma$, which in turn is the update to the scattering potential determined by this particular Gauss-Newton step. In Step 715 a) the point-wise product is stored in vector x. In Step 715 b) the Fast Fourier Transform (FFT) of the point-wise product is computed and in Step 715 c) this Fast Fourier Transform (FFT) is taken with a point-wise product with the Fast Fourier Transform (FFT) of the Green's function for this particular frequency $\omega$, and the inverse Fast Fourier Transform (FFT) of the point-wise product is taken to yield G convolved with the product f*$\delta\gamma$ which result is stored in vector y. In Step 715 d) the point-wise product of vector y is taken with $\gamma$ and the vector x computed and stored in Step 715 a) is added to it. The Fast Fourier Transform (FFT) of this sum is calculated in Step 716 of FIGS. 20A through 20C and the algorithm finishes exactly as described previously. Recall that transportation takes place in the scenario where the receivers exist at some finite distance from the image space in contradistinction to the truncation operation which takes place when the receivers exist at the border pixels of the image space. The truncation or transportation operator is discussed in FIG. 21 for the general case in which correlation, i.e. layering, is present or absent.

It is very important to note that the correlation that is calculated in the case of layering is, without exception, calculated as a convolution by a change of variables. It is the presence of the convolution which allows the introduction of the Fast Fourier Transform (FFT) and allows this algorithm to be completed in real time when the Fast Fourier Transform (FFT) is used in conjunction with the other specific algorithms and devices of this apparatus.

Figure 23A:
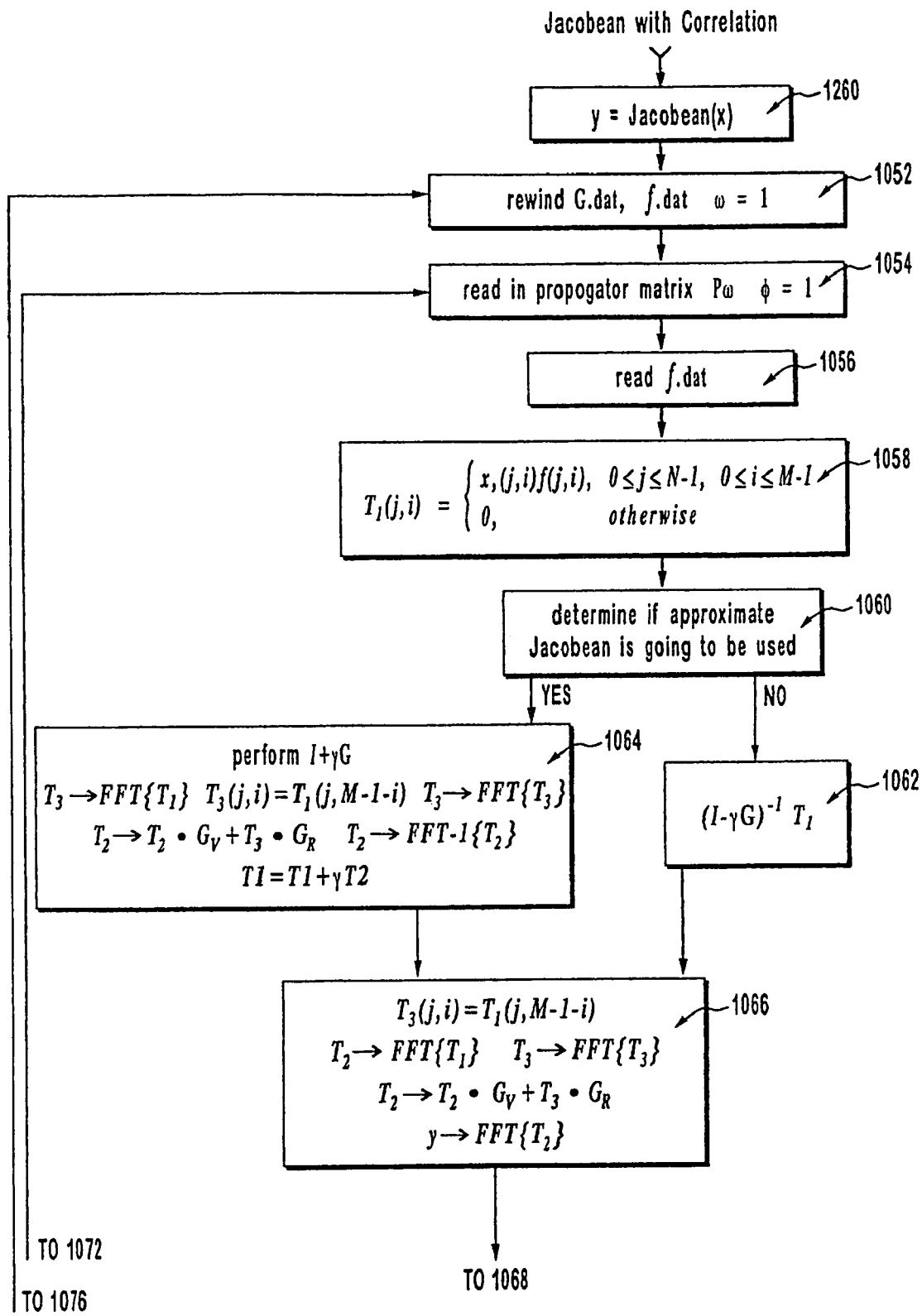
FIGS. 23A and B illustrates application the Jacobian Matrix with correlation, according to the present invention.
Figure 23B:
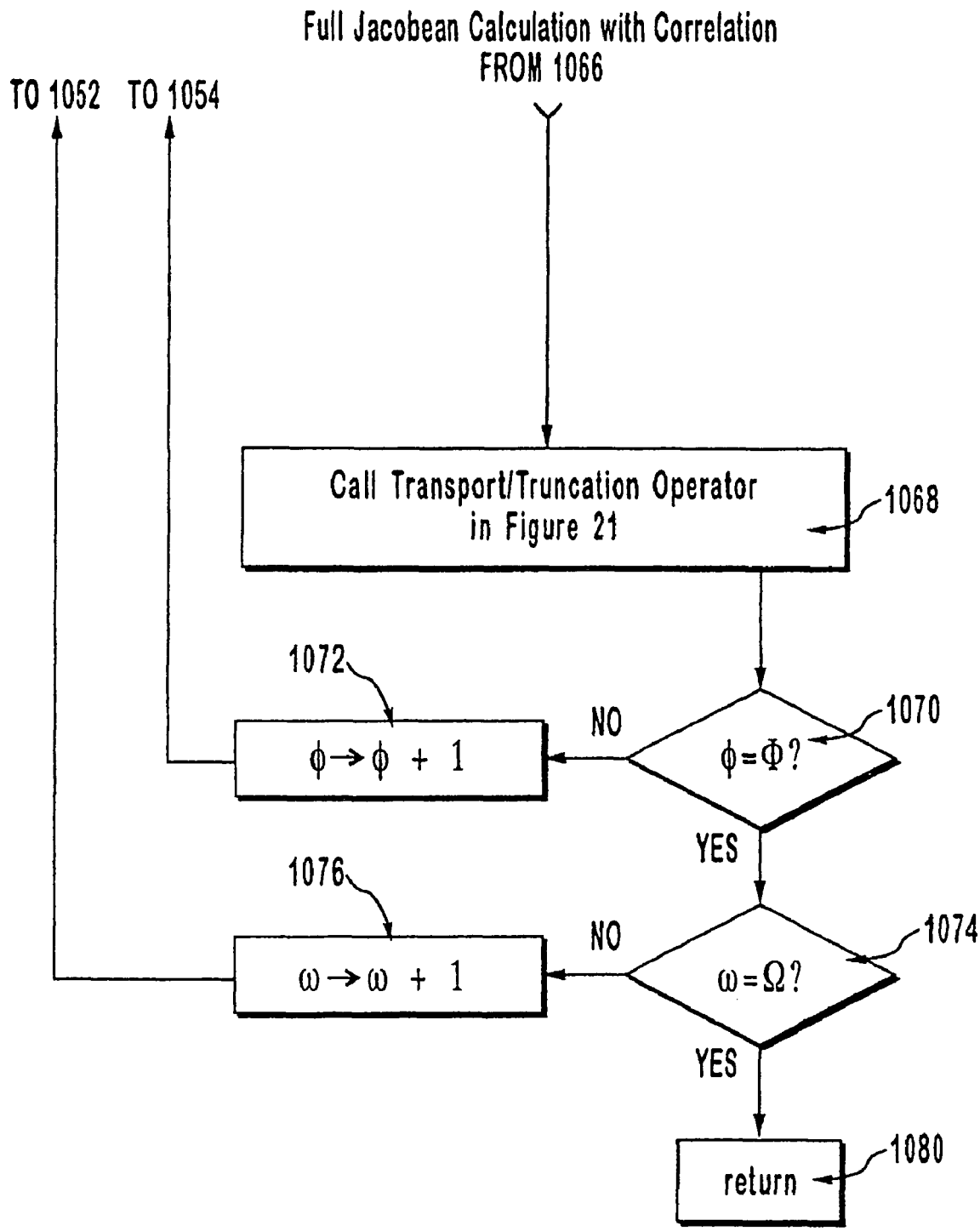

It is now appropriate to consider in detail the action of the Lippmann-Schwinger operator and the Jacobian in the case when layering is present. FIGS. 23A and B displays this case.

It is also important to note regarding the Jacobian calculation with correlation, that both the reduced and the exact form have their counterpart in the Hermitian conjugate. This is discussed in FIGS. 19A/B. In Step 654, the re-winding of the disk with the Green's function and the disk with the internal fields is carried out, and $\omega$ is set equal to 1. In Step 658 the complex Fast Fourier Transform (FFT) of the Green's function at this particular frequency $\omega$ is retrieved. Step 658 also sets $\phi$ (source position) equal to 1. Step 660 retrieves the internal field for this $\phi$. Step 662 calculates the Hermitian conjugate of the truncation operator which puts values in border positions of the image space of the appropriate field and zeros everywhere else. Step 664 point-wise multiplies the result of 662 by complex conjugate of the Fast Fourier Transform (FFT) of the Green's function. Step 668 takes the inverse Fast Fourier Transform (FFT) and stores this in vector y. Now, in Step 670 depending upon the value for JACFLAG, either the full inverse $(I-G^*\gamma^*)^{-1}$ (via BCG or BiSTAB, etc.) or $(I+G^*\gamma^*)$ is applied directly to y. The second alternative is carried out in the standard manner. That is, one takes the point-wise multiplication of the complex conjugate of $\gamma$, the scattering potential estimate at this time with the vector y. The one takes the Fast Fourier Transform (FFT) of the result and takes the point-wise multiplication of the complex conjugate of the Fast Fourier Transform (FFT) with this result. Finally one adds the vector y and stores it in vector y, (overwriting y).

The Step 672 multiplies the final result point-wise, with the complex conjugate of the internal field for this particular frequency and source position, and stores the result. Step 672 transfers control to 674 where it is determined if $\phi$ is equal to $\Phi$. If no, then $\phi$ is incremented by 1 and returned to Step 660 in Step 676. If yes, control is transferred to 680 where it is determined if $\omega$ is equal to $\Omega$; if yes, increment $\omega$ by 1 in Step 682, and transfer control to Step 656. If no, transfer control to Step 684 where control is transferred back to the inverse scattering main algorithm, FIGS. 9A through 9D.

Figure 12:
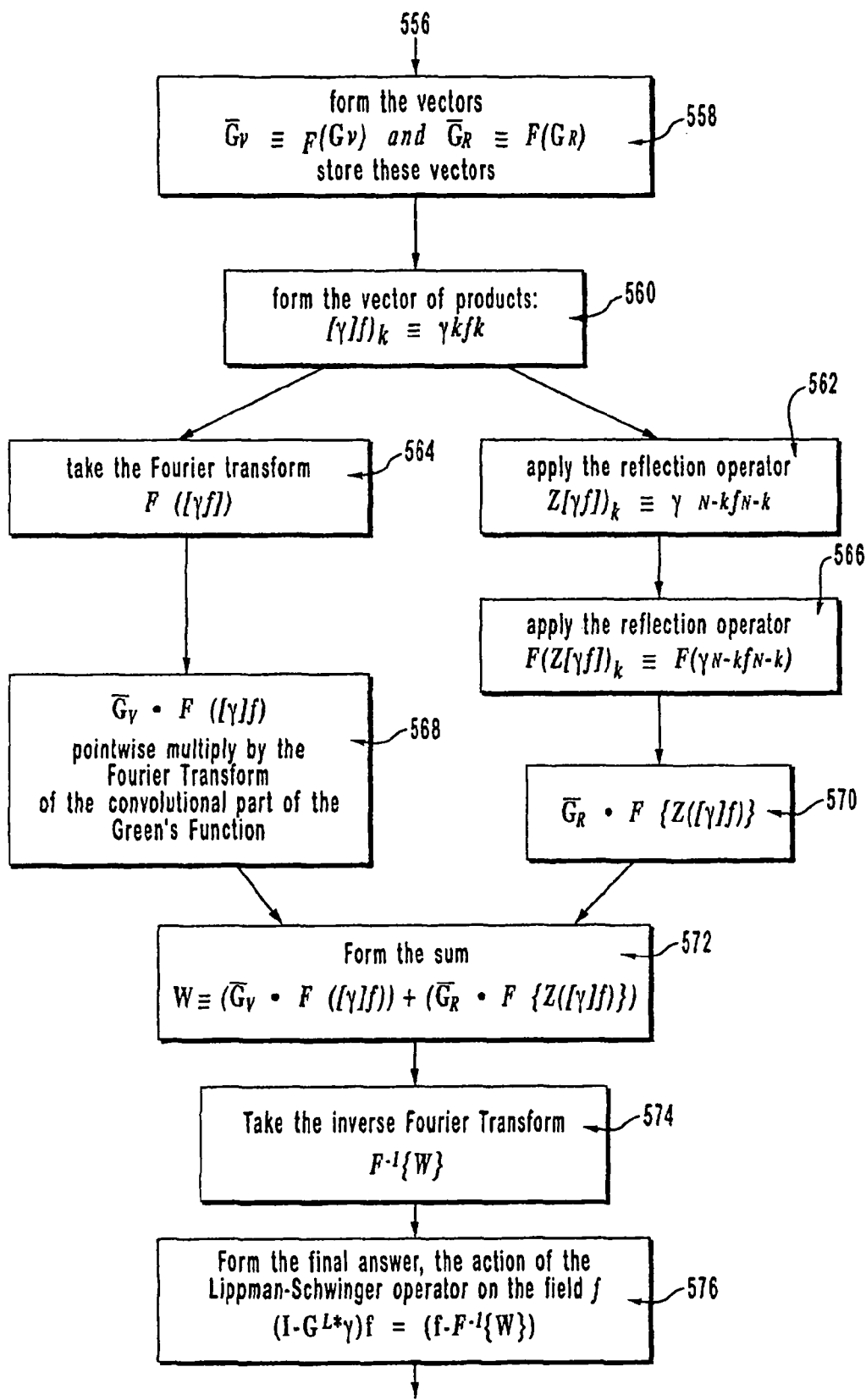
FIG. 12 illustrates the application of the Lippmann-Schwinger Operator in the presence of layering to the internal field estimate according to the present invention.

It is important to note at this point that when the operator $I-G\gamma$ is applied to the vector $T_1$, and also when the Lippmann-Schwinger operator $I-G\gamma$ is applied to any input vector in the layering scenario, FIG. 12 must be followed. Step 556 of FIG. 12 forms the vectors which store the Fast Fourier Transform (FFT) of the convolutional and the correlational parts of the layered Green's function separately. These convolutional and correlational parts are computed by appendices C and G for the two and three-dimensional cases, respectively, and are given explicitly by the formulas given on page 35 of the Summary of the Invention section.

The step 558 passes control to step 560 where the vector of pointwise products shown explicitly there, is formed. This pointwise produce of $\gamma$, the scattering potential estimate, and F, the internal field, is Fourier transformed in step 564 and in parallel simultaneously in step 562, the reflection operator is applied to this pointwise product $\gamma F$ computed in step 560. In step 566, following step 562, the Fourier Transform of the reflected product $\gamma F$ is taken. In step 570 and in step 568, there is pointwise multiplication by the correlational part and the convolutional part of the layered Green's function, respectively. The correlational part of the layered Green's function is pointwise multiplied by the Fast Fourier Transform (FFT) computed in step 566, the convolutional part of layered Green's function fast Fourier transformed is pointwise multiplied by the Fast Fourier Transform (FFT) which was computed in step 564. In step 572, the vector W, which is the difference of the results of step 568 and 570, is computed and stored. In step 574, the inverse Fast Fourier Transform (FFT) of the vector W is computed. In step 576, the final answer which is the action of the Lippmann-Schwinger operator acting upon the field f is computed for the layered medium case, i.e., the case in which correlation exists. This process of applying a Lippmann-Schwinger operator in the presence of layering established in FIG. 12 is used explicitly in the calculation of the forward problems in step 222 of FIG. 9A in the presence of layering. It is also carried out explicitly in Appendices B and F for the two and three-dimensional cases, respectively. It is also required in some of the calculations of the application of the Jacobian in the layered medium case.

Figure 14:
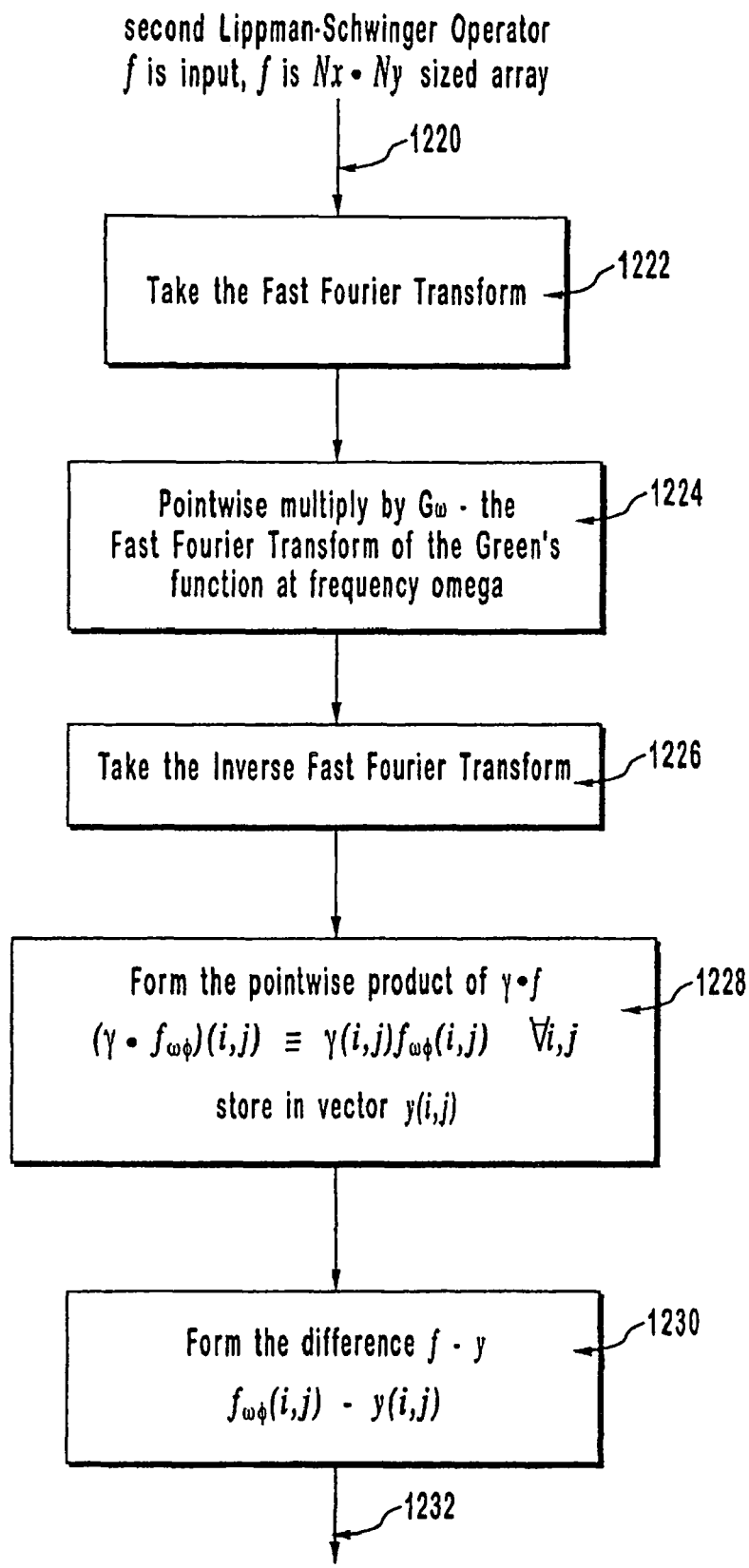
FIG. 14 illustrates the application of the second Lippmann-Schwinger operator in the generic case.

The operator described by FIG. 14, $(I-\gamma G)$, is called the "Second Lippmann-Schwinger operator". This operator is in fact the transpose of the "Lippmann-Schwinger" operator so-called, i.e. $(I-G\gamma)$. Note that this is not the Hermitian adjoint of the Lippmann-Schwinger operator, precisely because no complex conjugate is taken.

The input to FIG. 14 is Fast Fourier Transformed in step 1222. The result is then pointwise multiplied by the Fast Fourier Transform (FFT) of the Green's function for this particular frequency. The result is inverse Fast Fourier Transformed and stored in vector y, in step 1226. The pointwise product $\gamma \cdot y$ is computed and stored in vector y. Finally the difference between input vector x, and y is formed in step 1230. Finally, the control is transferred back to the calling subroutine.

FIG. 15 details the application of the hermitian conjugate of the "second Lippmann-Schwinger" operator In 15 control is transferred to step 1242, where the pointwise product is formed, between the complex conjugate of the scattering potential estimate, and the input to this subroutine, x. The Fast Fourier Transform (FFT) is then applied to this product in step 1244. In step 1246 the pointwise multiplication by G*, the complex conjugate of the Fast Fourier Transform (FFT) of the Green's function at frequency ω, is effected. In step 1248, the Inverse Fast Fourier Transform (FFT) of the product is taken, and finally the result is stored in y. In step 1252, the difference is formed between the input to this subroutine, x, and the computed vector y, and the result is stored in y.

FIG. 21 delineates the propagation operator that takes fields in the image space, and propagates them to the remote receivers at some distance from the image space. This propagator is discussed elsewhere in more detail.

In FIG. 21, the input is truncated to the border pixels, in step 1122. Next it is determined if the receivers are remote, or juxtaposed to the image space. If the detectors are in fact juxtaposed to the image space, the control is returned to the calling subroutine.

If the detectors are remote, the field is propagated with the aid of the propagator matrix P (described in section EXTENSION OF THE METHOD TO REMOTE RECEIVERS WITH ARBITRARY CHARACTERISTICS), in step 1128. Control is then transferred to the calling subroutine in the situation where the detectors are remote.

Figure 22:
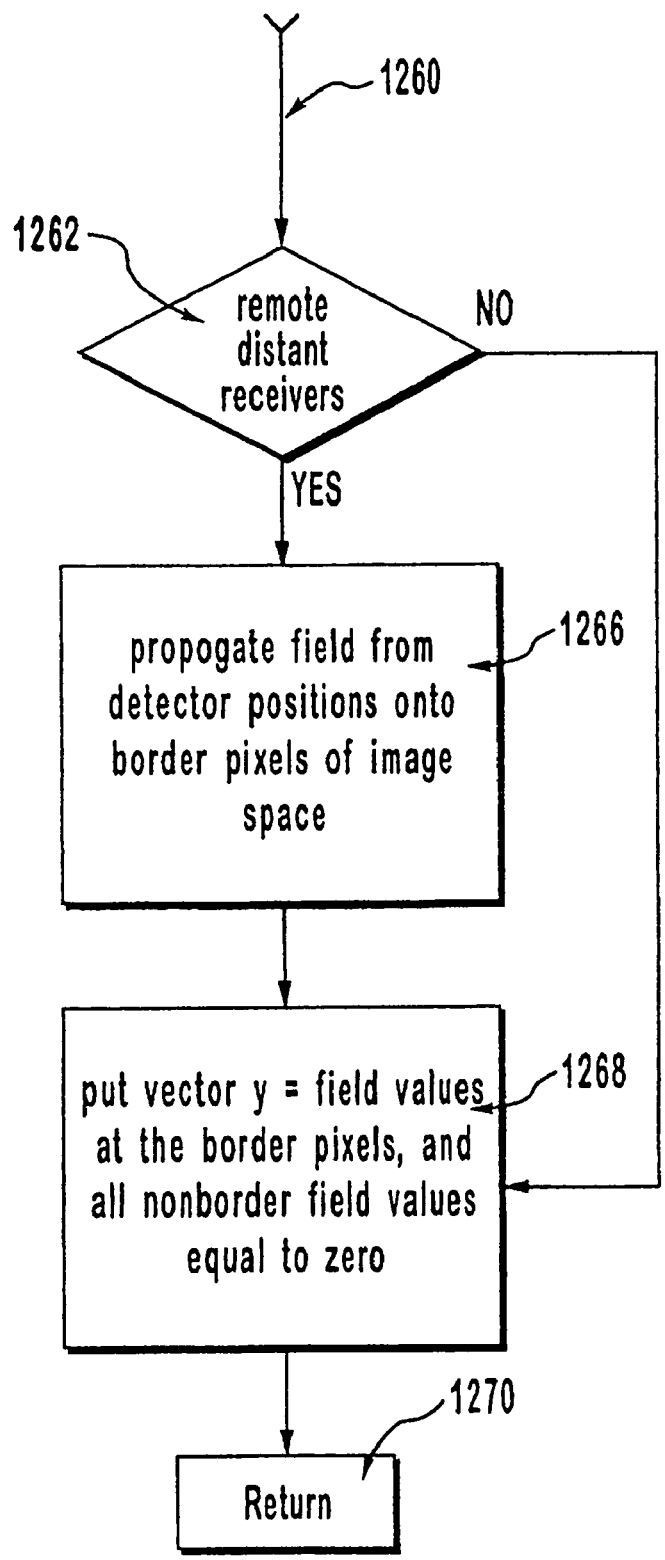
FIG. 22 the illustrates application the Hermitian conjugate of transportation of fields from image space to detector position.

FIG. 22 details the Hermitian conjugate of the propagation operator discussed in FIG. 21.

In FIG. 22, the Hermitian conjugate of the Propagation operator P, it is first determined in step 1262, whether the receivers are at some remote location. If not, then control is transferred directly to step 1268. If the detectors are in fact remote, then control is passed to step 1266, where the fields are propagated via the propagation matrix to the border pixels of the image space. In either case, control is passed then to step 1270, and on to the calling subroutine.

FIG. 23A/B determines the effect of the Jacobian on an input vector x in the presence of layering. Step 1050 transfers control to step 1052 where ω is set equal to 1. Also the files containing the Greens function for this frequency (both the correlations and the convolutional parts), and the internal field estimates, and the propagator matrix are rewound. Control is then transferred to step 1054 where the propagator matrix for this frequency is read in and also the Greens function for this particular frequency is read into memory. Also in step 1054 φ resource position index is set equal to 1. Control is then transferred to step 1056 where the file that contains the internal field estimate for this particular frequency and source position is read into memory. Control is then transferred to step 1058 where the pointwise product of the internal field estimate and the input vector x is computed. Next in step 1060 it is determined if the approximate Jacobian or the full Jacobian will be used. If the full Jacobian is to be used then control is transferred to step 1062 where biconjugate gradients or biconjugate gradients stabilized is used to solve for the action of the inverse matrix of I–γG acting on $T_1$. Recall $T_1$ is the temporary matrix which holds the pointwise product computed in step 1058. Control is then transferred to step 1066. If in step 1060 the determination is made to perform the approximate Jacobian operation then control is transferred to step 1064. In step 1064 the Fast Fourier Transform (FFT) is taken of the vector $T_1$ and it is stored in temporary vector $T_2$. Also the reflection operator is applied to the vector $T_1$ and the result is stored in vector $T_3$. Also the Fast Fourier Transform (FFT) is taken of the result of the planar reflection operator which is stored in $T_3$ and $T_2$ now contains the pointwise product of the convolutional part of the Greens function and the previous $T_2$ added to the pointwise product of $T_3$ with the correlational part of the Greens function for this particular frequency. The inverse Fast Fourier Transform (FFT) is applied to vector $T_2$ and the result is stored in vector $T_2$. Finally, the pointwise product between γ and $T_2$ is formed and the result is added to vector $T_1$ and the result is stored in vector $T_1$. Regardless of whether step 1064 or 1062 has just been completed in step 1066 the reflection operator is applied to the result of either box 1062 or 1064 and the result is Fast Fourier transformed in vector $T_3$ Also the original vector $T_1$ is Fast Fourier transformed and the result is stored in Vector $T_2$. $T_2$ is the pointwise multiplied by the convolutional part of the layered Greens function at this particular frequency and the result is added to the pointwise product of $T_3$ with the correlational part of the layered Greens function at this frequency. The result is stored in vector $T_2$. Finally a Fast Fourier Transform (FFT) is applied to the resulting vector $T_2$ control is then transferred to step 1068 where the transportation or truncation operator given in FIG. 21 is applied to the result. In step 1070 it is determined if φ is equal to Φ if in fact φ is equal to Φ control is transferred to step 1074 where it is determined if ω is equal to ω. If φ is not equal to Φ control is transferred to step 1072 where φ is incremented by 1 and control is then transferred back to step 1056. If in step 1074 ω is determined to be equal to Ω control is transferred to step 1076 where ω is incremented by 1 and control is transferred back to step 1054. If ω is equal to ω in step 1074 control is transferred step 1080 from there control is returned to the calling subroutine.

Figure 19A:
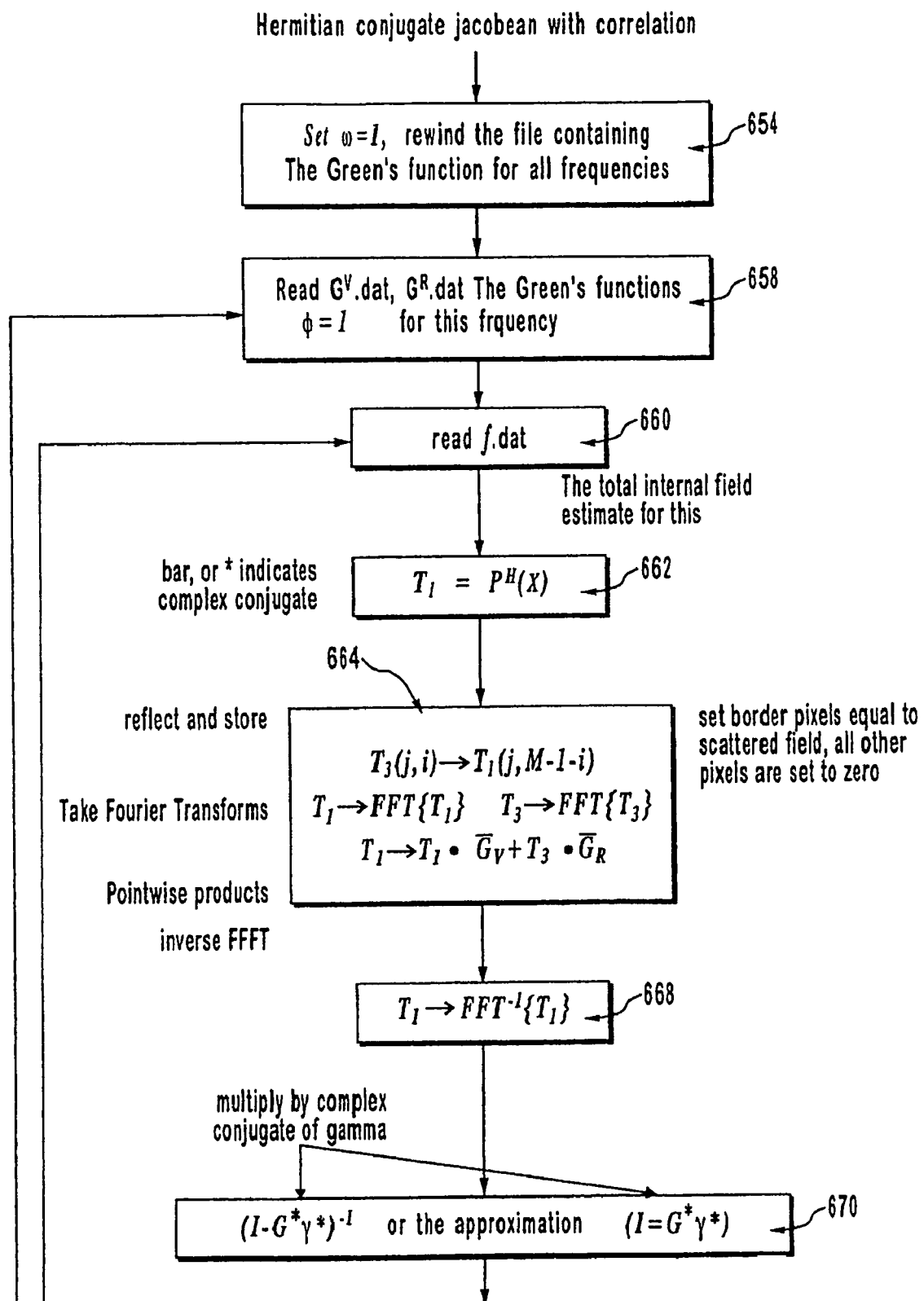
FIGS. 19A and B illustrate application of the Hermitian conjugate of the Jacobian Matrix in the presence of layering according to the present invention.
Figure 19B:
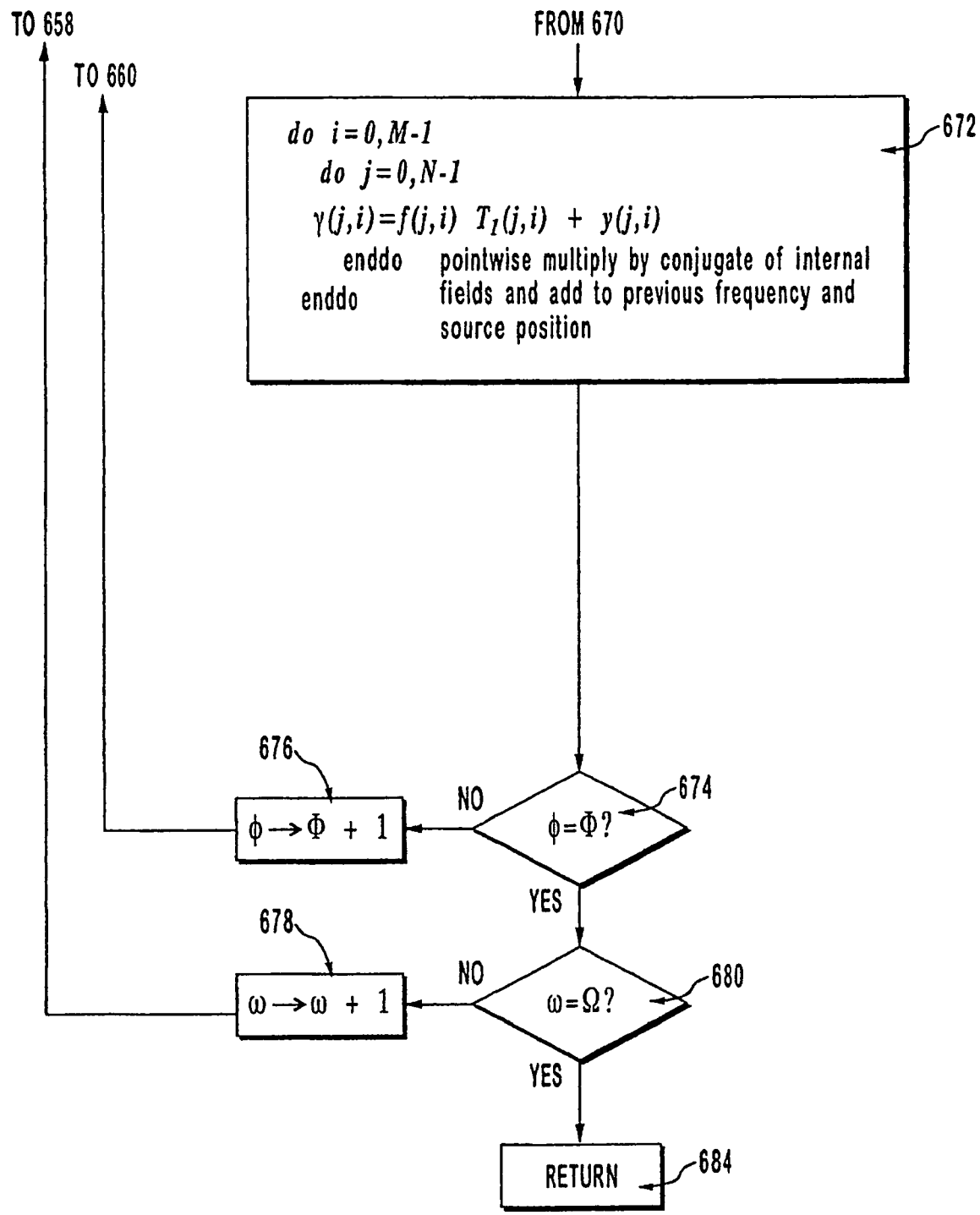

In FIG. 19A the Hermitian conjugate Jacobian with correlation present is applied to an input vector x in step 654 of FIG. 19A ω is set equal to 0 and the files containing the Greens functions for all frequencies are rewound in step 658. The Greens function both the convolutional and the correlational parts for this particular frequency are read into memory, also φ is set equal to 1. In step 660 the file containing the internal field estimate for this particular source position and frequency is read into memory in step 662 the Hermitian conjugate of the propagation operator is applied to the vector x the result is stored in vector $T_1$. In step 664 the reflection operator is applied to the vector $T_1$ and the result is stored in vector $T_3$ also Fast Fourier transforms are applied to both vector $T_1$ and vector $T_3$. Finally the pointwise product of the complex conjugate of the FFT of the convolution part of the layered Greens function is formed with T1 and the result is added to the pointwise product of $T_3$ with the FFT of the correlational part of the layered Greens function with its complex conjugate taken. The result is stored in vector $T_1$. Control is then transferred to step 668 where the inverse Fast Fourier Transform (FFT) of $T_1$ is taken and the result is stored in vector $T_1$. In step 670 either the approximation or the full action of the inverse of the second Lippmann-Schwinger operator with Hermitian conjugate taken is applied as before. If the inverse operator is applied it is approximated by the solution to a system via biconjugate gradients or biconjugate gradients stabilized. In step 670 also, the approximation I+G*γ* is applied to the vector $T_1$ resulting from step 668, and the pointwise product with Gamma* ie the complex conjugate of γ is taken. The Fast Fourier Transform (FFT) of the result is then pointwise multiplied by G* the complex conjugate of the Greens function, with care being taken to insure that the convolution and the correlational parts are performed separately as before. This result is added to $T_1$, then stored in $T_1$ and control is then transferred to step 672 where the result is pointwise multiplied by the complex conjugate of the internal field estimates and the result is added to the previous frequency and source position result. Then control is transferred to step 674 where it is determined if φ is equal to Φ if not φ is incremented by 1 and control is transferred to step 660 if it is, control is transferred to step 680 where it is determined if ω is equal to Ω. If not the ω in incremented by 1 and control is transferred back to step 658. If it is, control is transferred back to the calling subroutine.

Having seen in the previous pages how the full nonlinear inversion yields substantial increases in resolution and utility of image, we are now prepared to discuss the advanced marching technique employed in both the forward problem and the Jacobian calculations (as well as the closely related Hermitian conjugate of the Jacobian calculation) in the following algorithm.

Scientific Background to Advanced Parabolic Marching Method

The parabolic equation method is a very efficient method for modelling acoustic wave propagation through low contrast acoustic materials (such as breast tissue). The original or classical method requires for its applicability that energy propagate within approximately ±20° from the incident field direction. Later versions allow propagation at angles up to ±90° from the incident field direction. Further modifications provide accurate backscattering information, and thus are applicable to the higher contrasts encountered in nondestructive imaging, EM and seismic applications. [M. D. Collins, A two-way parabolic equation for acoustic backscattering in the ocean, Journ. Acoustical Society of America, 1992, 91, 1357-1368, F. Natterer and F. Wubbeling, "A Finite Difference Method for the Inverse Scattering Problem at Fixed Frequency," Lecture Notes in Physics, 1993, vol. 422:157-166, herein included as reference]. The source/receiver geometry we use in this device, and the relatively low contrast of breast tissue, allow us to utilize this efficient approximation. The resulting speed up relative to the Gauss Newton, conjugate gradient method [Borup et al., 1992] described in the previous patent, is dependent upon the contrast but is estimated to be 100-400 times. This allows us, for the first time, to apply inverse scattering to fully 3-D reconstruction of the human breast. Furthermore the coarse grain parallelization employed in the integral equation method is equally applicable to the parabolic algorithm. The basic structure of the inversion algorithm is essentially unchanged over our previous patent. The main difference is in the use of the Parabolic equation approximation, and more exactly, the "split step Fourier Method" [R. H. Hardin and F. D. Tappert "Applications of the split-step fourier method to the solution of nonlinear and variable coefficient wave equations," SIAM Rev. 15, 423 (1973). and M. D. Collins, "A Split-step Pade' solution for the parabolic equation method," J. Acoust. Soc. Am. 93, 1736-1742 (1993), herein included as reference] in the implementation of both the Jacobian of the residual function, and the solution to the forward problems for each view. The source/receiver geometry requirements and the relatively low contrast of breast tissue, allow us to utilize this efficient approximation for breast cancer scanner applications, for example. In particular because we may elect to use only transmission data in the breast problem, we are able to use this "parabolic approximation" in a straightforward, simple manner [see Hardin and Tappert].

To derive and elucidate our parabolic equation method in 2-D, we begin with the 2-D Helmholtz wave equation governing wave propagation in inhomogeneous media:

$$\left\{\frac{\partial^2}{\partial x^2} + \left(k^2(x,y) + \frac{\partial^2}{\partial y^2}\right)\right\}f(x,y) = 0 \qquad 1$$

Now Fourier transforming y to λ results in:

$$\left[\frac{\partial^2}{\partial x^2} + \left(\frac{1}{2\pi}\tilde{k}^2(\lambda)^* - \lambda^2\right)\right]\tilde{f}(x,\lambda) = 0 \qquad 2$$

where:

$$\tilde{k}^2(\lambda) \equiv \tilde{k}^2(x,\lambda) \equiv \int_{-\infty}^{\infty} k^2(x,y)e^{-i\lambda y}dy \qquad 3$$

and the * notation denotes convolution:

$$f(\lambda)^*g(\lambda) = \int_{-\infty}^{\infty} f(\lambda-\lambda')g(\lambda')d\lambda' \qquad 4$$

Eqn (2) can be factored in the sense of pseudo-differential operators [M. E. Taylor, "Pseudo-differential Operators," Princeton University Press, Princeton, 1981, herein included as reference]

$$\left(\frac{\partial}{\partial x} + i\sqrt{\frac{1}{2\pi}\tilde{k}^2(\lambda)^* - \lambda^2}\right)\left(\frac{\partial}{\partial x} - i\sqrt{\frac{1}{2\pi}\tilde{k}^2(\lambda)^* - \lambda^2}\right)\tilde{f}(x,\lambda) = 0 \qquad 5$$

An intuitive feel for the manner in which the Parabolic equation arises can be seen by looking at particularly simple case: when k is a constant. Then we have, upon Fourier Transforming (1):

$$\left(\frac{\partial}{\partial x} + i\sqrt{k^2-\lambda^2}\right)\left(\frac{\partial}{\partial x} - i\sqrt{k^2-\lambda^2}\right)\tilde{f}(x,\lambda) = 0 \qquad 6$$

where the square root is now simply the square root of a scalar value. From 6, it is clear that in this special case, two solutions exist:

$$\left(\frac{\partial}{\partial x} + i\sqrt{k^2-\lambda^2}\right)\tilde{f}(x,\lambda) = 0, \quad \tilde{f}(x,\lambda) = g(\lambda)e^{-ix\sqrt{k^2-\lambda^2}} \qquad 7$$

for an arbitrary function g, which represents a rightmoving wave for $e^{i\omega t}$ time dependence and:

$$\left(\frac{\partial}{\partial x} - i\sqrt{k^2-\lambda^2}\right)\tilde{f}(x,\lambda) = 0, \quad \tilde{f}(x,\lambda) = g(\lambda)e^{ix\sqrt{k^2-\lambda^2}} \qquad 8$$

representing a wave which "moves" to the left. Suppose that we know that the field is due to sources entirely on the LHS of the x-y plane. Then, for x>0 we must have:

$$\tilde{f}(x,\lambda) = g(\lambda)e^{-ix\sqrt{k^2-\lambda^2}} \qquad 9$$

Note that knowledge of f on the line x=0 (boundary condition) completes the solution since:

$$\tilde{f}(0,\lambda) = g(\lambda) \qquad 10$$

and so, on inverse Fourier Transforming:

$$f(x, y) = \frac{1}{2\pi}\int_{-\infty}^{\infty} \tilde{f}(0, \lambda) e^{-ix\sqrt{k^2-\lambda^2}} e^{i\lambda y} d\lambda, \quad x > 0 \qquad 11$$

In fact, for any $x_o > 0$:

$$f(x, y) = \frac{1}{2\pi}\int_{-\infty}^{\infty} \tilde{f}(x_0, \lambda) e^{-i(x-x_0)\sqrt{k^2-\lambda^2}} e^{i\lambda y} d\lambda, \quad x > x_0 > 0 \qquad 12$$

The idea behind the parabolic equation method is to try to factor a general inhomogeneous (i.e. k=k(x,y)) problem into forward and backward moving (in x) factors and then solve only the forward (+x) moving part (assuming that the field source is to the left (on the x-axis) of the scatterer).

Let $x_n = n\Delta$, $n = 0, \ldots$ then 12 is:

$$f_{n+1}(y) = \frac{1}{2\pi}\int_{-\infty}^{\infty} \tilde{f}_n(\lambda) e^{-i\Delta\sqrt{k^2-\lambda^2}} e^{i\lambda y} d\lambda \qquad 13$$

Since 13 is local to $x=(n+\frac{1}{2})\Delta$ we consider the discretization/approximation:

$$f_{n+1}(y) = \frac{1}{2\pi}\int_{-\infty}^{\infty} \tilde{f}_n(\lambda) e^{-i\Delta\sqrt{k^2(x_{n+1/2},y)-\lambda^2}} e^{i\lambda y} d\lambda \qquad 14$$

Detailed Description of Advanced Parabolic Marching Method Now we desire to take the y-dependence out from under the square root in order that it may then be factored out from under the integral, which will result in the integral being an inverse Fourier Transform, yielding a substantial increase in efficiency. This goal can be achieved approximately in the following manner:

$$e^{-i\Delta k_{n,m}\sqrt{1-(\lambda/k_{n,m})^2}} \approx e^{-i\Delta(k_{n,m}-k_n)} e^{-i\Delta k_n\sqrt{1-(\lambda/k_n)^2}} \qquad 45$$

where $k_{n,m} \equiv k(x_{n+1/2}, y_m) \cdot y_m = m\Delta$.

and $k_n$ is the wave number averaged over y. Equation 14 is then:

$$f_{n+1}(y_m) \approx \frac{1}{2\pi}\int_{-\infty}^{\infty} \tilde{f}_n(\lambda) e^{-i\Delta(k_{n,m}-k_n)} e^{-i\Delta k_n\sqrt{1-(\lambda/k_n)^2}} e^{i\lambda y_m} d\lambda \qquad 15$$

or $$f_{n+1}(y_m) \approx \frac{e^{-i\Delta(k_{n,m}-k_n)}}{2\pi}\int_{-\infty}^{\infty} \tilde{f}_n(\lambda) e^{-i\Delta k_n\sqrt{1-(\lambda/k_n)^2}} e^{i\lambda y_m} d\lambda$$

We have thus approximately maintained the y variation in k, while simultaneously giving a Fourier Transform formulation for the field $f_{n+1}$ and maintaining the exact Fourier propagator which is exact for all angle of scattering in homogeneous medium $k_n$.

Using the notation:

$$f(y) = F^{-1}\{\tilde{f}(\lambda)\}(y) \equiv \frac{1}{2\pi}\int_{-\infty}^{\infty} \tilde{f}(\lambda) e^{-i\lambda y} d\lambda$$

to indicate the Inverse Fourier Transform, gives:

$$f_{n+1}(y) = F^{-1}\{\tilde{f}_n(\lambda) P_n(\lambda)\}(y)$$

where $P_n$ is the range (x) dependent propagator defined as:

$$P_n(\lambda) \equiv e^{-i\Delta\sqrt{k^2(x_{n+1/2})-\lambda^2}}$$

This is our basic equation for the parabolic split step method. The "standard" form of the parabolic equation with approximate propagator is derived by using the binomial approximation:

$$\sqrt{1-(\lambda/k_n)^2} \approx 1 - \frac{1}{2}\left(\frac{\lambda}{k_n}\right)^2$$

In the above integral this approximation is valid only for angular deviations of approximately 20° from the incident propagation direction. This yields the "standard" form of the split-step parabolic equation method:

$$f_{n+1}(y_m) = \frac{e^{-i\Delta k_{n,m}}}{2\pi}\int_{-\infty}^{\infty} \tilde{f}_n(\lambda) e^{i\Delta\frac{\lambda^2}{2k_0}} e^{i\lambda y_m} d\lambda \qquad 16$$

Our numerical experiments have proven the superiority of 15 over 16 due to the occurance of the exact propagator in our approach, 15. In Fourier notation, 16 is:

$$f_{n+1}(y_m) = e^{-i\Delta k_{n,m}} F^{-1}\left\{e^{i\Delta\frac{\lambda^2}{2k_0}} F\{f_n\}(\lambda)\right\}(y_m) \qquad 17$$

This is the usual form of the split-step PE method. Our more general equation is (in Fourier notation):

$$f_{n+1}(y_m) = e^{-i\Delta(k_{n,m}-k_n)} F^{-1}\left\{e^{-i\Delta k_n\sqrt{1-(\lambda/k_n)^2}} F\{f_n\}(\lambda)\right\}(y_m).$$

An interesting interpretation of our split step method is evident from this: The algorithm step consists of an exact propagation a distance of $\Delta$ in $k_n$ (which includes diffraction) followed by a phase shift correction, i.e, multiplication by $$e^{-i\Delta(k_{n,m}-k_n)} \qquad 18$$

which corrects the phase of a plane wave travelling forward.

Relation to the Generalized Born approximation The above split step Fourier method can be seen to be a generalization of the "Generalized Born" method as developed at TechniScan scientific research division in the following manner. Suppose that we assume that the f-eld variation in y is very slow, i.e., $F\{f_n\}(\lambda) \approx 0$ for $\lambda \neq 0$ so that we may replace $$e^{-i\Delta k_n \sqrt{1-(\lambda/k_n)^2}} \approx e^{-i\Delta k_n}$$

in the above integral, 15, which gives $$\frac{1}{2\pi} \int_{-\infty}^{\infty} \tilde{f}_n(\lambda) e^{-i\Delta\sqrt{k_0^2-\lambda^2}} e^{i\lambda y} d\lambda \approx f_n(y) e^{-ik_n\Delta} \quad 19$$

Then 15 becomes:

$$f_{n+1}(y_m) = e^{-i\Delta k_{n,m}} f_n(y_m), \ f_{n+1}(y_m) = e^{-i\Delta \sum_{n=0}^{n} k_{n,m}} \quad 20$$

(assuming $f_0(y) = 1$)

which, in integral form, is:

$$f(x,y) = e^{-i\int_0^x k(x',y)dx'} \quad 21$$

This is our generalized Born approximation to the field. Thus, our PE formula 15 reduces to the GB formula if straight line propagation and no diffraction are assumed. In order to reintroduce diffraction in the GB approach, we must now "rescatter" the internal field approximation, 21, via:

$$f^S(\rho) = k_0^2 \iint \gamma(\rho') f^{GB}(\rho') \frac{H_0^{(2)}(k_0|\rho-\rho'|)}{4i} ds' \quad 22$$

$$\gamma(x,y) \equiv \frac{k^2(x,y)}{k_0^2} - 1$$

where $f^{GB}$ is computed from 21.

This "rescattering" will also improve the calculation of backscatter in our PE method. The PE formulation has no explicit backscatter in it. Equation 22 is one way to put it back in, in a manner that gives a good approximation for weak scattering.

It is important to note that the above formulation of the parabolic equation inversion method does not require the storage of any fields (ru~like the integral equation method of the previous patent). Of course, our PE method (as in the method described in our previous proposal) does not require the explicit storage of a large Jacobian, or its adjoint.

Inverse Problem and Implementation of the Jacobian.

A computational formula for the Jacobian is desired for the construction of the inversion algorithm $$\frac{\partial}{\partial k_{i,j}} f_{n+1}(y_m) =$$

$$e^{-i\Delta(k_{n,m}-k_O)}\left(-i\Delta\delta_{[n,m]}^{[i,j]}\right) F^{-1}\left\{e^{-i\Delta k_O\sqrt{1-(\lambda/k_O)^2}} F\{f_n\}(\lambda)\right\}(y_m) +$$

$$e^{-i\Delta(k_{n,m}-k_O)} F^{-1}\left\{e^{-i\Delta k_O\sqrt{1-(\lambda/k_O)^2}} F\left\{\frac{\partial}{\partial k_{i,j}} f_n\right\}(\lambda)\right\}(y_m)$$

More exactly, we use the conjugate gradient algorithms in our inversion, and consequently desire only the action of the Jacobian defined above on a wavenumber perturbation $\delta k_{i,j}$, i.e. the total variation of f due to perturbation $\delta k$:

$$\delta f_{n+1}(y_m) \equiv \sum_{i,j} \frac{\partial f_{n+1}}{\partial k_{i,j}}(y_m) \delta k_{i,j}$$

The recursion formula for the action of the Jacobian on the perturbation in k is given by $$\delta f_{n+1}(y_m) = e^{-i\Delta(k_{n,m}-k_O)}(-i\Delta\delta k_{n,m}) F^{-1}\left\{e^{-i\Delta k_O\sqrt{1-(\lambda/k_O)^2}} F\{f_n\}(\lambda)\right\}(y_m) +$$

$$e^{-i\Delta(k_{n,m}-k_O)} F^{-1}\left\{e^{-i\Delta k_O\sqrt{1-(\lambda/k_O)^2}} F\{\delta f_n\}(\lambda)\right\}(y_m)$$

It is advisable to rewrite the recursion expression for the field values $f_{n+1}(Ym)$ as:

$$f_{n+1}(y_m) = t_{n,m} \int_{-\infty}^{\infty} \tilde{f}_n(\lambda) e^{-i\Delta\sqrt{k_0^2-\lambda^2}} e^{i\lambda y_m} d\lambda$$

Where $$t_{n,m} \equiv \frac{4}{2 + \sqrt{\gamma_{n,m}+1} + 1/\sqrt{\gamma_{n,m}+1}} e^{-i\Delta(k_{O,m}-k_O)}$$

is the transmission coefficient of pixel n,m. The equation for the Jacobian with repect to the new unknown variable t is:

$$\frac{\partial}{\partial t_{i,j}} f_{n+1}(y_m) = \delta_{[n,m]}^{[i,j]} F^{-1}\left\{e^{-i\Delta\sqrt{k_0^2-\lambda^2}} F\{f_n\}(\lambda)\right\}(y_m) +$$

$$t_{n,m} F^{-1}\left\{e^{-i\Delta\sqrt{k_0^2-\lambda^2}} F\left\{\frac{\partial f_n}{\partial t_{i,j}}\right\}(\lambda)\right\}(y_m)$$

and the total field variation in terms of a perturbation in t, $\delta$ t, is:

$$\delta f_{n+1}(y_m) \equiv \sum_{i,j} \frac{\partial f_{n+1}}{\partial t_{i,j}}(y_m) \delta t_{i,j}$$

The recursion formula for $\delta$ f is therefor:

$$\delta f_{n+1}(y_m) =$$

$$\delta t_{n,m} F^{-1}\left\{e^{-i\Delta\sqrt{k_0^2-\lambda^2}} F\{f_n\}(\lambda)\right\}(y_m) + t_{n,m} F^{-1}\left\{e^{-i\Delta\sqrt{k_0^2-\lambda^2}} F\{\delta f_n\}(\lambda)\right\}(y_m)$$

The Formula for the Adjoint (Conjugate Transpose) of the Jacobian:

The recursion for the total variation in the data $\delta f_N$ (on a detector line at $x=N\Delta$) can be written as:

$$\delta f_N = \delta t_N \otimes v_N + W_N \delta f_{N-1}$$

where the matrix $W_j$ is defined as:

$$W_j = t_j \otimes A_j = [t_j]A_j$$

where $\otimes$ denotes the Hadamard product, $[t_j]$ represents the diagonal matrix:

$$[t_j] \equiv \begin{bmatrix} t_{j,1} & 0 & 0 & 0 \\ 0 & t_{j,2} & 0 & 0 \\ 0 & 0 & \ddots & 0 \\ 0 & 0 & 0 & t_{j,M} \end{bmatrix}$$

whose diagonal terms consist of the elements of the vector $t_j$ and $A_j$ is the matrix defined as (where juxtaposition always indicates matrix multiplication):

$$A_j = F^{-1} P_j F$$

Also the vector Vj is defined as $$V_j \equiv A_j f_{j-1}$$

i.e.

$$v_j = F^{-1} P_j F f_{j-1}$$

With these notational conventions, the recursion for the total variation becomes:

$$\delta f_N = [v_N]\delta t_N + W_N[v_{N-1}]\delta t_{N-1} + $$
$$W_N W_{N-1}[v_{N-2}]\delta t_{N-2} + \ldots + (W_N W_{N-1} \cdots W_1)[v_o]\delta t_o$$

The total variation can be written as a matrix product to facilitate the formation of the adjoins (conjugate transpose):

$$[\delta f_N] = ([v_N]W_N[v_{N-1}] \cdots (W_N W_{N-1} \cdots W_1)[v_o]) \begin{bmatrix} [\delta t_N] \\ [\delta t_{N-1}] \\ [\delta t_{N-2}] \\ \vdots \\ [\delta t_o] \end{bmatrix}$$

Defining the matux M as:

$$M = ([V_N] W_N[v_{N-1}] \ldots (W_N W_{N-1} \ldots W_1)[v_o])$$

one can form the conjugate transpose, which is (using the symmetry of the diagonal matrices $[v_k]$):

$$M^H = \begin{bmatrix} \overline{[v_N]} \\ \overline{[v_{N-1}]}W_N^H \\ \overline{[v_{N-2}]}W_{N-1}^H W_N^H \\ \vdots \\ \overline{[v_o]}(W_1^H \cdots W_{N-1}^H W_N^H) \end{bmatrix}$$

The equation for the action of the conjucate transpose of the Jacobian acting on $\delta f_N$ is then:

$$\begin{bmatrix} [\delta t_N] \\ [\delta t_{N-1}] \\ [\delta t_{N-2}] \\ \vdots \\ [\delta t_0] \end{bmatrix} = \begin{bmatrix} \overline{[v_N]} \\ \overline{[v_{N-1}]}W_N^H \\ \overline{[v_{N-2}]}W_{N-1}^H W_N^H \\ \vdots \\ \overline{[v_0]}(W_1^H \cdots W_{N-1}^H W_N^H) \end{bmatrix} [\delta f_N]$$

For computational purposes it is advantageous to write this equation in conjugate form:

$$\overline{\begin{bmatrix} [\delta t_N] \\ [\delta t_{N-1}] \\ [\delta t_{N-2}] \\ \vdots \\ [\delta t_0] \end{bmatrix}} = \overline{M^H[\delta f_N]} = M^T\overline{[\delta f_N]}$$

This reduces the number of conjugation operations needed for computer implementation. Thus the matrix required is actually $M^T$:

$$M^T = \begin{bmatrix} [v_N] \\ [v_{N-1}]W_N^T \\ [v_{N-2}]W_{N-1}^T W_N^T \\ \vdots \\ [v_o](W_1^T \cdots W_{N-1}^T W_N^T) \end{bmatrix}$$

The expression for $W^T$ is (as usual F will denote Fourier Transform.):

$$(W_j)^T = A_j^T[t_j] = FP_j F^{-1}[t_j]$$

where use has been made of the fact that since the propagator P is a diagonal operator:

$$P_j = P_j^T$$

The $v_j = F^{-1}P_j F f_{j-1}$ computed and stored as the forward fields are computed within the "subroutine jach" which computes the action of the transpose of the jacobian on the complex conjugate of the residual vector, followed by condgugation of the result.

The updates for one view, then, are constructed in sequence using the formulae:

$$\overline{[\delta t_N]} = [v_N]\overline{[\delta f_N]}$$

$$\overline{[\delta t_{N-1}]} = [v_{N-1}]W_N^T\overline{[\delta f_N]} = [v_{N-1}]FP_N F^{-1}[t_j]\overline{[\delta f_N]} \text{ etc.}$$

Figure 35:
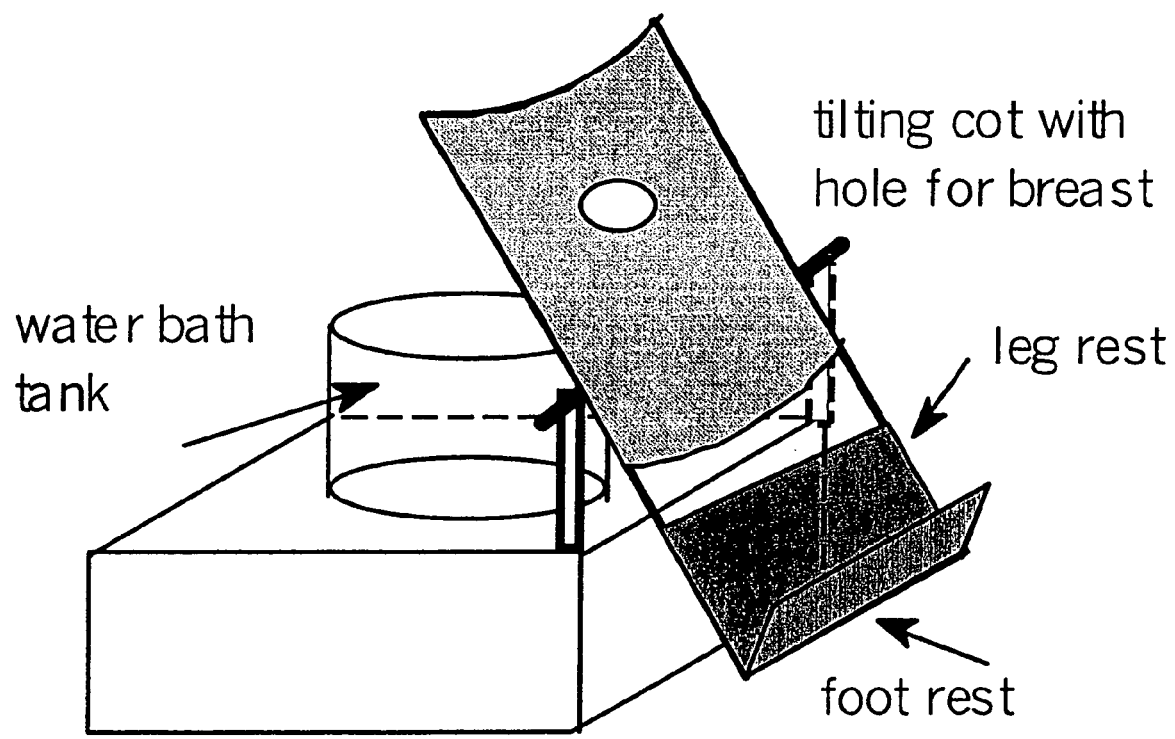
FIG. 35: Tilting cot for patient positioning when scanning using the water bath scanner.

See FIG. 35 and forward, for the flowohart, and the microfiche documentation for the source code.

Preconditioned Inversion

General Discussion of Conditioning

Suppose that the goal is to find $\min_t\|At-r\|_2$, where A is m by n matrix (m<n), t is an n-dimensional vector, and r is m-dimensional "residual" vector. By making a change of variables BS=t, to s, where B is n by m., the system to be solved is now $$ABs=r$$

is a square system. Therefore the BiConjugate gradient method or BiCGsquared algorithm can be applied to this system. BiCG squared has much better convergence behaviour than standard conjugate gradient methods for non-square systems [see references in previous patent]. Consequently the convergence to a solution ŝ will generally be much quicker, whereupon $\hat{t}=B\hat{s}$ computes the answer to the original problem. Due to the position of the conditioning matrix B, this procedure is hereafter referred to as 'postconditioning'

Two special cases:

1. $B=A^T$ in which case s is the minimum norm solution to an underdetemined problem 2. $A(\gamma) = \bigoplus_{\omega\phi} G^{sc}_\omega (I - G_\omega \gamma)^{-1} f^{inc}_{\omega\phi}$.

where $$\bigoplus_{\omega\phi}$$

indicates the direct sum in the sense of vector spaces over all frequencies, ω, and views, φ, ie concatenation. In fact, for operators $A_j$, j=1, ..., N, we have explicitly:

$$\bigoplus_j A_j \equiv \begin{bmatrix} A_1 & 0 & 0 & 0 \\ 0 & A_2 & 0 & 0 \\ 0 & 0 & \ddots & 0 \\ 0 & 0 & 0 & A_N \end{bmatrix}$$

Of course, this is a nonlinear operator, and the corresponding Jacobian $$\frac{\partial AB}{\partial g} \equiv \frac{\partial A(\gamma)}{\partial \gamma}\frac{\partial B}{\partial g} = \left(\begin{array}{c}\text{by}\\\text{linearity}\end{array}\right) = \frac{\partial A(\gamma)}{\partial \gamma}B \quad (1)$$

evaluated at some iterated guess is the object that is used in the BiCG minimization routine. B in this case is the Born or Rytov reconstruction. The general procedure for the solution of the Jacobian equation:

$$\frac{\partial A(\gamma)}{\partial \gamma} B \delta g^{sc} = -r^{(n)}$$

then involves the application of said Jacobian (1), and its conjugate transpose:

$$B^H \frac{\partial A(\gamma)^H}{\partial \gamma} r^{(n)}$$

$g^{sc}$ is the scattered field to which the Born reconstruction procedure is applied to yield γ, $$\gamma = Bg^{sc}$$

where the standard Born approximation is utilized:

$$g^{sc}(x) = \int_\Omega G(x,x')\gamma(x')f^{inc}(x')dx'$$

which upon discretization reads:

$$g^{sc} = G[f^{inc}]\gamma$$

where the standard notation for the matrix whose diagonal elements are the components of the vector $f^{inc}$ has been used:

$$[f^{inc}] \equiv \begin{bmatrix} f^{inc}_1 & & & \\ & f^{inc}_2 & & \\ & & \ddots & \\ & & & f^{inc}_N \end{bmatrix}$$

It is important to realize that the explicit matrix inversion of B is never carried out: rather, the standard Born reconstruction based upon the Fourier Diffraction Theorem is used, for computational efficiency.

Subroutine "scatter" is called from main program in FIG. 9A, in order to effect the forward calculation of the fields for each view. Control is transferred to box 2000, where inv is set=1 (inv is the index of views). Next, in box 2002, is the calculation of rotation angle θ=(inv−1)δθ. and the setting up of rotation matrix M(θ), which is then applied to transmission coefficient matrix T to yield $$T_v(x) \equiv M(\theta)T(x) x \in R^3$$

Next control is moved to box 2004, where the field for the first "slice" (ie. j=1) is set to predetermined values: s(ik), and the y index, "j" is set=

$$1, f_0(x,z) \equiv f(x,j\delta y,z)|_{j=0} \leftarrow s(z)$$

Control is then transferred to box 2006, where the Fourier Transform is applied to field slice $$j-1. F(f_{j-1})$$

Control is then transferred to box 2008, where the pointwise product is taken between the propagator $P_j$, defined as $$P_j = \text{propagator} = e^{-i\Delta\sqrt{k_0^2 - \lambda^2}},$$

and the result from box 2006, to get $$P_j F(f_{j-1}).$$

Now transfer to box 2012 where we take the Inverse Fourier transform in z-direction to get $$v_j = F^{-1}(P_j F(f_{j-1})).$$

Then move to box 2014, where $j^{th}$ field slice is given by pointwise product of transmission coefficient $T_j$ and $v_j$.

$$f_j = T_j(x)v_j.$$

Then transfer control to decision box 2016, whereupon: if j is strictly less than $N_y$, then control moves to box 2018, where indexj is increased by 1, and control is directed along arrow 2020 to box 2006. If j is exactly $N_y$, control is transferred to decision box 2024. Then, if inv<$N_{view}$, control is transferred to box 2030 where inv is incremented by 1 to inv+1, and control is then transferred along arrow 2026 to box 2002. When inv=$N_{view}$, control is returned to the main program.

Figure 32A:
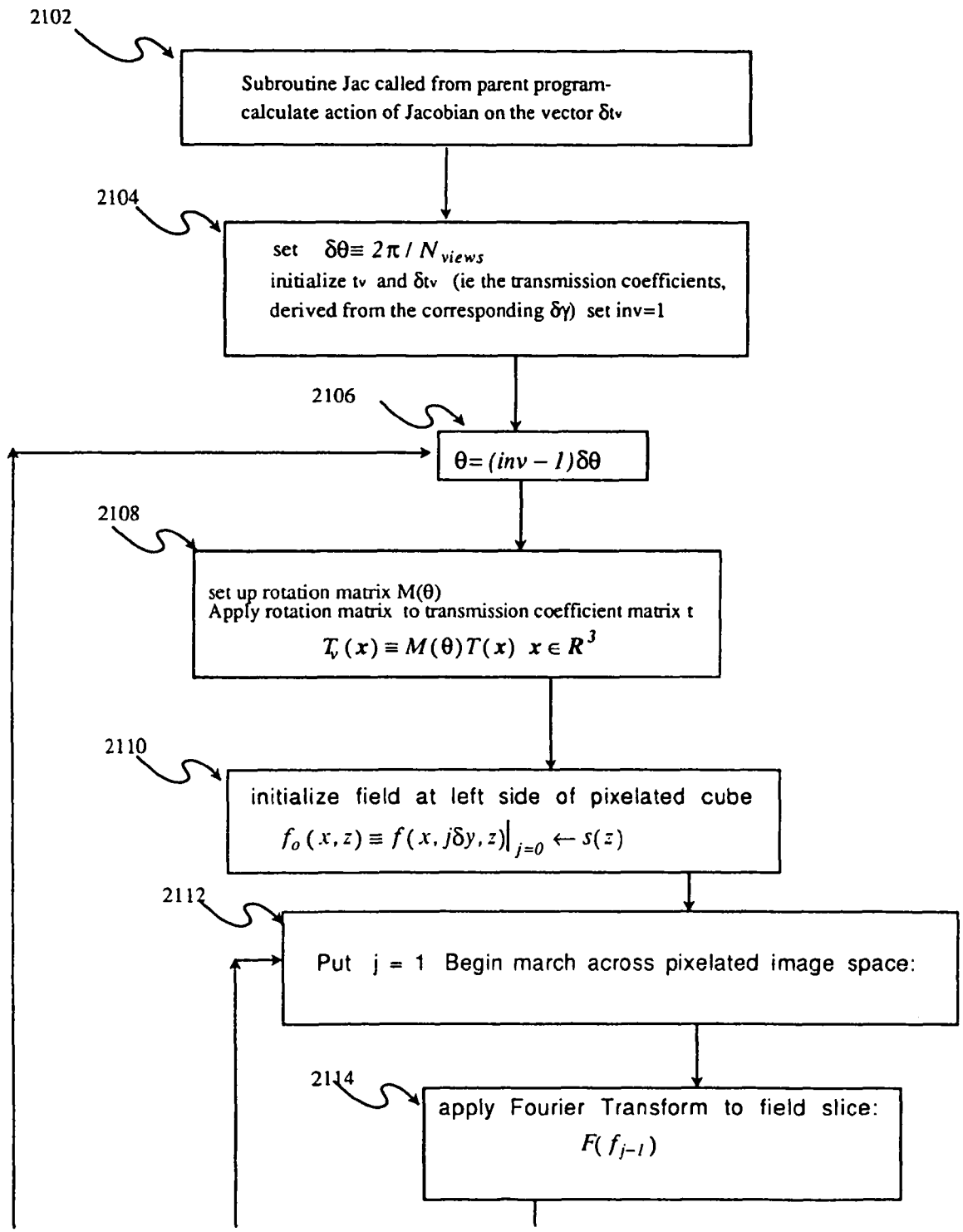
FIG. 32A. Example of subroutine Jac called from parent program.

Referring to FIGS. 32A, B, and C, control is passed to subroutine Jac from the parent program in box 2102 It will calculate the action of the Jacobian of the forward problem on the vector δy. Control is transferred to box 2104 where δθ is determined via the formula $\delta\theta \equiv 2\pi/N_{views}$, the spatially dependent transmission coefficient $T_v = t_v + 1(T_v = T_v(x,y,z)$ and the input δt, or the corresponding δγ (object function) are also initialized, and inv is set=1, ie. the index corresponding to view number Control is then transferred to box 2106 where one sets θ=(inv−1)δθ, and thus to box 2108 which sets up rotation matrix M(θ), and applies rotation matrix to transmission coefficient matrix T: $T_v(x) \equiv M(\theta)T(x)x \in R^3$. Control is then transferred to box 2110 which initializes filed at left side of pixelated cube using the formula $$f_o(x,z) \equiv f(x,j\delta y,z)|_{j=0} \leftarrow s(z)$$

Now begin the march across the pixelated image space by transferring control to box 2112 where j (y index) is set=1. Then control moves to box 2114 where we apply Fourier Transform to field slice j−1:

$$F(f_{j-1}).$$

Figure 32B:
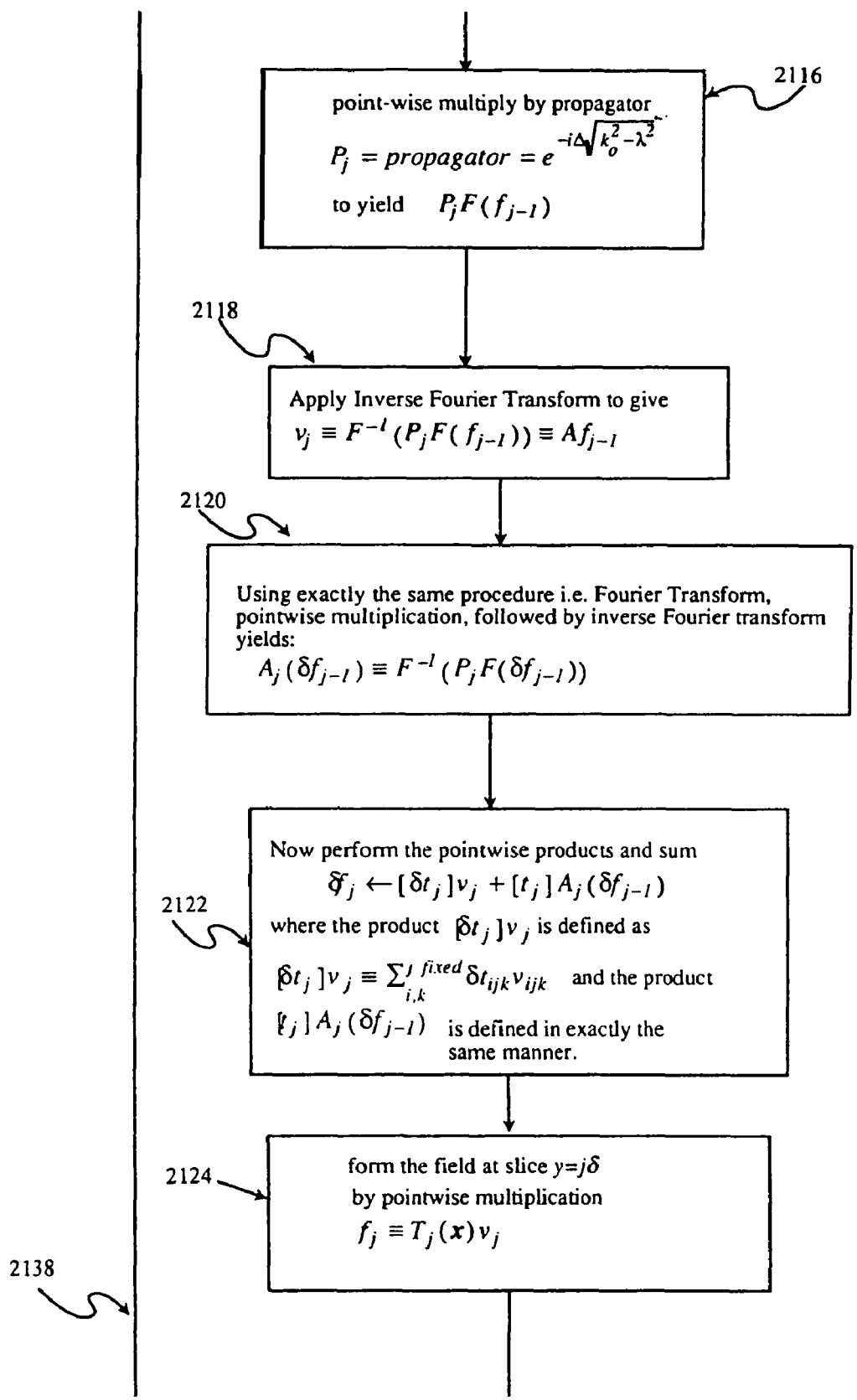
FIG. 32B. Example of subroutine Jac called from parent program continued.

Then control is transferred to box 2116 of FIG. 32B where we multiply pointwise by propagator $P_j$.

$$P_j = \text{propagator} = e^{-i\Delta\sqrt{k_o^2-\lambda^2}} \text{ to get } P_j F(f_{j-1}).$$

We now move to box 2118 where the Inverse Foufier transform in z-direction is applied to get $$v_j = F^{-1}(P_j F(f_{j-1})) \equiv A f_{j-1}$$

(this slice $v_j$ will be used later, and so is not overwritten). Control is then transferred to box 2120, where $$A_j(\delta f_{j-1}) \equiv F^{-1}(P_j F(\delta f_{j-1}))$$

is computed in exactly the same manner, i.e. the Fourier transform is applied to $\delta f_{j-1}$, then the propagator is pointwise multiplied, and finally the inverse Fourier Transform is taken. Control is then transferred to box 2122, where the pointwise product between the $v_j$ (calculated above) and $\delta t_j$, $[\delta t_j]v_j$ is formed. Also the pointwise product involving $t_j$: $[t_j]A_j(\delta f_{j-1})$ is formed. The definition of the pointwise product is given explicitly by $$[\delta t_j]v_j \equiv \sum_{i,k}^{j fixed} \delta t_{ijk} v_{ijk}.$$

Finally form the sum of the resulting "vectors", $$\delta f_j \leftarrow [\delta t_j]v_j + [t_j]A_j(\delta f_{j-1}).$$

Figure 32C:
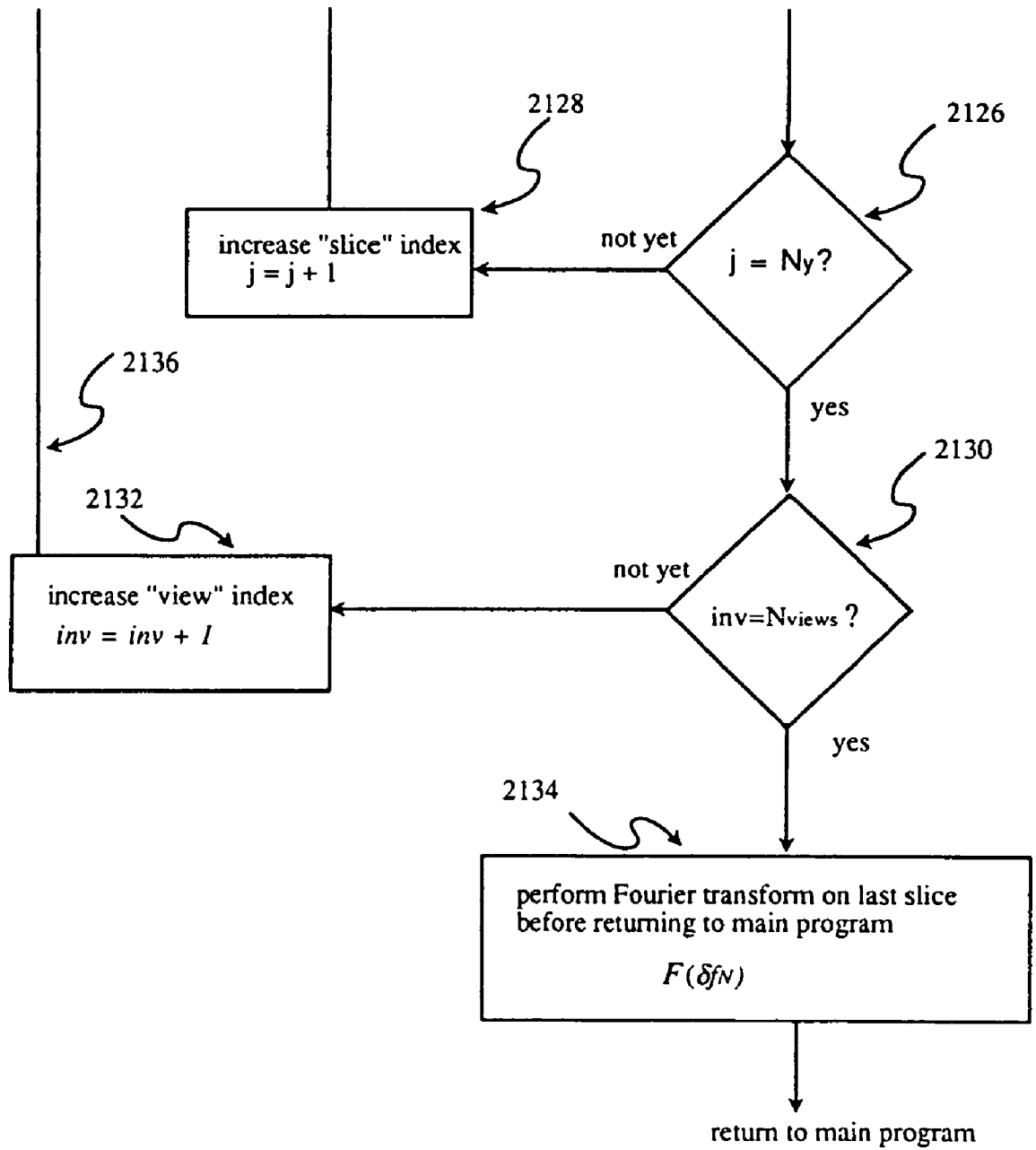
FIG. 32C. Example of subroutine Jac called from parent program continued.

If control has been transferred to decision box 2130 of FIG. 32C, and if the index for "view", inv=$N_{view}$ then control moves to box 2134, where the Fourier Transform is applied to the error on the detectors $\delta f_N$: fc←F(r≡$\delta f_N$), The resulting fc is pointwise multiplied by a scaling which in some cases, leads to more rapid convergence. This scaling is not critical to the implementation of the algorithm. The vector fc (scaled or not) is the output for the subroutine.

Figure 33A:
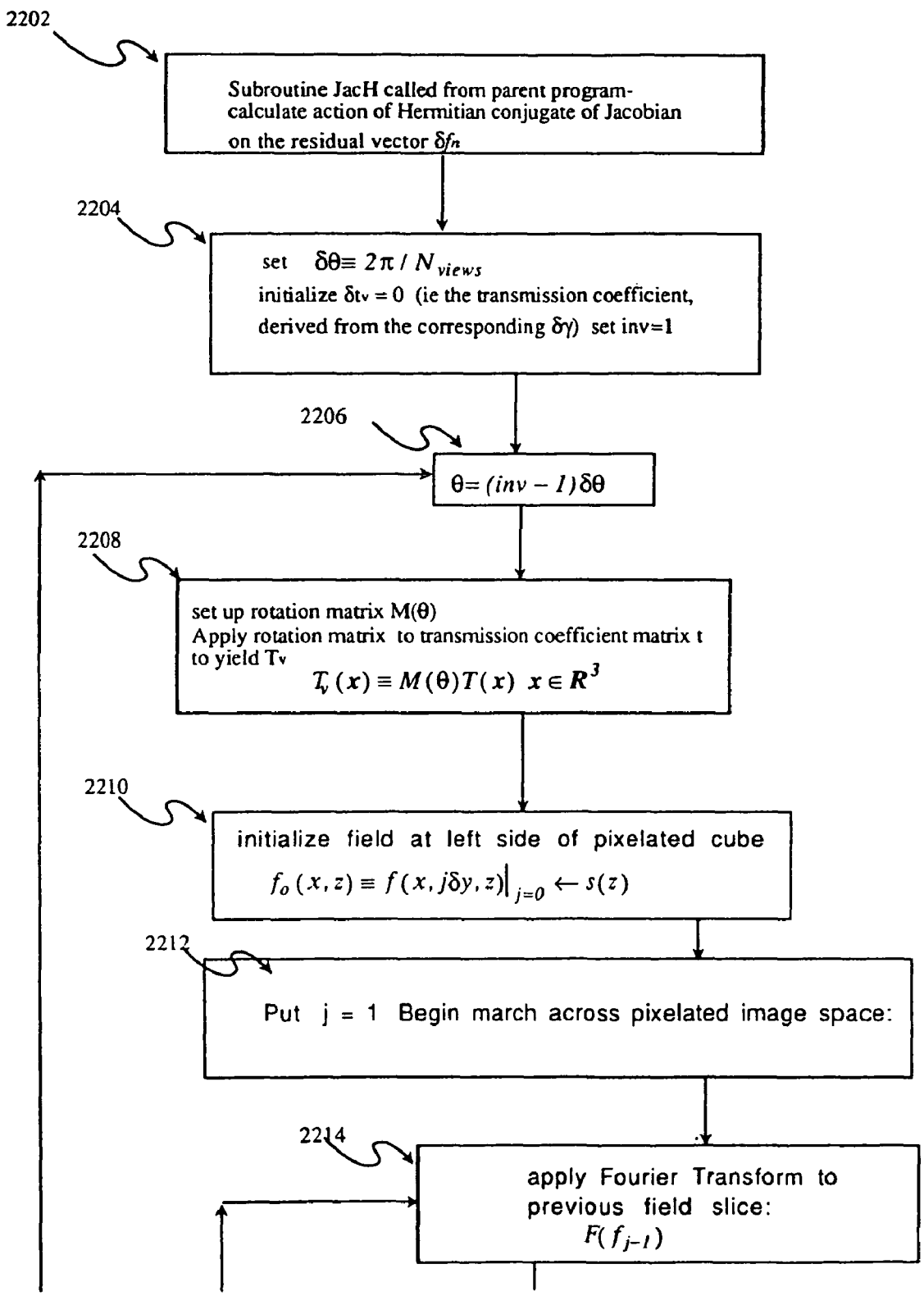
FIG. 33A. Example of subroutine JacH called from parent program.

Referring to FIGS. 33A, B, and C, subroutine JacH(r) is called from parent program—it will calculate action of Hermitian conjugate of Jacobian on the residual vector r. Control is transferred from box 2202 to box 2204 where δθ is determined: $\delta\theta \equiv 2\pi/N_{views}$ also δt is initialized=0 and invis set=1. Control is transferred then, to box 2206 where θ is defined according to: θ=(inv−1)δθ. Control is transferred to box 2208, where the rotation matrix M(θ) is defined, and applied to transmission coefficient matrix T to yield $T_v T_v(x) \equiv M(\theta)T(x)x \in R^3$. Then control is transferred to box 2210, where the field at the left side of the pixelated cube is initialized:

$$f_o(x,z) \equiv f(x,j\delta y,z)|_{j=0} \leftarrow s(z)$$

Next control is transferred to box 2212, where j is set=1, and the march across the pixelated image space is begun.

Next control is transferred to box 2214 the Fourier transform is applied to the field slice $f_{j-1}$:F($f_{j-1}$) and control is transferred to box 2216, where pointwise multiplication by the propagator $P_j$ is carried out, where $$P_j = \text{propagator} = : e^{-i\Delta\sqrt{k_o^2-\lambda^2}}.$$

The result, $P_j F(f_{j-1})$ is then transferred to box 2218 where the inverse Fourier transform in the z (vertical) direction is applied, yielding $$v_j = F^{-1}(P_j F(f_{j-1})).$$

This $v_j$ will be used below, and so is saved.

Figure 33B:
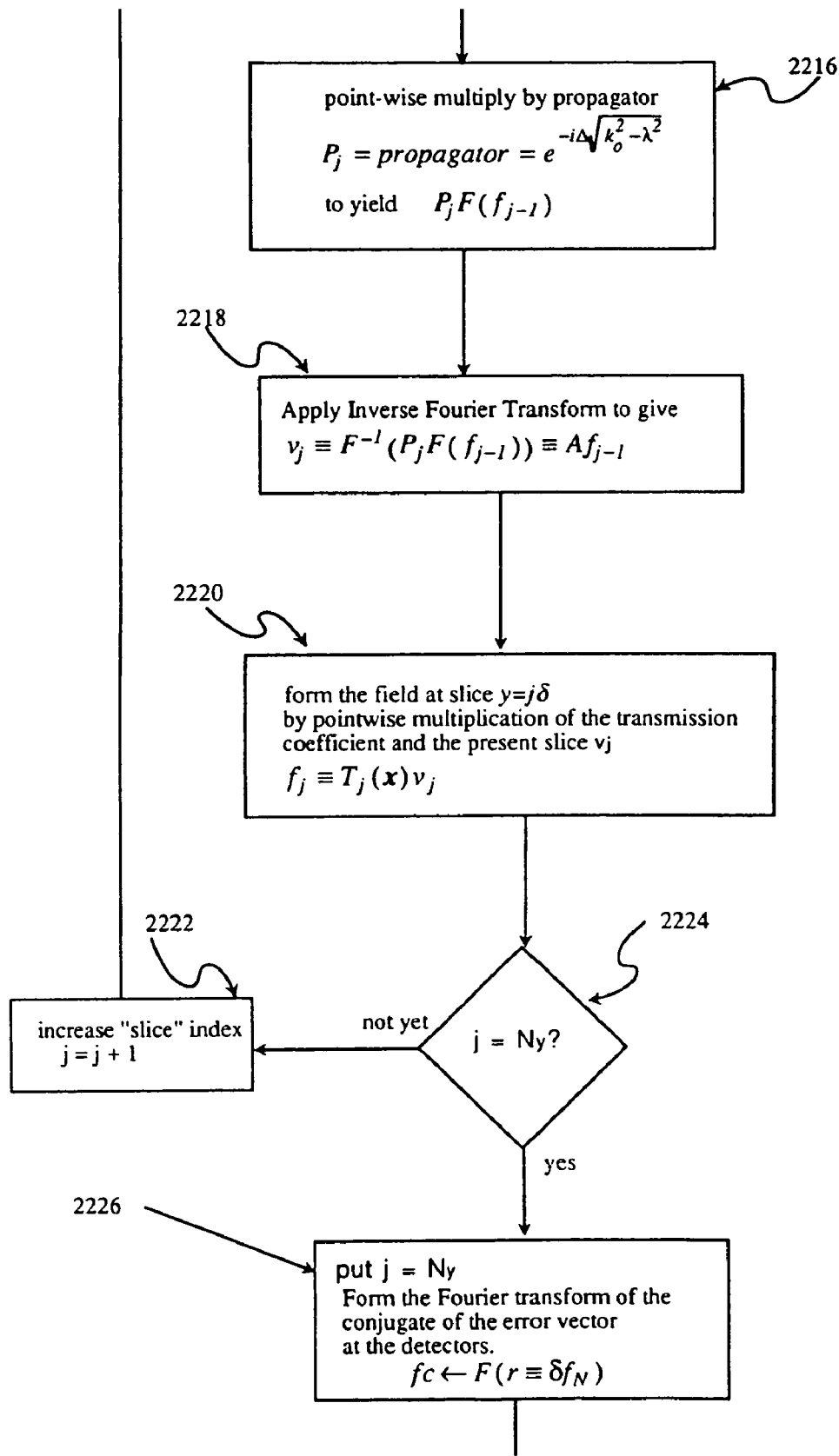
FIG. 33B. Example of subroutine JacH called from parent program continued.
Figure 33C:
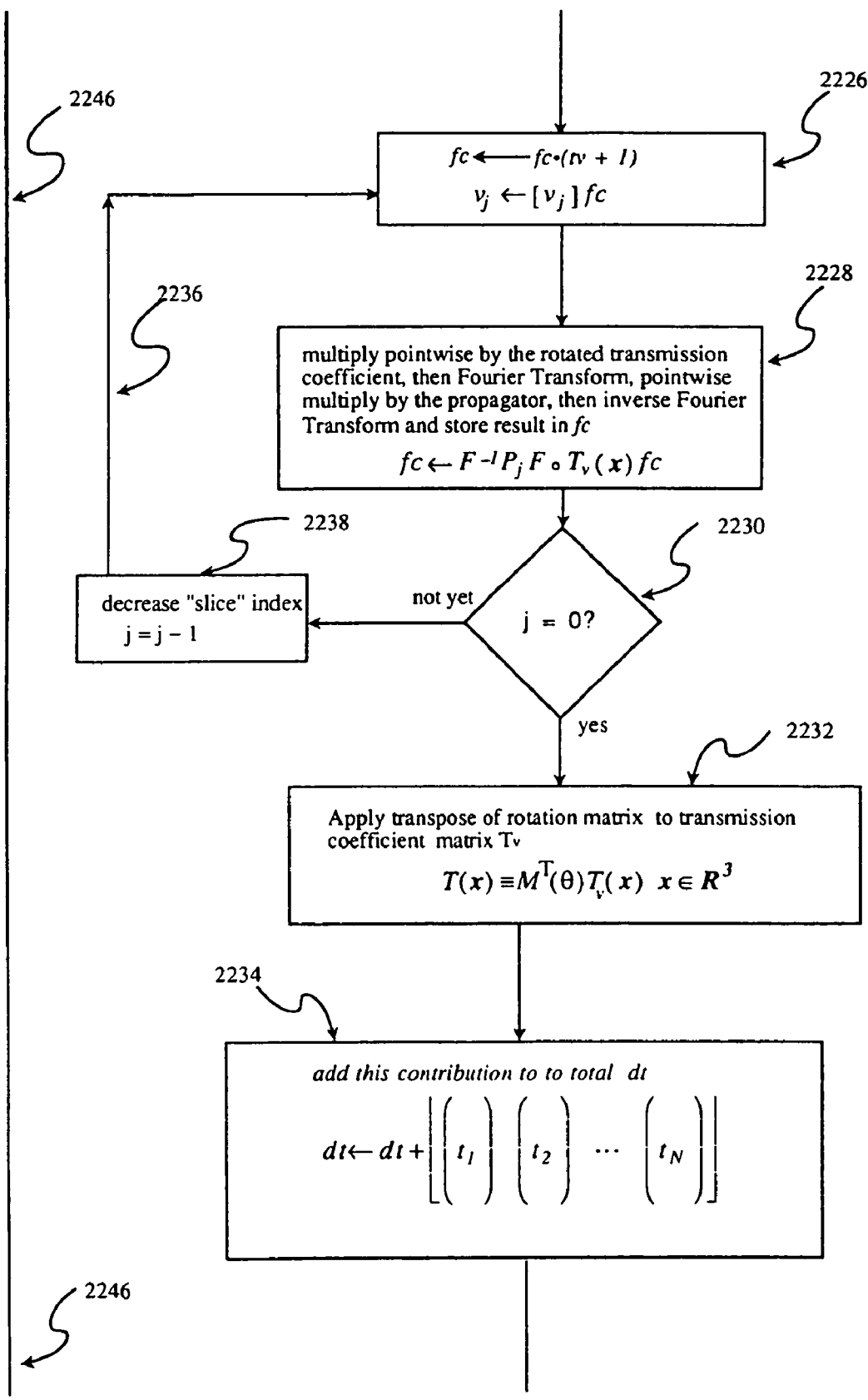
FIG. 33C. Example of subroutine JacH called from parent program continued.
Figure 33D:
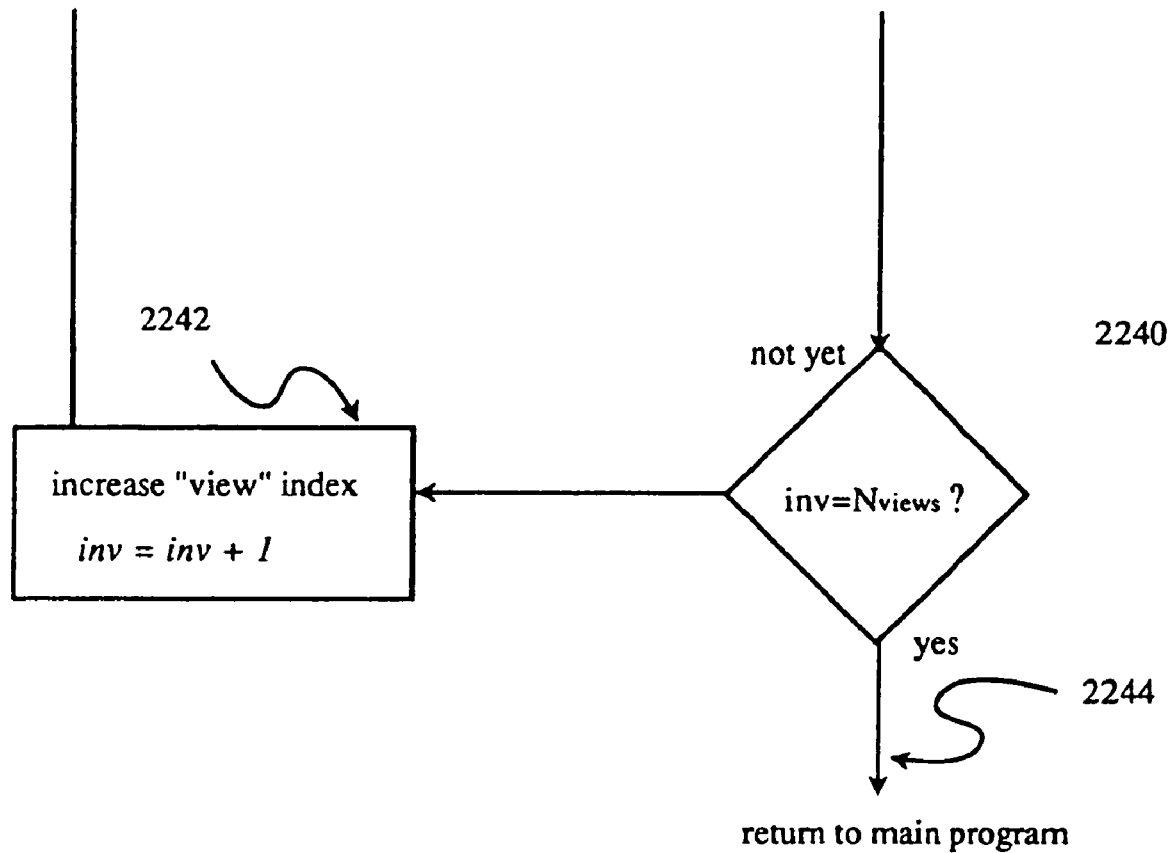
FIG. 33D. Example of subroutine JacH called from parent program continued.

From this, control moves to box 2220, where the field slice at y=jδ (recall that field values are recomputed to obviate the time consuming storage/retrieval of these on disk) is given by pointwise product of transmission coefficient $T_j$ and $v_j$. $f_j \equiv T_j(x)v_j$. Control now goes to decision box 224, whereupon if j is strictly less than $N_y$, control is switched to box 2222, where index j is increased by 1, and control reverts to box 2214, where the Fourier transform of the next field slice is taken. Whenj is equal to $N_y$, control is transferred to box 2226 of FIG. 33B. This is the beginning of the backward moving loop (ie. j decreases from $N_y$ to 1). Here we form the Fourier transform of the conjugate of the error vector at the detectors, and store result $$fc: fc \leftarrow F(r \equiv \delta f_N).$$

Now use $V_j$ (calculated in loop above) and fields fcj to calculate action of Jacobian on r, the error in field at the detector (far side of image space) in the following manner:

Control then moves to box 2226 where fc is redefined as fc·($t_v$+1) and the pointwise product between the resulting fc, and $v_j$ is taken, and stored in $v_j \leftarrow [v_j]$fc. Control is then transferred to box 2228 where we pointwise multiply fc by rotated transmission coefficient $T_v$, Fourier Transform the result, pointwise multiply by propagator $P_j$, then inverse Fourier Transform (in z direction) the result; finally store the resulting slice in fc (overwriting previous contents) fc←$F^{-1}P_j F \circ T_v(x)$ fc. Next, control is transferred to box 2230, in order to test whether j=0. If not, then control is transferred to box 2238, where the y index, "j", is decreased by one (put j←j−1), and control is transferred along arrow 2236, back to box 2226. If, however, j does=0, then the loop is done, and control moves to box 2232, where the hermitian conjugate of rotation matrix is applied to matrix of transmission coefficients tu computed in the above loop, where:

$$tv \equiv [(v_1)(v_2)\cdots(v_N)]$$

in order to rotate (estimate of) object back to original orientation $$[(t_1)(t_2)\cdots(t_N)] \equiv Rot^H(tv)$$

Then, control moves to box 2234, where we add contribution for this view to total transmission coefficient adjustment dt $$dt \leftarrow dt + [(t_1)(t_2)\cdots(t_N)]$$

Now control is transferred over to decision box 2240, where it is determined if index inv=$N_{views}$. If it is, then control is transferred over to box 2242, where index inv is increased by 1: inv←inv+1, and control is transferred up arrow 2242 to box 2246 to do the next view. If it is determined that index inv does in fact=$N_{views}$, the control is passed along arrow 2244, to return to the calling program, with output--->(δt)

Embodiments within the scope of the present invention also include computer-readable media having computer-executable instructions or data structures stored thereon. Such computer-executable media can comprise RAM, ROM, EEPROM, CD-ROM or other optical disk storage, magnetic disk storage or other magnetic storage devices, or any other medium which can be used to store desired computer-executable instructions or data structures and which can be accessed by a general purpose or special purpose computer. When information is transferred or provided over a network or another communications connection to a computer, the computer properly views the connection as a computer-readable medium. Thus, such connection is also properly termed a computer-readable medium. Combinations of the above should also be included within the scope of computer readable media. Computer-executable instructions comprise, for example, instructions and data which cause a general purpose computer, special purpose computer, or special purpose processing device to perform a certain function or group of functions.

The following discussion is intended to provide a brief, general description of a suitable computing environment in which the invention may be implemented. Although not required, the invention can be implemented in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein.

Those skilled in the art will appreciate that the invention may be practiced in network computing environments with many types of computer system configurations, including personal computers, hand-held devices, multi-processor systems, microprocessor-based or programmable consumer electronics, network PCs, minicomputers, mainframe computers, and the like. The invention may also be practiced in distributed computing environments where tasks are performed by local and remote processing devices that are linked through a communications network. In the distributed computing environment, program modules may be located in both local and remote memory storage devices.

Figure 34:
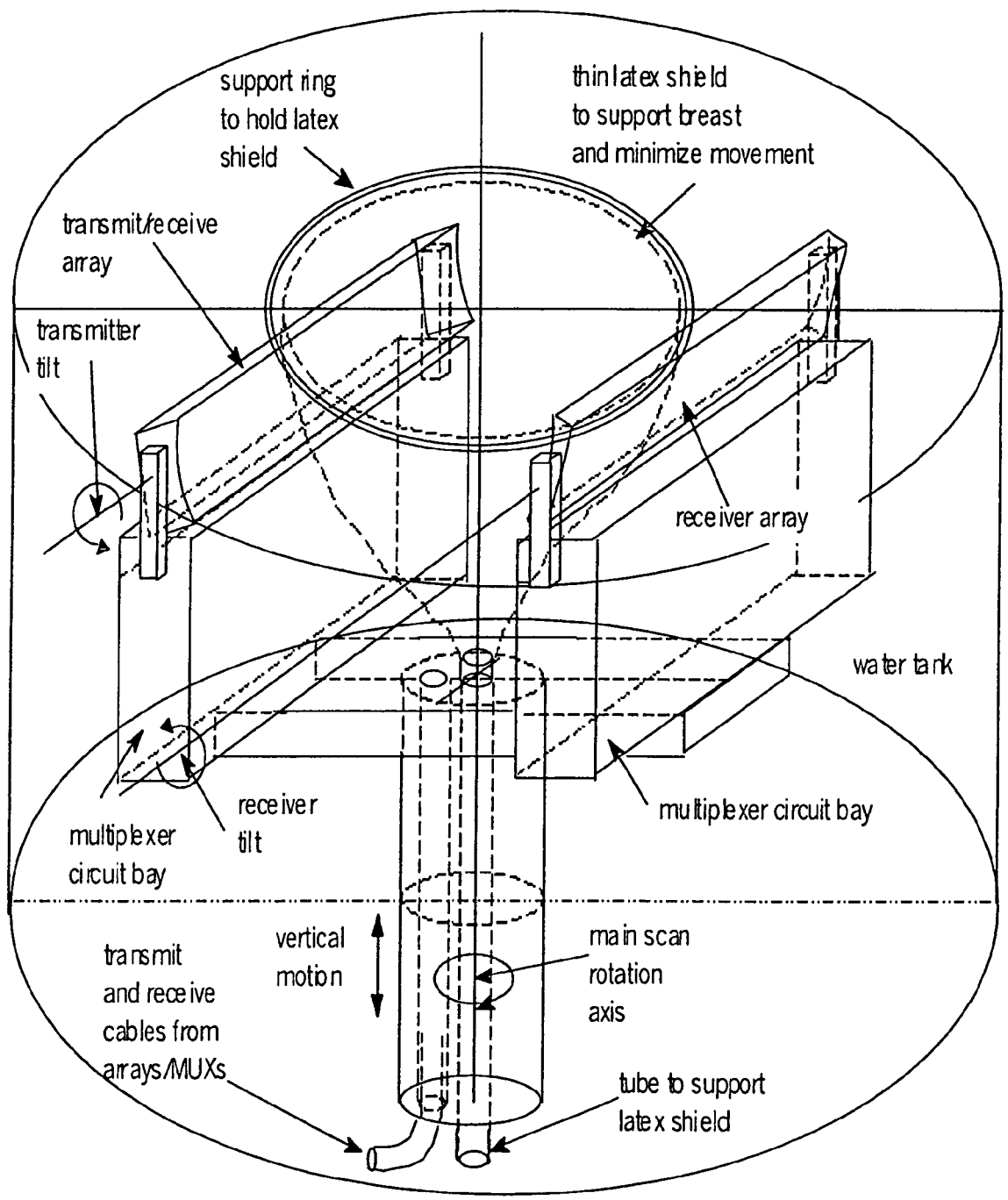
FIG. 34: Illustration of the water bath scanner and the associated two transducer arrays.

Water Bath Scanner Compatible with Reflection Tomography and Large Pixel Inverse Scattering General features of the proposed water bath scanner are shown in FIG. 34. It is seen that the general architecture is a pair of 2-D arrays (actually 1.75-D arrays) that are rotated about a vertical axis below the water surface. Each array can act as a transmitter or a receiver in both pulse echo mode (B-scan and reflection tomography) and in transmission mode (inverse scattering tomography). This arrangement allows a complete 360 degree tomographic scan to be obtained in only 180 degrees of rotation. Each array can be tilted up to image features close to the chest wall. The respective tilt axes are mutually parallel. The arrays as a group can be raised and lowered to image different slices of the breast. An optional latex rubber shield (or a woven nylon stocking-like shield) holds the breast stationary to minimize motion artifacts during scanning. The shield is held at the top of the water tank by a ring and at the bottom by a tube that passes through a hole in the rotation shaft.

A slight vacuum can be applied to the tube to make a tighter fit as needed for the latex version. This shield is disposable and contributes to the esthetics and sanitation of the scanner. A tilting cot provides a comfortable means in patient positioning, shown in FIG. 35. The patient stands on the foot rest when the cot is vertical. Then the cot tilts to the horizontal position for the scanning process. The breast is then pendant in the water bath tank. One breast at a time is scanned. The tilt process is reversed for patient exit.

Some of the important specifications for the scanner are given in TABLE 1 below. Said table illustrates the performance of both reflection tomography and inverse scattering transmission tomography. The in-plane and normal to plane spatial resolution of reflection tomography will approach 0.2 mm and 2 to 3 mm respectively (the vertical resolution may be increased to 1 to 1.5 mm with special apodizing functions).

The number of views for reflection tomography will be determined experimentally, but best estimated as equal to be the number of depth resolution lengths per circumference of a circle of diameter equal to the lateral resolution of a single view. Thus, N=λπ[2R/A]/[c/(2Pf)]=4π λRPf/[cA]=4π RP/A where λ is wavelength, R is range to target from array, A is the active lateral aperture of the array, c is the speed of sound, P is the fractional bandwidth, and f is the center frequency of the signal. The total data collection time for one slice is 12 seconds for the system specified in TABLE 1.

The in-plane spatial resolution of inverse scattering can be varied by choice of the pixel size (this ability is not possible with reflection tomography and is one of the new developments we report). In TABLE 1 we use 2 wavelength pixels (0.6 mm at 5 MHz) as an example.

The number of views for inverse scattering tomography will be taken to be the same as for diffraction tomography which is N=πD/λ where D is the breast diameter. For inverse scattering this generalizes to N=πD/p=667 at 5 MHz for D=5 inches and for p=pixel size=2 wavelengths. Using many views at one frequency is equivalent to using fewer views with more frequencies per view. This creates a speed up factor in data collection since many frequencies can be collected at each view in the same time required to collect a single frequency after 2 wavelengths. The frequency sample interval required to reduce the view-to-view angle separation for a complete high quality image reconstruction is given by $\Delta f=2\pi f/N=2\pi f/[\pi D/p]=2pf/D=0.047$ MHz. The frequency bandwidth for 16 frequencies is then 0.047 MHz×16=0.752 MHz and requires only 667/16=42 views. For this example with p=2 wavelengths, the spatial resolution is 0.6 mm. If p=1 wavelength were used, then the spatial resolution would be 0.3 mm. The total single slice, data collection time for 42 views and 16 frequencies is 4.3 seconds for the system specified in TABLE 1.

Figure 36A:
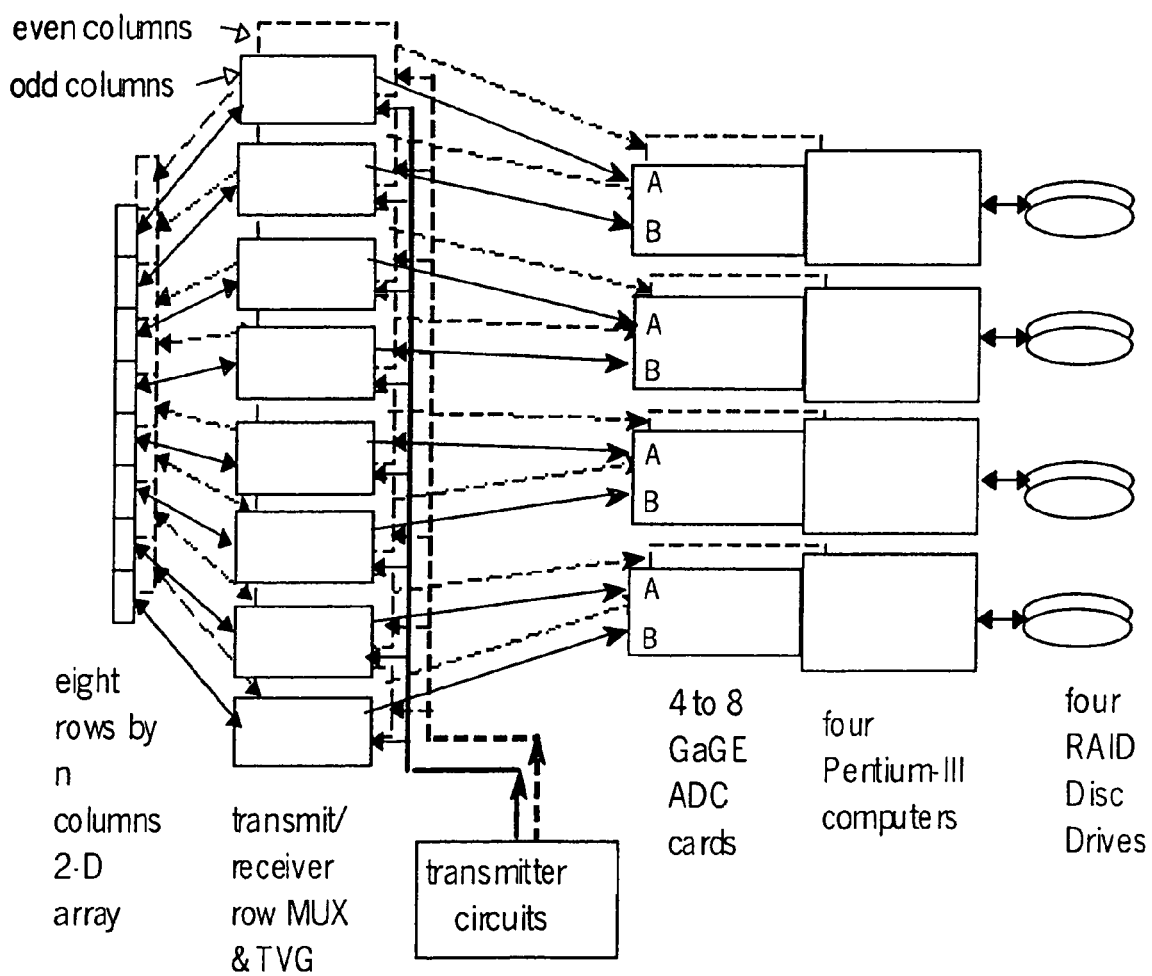
FIG. 36A: Block Diagram of the total water bath scanner system.

The block diagram of the scanner electronics is shown in FIG. 36A. Starting on the left, the transducer array is 8 by 96 elements. Each row has a receiver multiplexer (MUX) that feeds one of 8 analog to digital converters (ADC). Two ADCs are packaged on one GaGe™, Montreal, QC, Canada, "CompuScope 12100™", card and is clocked at 30 million samples per second (www.gageapplied.com). Each of the 8 channels digitizes 6,000 samples simultaneously per transmit event. Each transmit event is a transmission from a single element or from a single column (or part of a column) of elements. Also shown is a potential future expansion (using even and odd columns to separate MUXs) where 4 more GaGe cards are added to each computer or to 4 additional separate computers. If the PCI bus in each computer runs at 100 Mbytes/sec then each channel on the GaGe card runs at 25 sample/micro-sec (two Bytes/sample) into the PCI bus. Then 6000 samples will be transferred in 6000/25=240 microseconds on a single channel. This closely matches the 30 samples/micro-sec digitization rate. The computational load can be handled is several ways: (1) array processor boards; (2) Apple G4 computers with their velocity engine that, when programmed properly and matched to compatible problems, operates up to 4 GFLOPS (4 billion floating operations per second); or (3) by parallel computers. Our first choice would be to place one dual G4 PCI card in one slot of each of the 4 computers. This would provide 4×2=8 G4 computers, which would provide a maximum of 32 GFLOPS. We could also put two G4 cards in each computer for a maximum of 64 GFLOPS.

The question of over loading the PCI bus has been examined and is not a problem since our algorithms are coarse grained and each distributed process needs minimum communication with the other processes. Thus, similar operations can run in parallel on all the G4s nodes and possibly parts of each node (each G4 has 4 parallel SIMD processors). SIMD (single instruction multiple data) computers also work well with our coarse grained algorithms. The natural process divisions are frequency, view angle and slice height.

The signals to the transmitter elements are generated by an arbitrary wave form generator card (such as the GaGe™ CompuGen 1100) that is placed in the PCI bus of one of the computers that acts as the master computer. This master computer synchronizes the actions of the other computers. This is not a time consuming task since each computer's processing is largely independent of the other nodes. The output of the waveform generator is amplified by a linear amplifier and sent to the transmitter MUX. The MUX will be designed to allow future expansion for using 2 to 8 linear amplifiers to be placed after respectively 2 to 8 delay lines (connected to the common wave form generator) to form transmit beams. The MUX circuits will be solid state analog switches of either the diode network type or of the Supertex™ (Sunnyvale, Calif. 94089) MOS (metal oxide semiconductor) type. We have used the diode network type with success in one of our present scanners. The diode network requires more printed circuit (PC) board space, but has lower series resistance (about 5 Ohms) and low shunt capacitance. The Supertex approach uses less PC board space (the HV20822 has 16 switches in a 0.354 inch square package) but has higher series resistance (about 25 Ohms) and shunt capacitance (20 pf off, 50 pf on). The diode network is a safe bet. However, we will look at placing the Supertex switches in the MUX circuit bays close to the arrays to reduce cable capacitance. We will also consider using preamplifiers or buffer amplifiers after the Supertex switches to reduce the effect of their higher resistance and capacitance. The Supertex is not a bad choice and is used in many commercial ultrasound scanners with normal cable lengths from

TABLE 1

Scanner Specifications

| | | | |
|---|---|---|---|
| Diameter of water bath tank | 9 inches | Depth of water bath tank | 13 inches |
| Water temperature stability | ±0.1 degrees F. | Ground fault and safety protection | yes |
| Patient hand controlled interrupt | Yes | Breast stabilizing disposable liner | yes |
| Antibacterial water in tank | Yes | Disposable sanitary liners per patient | yes |
| Inter array separation | 5 ± 2 inches | | |
| Center frequency of arrays | 5 MHz | Percent bandwidth of arrays | 70 percent |
| Size of each array (elements) | 8 by 96 | Waterproof cable built in | yes |
| Number of sub cables/array | 768 | Impedance of sub cable (Ohms) | 50 |
| Length of arrays | 4.91 inches | Height of arrays | 0.736 inches |
| Vert. rotation of arrays | 370 degrees | Vert. motion of arrays | 6 inches |
| Tilt of arrays | 0 ± 30 degrees | Arrays identical | yes |
| Center lateral resolution/view, r = 3" | 1.47 mm | | |
| Collection time per reflection view | .34 sec | # views for reflection tomography | 19 to 36 |
| | | Total collect time for reflection slice | 12 sec |
| Spatial resolution for reflect tomog | 0.2 mm planar 2-3 mm vert. | Contrast resolution: reflect tomog | 15 to 1 |
| Number of reflection vertical slices | up to 153 | | |
| Collect time for inverse scat view | 0.102 sec | # views for inverse scat tomogra'y | 667 @ 1 freq 42 @16 freq |
| | | Total collect time/slice for inv. scat | 68 sec @ 1 freq 4.3 sec@16 freq |
| Spatial resolution: Inv. Scat. tomog | 0.3-0.6 mm pln 2-3 mm vert | Contrast resol'n: Inv. Scat. tomog | 100 to 1 |
| Frequency separation to replace angle separation for 667 views | 47 kHz | Frequency band = 16 × 47 kHz = | 752 kHz |
| Number of inv scat. vertical slices | up to 153 | | | probe to chassis where space-savings is important in the chassis. The MUX circuits will use two stages, for both the transmitter and receiver connections.

The tank and scan motion control will be constructed and assembled as per well known methods and components known to the art. The arrays can be built by transducer jobbers such as Blatek, State College, Pa. The engineering and tooling for the arrays has already been completed; and allows the present array we are using (8 rows and 16 columns) to be replicated 6 times per new array to make a 96 by 8 element array.

Figure 36B:
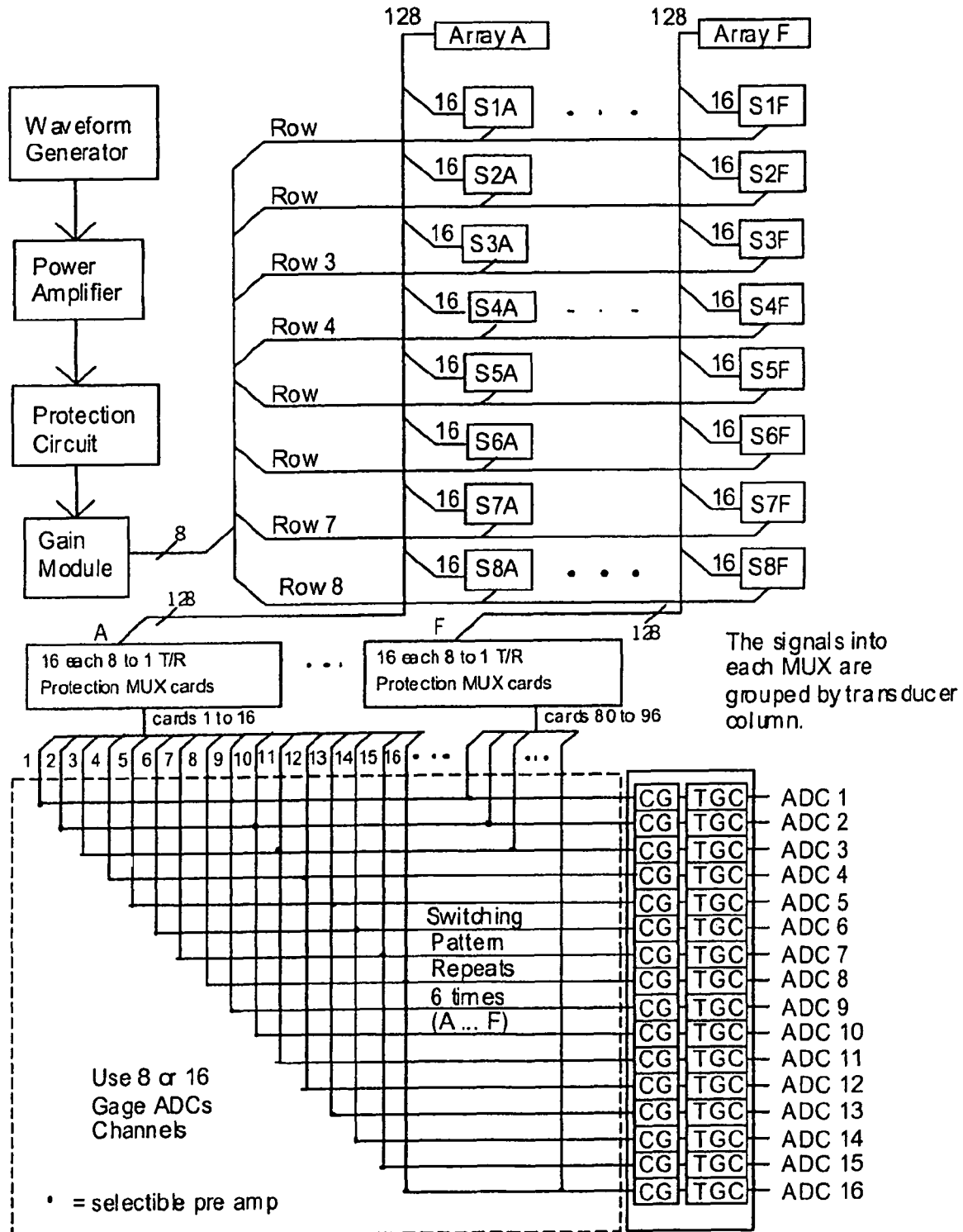
FIG. 36B: Block Diagram of the transmit and receive MUX.

A more detailed understanding of the MUX shown in FIG. 36A is given in FIG. 36B. The MUX circuit is divided into two natural parts, the transmitter MUX and the receiver MUX. The transmitter MUX is shown in the top part of FIG. 36B. The transmitter portion consists of a programmable arbitrary waveform generator, a power amplifier, a protection circuit (which blocks the signal if the voltage exceeds a critical threshold), and a programmable gain module that can provide independent gains to each of 8 separate output lines. The 8 independent output lines drive 8 independent rows of the 96-column transducer. Each row has six multiplexers, labeled A through F, that multiplex to 16 respective elements on that row, so that 6×16=96 elements per row. Each of the said six multiplexers drives one row of an 8 row by 16-column subarray. The 6×8=48 multiplexers labeled S1A through S8A for column A through SiF through S8F for column F are 16 to 1 supertex MOS, analog, high voltage switches.

The receiver multiplexer is shown in the bottom half of FIG. 36B and consists of two subsections. The first subsection consists of six modules that multiplex 128 to 16. This is accomplished by 16 daughter cards that each multiplex 8 to 1 using divide gates, 8×16=128 inputs; each subarray has 8 rows and 16 column=128 elements to match. The outputs of the six modules in the first subsection then are routed to a matrix switch that selects which of 16 outputs of each module are connected to either 8 or 16 analog to digital converters. The matrix switch has 2×6×16 nodes that thus allows either 8 or 16 ADC to be used. The node switches can be diode switches or selectable preamps. Outputs can be parallel when deselected without loading the input to any ADC channel.

The design and construction of multiplexer circuit boards is a process well known in the art. We have experience in designing such multiplexers for the compression plate inverse scattering scanner and other scanners in our lab.

The circuit board fabrication can be sent to a jobber. The circuit boards layout work can be done by Orcad or similar software. The design and coding of the software for data acquisition is a well known process in the art. For example, one can use C++ or the Labview™ application software from National Instruments™ (Austin, Tex. 78759-3504) for the main data acquisition program to allow the use of a virtual instrument panel (showing scanner array position, digitized waveforms, gain settings, etc.). The inner loops of the Labview program will be written in C or C++ for speed. Algorithm implementation and programming may be done in Fortran or C or C++.

Reflection Tomography and Inverse Scattering Imaging Algorithms

The algorithms used for reflection tomography are described further below. The exact algorithms for inverse scattering are given by Borup et al in [D. T. Borup, S. A. Johnson, W. W. Kim, and M. J. Berggren, "Nonperturbative diffraction tomography via Gauss-Newton iteration applied to the scattering integral equation," *Ultrasonic Imaging* 14, 69-85, (1992), and Wiskin, J W, Borup, D T, and Johnson, S A, "Inverse Scattering from arbitrary two-dimensional objects in stratified environments via a Green's Operator", J. Acoust. Soc. Am. Pt.1, August 1997.]. We show here an improved faster version of the parabolic method which is one of three faster versions of inverse scattering that uses forward propagating wave solutions. This method is an approximate method that is much more accurate than the Born or Rytov methods, and even approaches closely the accuracy of the exact solution. An outline of the theory will be given here, but a full account of several approaches using this method may be found in the literature and our patent.

We start with the Helmholtz wave equation $$[\partial^2/\partial x^2 + [k^2(x,y) + \partial^2/\partial y^2]]f(x,y) = 0.$$

Next we take the Fourier transform with respect to y and then assume an approximate factor of the resultant equation. Note that the convolution theorem of Fourier transforms is used, where $\otimes$ denotes the convolution operator. Let $\tilde{f}(x,\lambda)$ denote the Fourier transform of f(x, y) with respect to y. The approximate factored equation (by forcing commutation of all variables) is then:

$$\left(\frac{\partial}{\partial x} + i\sqrt{\tilde{k}^2(x,\lambda) \otimes -\lambda^2}\right)\left(\frac{\partial}{\partial x} - i\sqrt{\tilde{k}^2(x,\lambda) \otimes -\lambda^2}\right)\tilde{f}(x,\lambda) = 0.$$

We next note that the two factors represent waves moving to the left and to the right along the x axis. Taking only the wave moving from left to right (the first factor), we have $$\left(\frac{\partial}{\partial x} + i\sqrt{\tilde{k}^2(x,\lambda) \otimes -\lambda^2}\right)\tilde{f}^+(x,\lambda) = 0,$$

where the superscript + indicates that part of $\tilde{f}(x,\lambda)$ moving in the +x direction (left to right). It is a parabolic differential equation. For the special case, $k^2(x, y) = k_0^2 = \text{const} \ldots$, the factorization is exact and convolution becomes multiplication and we can solve the equation for $\tilde{f}^+(x,\lambda)$ and then take the inverse Fourier transform to get the propagation formula:

$$f^+(x, y) = \frac{1}{2\pi}\int_{-\infty}^{\infty} \tilde{f}^+(x_0, \lambda) e^{-i(x-x_0)\sqrt{k_0^2 - \lambda^2}} e^{i\lambda y} d\lambda, x > x_0 > 0,$$

which approximation propogation in breast tissue where contrast in $k^2$ is small, i.e. $k^2 \approx k_0^2$.

This formula is the basis for a multitude of marching approaches for solving the direct scattering problem. The general idea is to perform the integral on a line parallel to the y-axis and to propagate the angular spectra forward by an increment of x. Then the process is repeated for additional increments of x. The method for dealing with $k^2(x,y) \neq \text{const.}$ varies between methods (including a binomial expansion of the square root). Our approach follows this general pattern but adds additional refinements to improve accuracy and speed. This completes the outline of the parabolic method.

The parabolic method has allowed us to design the proposed scanner to use inverse scattering at 5 MHz. Using several tricks has accomplished this. One trick is to use larger pixels to reduce the computational load. Other tricks involve further approximations that increase speed but do not degrade performance. The basis of inverse scattering imaging is to solve by optimization methods the following least squares problem for the vector of independent variable y or (x,y)*, whose components are the image parameters. Let $f^{(measured)}(x_{det})$ be the measured field on detectors and let $f^{(calculated)}(x_{det},\gamma,f^{(inc)})$ be the computed received field as a function of an estimate of $\gamma$ and the incident field $f^{(inc)}(x)$ in the body and on the detectors. Then the scattering potential is found by finding the minimum value of the norm of the measurement residual R, where, R is defined as the square of the difference, in Hilbert space, between the measured and computed fields on the detector.

$$\min_{\gamma}\{\|f^{(measured)}(x_{det}) - f^{(calculated)}(x_{det}, \gamma, f^{(inc)})\|^2\} = \min_{\gamma}\{\|R\|^2\}$$

We have shown how this optimization problem may be solved by Gauss Newton, Fletcher Reeves, Ribiere Polak and other methods [D. T. Borup, S. A. Johnson, W. W. Kim, and M. J. Berggren, "Nonperturbative diffraction tomography via Gauss-Newton iteration applied to the scattering integral equation," *Ultrasonic Imaging* 14, 69-85, (1992), J W Wiskin, D T Borup, S A Johnson, "Inverse Scattering from arbitrary two dimensional objects in Stratified Environments via a Green's Operator", APPARATUS AND METHOD FOR IMAGING WITH WAVEFIELDS USING INVERSE SCATTERING TECHNIQUES, S. A. JOHNSON ET AL.], herein included by reference. Formerly we used integral equations or finite difference time domain (FDTD) methods to solve the forward problem (given $\gamma$ and $f^{(inc)}(x)$, compute $f^{(calculated)}(x_{det},\gamma,f^{(inc)})$). The Jacobian is defined as $$J \equiv \frac{\delta f^{(calculated)}}{\delta \gamma}$$

The solution, $\gamma$, is found by the iteration $$J^{(n)}\delta\gamma^{(n)} = -R^{(n)}$$

$$\gamma^{(n+1)} = \gamma^{(n)} + \delta\gamma^{(n)}$$

The derivation and use of the Parabolic Jacobian is based on a recursion process and is found in our patent [APPARATUS AND METHOD FOR IMAGING WITH WAVEFIELDS USING INVERSE SCATTERING TECHNIQUES, S. A. JOHNSON ET AL.] in a subsection called "Inverse problem and construction of Jacobian" in section call "EXAMPLE 12, PARABOLIC MARCHING METHODS".

We form a Jacobian for the parabolic method and incorporate it as part of the above iterative formula. We next show how the new parabolic method performs in terms of speed and accuracy by simulating the geometry and parameters for scanners similar to the proposed scanner specified in TABLE 1.

EXAMPLES OF EMBODIMENT OF INVENTION

Example 1

In this example we consider the design of a compression plate ultrasound scanner combining both reflection imaging and transmission inverse scattering imaging. This is not the geometry for the water bath scanner, yet we show that both geometries can produce images of sound speed and attenuation.

Figure 37A:
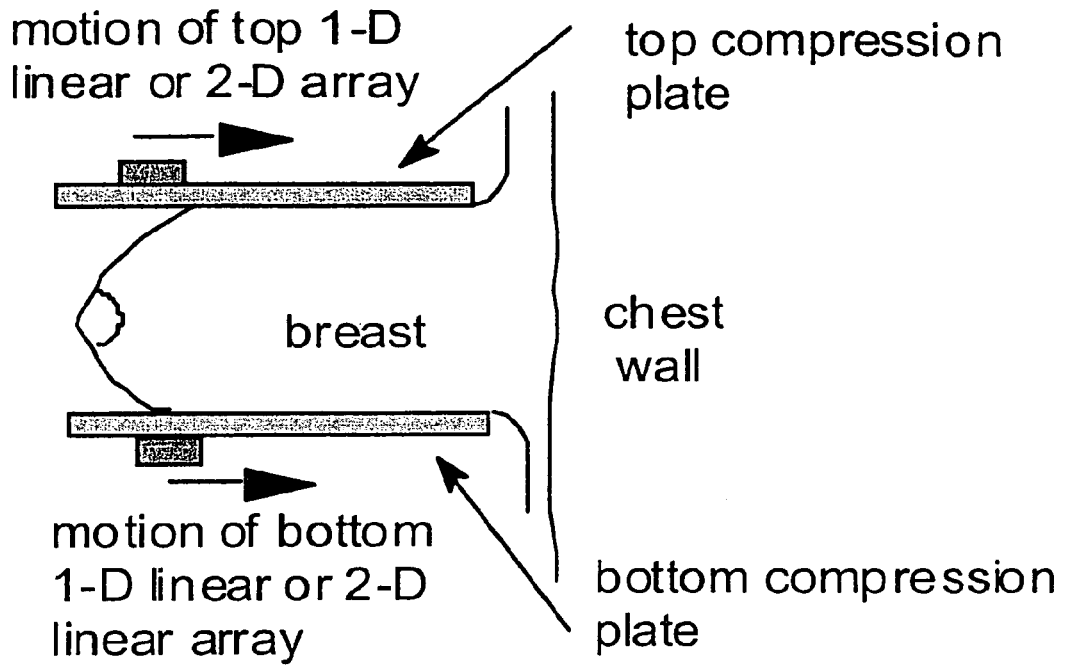
FIG. 37A: Side view of the ultrasound compression plate scanner for transmission inverse scattering and reflection ultrasound.
Figure 37B:
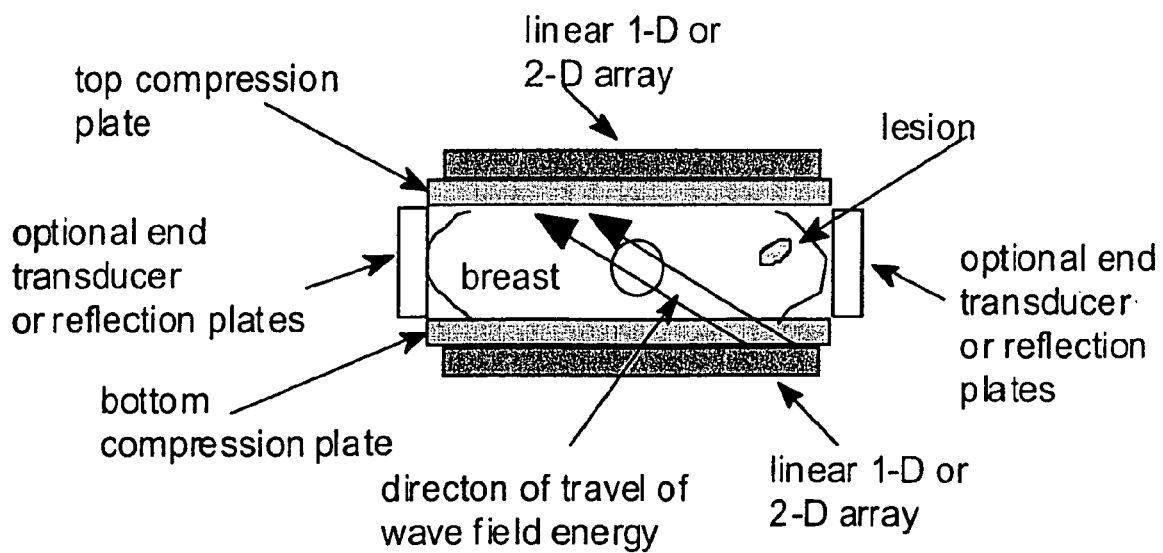
FIG. 37B: End view of the ultrasound compression plate scanner for transmission inverse scattering and reflection ultrasound.

We specify two arrays facing each other, with their faces mutually parallel. Each array can be a 1-D array or a 2-D array of transducer elements. We have constructed a compression plate scanner where each array is a 1-D array with 256 elements with $\lambda/2$ element separation at 2 MHz. A drawing of this compression plate configuration is shown in FIGS. 37A and 37B. Therein is shown the side view of a breast between two compression plates and an end view of the top and bottom linear array transducers and their translation motions. The two opposing transducers allow transmission data to be collected that includes scattering and diffraction into wide angles thus improving spatial resolution. The motion of the top and bottom linear 1-D array or 2-D array is included to image successive slices of the breast. The top and bottom compression plates are also shown.

Figure 37C:
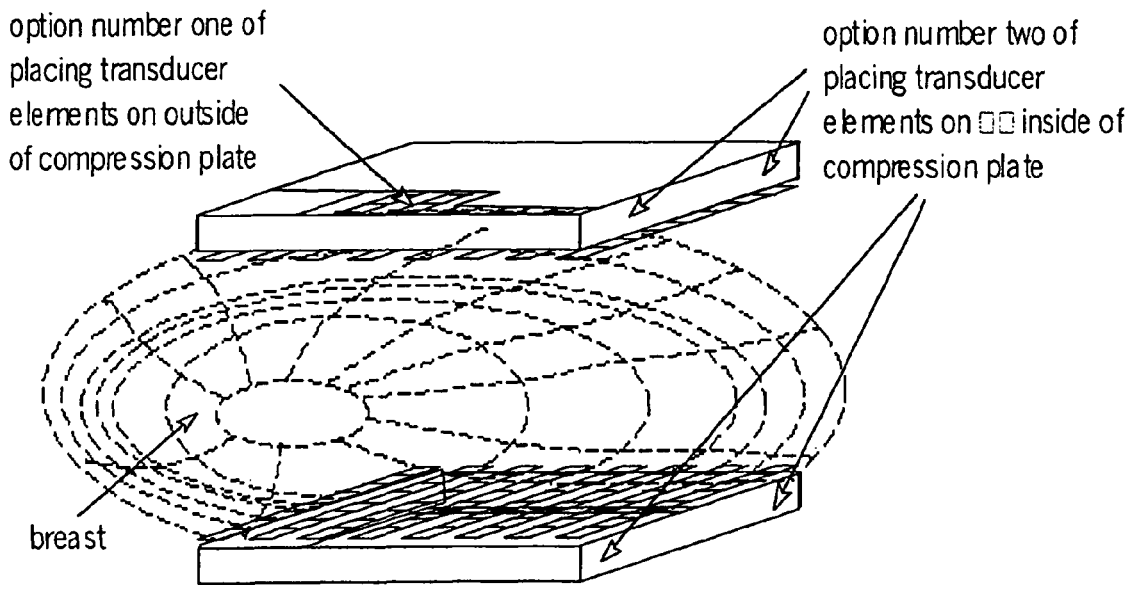
FIG. 37C: Isometric view of the compression plate scanner showing options for placing transducer elements either inside or outside of the top and bottom compression plates.
Figure 37D:
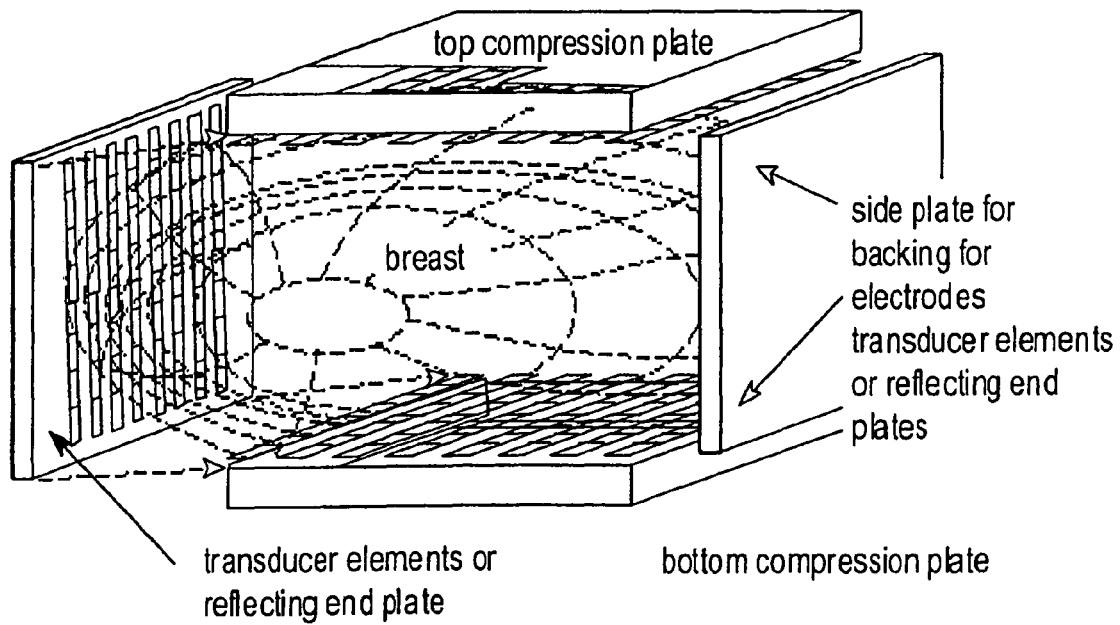
FIG. 37D: Isometric view of the compression plate scanner showing options for placing side compression plates with optional transducer elements either inside or outside of the side compression plates.
Figure 37E:
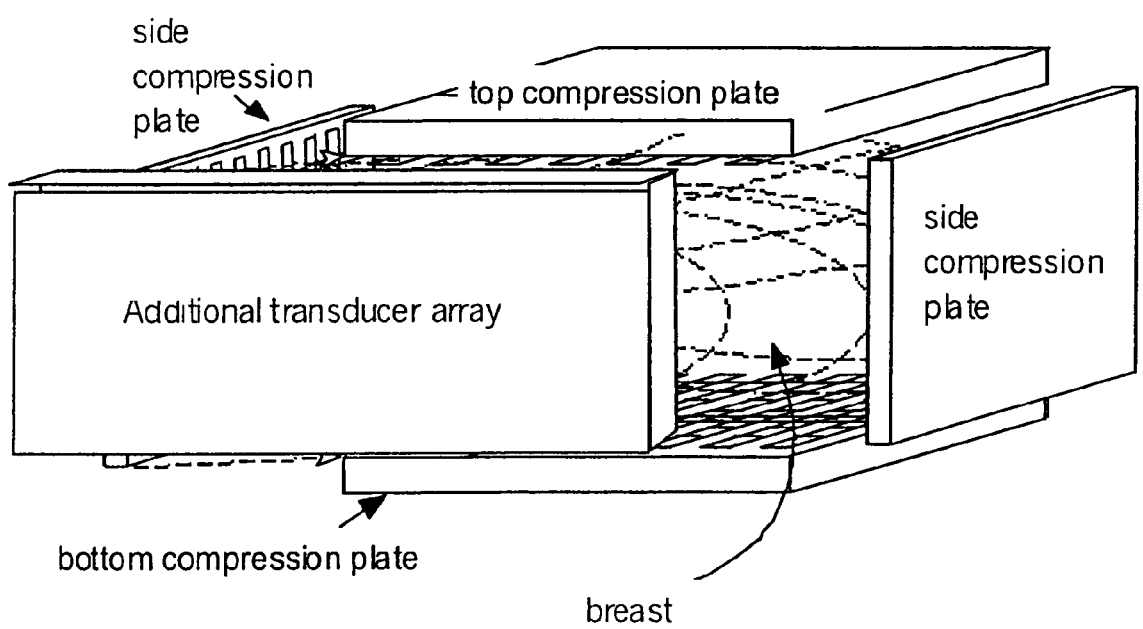
FIG. 37E: Isometric view of the compression plate scanner showing the option for placing front compression plates with optional transducer elements either inside or outside of the front compression plates.

The array geometry can be extended to provide improved imaging by adding side reflecting plates or side transducer arrays which also serve as side compression plates. This extension in function is shown in FIGS. 37C and 37D. In particular, FIG. 37C shows an isometric view of a compression plate scanner showing options for placing transducer elements either inside or outside of the top and bottom compression plates. We also note that the top and bottom transducer arrays can be used for reflection imaging as well. The side plates with transducers may also be used for reflection imaging. FIG. 37D shows an isometric view of a compression plate scanner showing options for placing side compression plates with optional transducer elements either inside or outside of the side compression plates. A front compression plate and optional reflector or transducer array can also be added as a front plate as is shown in FIG. 37E.

A simulation of the compression plate scanner is described next. The bandwidth for the reflection imaging mode was set equal to a Blackmann window from 0 to 2 MHz with a center frequency of 1 MHz. The reflection mode beam former used a 16-element segment of the array to create a beam perpendicular to the array face which was then translated across the array. The beam former was focused at all ranges for both the transmitter and receiver elements and a Hamming window was used to apodize both the transmitter and receiver beams FIG. 38A. Shows the speed of sound model of a breast compressed between two plates as in a mammogram. FIG. 38C. Shows the corresponding attenuation model. The tissue model for the simulation was constructed with five tissue speeds of sound and attenuations. For speed of sound: $C_{fat}$=1458 m/s, $C_{parenchyma}$=1519 m/s, $C_{tumor}$=1564 m/s, $C_{cyst}$=1568 m/s, $C_{skin}$=1525 m/s. For attenuation: $a_{fat}$=0.41 dB/cm/MHz, $a_{parenchyma}$=0.81 dB/cm/MHz, $a_{tumor}$=1.18 dB/cm/MHz, $a_{cyst}$=0.10 dB/cm/MHz, $a_{skin}$=0.81 dB/cm/MHz. A value of 1500 m/s for water was assumed. A random component with mean 0 and uniformly distributed from −5% to 5% of the average speed of sound-was added to the speed of sound model. The data was generated with the generalized Born approximation corrected for time delay and attenuation loss through the tissue. The generalized Born scattering model and image arrays were 512 by 200 with a $\lambda/4$ at 2 MHz pixel size. A reflection image was made by software that simulates a reflection mode scanner. FIG. 38E shows the reflection mode image created from the simulated data for the model defined in FIGS. 38A and 38C. The image range is −50 dB (black) to 0 dB (white). Notice the noise and speckle caused by the random speed of sound component. The speckle caused by the random component prevents the identification of the targets (except possibly the cyst although there are speckle artifacts at least as bright).

The inverse scattering data was generated by computer simulation using a direct scattering solver. This solver generated data at all elements on the receiving array for each element transmitting on the opposite transmitter array. The inverse scattering image was formed by software that inverted this simulated data. Perfectly reflecting plates (infinite impedance) were assumed to exist on the other two sides. Two frequencies, 1 MHz and 2 MHz, were used. The image array was 256 by 100, $\lambda/2$ at 2 MHz, pixels. For 30 iterations, the algorithm required 1.5 hr. of CPU time on a 400 MHz Pentium II. The model defined in FIGS. 38A and 38C was used to generate data which was then inverted with the parabolic inverse scattering algorithm.

The performance of the standard parabolic method with ½ wavelength pixels is shown if FIG. 38A through 38D.

Figure 38A:
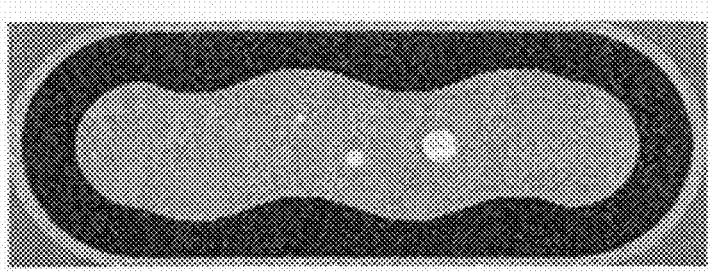
FIG. 38A: Speed of sound model of a breast compressed between two plates as in a mammogram.
Figure 38B:
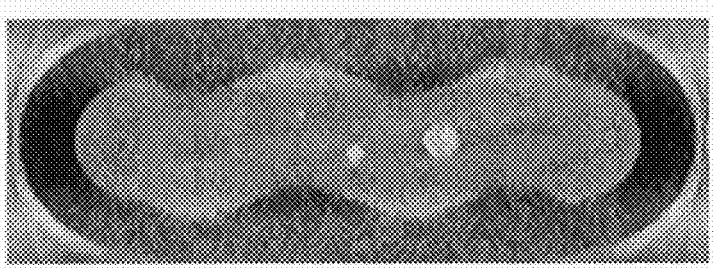
FIG. 38B: Reconstructed image of sound speed (including a random component) using a ½ wavelength pixel parabolic inverse scattering algorithm.
Figure 38C:
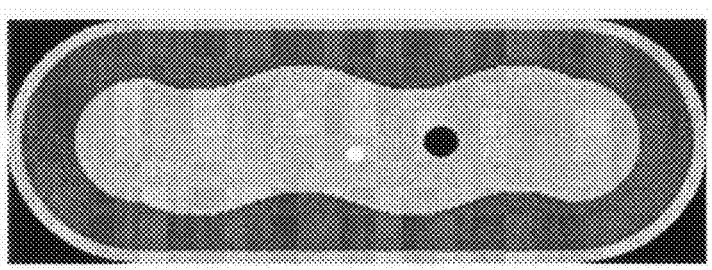
FIG. 38C: Attenuation model of a breast compressed between two plates as in a mammogram.

FIG. 38A. Shows the true speed of sound model. FIG. 38B shows the reconstructed image of sound speed using the ½ wavelength pixel parabolic inverse scattering algorithm. Values range from 1419 m/s (black) to 1602 m/s (white). Notice that unlike the reflection mode image, all targets are visible. If sources & receivers are added to the sides, the reconstructed image becomes almost identical to original, but this simulation has only the top and bottom arrays. Note the accurately reproduced random component of the speed of sound.

Figure 38D:
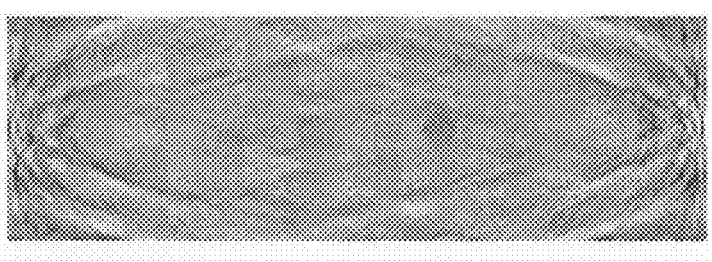
FIG. 38D: Reconstructed image of the acoustic attenuation using a ½ wavelength pixel parabolic inverse scattering algorithm.
Figure 38E:
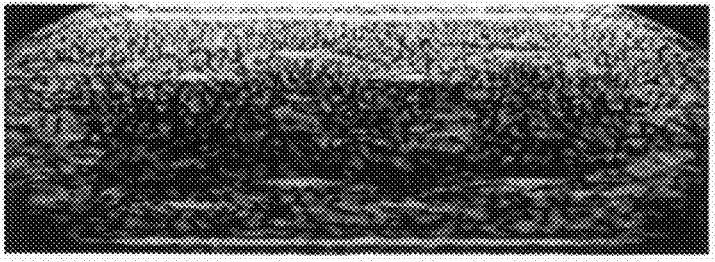
FIG. 38E: B-scan image created from simulated data for the model defined in FIGS. 5.$a$ and 5.$c$ with scattering from changes in speed of sound.

FIG. 38C. Shows the true corresponding attenuation model. Note that no random components were added to the attenuation for this simulation. FIG. 38D. Shows the reconstructed image of the acoustic attenuation using the ½ wavelength pixel parabolic inverse scattering algorithm. Notice that all of the targets are clearly visible. The original parabolic method used $\lambda/2$ pixels. With $2\lambda$ pixels, there are $4\times4=16$ times fewer pixels, and 4 times fewer sources and 4 times the inner loop speed, for a factor of $4^4=256$. At 5 MHz the $2\lambda$ pixel spatial resolution is 0.6 mm. With the new parabolic method two options still exist: (1) use $\lambda/2$ or $\lambda$ pixels and run the imaging program over night for those slices that are wanted at 0.3 mm spatial resolution; or (2) increase computing power. By Moore's law, computing speed increases 2.5 times per 2 years, so in about 12 years 0.3 mm resolution may be possible in some breast types.

Example 2

Inverse scattering images from real lab data from two ¼ inch, 5 Hz Panametrics™ video scan transducers facing each other and using parabolic inverse scattering algorithm.

This example illustrates that our breakthrough in large pixel parabolic codes is practical. We applied it to existing time of flight data (digitized waveforms) that were collected to be analyzed by time of flight tomography (a modified x-ray CT algorithm). No transducer array was used as a receiver (thus no diffraction pattern was recorded). Nevertheless, the parabolic inverse scattering method has defined the two holes in an agar phantom somewhat better than the straight line time of flight method (see FIG. 39).

Figure 39A:
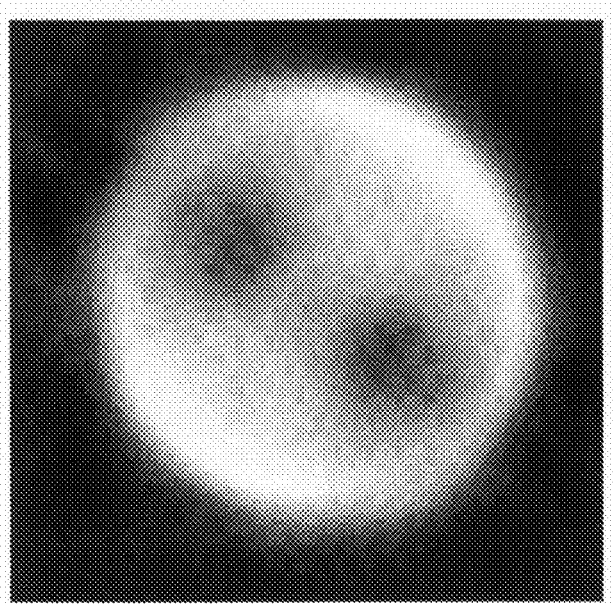
FIG. 39A: "Time of flight image" i.e., speed of sound map (image) obtained from real time of flight data collected on a laboratory scanner through application of a time of flight CT algorithm.

FIG. 39A. shows the "time of flight image" i.e., speed of sound map (image) obtained from real time of flight data collected on a laboratory scanner through application of a time of flight CT algorithm. Minimum=black=1477 m/s, Maximum=white=1560 m/s.

Figure 39B:
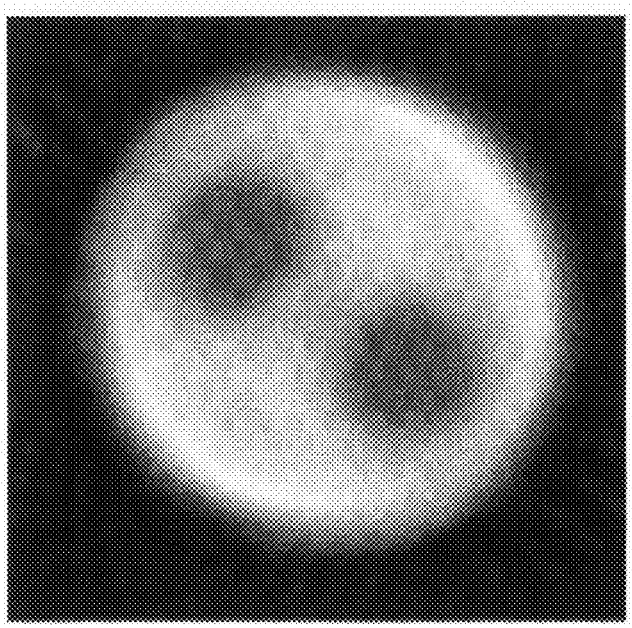
FIG. 39B: Sound speed map (image) obtained after 15 steps of the new fast 2 wavelength pixel algorithm starting with the same data as the time of flight CT algorithm.

FIG. 39B Shows the sound speed map (image) obtained after 15 steps of the new fast 2 wavelength pixel algorithm starting with the same real lab data as used by the time of flight CT algorithm. Minimum=black=1465 m/s, Maximum=white=1560 m/s. Although the data used was not designed for this new algorithm, the image is better than the corresponding "time of flight image". Based on this evidence we therefore point out that with hardware designed to be compatible with and optimized for this new method, we can rapidly compute images of speed of sound at 5 MHz that exceed the spatial resolution of time of flight images by a factor of 10 (0.6 mm vs. 6 mm). With further effort we can obtain images of 0.3 mm and even 0.15 mm resolution (by combining reflection and transmission data). We have tested this claim with computer simulation and the results support the claim as we show in FIGS. 40 and 41 in the next example.

Conclusion for Example 2: The new fast algorithm has been tested in adverse conditions with poor data (incomplete angular spectrum) from the laboratory and performs better than the "gold standard" time of flight CT algorithm. Its predicted performance should be about 10 times better when using data that is designed to meet it's computational and interface requirements. This will be verified in the next two examples.

Example 3

Inverse scattering images from simulated data from ¼ inch piston transducers using the parabolic inverse scattering algorithm.

Figure 40A:
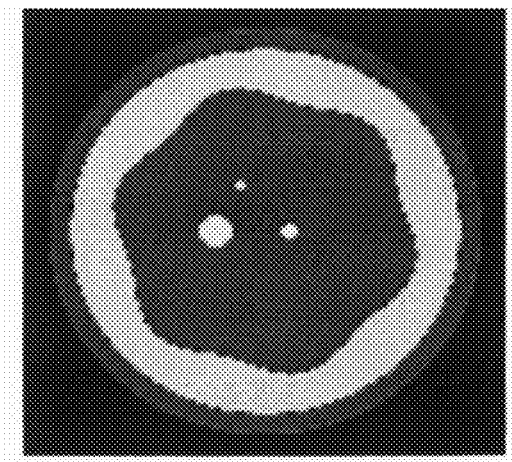
FIG. 40A: Normalized true speed of sound image, $\gamma=[c_o/c(x,y)-1]$, used to generate simulated data to test the 2 wavelength pixel algorithm.
Figure 40B:
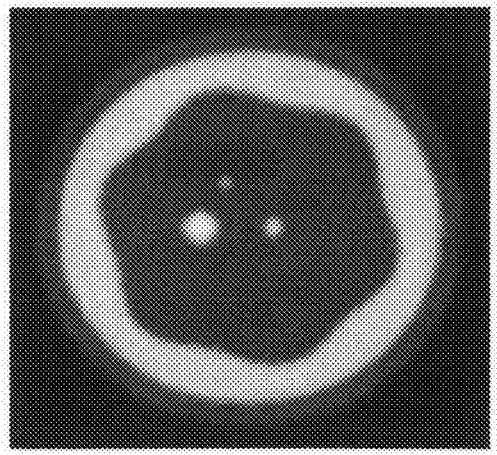
FIG. 40B: Normalized speed of sound image, $\gamma=[c_o/c(x,y)-1]$, reconstructed by the 2 wavelength pixel algorithm.
Figure 40C:
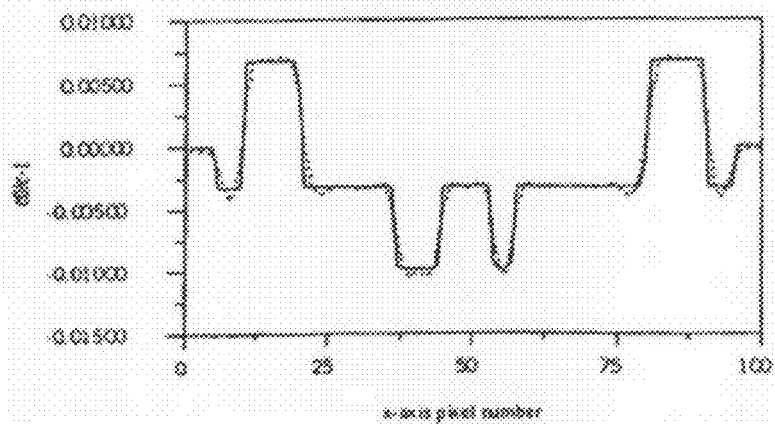
FIG. 40C: Sampled true and reconstructed 2 wavelength pixel images through the horizontal center-line.

For this computer simulation example we use the following parameters: Frequency=5 MHz. Number of frequencies=1. Pixel dimension=2) Image size 100 by 100 pixels=2.36 by 2.36 inches. Element aperture=0.236 inches. 90 element translation positions for 90 view angles. Speed of sound values (m/s): cwater=1500, cskin=1505, cfat=1490, cparenchyma=1505, ctumor=1510. The image size can easily be doubled or beyond for real data. The results of this simulation are shown in FIGS. 40A and 40B. FIG. 40A shows the normalized true speed of sound image, $[c_o/c(x,y)-1]$, used to generate the simulated data. FIG. 40B shows the normalized image, $[c_o/c(x,y)-1]$, reconstructed by the 2 wavelength pixel algorithm.

Conclusion for Example 3: Using an accurate model of the two, 5 MHz, ¼ inch diameter piston transducers rather than lab data that was not designed with the transducers accurately aligned and calibrated, the spatial resolution is about 4 times better than the lab data. In fact, the images are remarkable. This simulation experiment suggest a follow up simulation experiment where a much larger receiver aperture is used to sample a much greater part of the scattered (diffracted) waves in the forward direction. In this case an additional factor of improvement should be obtained. This experiment is performed in the next example.

Example 4

Images made from simulated data for the same phantom as in EXAMPLE 3, but with the ¼ inch diameter piston transducers replaced with an transducer array of 120 elements, each 2 wavelengths in width and center to center separation.

See FIG. 41 for the comparison of the time of flight image using the CT algorithm with straight acoustic rays vs. the new, high speed inverse scattering method with $2\lambda$ (two wavelength) size square pixels. The phantom for generating the computer simulated data (used by the inversion algorithm in FIGS. 40 and 41) are the same, but the transducers are different (FIG. 40 uses piston transducers, while FIG. 41 uses a 120 element array). The parameters used in FIG. 41 are: D=pixel size=$2\lambda$ at 5 MHz=0.6 mm; Numeric array size=180 by 120 pixels=10.8 by 7.2 cm=4.25 by 2.84 in; outside circle diameter=6 cm=2.36 in; the receivers are located at 151 points centered on the 180 pixel border; the left and right hand sides of the 180 by 120 array are assumed to be perfectly reflecting (infinite impedance) boundaries; 120 views, 2 frequencies at 2.5 MHz and 5 MHz; cfat=1485; cparen=1515; ctumor=1520; ccyst=1520; and cskin=1515.

Figure 41A:
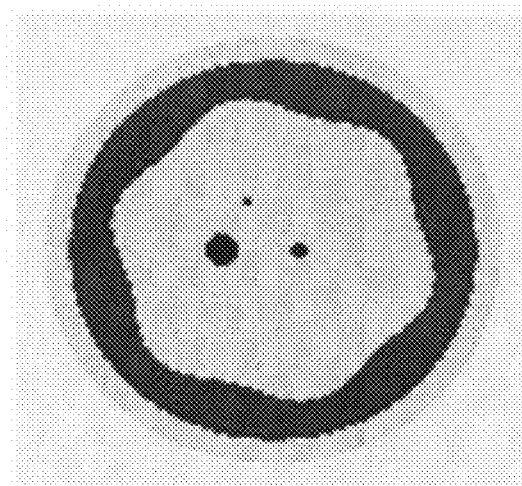
FIG. 41A: A 120 by 120 pixel image of Re($\gamma$) for the true object.
Figure 41B:
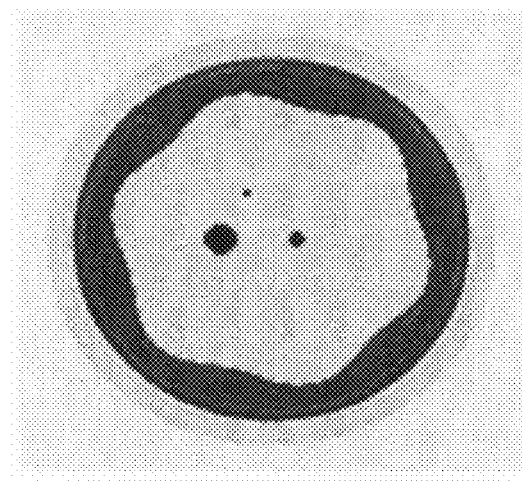
FIG. 41B: A 120 by 120 pixel image of the Re($\gamma$) reconstructed using the straight line, time of flight CT algorithm.
Figure 41C:
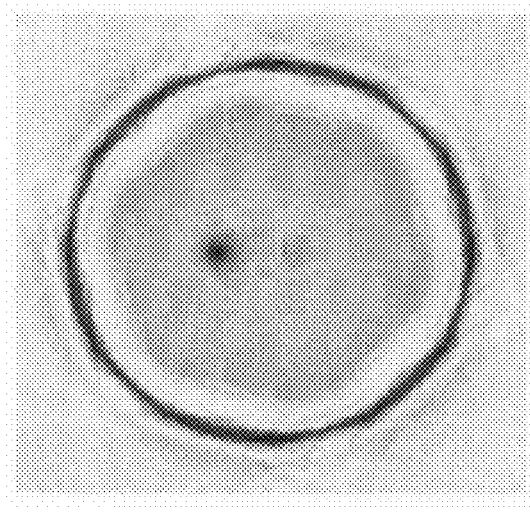
FIG. 41C: A 120 by 120 pixel image made by the new fast parabolic algorithm.

FIG. 41A shows a 120 by 120 pixel image of $[c_o/c(x,y)-1]$ for the true object. FIG. 41B shows a 120 by 120 pixel image of the $[c_o/c(x,y)-1]$ reconstructed using the straight line, time of flight CT algorithm. FIG. 41C shows a 120 by 120 pixel image by the new fast parabolic algorithm. Note the big improvement over the CT method.

Note the greater accuracy of the image from the new algorithm (right) vs. the time of flight (i.e. CT) image (center). Also note that using an array (FIG. 41C) produces a much better image than a single piston receiver (FIG. 40B).

Conclusion for Example 4: Increasing the receiver aperture does indeed improve spatial resolution as predicted by theory. The new algorithm is stable, accurate and fast and can use this increased data set size. The results of the four (4) Examples are self consistent and a speed up factor of 256 over previous parabolic methods is verified.

Transition to 3-D Imaging

Figure 42A:
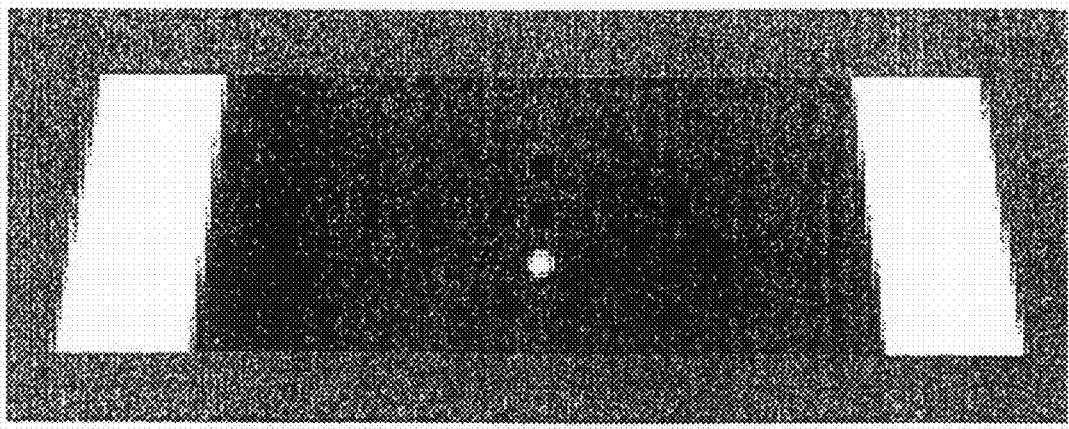
FIG. 42A: True 3-D speed of sound x-y image for breast cancer model on plane y=75.
Figure 42B:
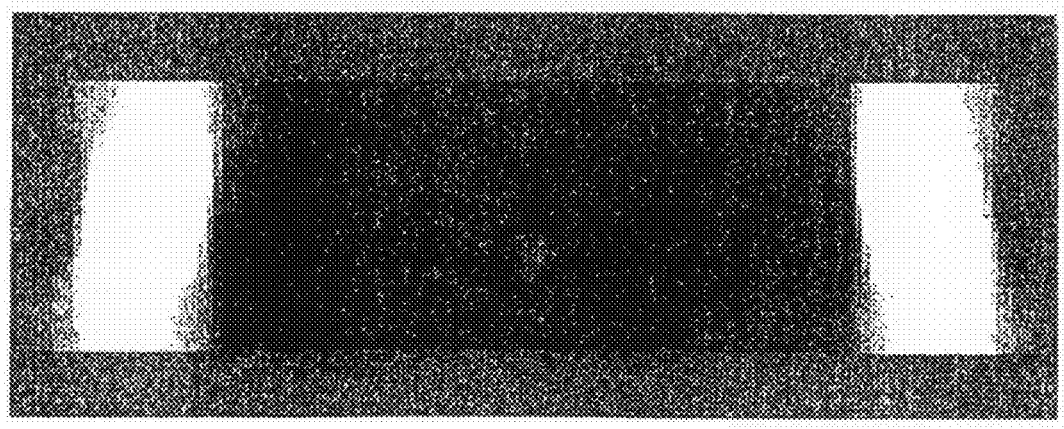
FIG. 42B: Parabolic reconstructed 3-D speed of sound image for the breast cancer model on plane y=75.

The transition from 2-D algorithms (either standard parabolic or fast multi pixel parabolic) is straight forward and only involves replacing the 1-D convolution kernel by a 2-D convolution kernel and other obvious dimensional changes. We have reprogrammed our standard 2-D parabolic algorithm to make 3-D inverse scattering images. The image pixel space for the following test case was 150 by 150 in the (x,y) topographic plane with 60 stacked planes (z axis direction). FIGS. 42A and 42B show the results of this simulation.

FIG. 42A shows the 3-D breast model with the true speed on sound on a z-x plane at y=75. In particular, the image is given by: speed of sound c(x, 75, z); positive contrast=4.6%; negative contrast=5.4%; gray scale limits are max black=–6% and max white=8%. Note that the three simulated tumors near the center are spatially resolved and reconstructed accurately.

We conclude from these images that 3-D imaging is a straight forward modification of 2-D imaging.

Value of Incorporating Reflectivity Imaging by Reflection Tomography.

We show next that incorporating reflection tomography imaging with the inverse scattering algorithm is straightforward and valuable. The speed of sound image made by inverse scattering can be used with ray tracing (either straight ray approximation or actual ray tracing) as a correction map or correction table to adjust the delay times for back propagation of data from a common transmission and reception transducer array. This process is well known to the art. The main difficulty to date has been obtaining an accurate speed of sound image to proceed with the mapping process to generate the correction table. The inverse scattering method fulfills this requirement almost perfectly. We show the result of straight line ray tracing through a speed of sound image made by time of flight tomography to correct a reflection tomography image of human breast tissue in a thin plastic cylinder.

Figure 43A:
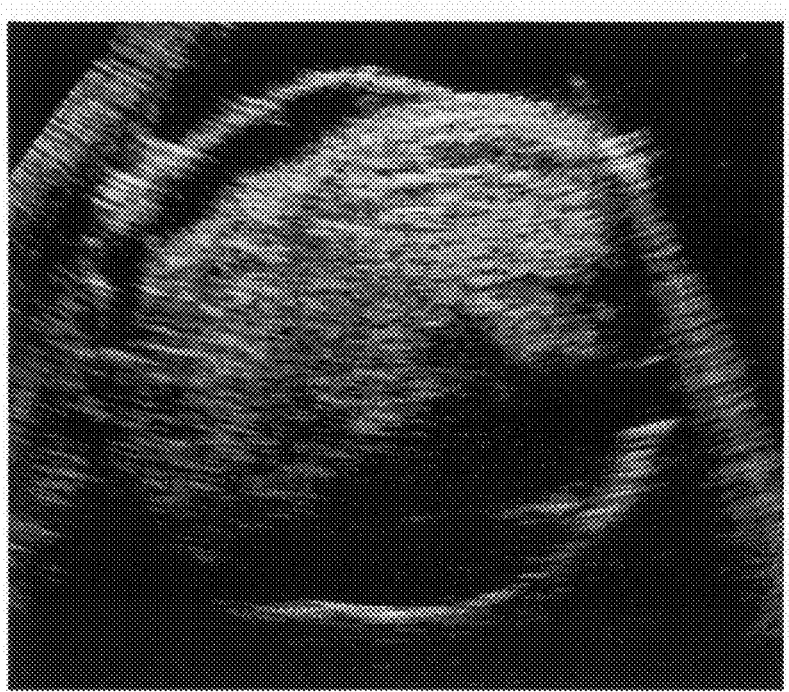
FIG. 43A: Commercial B-scan Image of the cancerous breast tissue.

FIG. 43A shows an image system made with a commercial B-scan of the cancerous breast tissue in the cylinder. A 3.5 MHz ultrasound sector probe was used while the phantom was submerged under water. The commercial scanner used 32 beam former channels.

Figure 43B:
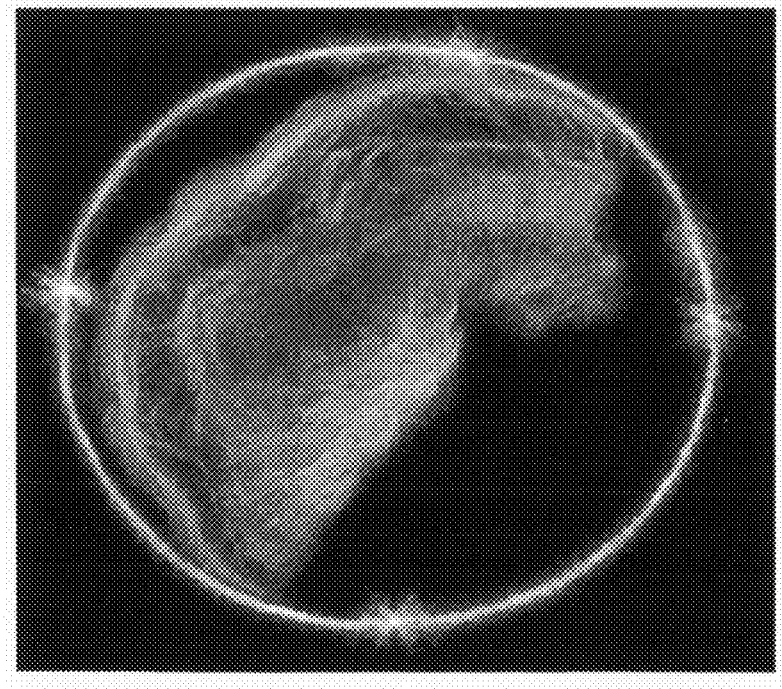
FIG. 43B: Reflection tomography image of the corresponding slice of the cancerous breast tissue shown in the companion B-scan image, FIG. 10.$a$.

FIG. 43B shows a reconstructed image made by reflection tomography of the same breast tissue sample at approximately the same level, made with a Water Bath, Reflection Tomography scanner at 5 MHz. This image was reconstructed from 12 vertical source/receiver pairs on a 420×420 grid using 0.25 mm wide pixels. Corrections in time delays were made for speed of sound variations (but not for refraction effects). It takes approximately 1.5 hr. of CPU time to compute this image on a 27 MFLOP computer. The breast is encapsulated in a plastic container whose walls are clearly visible and the bright spots on the walls are four marker strings. The greatly improved quality of the reflection tomography image is obvious.

Invention Disclosures for the Parabolic Inverse Scattering Algorithm—Large (2λ) Pixels In our original parabolic disclosure: example 12 of APPARATUS AND METHOD FOR IMAGING WITH WAVEFIELDS USING INVERSE SCATTERING TECHNIQUES, S. A. JOHNSON ET AL., the forward propagation of the wavefield from f(x,y) to f(x, y+Δ) where Δ is the pixel site, was performed by Fourier transforms via:

$$f(x,y+\Delta) = F_{\lambda \to x}^{-1}\{p(\lambda) F_{x' \to \lambda}\{f(x',y)\}\} \qquad 101.1$$

where F and $F^{-1}$ denote the forward and inverse Fourier transforms and the exact propagator, p, is given by:

$$p(\lambda) = e^{-i\Delta\sqrt{k_0^2 - \lambda^2}} \qquad 101.2$$

This propagator is exact. By the convolution theorem, 101.1 can be rewritten as:

$$f(x,y+\Delta) = \int f(x',y) p(x-x') dx' \qquad 101.3$$

where $$p(x) = F_{\lambda \to x}^{-1}\{p(\lambda)\} \qquad 101.4$$

Figure 44:
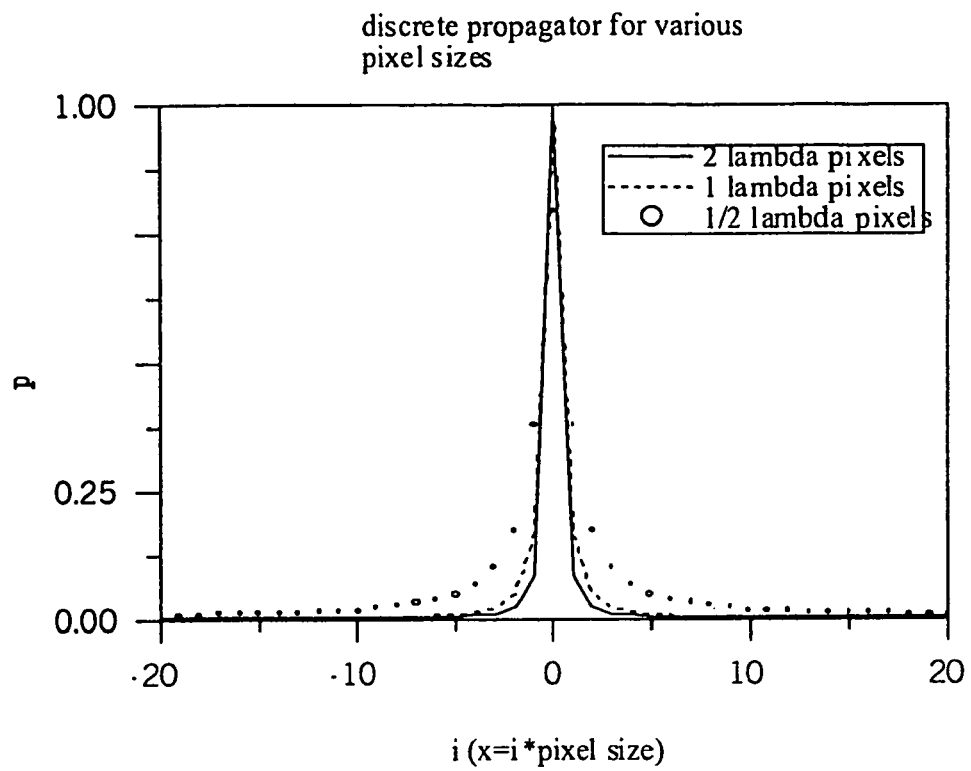
FIG. 44 The discrete propagator for $\Delta=2\lambda$, $\Delta=\lambda$ and $\Delta=\lambda/2$ for the new 'big pixel' parabolic method.

In other words, the propagator can be implemented by convolution. The question is, for a discrete version of these equations, which is faster, FFT's and multiplication in the frequency domain or convolution in the spatial domain? FIG. 44 shows our discrete propagator, p(iΔ), for 3 cases: Δ=2λ, Δ=λ and Δ=λ/2 where λ is the wavelength.

Notice that for Δ=λ/2, if we assume that we can cut off the propagator at i=±20 then the implementation of the propagator by a direct convolution sum would require N*41 operations. This convolution length is probably too long to be any faster than the FFT implementation. However, the Δ=λ case can be cut off at i=±6 and the Δ=2λ case can be cut off at i=±3. In particular, we have found that the Δ=2λ case can be implemented with a cut off at i=±3 with no discernible error over the FFT implementation providing that the propagator is multiplied by a Blackmann window:

$\hat{p}(i) = p(i)(0.42+0.5\ \cos(\pi i/(\text{nfilt}+1))+0.08\ \cos(2\pi i/(\text{nfilt}+1)))$, i=–nfilt, . . . , nfilt where nfilt=3 for the Δ=2λ case. Without this filter multiplication, the parabolic propagation was found to be unstable. Apparently, even though the neglected values are small, simple truncation of the propagator results in at least one eigenvalue slightly greater than 1 resulting in exponential growth for large numbers of parabolic steps.

We had originally thought that the parabolic algorithm required Δ≦λ/2 in order to maintain accuracy for scattering from biological tissue contrasts. This is certainly true if one requires scattering at angles out to 45 deg. from the incident field propagation direction. However, for computation of all scattering in a ±15 deg. cone, Δ=2λ sampling is sufficient. Of course, in a typical medical imaging problem, there will be scattering at large angles, however, suppose that the receivers are 2λ segments. Then the receivers do not see this large angle scattering energy anyway. Thus, the Δ=2λ algorithm will accurately compute the received data. Since the pixel size is now larger, the number of views needed for a complete dataset is also reduced by a factor of 4 over the Δ=λ/2 algorithm.

Compared with the previous $\Delta=\lambda/2$ algorithm, the speedup in compute time is given by: 4 times fewer views*16 times fewer pixels*speedup factor of short convolution vs. FFT propagator.

Even assuming that the short convolution buys only a factor of 4 over the FFT (it is likely better than this for nfilt=3), the algorithm is still 256 times faster than the previous algorithm for the same sized object at the same frequency.

Pseudo code definitions of the plane wave parabolic algorithms for the frequency domain
    Parameter Definitions

```
c₀ = background medium speed of sound in m/s
denotes the complex conjugate
||x²|| = x x*
||array||² = Σ_{i,j,...} ||array(i,j,...)||² where i,j,... are the indices of the array
<array1,array2> = Σ_{i,j,...} array1(i,j,...)* array2(i,j,...)
        denotes discrete convolution
             = pixel dimension
nx = x-axis array dimension (x is normal to the parabolic
    propagation direction)
ny = y-axis array dimension (y is parallel to the parabolic
    propagation direction)
nr = the number of receivers per view
nv = the number of plane wave views from 0 to 360 deg.
nf = the number of frequencies used
nfilt defines the width of the short convolution propagator:
the values f(-nfilt+n) to f(n+nfilt) are used to propagate one step
for field index f(n).
    ne defines the number of samples used to define a receiver element.
Each receiver is -ne to ne, Δ samples long. For a point receiver,
ne is set equal to 0.
```

Propagator Definition

The following pseudo code defines the short convolution propagator generation.

```
δλ = 2π/(nxΔ)
for lf=1,...,nf
    for n=1,...,nx
           = (n-1)δλ
       if n > nx/2, λ = (n-nx-1)δλ
       if λ<k₀(lf) then
           temp(n) = exp(-i Δ sqrt(k₀(lf)²-λ²))
       else
           temp(n) = exp(- Δ sqrt(λ²-k₀(lf)²))
       endif
    next n
```

The next step is done by the FFT algorithm:

```
for m=1,nx
    temp2(m)=0
    for n=1,nx
        temp2(m)=temp2(m)+temp(n) exp(i 2π(n-1)(m-1)/nx)/nx
    next n
next m
for n=0,nfilt
    wind=0.42+0.5cos(πn/(nfilt+1))+0.08cos(2πn/(nfilt+1))
    prop(n,lf)=temp2(n+1) wind
next n
for n=-nfilt,-1
    prop(n,lf)=prop(-n,lf)
next n
next lf
```

The window (wind = Blackmann in the present case) applied above to the short convolution propagator is essential for stability.

Definition of the Propagator Operation

The notation:
    temp→temp⊛prop(.,lf) will henceforth be used to denote
    the following computation:
```
for n=1,...,nx
    temp2(n)=temp(n)
next n
for n=-nfilt+1,0
    temp2(n)=temp(1-n)
next n
for n=nx+1,nx+nfilt
    temp2(n)=temp(2nx-n+1)
next n
for m=1,...,nx
    temp(m)=0
    for n=n-filt,n+nfilt
        temp(m)=temp(m)+temp2(n)prop(m-n,lf)
    next n
next m
```
Note that this implementation applies the boundary condition for an infinite impedance boundary (f'=0) at the array ends 1 and nx.

Definition of the Rotation Operator

The notation $$tr = Rot(t, \phi)$$

will henceforth denote the rotation of the function in array t(nx,ny) by $\phi$ radians followed by placement into array tr(nx, ny) via bilinear interpolation.

Definition of the Receiver Location Array

The nr receivers are located at the points mr(lr), lr=1, ..., nr where each mr(lr) is an element of [1+ne, ..., nx-ne]

Definition of the Receiver Sensitivity Function

Receiver lr is centered at point mr(lr) and extends from mr(lr)-ne to mr(lr)+ne. The array wr(-ne:ne,nf) is set to be the receiver sensitivity function on the support of the receiver for each frequency 1, ..., nf.

```
Code 1. Frequency domain, plane wave source, parabolic algorithm
common k₀,Δ,prop,wr,mr
common /gamma/ γ
complex γ(nx,ny), grad(nx,ny), tg(nx,ny), p(nx,ny)
        f(nr,nv,nf), r(nr,nv,nf),tr(nr,nv,nf), wr(-ne:ne,nf), prop(-nfilt:nfilt,nf)
real k₀(nf),freq(nf)
integer mr(nr)
set Δ = pixel size in m.
set freq(lf), lf=1,...,nf in Hz.
```

-continued

```
k₀(lf)=2π freq(lf)/c₀, lf=1,...,nf
set the prop() array as described in "Definition of the propagator operation" section above.
set wr as described in "Definition of the receiver location array" section above.
set mr as described in "Definition of the receiver sensitivity function" section above.
select a residual termination tolerance ε₁
select a gradient magnitude termination tolerance ε₂
select a maximum number of iterations, nrp
read the data f(nr,nv,nf)
resdata=||f||
set γ equal to a starting guess
call scatter(γ,r)
r→r-f
res0=||r||/resdata
call jacobian_adjoint(r,grad)
r₁ = ||grad||²
p→-grad
g0=||grad||
for lrp=1,...,nrp
call jacobian(p,tr)
α=-Re{<r,tr>}/||tr||²
γ→γ+αp
call scatter(γ,r)
r→r-f
res(lrp)=||r||/resdata
call jacobian_adjoint(r,tg)
g(lrp)= ||tg||/g0
if res(lrp) < ε₁, go to line 100
if g(lrp) < ε₂, go to line 100
β=Re{<tg,tg-grad>}/r₁
if β < 0, β→0
r₁ = ||tg||²
p→-tg+βp
grad→tg
next lrp
100 write γ to a datafile
stop
subroutine scatter(γ,f)
common k₀,Δ,prop,wr,mr
complex t(nx,ny),γ(nx,ny),temp(nx),f(nr,nv,nf),wr(-ne:ne,nf),
        prop(-nfilt:nfilt,nf),tr(nx,ny)
real ko(nf)
integer mr(nr)
for lf=1,...,nf
t(n,m)= exp(-i k₀(lf)Δ γ(n,m)), n=1,...,nx, m=1,...,ny
for lv=1,...,nv
    φ=2π (lv-1)/nv
    tr = Rot(t,φ)
    temp(n) = 1, n=1,...,nx
    for m=1,...,ny
    temp→temp⊛prop(.,lf)
    temp(n) = temp(n) tr(n,m), n=1,...,nx
    next m
    for lr=1,...,nr
    f(lr,lv,lf) = 0
    for le=-ne,...,ne
        f(lr,lv,lf) = f(lr,lv,lf)+temp(mr(lr)+le)wr(le,lf)
    next le
    next lr
next lv
next lf
return
subroutine jacobian(δγ,δf)
common k₀,Δ,prop,wr,mr
common /gamma/ γ
complex t(nx,ny),γ(nx,ny),temp(nx),wr(-ne:ne,nf),prop(-nfilt:nfilt,nf),tr(nx,ny)
        δt(nx,ny),δtr(nx,ny),temp2(nx),δf(nr,nv,nf)
real ko(nf)
integer mr(nr)
for lf=1,...,nf
t(n,m)= exp(-i k₀(lf)Δ γ(n,m)), n=1,...,nx, m=1,...,ny
coeff = -i k₀(lf)Δ
for lv=1,...,nv
    φ=2π (lv-1)/nv
    tr = Rot(t,φ)
    δtr = Rot(δt,φ)
    temp(n) = 1, n=1,...,nx
    temp2(n) = 0, n=1,...,nx
    for m=1,...,ny
    temp→temp⊛prop(.,lf)
```

-continued

```
        temp2→temp2⊛prop(.,lf)
        for n=1,...,nx
            temp2(n) = (temp2(n)+temp(n) δtr(n,m) coeff) tr(n,m)
            temp(n) = temp(n) tr(n,m)
        next n
        next m
        for lr=1,...,nr
        δf(lr,lv,lf) = 0
        for le=-ne,...,ne
            δf(lr,lv,lf) = δf(lr,lv,lf)+temp(mr(lr)+le)wr(le,lf)
        next le
        next lr
    next lv
    next lf
    return
    subroutine jacobian_adjoint(δf,δγ)
    common k₀,Δ,prop,wr,mr
    common /gamma/ γ
    complex t(nx,ny),γ(nx,ny),temp(nx),wr(-ne:ne,nf),prop(-nfilt:nfilt,nf),tr(nx,ny)
        δt(nx,ny),δtv(nx,ny),δtvr(nx,ny),δf(nr,nv,nf)
    real ko(nf)
    integer mr(nr)
    δt(n,m)=0, n=1,...,nx m=1,...,ny
    for lf=1,...,nf
    t(n,m)= exp(-i k₀(lf)Δ γ(n,m)), n=1,...,nx, m=1,...,ny
    coeff = -i k₀(lf)Δ
    for lv=1,...,nv
        =2π (lv-1)/nv
        tr = Rot(t,φ)
        temp(n) = 1, n=1,...,nx
        for m=1,...,ny
        temp→temp⊛prop(.,lf)
        for n=1,...,nx
            δtv(n,m)=temp(n)
            temp(n) =t emp(n) tr(n,m)
        next n
        next m
        temp(n) = 0, n=1,...,nx
        for lr=1,...,nr
        for le=-ne,...,ne
            temp(mr(lr)+le) =temp(mr(lr)+le)+δf*(lr,lv,lf)wr(le,lf)
        next le
        next lr
        for m = nx,...,1
        for n = 1,...,nx
            δtv(n,m) = δtv(n,m)*temp(n)
            temp(n) = temp(n) tr(n,m)
        next n
        temp→temp⊛prop(.,lf)
        next m
        δtvr = Rot(δtv,-φ)
        δt(n,m) = δt(n,m)+δtvr(n,m) tr(n,m) coeff, n=1,...,nx m=1,...,ny
    next lv
    next lf
    δt(n,m) = δt*(n,m), n=1,...,nx m=1,...,ny
    return
```

The Enveloped Time Domain Parabolic Algorithm

The second invention disclosure for the parabolic inverse scattering algorithm is a means of avoiding local minima when imaging an object with many π phase shifts and when starting from a zero (or a somewhat poor) initial guess. If one has only one frequency and the phase shift through the object is less than π radians then one can converge to the global, correct solution from a starting guess of zero. If the phase shift is greater than π then the algorithm will converge to a local minimum if a zero starting guess is used. Extrapolating this, if one has a bandwidth from fmin to fmax then convergence to the correct solution will occur from a zero starting guess only if the phase shift through the object is less than π at fmin. For biological tissue at ultrasound frequencies, say 5 MHz, phase shifts of on the order of 10 π are encountered. This means that fmin needs to be on the order of 1/10 th finax. This is not possible with the typically 50% bandwidth transducers available at present.

In order to get around this difficulty, we have examined the use of starting guesses computed by straight line time of flight imaging. In this approach the time delay of the acoustic time pulse through the body is extracted from the data. Assuming that the energy took a straight line path through the body for each receiver (not a good assumption due to ray bending (refraction) and diffraction effects) then the speed of sound image can be reconstructed by well known x-ray CT type algorithms. We have found that these starting guesses will work up to a point but as we increase the size and contrast of the body up to that of tissue, we find that the time of flight image is not sufficiently close to the truth to allow inverse scatter imaging with 50% bandwidth transducers.

One may reasonably ask the question: why does the time of flight algorithm work with 50% bandwidth transducers? The answer is that even though the time pulse that travels through the target has only 50% bandwidth, it is still possible to deduce the time delays.

FIG. 35 shows the time signal computed for a 2.4 cm dia. 1520 m/s cylinder illuminated by a plane wave for 20 frequencies from 2.5 to 5 MHz at a receiver located at the center of the receiving array. The frequency domain data for this case is $f^{total}(\omega)\overline{f^{inc}(\omega)}$ which was then transformed to time. Note that this division by $f^{inc}$ in the frequency domain removes the time delay due to the propagation from source to receiver through the background medium (water 1500 m/s) and so the center of the time pulse gives the time shift due to the cylinder.

Figure 45:
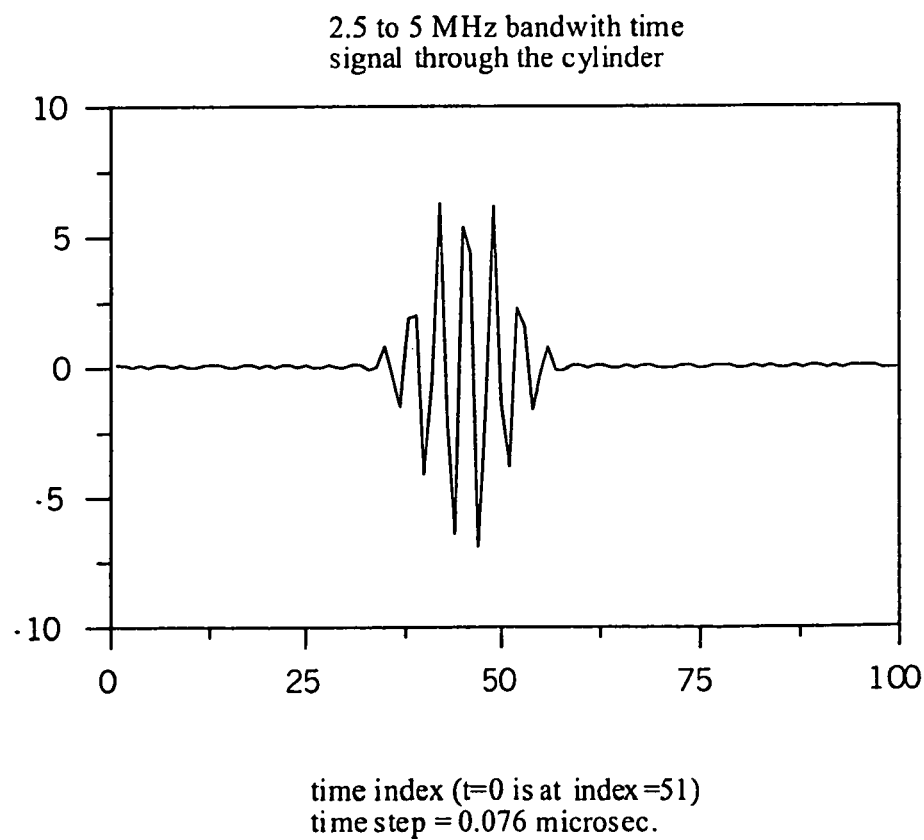

Suppose now that we attempted to find the center of the waveform in FIG. 45 with a optimization algorithm (say Newton's method) starting with t=0 (sample 51) as the starting guess. Further suppose that we defined the center as coincident with the maximum wave magnitude.

Figure 46:
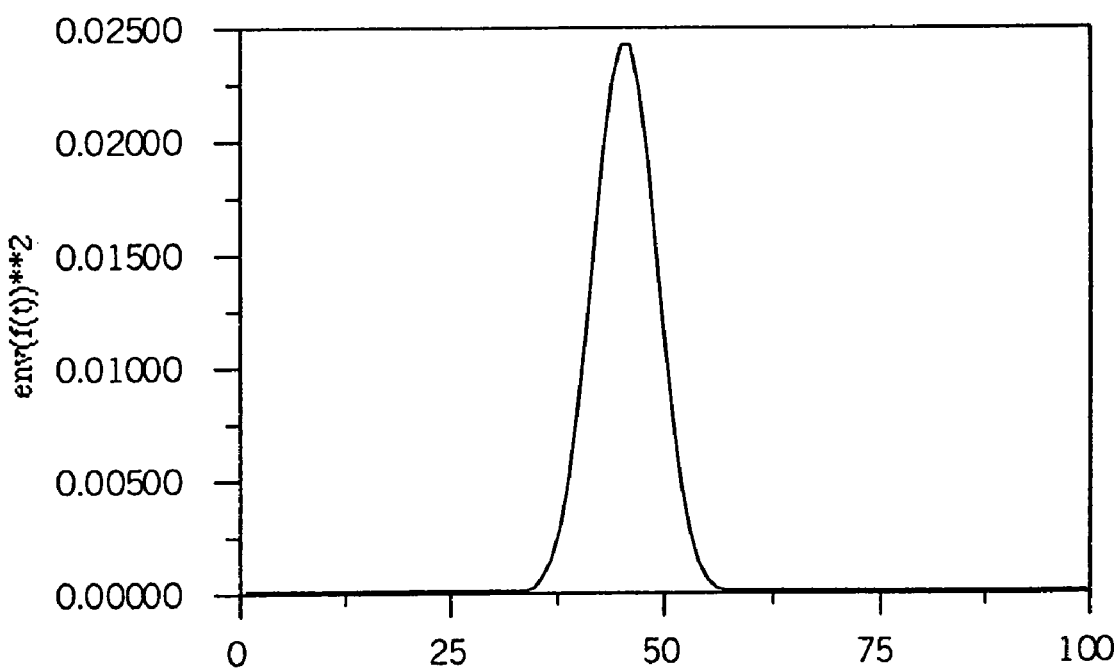
FIG. 46 Squared envelope of the 2.5 MHz to 5 MHz bandwidth time signal through a cylinder.

Clearly we would find the negative peak near sample 51—a local maximum. This is analogous to what happens with the parabolic inversion algorithm starting with a zero guess. The time of flight algorithm, on the other hand, finds the time delay by first taking the envelope of the waveform. The envelope squared of the signal shown in FIG. 45 is shown in FIG. 46.

It is now a simple matter to find the time delay to the waveform center with either an optimization algorithm or by simply detecting the index of the maximum value.

The preceding discussion suggests that the parabolic inversion algorithm might avoid local minima, even with 50% bandwidth transducers, if one operated on the envelope of the time waveform as the data. It is a simple matter to take the frequency domain output of the parabolic algorithm, transform to time, and then take the envelope. Unfortunately, the envelope operator is not differentiable and the parabolic inversion algorithm relies on gradient direction optimization (conjugate gradients). This difficulty can, however, be overcome by making the square of the envelope the time domain output data. This function is differentiable and a conjugate gradient optimization algorithm can be applied. Specifically, the new functional to be minimized is:

$$F[\gamma] = \|env(f^{parabolic}(\gamma,t))^2 - env(f^{data}(t))^2\|^2 \qquad 102.1$$

(with multiple receivers and views of course). Derivation of the Jacobian and its adjoint for the new functional is straightforward. The resulting forward scattering calculations and the Jacobian and its adjoint are best viewed in the following pseudo code form.

PseudoCode for Time Domain Parabolic Code Algorithm:

For the time domain code, we first set the parameter $\Delta f$=the frequency domain sample interval so that the total time period T=1./$\Delta f$ is sufficient to contain the minimum and maximum time shifts in the data. We then specify the minimum and maximum frequencies by their indices nmin and nmax:

fmin=minimum frequency=nmin $\Delta f$, fmax=maximum frequency=nmax $\Delta f$, using the desired fmax and fmin.

We then select the number of time steps, nt>nmax and set the time domain sample interval as:

$\Delta t = 1/(nt\ \Delta f)$.

Then, nf=the number of frequencies, is set=nmax−nmin+1 and the frequency list is set as:

freq($lf$)=($lf$−1+nmin)$\Delta f$, $lf$=1, ..., $nf$

Now, suppose that the array fc(m,nv,nf) contains the frequency domain total field computed by the parabolic algorithm for nr receivers and nv views and let the array fi$\omega$(nr,nf) contain the incident field for the parabolic algorithm. We then transform this frequency domain to the envelope squared of the time domain data via the operations:

```
for lv = 1,...,nv
  for lr = 1,...,nr
    fctemp(i)=0, i = 1,...,nt
    for lf = 1,...,nf
      fctemp(lf+nfmin)=(fc(lr,lv,lf)/fiω(lr,lf)) wt(lf)
    next lf
    fctemp→FFT⁻¹ₙₜ{fctemp}
    for n = 1,...,nt
      fω(lr,lv,n)=fctemp(n)
      f(lr,lv,n)=fctemp(n) fctemp*(n)
    next n
  next lr
next lv
```

Now, f(nr,nv,nt) contains the time envelope squared of the simulated signals. Note we have also computed the array f$\omega$(nr,nv,nt) which contains the complex analytic time domain waveforms. This function is needed for the Jacobian and Jacobian adjoint calculations. The frequency domain filter wt(nf) is given by:

freq$c$=($f$max+$f$min)/2 freq$b$=($f$max−$f$min)/2 wt($lf$)=(0.42+0.5 cos($\pi$(freq($lf$)−freq$c$)/freq$b$)+0.08 cos(2$\pi$(freq($lf$)−freq$c$)/freq$b$))*exp(−$i$2$\pi$freq($lf$)$\Delta t$ ($nt$/2)), $lf$=1, ..., $nf$ and is applied to prevent sidelobes in the envelope and to shift the time=0 index in the array from 1 to nt/2+1.

In order to compute the gradient (Jacobian adjoint operating on the residual), we first compute the time domain residual array:

$r(lr,lv,lt) = f^{data}(lr,lv,lt) - f(lr,lv,lt)$, $lt$=1, ..., $nt$, $lv$= 1, ..., $lv$, $lr$=1, ..., $nr$.

We then compute the frequency domain residual, r$\omega$(m,nv, nf) by the calculation:

```
for lv = 1,...,nv
  for lr = 1,...,nr
    for n = 1,...,nt
      fctemp(n)=2 r(lr,lv,n) fω(lr,lv,n)
    next n
    fctemp→FFTₙₜ{fctemp}
    for lf = 1,...,nf
      rω(lr,lv,lf)=fctemp(lf+nfmin) (wt(lf)/fiω(lr,lf))*
    next lf
  next lr
next lv
```

Once the frequency domain residual array is computed, we then apply the original Jacobian adjoint of the frequency domain parabolic algorithm:

$\nabla F = J$(frequency domain parabolic Jacobian)$^H \cdot r\omega$

The Jacobian operating on a perturbation to γ (which is also needed to perform a conjugate gradient optimization) is similarly computed.

Note on the Jacobian implementation: observe that the operation of converting to time domain data, then taking the envelope and squaring is concatenated onto the operation of propagating the fields via the parabolic algorithm at the respective frequencies, therefore, it follows that the implementation of the Jacobian will follow from the standard chain rule of vector calculus. This implementation is in fact given explicitly in the above pseudo-code, but is restated explicitly here for further elucidation of the process.

CONCLUSION

We have implemented this enveloped time domain parabolic algorithm and have verified that it does indeed converge from a zero starting guess. The final image is somewhat degraded (lower resolution) relative to the frequency domain algorithm with a good starting guess due to the loss of some information from the envelope operation. However, this code does produce a sufficiently accurate starting guess for the frequency domain algorithm which can then refine the resolution of the image.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A transmission wave field imaging method, comprising:
    transmitting an incident wave field into an object, the incident wave field propagating into the object and, at least, partially scattering;
    measuring a wave field transmitted, at least in part, through the object to obtain a measured wave field, the measured wave field being defined, in part, by the incident wave field and the object; and
    processing the measured wave field utilizing a parabolic approximation reconstruction algorithm to generate an image data set representing at least one image of the object.

2. The method of claim 1, wherein the parabolic approximation reconstruction algorithm calculates a predicted total wave field utilizing a single independent variable, the single independent variable representing scattering potential.

3. The method of claim 1, wherein the parabolic approximation reconstruction algorithm utilizes a parabolic binomial approximation.

4. The method of claim 1, wherein the object is tissue, the incident wave field is an acoustic wave field and the parabolic approximation reconstruction algorithm models acoustic wave propagation through the tissue.

5. The method of claiml, wherein the parabolic approximation reconstruction algorithm models forward wave propagation of the incident wave field.

6. The method of claim 1, wherein the object is a breast scanner and the processing generates the image of a breast during a breast scan.

7. The method of claim 1, wherein the image represents quantitative estimates of a speed-of-sound associated with the object.

8. The method of claim 1, wherein the image represents quantitative estimates of an attenuation associated with the object.

9. The method of claim 1, wherein the incident wave field represents an ultrasound wave field and the method further comprises displaying the at least one image as at least two images co-displayed, the at least two images including a speed-of-sound image and an attenuation image.

10. The method of claim 1, wherein the incident wave field represents an ultrasound wave field and the method further comprises displaying the at least one transmissive image as at least two images co-displayed, the at least two images including a speed-of-sound image and an attenuation image.

11. The method of claim 1, wherein the incident wave field comprises at least one of acoustic energy, elastic energy, electromagnetic energy and microwave energy.

12. The method of claim 1, wherein the transmitting and measuring are performed by a transmitter and receiver, respectively, the method further comprising moving at least one of the transmitter and receiver with respect to the object.

13. The method of claim 1, further comprising repeating the transmitting and receiving at multiple slices within the object to generate a 3D volume of data.

14. The method of claim 1, further comprising displaying 2-D images representative of slices through the object.

15. The method of claim 1, further comprising displaying a 3-D image of at least a portion of the object.

16. The method of claim 1, further comprising:
    obtaining speed-of-sound and attenuation values from the image data set, the speed-of-sound values corresponding to a speed of ultrasound wave fields through tissue, the attenuation values corresponding to an amount of attenuation of ultrasound wave fields propagating through the tissue.

17. The method of claim 1, further comprising:
    constructing a speed-of-sound image from the measured wave field;
    constructing an attenuation image from the measured wave field; and
    displaying the speed-of-sound image and the attenuation image.

18. A transmission wave field imaging device, comprising:
    a transmitter for transmitting an incident wave field into an object, the incident wave field propagating into the object and, at least, partially scattering;
    a receiver measuring a total wave field transmitted, at least in part, through the object to obtain a measured wave field, the measured wave field being defined, in part, by the incident wave field and the object; and
    a processing module processing the measured wave field utilizing a parabolic approximation reconstruction algorithm to generate an image data set representing at least one image of the object.

19. The device of claim 18, wherein the processor module comprises a plurality of processors operated in parallel.

20. The device of claim 18, wherein the processor module is implemented on one of a personal computer, a hand-held device, a multi-processor system and a network PC.

21. The device of claim 18, wherein the receiver is rotated about the object to obtain measured data at multiple receive positions around the object, the measured data defining the measured wave field.

22. The device of claim 18, further comprising a display for displaying an image based on the image data set as at least one of a speed of sound image and an attenuation image.

23. The device of claim 18, wherein at least one of the receiver and the transmitter includes transducer elements arranged in at least one of a circular array, a linear array, a 2D planar array and a checkerboard 2D array.

24. The device of claim 18, wherein the transmitter sequentially transmits first and second incident wave fields into the object having different first and second fundamental frequencies, respectively.

25. A transmission wave field imaging system, comprising:
a transmitter for transmitting an incident wave field into an object, the incident wave field propagating into the object and, at least, partially scattering;
a receiver measuring a total wave field transmitted, at least in part, through the object to obtain a measured wave field, the measured wave field being defined, in part, by the incident wave field, a scattering potential and the object, the measured wave field including at least one of speed of sound information and attenuation information characterizing the object;
a processing module for processing, on-site and in real-time, the measured wave field utilizing a parabolic approximation reconstruction algorithm to generate an image data set representing at least one image of the object, the image comprising pixel values based on at least one of the speed of sound information and the attenuation information characterizing the object; and
a display for displaying, on-site and in real-time, the image containing at least one of the speed of sound information and the attenuation information of the object.

26. The system of claim 25, wherein the system is a breast scanner and the processing module generates the image during a breast scan.

27. The system of claim 25, further comprising a phase detector joined to the receiver, the phase detector outputting real and imaginary signal components.

28. The system of claim 25, wherein the transmitter and receiver repeat the transmitting and receiving operations at multiple slices within the object to collect a 3D volume of data.

29. The system of claim 25, wherein the display displays 2-D images representative of slices through the object.

30. The system of claim 25, wherein the display displays a 3-D image of at least a portion of the object.

31. The system of claim 25, further comprising a movable carriage supporting the transmitter and receiver, the movable carriage rotating about an axis of a cylindrical chamber that is configured to receive the object.

32. The system of claim 25, further comprising a movable carriage supporting the transmitter and receiver, the movable carriage being vertically adjusted along an axis of a cylindrical chamber that is configured to receive the object.

33. The system of claim 25, further comprising a fluid tank configured to receive at least one of the object, the transmitter and receiver.

* * * * *